(12) United States Patent
Ren et al.

(10) Patent No.: US 9,637,492 B2
(45) Date of Patent: May 2, 2017

(54) BENZOTHIAZOLE KINASE INHIBITORS AND METHODS OF USE

(71) Applicant: Intellikine LLC, La Jolla, CA (US)

(72) Inventors: Pingda Ren, San Diego, CA (US); Yi Liu, San Diego, CA (US); Troy Edward Wilson, San Marino, CA (US); Liansheng Li, San Diego, CA (US); Katrina Chan, San Diego, CA (US)

(73) Assignee: Intellikine LLC, La Jolla, CA (US)

( * ) Notice: Subject to any disclaimer, the term of this patent is extended or adjusted under 35 U.S.C. 154(b) by 0 days.

(21) Appl. No.: 14/619,556

(22) Filed: Feb. 11, 2015

(65) Prior Publication Data

US 2015/0225407 A1    Aug. 13, 2015

Related U.S. Application Data

(63) Continuation of application No. 12/920,966, filed as application No. PCT/US2009/037324 on Mar. 16, 2009, now Pat. No. 8,993,580.

(60) Provisional application No. 61/069,637, filed on Mar. 14, 2008.

(51) Int. Cl.

| | | |
|---|---|---|
| C07D 487/04 | (2006.01) | |
| A61K 31/519 | (2006.01) | |
| A61P 35/02 | (2006.01) | |
| A61P 37/06 | (2006.01) | |
| A61P 35/04 | (2006.01) | |
| A61K 31/5377 | (2006.01) | |

(52) U.S. Cl.
CPC .......... *C07D 487/04* (2013.01); *A61K 31/519* (2013.01); *A61K 31/5377* (2013.01)

(58) Field of Classification Search
CPC ........................ C07D 487/04; A61K 31/519
See application file for complete search history.

(56) References Cited

U.S. PATENT DOCUMENTS

| | | | |
|---|---|---|---|
| 4,704,381 A | 11/1987 | Schaumann et al. | |
| 5,240,941 A | 8/1993 | Bruneau | |
| 5,310,731 A | 5/1994 | Olsson et al. | |
| 5,364,862 A | 11/1994 | Spada et al. | |
| 5,420,419 A | 5/1995 | Wood | |
| 5,428,125 A | 6/1995 | Hefner, Jr. et al. | |
| 5,442,039 A | 8/1995 | Hefner, Jr. et al. | |
| 5,506,347 A | 4/1996 | Erion et al. | |
| 5,561,134 A | 10/1996 | Spada et al. | |
| 5,563,257 A | 10/1996 | Zilch et al. | |
| 5,593,997 A | 1/1997 | Dow et al. | |
| 5,646,128 A | 7/1997 | Firestein et al. | |
| 5,652,366 A | 7/1997 | Spada et al. | |
| 5,654,307 A | 8/1997 | Bridges et al. | |
| 5,665,721 A | 9/1997 | Bhagwat et al. | |
| 5,674,998 A | 10/1997 | Boyer et al. | |
| 5,686,455 A | 11/1997 | Adams et al. | |
| 5,736,554 A | 4/1998 | Spada et al. | |
| 5,747,235 A | 5/1998 | Farid et al. | |
| 5,756,711 A | 5/1998 | Zilch et al. | |
| 5,763,596 A | 6/1998 | Boyer et al. | |
| 5,763,597 A | 6/1998 | Ugarkar et al. | |
| 5,763,885 A | 6/1998 | Murphy et al. | |
| 5,795,977 A | 8/1998 | Ugarkar et al. | |
| 5,824,492 A | 10/1998 | Hiles et al. | |
| 5,858,753 A | 1/1999 | Chantry et al. | |
| 5,914,488 A | 6/1999 | Sone | |
| 5,919,808 A | 7/1999 | Petrie et al. | |
| 5,922,753 A | 7/1999 | Petrie et al. | |
| 5,948,776 A | 9/1999 | Petrie et al. | |
| 5,965,573 A | 10/1999 | Petrie et al. | |
| 5,977,061 A | 11/1999 | Holy et al. | |
| 5,981,533 A | 11/1999 | Traxler et al. | |
| 5,985,589 A | 11/1999 | Chantry et al. | |
| 5,990,169 A | 11/1999 | Petrie et al. | |
| 5,994,358 A | 11/1999 | Petrie et al. | |
| 6,001,839 A | 12/1999 | Calderwood et al. | |
| 6,057,305 A | 5/2000 | Holy et al. | |
| 6,084,095 A | 7/2000 | Bridges et al. | |
| 6,093,737 A | 7/2000 | Anthony et al. | |
| 6,127,121 A | 10/2000 | Meyer, Jr. et al. | |
| 6,153,631 A | 11/2000 | Petrie et al. | |
| 6,191,170 B1 | 2/2001 | Medina | |
| 6,214,834 B1 | 4/2001 | Jadhav et al. | |
| 6,251,901 B1 | 6/2001 | Petrie et al. | |

(Continued)

FOREIGN PATENT DOCUMENTS

| | | |
|---|---|---|
| CA | 1338379 | 6/1996 |
| CN | 101602768 | 12/2009 |

(Continued)

OTHER PUBLICATIONS

Neidle, Stephen (Cancer Drug Design and Discovery, Elsevier/Academic Press, 2008 p. 427-431).*
U.S. Appl. No. 14/106,479, filed Dec. 13, 2013, Knight et al.
U.S. Appl. No. 14/139,723, filed Dec. 23, 2013, Ren et al.
U.S. Appl. No. 14/186,486, filed Feb. 21, 2014, Tanaka et al.
Bogert, et al. "Researches on quinazolines (Fifteenth paper), on a 3-aminoquinazoline, and the corresponding 3.3'-diquinazolyl, from 6-nitroacetanthranil and hydrazine hydrate" Journal of the American Chemical Society, (1906), 28(7), 884-893.
Elslager, et al. "Synthetic schistosomicides. VII. 6-Alkoxy-8-(aminoalkyl)amino-5-azoquinolines" Journal of Medicinal Chemistry (1964), 7(5) 663-4.
Hansch, et al. "Quantitative structure-activity relation of antimalarial and dihydrofolate reductase inhibition by quinazolines and 5-substituted benzyl-2,4-diaminopyrimidines" Journal of Medicinal Chemistry (1977), 20(1), 96-102.

(Continued)

*Primary Examiner* — Susanna Moore
(74) *Attorney, Agent, or Firm* — Honigman Miller Schwarz and Cohn LLP; Lucy X. Yang; Jonathan P. O'Brien

(57) ABSTRACT

The present invention provides chemical entities or compounds and pharmaceutical compositions thereof that are capable of modulating lipid kinases such PI3 kinases, tryosine kinases and protein kinases such as mTOR. Also provided in the present invention are methods of using these compositions to modulate these kinases especially for therapeutic applications.

19 Claims, 3 Drawing Sheets

(56) References Cited

U.S. PATENT DOCUMENTS

| | | |
|---|---|---|
| 6,265,410 B1 | 7/2001 | Bridges et al. |
| 6,268,370 B1 | 7/2001 | Adams et al. |
| 6,312,894 B1 | 11/2001 | Hedgpeth et al. |
| 6,319,660 B1 | 11/2001 | Allway et al. |
| 6,323,201 B1 | 11/2001 | Carson et al. |
| 6,342,514 B1 | 1/2002 | Petrie et al. |
| 6,350,741 B1 | 2/2002 | Golec et al. |
| 6,383,790 B1 | 5/2002 | Shokat |
| 6,384,039 B1 | 5/2002 | Fossa |
| 6,387,894 B1 | 5/2002 | Fossa |
| 6,390,821 B1 | 5/2002 | Shokat |
| 6,417,194 B1 | 7/2002 | Fox et al. |
| 6,455,534 B2 | 9/2002 | Bridges et al. |
| 6,472,153 B1 | 10/2002 | Dempcy et al. |
| 6,482,623 B1 | 11/2002 | Vanhaesebroeck et al. |
| 6,485,906 B2 | 11/2002 | Meyer, Jr. et al. |
| 6,492,346 B1 | 12/2002 | Hedgpeth et al. |
| 6,506,769 B2 | 1/2003 | Snow et al. |
| 6,518,277 B1 | 2/2003 | Sadhu et al. |
| 6,521,417 B1 | 2/2003 | Shokat |
| 6,521,620 B1 | 2/2003 | Bridges et al. |
| 6,531,491 B1 | 3/2003 | Kania et al. |
| 6,534,524 B1 | 3/2003 | Kania et al. |
| 6,545,005 B1 | 4/2003 | Baxter et al. |
| 6,552,192 B1 | 4/2003 | Hanu et al. |
| 6,562,819 B2 | 5/2003 | Carson et al. |
| 6,583,161 B1 | 6/2003 | Medina |
| 6,613,798 B1 | 9/2003 | Porter et al. |
| 6,624,119 B1 | 9/2003 | Reinhard et al. |
| 6,630,495 B1 | 10/2003 | Cooke et al. |
| 6,632,789 B1 | 10/2003 | June |
| 6,645,989 B2 | 11/2003 | Adams et al. |
| 6,649,631 B1 | 11/2003 | Orme et al. |
| 6,653,296 B1 | 11/2003 | Holy et al. |
| 6,653,306 B1 | 11/2003 | Alexander et al. |
| 6,660,744 B1 | 12/2003 | Hirst et al. |
| 6,660,845 B1 | 12/2003 | Gall et al. |
| 6,664,269 B2 | 12/2003 | Martin et al. |
| 6,667,300 B2 | 12/2003 | Sadhu et al. |
| 6,690,583 B1 | 2/2004 | Bergstedt et al. |
| 6,713,474 B2 | 3/2004 | Hirst et al. |
| 6,713,484 B2 | 3/2004 | Bridges et al. |
| 6,720,344 B2 | 4/2004 | Kerwin et al. |
| 6,734,187 B1 | 5/2004 | Tanaka et al. |
| 6,770,639 B2 | 8/2004 | Snow et al. |
| 6,777,425 B2 | 8/2004 | Burli et al. |
| 6,777,439 B2 | 8/2004 | Durden |
| 6,790,844 B2 | 9/2004 | Ueno et al. |
| 6,800,620 B2 | 10/2004 | Sadhu et al. |
| 6,800,633 B2 | 10/2004 | Castelhano et al. |
| 6,849,420 B2 | 2/2005 | Vanhasebroeck et al. |
| 6,849,713 B2 | 2/2005 | Zhang et al. |
| 6,852,727 B2 | 2/2005 | Goulet et al. |
| 6,906,103 B2 | 6/2005 | Zhang et al. |
| 6,919,332 B2 | 7/2005 | Noe et al. |
| 6,921,763 B2 | 7/2005 | Hirst et al. |
| 6,949,535 B2 | 9/2005 | Sadhu et al. |
| 7,026,461 B1 | 4/2006 | Shokat |
| 7,041,676 B2 | 5/2006 | McDonald et al. |
| 7,049,116 B2 | 5/2006 | Shokat |
| 7,049,312 B1 | 5/2006 | Rafferty et al. |
| 7,064,218 B2 | 6/2006 | Dyatkina et al. |
| 7,071,355 B2 | 7/2006 | Leban et al. |
| 7,115,627 B2 | 10/2006 | Pinto et al. |
| 7,115,653 B2 | 10/2006 | Baxter et al. |
| 7,144,903 B2 | 12/2006 | Collins et al. |
| 7,148,228 B2 | 12/2006 | Kasibhatla et al. |
| 7,157,487 B2 | 1/2007 | Nakayama et al. |
| 7,166,293 B2 | 1/2007 | Teng et al. |
| 7,208,601 B2 | 4/2007 | Mjalli et al. |
| 7,217,794 B2 | 5/2007 | Abdel-Meguid et al. |
| 7,241,890 B2 | 7/2007 | Kasibhatla et al. |
| 7,244,741 B2 | 7/2007 | Simon et al. |
| 7,247,736 B2 | 7/2007 | Leban et al. |
| 7,262,204 B2 | 8/2007 | Collins et al. |
| 7,265,111 B2 | 9/2007 | Bigot et al. |
| 7,265,131 B2 | 9/2007 | Johnson et al. |
| 7,271,262 B2 | 9/2007 | La Greca et al. |
| 7,329,765 B2 | 2/2008 | Burli et al. |
| 7,332,497 B2 | 2/2008 | Hirst et al. |
| 7,348,427 B2 | 3/2008 | Burli et al. |
| 7,365,094 B2 | 4/2008 | Leban et al. |
| 7,384,967 B2 | 6/2008 | Polisetti et al. |
| 7,396,836 B2 | 7/2008 | Harada et al. |
| 7,414,036 B2 | 8/2008 | Sevillano et al. |
| 7,429,596 B2 | 9/2008 | Tanaka et al. |
| 7,439,254 B2 | 10/2008 | Bergnes |
| 7,459,462 B2 | 12/2008 | Simon et al. |
| 7,459,472 B2 | 12/2008 | Mjalli et al. |
| 7,470,721 B2 | 12/2008 | Durden |
| 7,501,538 B2 | 3/2009 | Mjalli et al. |
| 7,534,797 B2 | 5/2009 | Arnold et al. |
| 7,541,373 B2 | 6/2009 | Polisetti et al. |
| 7,569,571 B2 | 8/2009 | Dong et al. |
| 7,572,913 B2 | 8/2009 | McKerracher et al. |
| 7,579,348 B2 | 8/2009 | Wang et al. |
| 7,585,868 B2 | 9/2009 | Knight et al. |
| 7,608,594 B2 | 10/2009 | Blagg et al. |
| 7,615,552 B2 | 11/2009 | Ono et al. |
| 7,622,451 B2 | 11/2009 | Blagg et al. |
| 7,678,803 B2 | 3/2010 | Huang et al. |
| 7,700,607 B2 | 4/2010 | Hu et al. |
| 7,745,485 B2 | 6/2010 | Durden |
| 7,932,260 B2 | 4/2011 | Fowler et al. |
| 2001/0024833 A1 | 9/2001 | Laborde et al. |
| 2001/0027197 A1 | 10/2001 | Bridges et al. |
| 2002/0016460 A1 | 2/2002 | Snow et al. |
| 2002/0016976 A1 | 2/2002 | Shokat |
| 2002/0037856 A1 | 3/2002 | Zhang et al. |
| 2002/0102590 A1 | 8/2002 | Taing et al. |
| 2002/0146690 A1 | 10/2002 | Meyer et al. |
| 2002/0147160 A1 | 10/2002 | Bhat et al. |
| 2002/0156081 A1 | 10/2002 | Hirst et al. |
| 2002/0161014 A1 | 10/2002 | Sadhu et al. |
| 2002/0173524 A1 | 11/2002 | Collins et al. |
| 2003/0001141 A1 | 1/2003 | Sun et al. |
| 2003/0008896 A1 | 1/2003 | Martin et al. |
| 2003/0018022 A1 | 1/2003 | Collins et al. |
| 2003/0022344 A1 | 1/2003 | Williams et al. |
| 2003/0064997 A1 | 4/2003 | Adams et al. |
| 2003/0073218 A1 | 4/2003 | Shokat et al. |
| 2003/0083268 A1 | 5/2003 | Burli et al. |
| 2003/0109248 A1 | 6/2003 | Lewis |
| 2003/0113765 A1 | 6/2003 | Dempcy et al. |
| 2003/0119479 A1 | 6/2003 | Arima et al. |
| 2003/0119791 A1 | 6/2003 | Kerwin et al. |
| 2003/0139427 A1 | 7/2003 | Castelhano et al. |
| 2003/0143602 A1 | 7/2003 | Meyer, Jr. et al. |
| 2003/0166929 A1 | 9/2003 | Snow et al. |
| 2003/0180924 A1 | 9/2003 | Desimone et al. |
| 2003/0186987 A1 | 10/2003 | Bridges et al. |
| 2003/0187001 A1 | 10/2003 | Calderwood et al. |
| 2003/0195211 A1 | 10/2003 | Sadhu et al. |
| 2003/0199516 A1 | 10/2003 | Moser et al. |
| 2003/0212113 A1 | 11/2003 | Dyatkina et al. |
| 2003/0225098 A1 | 12/2003 | Hirst et al. |
| 2003/0232849 A1 | 12/2003 | Noe et al. |
| 2003/0235822 A1 | 12/2003 | Lokhov et al. |
| 2004/0039035 A1 | 2/2004 | Collins et al. |
| 2004/0043983 A1 | 3/2004 | Li |
| 2004/0067901 A1 | 4/2004 | Bhat et al. |
| 2004/0067915 A1 | 4/2004 | McMahon et al. |
| 2004/0072766 A1 | 4/2004 | June |
| 2004/0072788 A1 | 4/2004 | Bhat et al. |
| 2004/0102423 A1 | 5/2004 | MacLaughlan et al. |
| 2004/0102437 A1 | 5/2004 | Takami et al. |
| 2004/0110717 A1 | 6/2004 | Carroll et al. |
| 2004/0110945 A1 | 6/2004 | Nakayama et al. |
| 2004/0116689 A1 | 6/2004 | Gall et al. |
| 2004/0122235 A1 | 6/2004 | Polisetti et al. |
| 2004/0127434 A1 | 7/2004 | Bigot et al. |
| 2004/0176458 A1 | 9/2004 | Leban et al. |
| 2004/0176601 A1 | 9/2004 | Goulet et al. |
| 2004/0192758 A1 | 9/2004 | Leban et al. |

(56) References Cited

U.S. PATENT DOCUMENTS

| | | |
|---|---|---|
| 2004/0266780 A1 | 12/2004 | Sadhu et al. |
| 2005/0004149 A1 | 1/2005 | Harada et al. |
| 2005/0043239 A1 | 2/2005 | Douangpanya et al. |
| 2005/0049310 A1 | 3/2005 | Mjalli et al. |
| 2005/0054614 A1 | 3/2005 | Diacovo et al. |
| 2005/0059713 A1 | 3/2005 | Mjalli et al. |
| 2005/0085472 A1 | 4/2005 | Tanaka et al. |
| 2005/0101551 A1 | 5/2005 | Sevillano et al. |
| 2005/0124637 A1 | 6/2005 | Cheng et al. |
| 2005/0143317 A1 | 6/2005 | Abdel-Meguid et al. |
| 2005/0153997 A1 | 7/2005 | Simon et al. |
| 2005/0171148 A1 | 8/2005 | Mjalli et al. |
| 2005/0182045 A1 | 8/2005 | Nagase et al. |
| 2005/0187230 A1 | 8/2005 | Ding et al. |
| 2005/0187418 A1 | 8/2005 | Small et al. |
| 2005/0197340 A1 | 9/2005 | Arora et al. |
| 2005/0215579 A1 | 9/2005 | Simon et al. |
| 2005/0222177 A1 | 10/2005 | Sim et al. |
| 2005/0239809 A1 | 10/2005 | Watts et al. |
| 2005/0250770 A1 | 11/2005 | Ono et al. |
| 2005/0256066 A1 | 11/2005 | Abel et al. |
| 2005/0261317 A1 | 11/2005 | Sadhu et al. |
| 2005/0272751 A1 | 12/2005 | McKerracher et al. |
| 2006/0019988 A1 | 1/2006 | McDonald et al. |
| 2006/0069034 A1 | 3/2006 | Burli et al. |
| 2006/0079538 A1 | 4/2006 | Hallahan et al. |
| 2006/0106038 A1 | 5/2006 | Bouscary et al. |
| 2006/0116326 A1 | 6/2006 | Burli et al. |
| 2006/0135790 A1 | 6/2006 | Hyett et al. |
| 2006/0156485 A1 | 7/2006 | Lim |
| 2006/0166997 A1 | 7/2006 | Zhang et al. |
| 2006/0183783 A1 | 8/2006 | Polisetti et al. |
| 2006/0199776 A1 | 9/2006 | Blagg et al. |
| 2006/0235031 A1 | 10/2006 | Arnold et al. |
| 2006/0246551 A1 | 11/2006 | Stack et al. |
| 2006/0276470 A1 | 12/2006 | Jackson et al. |
| 2006/0287295 A1 | 12/2006 | Barlaam et al. |
| 2007/0015773 A1 | 1/2007 | Bergeron et al. |
| 2007/0027193 A1 | 2/2007 | Leban et al. |
| 2007/0032640 A1 | 2/2007 | Varghese et al. |
| 2007/0054915 A1 | 3/2007 | Arora et al. |
| 2007/0072897 A1 | 3/2007 | Mahaney et al. |
| 2007/0099871 A1 | 5/2007 | Davis et al. |
| 2007/0112005 A1 | 5/2007 | Chen et al. |
| 2007/0142405 A1 | 6/2007 | Dong et al. |
| 2007/0149521 A1 | 6/2007 | Crew et al. |
| 2007/0203143 A1 | 8/2007 | Sheppard et al. |
| 2007/0213355 A1 | 9/2007 | Capraro et al. |
| 2007/0224672 A1 | 9/2007 | Leban et al. |
| 2007/0249598 A1 | 10/2007 | Wang et al. |
| 2007/0254883 A1 | 11/2007 | Cres et al. |
| 2007/0270452 A1 | 11/2007 | Blagg et al. |
| 2007/0293489 A1 | 12/2007 | Adams et al. |
| 2007/0293516 A1 | 12/2007 | Knight et al. |
| 2008/0003254 A1 | 1/2008 | Mack et al. |
| 2008/0032960 A1 | 2/2008 | Knight et al. |
| 2008/0039491 A1 | 2/2008 | Ronan et al. |
| 2008/0058521 A1 | 3/2008 | Krishnan et al. |
| 2008/0070935 A1 | 3/2008 | Huang et al. |
| 2008/0119454 A1 | 5/2008 | Polisetti et al. |
| 2008/0119455 A1 | 5/2008 | Polisetti et al. |
| 2008/0119461 A1 | 5/2008 | Sin et al. |
| 2008/0200465 A1 | 8/2008 | Burli et al. |
| 2008/0249090 A1 | 10/2008 | Hu et al. |
| 2008/0261956 A1 | 10/2008 | Choi et al. |
| 2008/0287469 A1 | 11/2008 | Diacovo et al. |
| 2008/0292626 A1 | 11/2008 | Wang et al. |
| 2008/0293674 A1 | 11/2008 | Schwarz et al. |
| 2008/0306053 A1 | 12/2008 | Tachdjian et al. |
| 2008/0306093 A1 | 12/2008 | Servant et al. |
| 2008/0312180 A1 | 12/2008 | Liang et al. |
| 2008/0318942 A1 | 12/2008 | Simon et al. |
| 2009/0030023 A1 | 1/2009 | Harada et al. |
| 2009/0053192 A1 | 2/2009 | Millan et al. |
| 2009/0088452 A1 | 4/2009 | Coleman et al. |
| 2009/0099214 A1 | 4/2009 | Fairhurst et al. |
| 2009/0105233 A1 | 4/2009 | Chua et al. |
| 2009/0118283 A1 | 5/2009 | Defert et al. |
| 2009/0124638 A1 | 5/2009 | Shokat et al. |
| 2009/0124654 A1 | 5/2009 | Mjalli et al. |
| 2009/0163481 A1 | 6/2009 | Murphy et al. |
| 2009/0163709 A1 | 6/2009 | Blagg |
| 2009/0170879 A1 | 7/2009 | Szucova et al. |
| 2009/0181920 A1 | 7/2009 | Watkins et al. |
| 2009/0181988 A1 | 7/2009 | Tanaka et al. |
| 2009/0187014 A1 | 7/2009 | Blagg |
| 2009/0203689 A1 | 8/2009 | Dhalla et al. |
| 2009/0232768 A1 | 9/2009 | Birkus et al. |
| 2009/0247513 A1 | 10/2009 | Burli et al. |
| 2009/0253694 A1 | 10/2009 | Ono et al. |
| 2009/0264409 A1 | 10/2009 | Dong et al. |
| 2009/0264423 A2 | 10/2009 | Chua et al. |
| 2009/0270567 A1 | 10/2009 | Small et al. |
| 2009/0312319 A1 | 12/2009 | Ren et al. |
| 2009/0312406 A1 | 12/2009 | Hsieh et al. |
| 2009/0325967 A1 | 12/2009 | Fairhurst et al. |
| 2010/0009963 A1 | 1/2010 | Knight et al. |
| 2010/0022585 A1 | 1/2010 | deLong et al. |
| 2010/0029658 A1 | 2/2010 | Gavish et al. |
| 2010/0029693 A1 | 2/2010 | Douangpanya et al. |
| 2010/0048540 A1 | 2/2010 | Boyle et al. |
| 2010/0048882 A1 | 2/2010 | Blagg et al. |
| 2010/0056494 A1 | 3/2010 | Winzeler et al. |
| 2010/0105630 A1 | 4/2010 | Blagg |
| 2010/0184760 A1 | 7/2010 | Ren et al. |
| 2010/0190749 A1 | 7/2010 | Ren et al. |
| 2010/0273776 A1 | 10/2010 | Lindquist et al. |
| 2011/0046165 A1 | 2/2011 | Ren et al. |
| 2011/0077268 A1 | 3/2011 | Liu et al. |
| 2011/0144134 A1 | 6/2011 | Shokat et al. |
| 2011/0160232 A1 | 6/2011 | Ren et al. |
| 2011/0172228 A1 | 7/2011 | Ren et al. |
| 2011/0224223 A1 | 9/2011 | Shokat et al. |
| 2011/0269779 A1 | 11/2011 | Wilson et al. |
| 2011/0281866 A1 | 11/2011 | Ren et al. |
| 2011/0301144 A1 | 12/2011 | Knight et al. |
| 2012/0294930 A1 | 11/2012 | Ren et al. |
| 2014/0030256 A1 | 1/2014 | Ren et al. |
| 2014/0128599 A1 | 5/2014 | Ren et al. |

FOREIGN PATENT DOCUMENTS

| | | |
|---|---|---|
| DE | 2004713 A1 | 8/1971 |
| EP | 0773023 A1 | 5/1997 |
| EP | 1020445 B1 | 8/2008 |
| GB | 812366 | 4/1959 |
| GB | 937725 | 9/1963 |
| GB | 1291417 A | 10/1972 |
| JP | 61109797 | 5/1986 |
| JP | 5256693 A | 10/1993 |
| JP | 8295667 A | 11/1996 |
| JP | 9143163 A | 6/1997 |
| JP | 10206995 A | 8/1998 |
| JP | 2000072773 A | 3/2000 |
| JP | 2002-037787 | 2/2002 |
| JP | 2002131859 A | 5/2002 |
| JP | 2003073357 A | 3/2003 |
| JP | 2004161716 A | 6/2004 |
| WO | WO 83/01446 A1 | 4/1983 |
| WO | WO 91/17161 A1 | 11/1991 |
| WO | WO 92/14733 A1 | 9/1992 |
| WO | WO 93/16091 A1 | 8/1993 |
| WO | WO 93/16092 A1 | 8/1993 |
| WO | WO 93/18035 A1 | 9/1993 |
| WO | WO 93/22443 A1 | 11/1993 |
| WO | WO 94/13677 A1 | 6/1994 |
| WO | WO 94/17803 A1 | 8/1994 |
| WO | WO 95/12588 A1 | 5/1995 |
| WO | WO 95/29673 A1 | 11/1995 |
| WO | WO 95/32984 A1 | 12/1995 |
| WO | WO 96/40706 A1 | 12/1996 |
| WO | WO 97/28133 A1 | 8/1997 |
| WO | WO 97/28161 A1 | 8/1997 |
| WO | WO 98/41525 A1 | 9/1998 |

(56) References Cited

FOREIGN PATENT DOCUMENTS

| | | |
|---|---|---|
| WO | WO 98/52611 A1 | 11/1998 |
| WO | WO 98/57952 A1 | 12/1998 |
| WO | WO 00/17202 A1 | 3/2000 |
| WO | WO 01/02369 A2 | 1/2001 |
| WO | WO 01/16114 A2 | 3/2001 |
| WO | WO 01/19829 A2 | 3/2001 |
| WO | WO 01/25238 A2 | 4/2001 |
| WO | WO 01/31063 A1 | 5/2001 |
| WO | WO 01/38584 A2 | 5/2001 |
| WO | WO 01/16114 A3 | 8/2001 |
| WO | WO 01/55140 A1 | 8/2001 |
| WO | WO 01/56988 A1 | 8/2001 |
| WO | WO 01/19829 A3 | 9/2001 |
| WO | WO 01/25238 A3 | 10/2001 |
| WO | WO 01/38584 A3 | 10/2001 |
| WO | WO 01/81346 A2 | 11/2001 |
| WO | WO 02/06192 A1 | 1/2002 |
| WO | WO 01/81346 A3 | 3/2002 |
| WO | WO 01/02369 A3 | 4/2002 |
| WO | WO 02/30944 A2 | 4/2002 |
| WO | WO 02/057425 A2 | 7/2002 |
| WO | WO 02/076986 A1 | 10/2002 |
| WO | WO 02/080926 A1 | 10/2002 |
| WO | WO 02/083143 A1 | 10/2002 |
| WO | WO 02/088025 A1 | 11/2002 |
| WO | WO 02/090334 A1 | 11/2002 |
| WO | WO 02/030944 A3 | 1/2003 |
| WO | WO 03/000187 A2 | 1/2003 |
| WO | WO 03/000688 A1 | 1/2003 |
| WO | WO 03/016275 A1 | 2/2003 |
| WO | WO 03/020880 A2 | 3/2003 |
| WO | WO 03/024969 A1 | 3/2003 |
| WO | WO 03/035075 A1 | 5/2003 |
| WO | WO 03/059884 A1 | 7/2003 |
| WO | WO 03/020880 A3 | 10/2003 |
| WO | WO 03/082341 A1 | 10/2003 |
| WO | WO 03/106426 A1 | 12/2003 |
| WO | WO 2004/006906 A2 | 1/2004 |
| WO | WO 2004/006906 A3 | 3/2004 |
| WO | WO 2004/018058 A2 | 3/2004 |
| WO | WO 2004/031177 A1 | 4/2004 |
| WO | WO 2004/039774 A2 | 5/2004 |
| WO | WO 2004/018058 A3 | 7/2004 |
| WO | WO 2004/039774 A3 | 7/2004 |
| WO | WO 03/000187 A3 | 8/2004 |
| WO | WO 2004/087053 A2 | 10/2004 |
| WO | WO 2004/111014 A1 | 12/2004 |
| WO | WO 2005/002585 A1 | 1/2005 |
| WO | WO 2005/007085 A2 | 1/2005 |
| WO | WO 2005/012323 A2 | 2/2005 |
| WO | WO 2005/016348 A1 | 2/2005 |
| WO | WO 2005/016349 A1 | 2/2005 |
| WO | WO 2005/016528 A2 | 2/2005 |
| WO | WO 2005/021533 A1 | 3/2005 |
| WO | WO 2002/057425 A3 | 4/2005 |
| WO | WO 2005/012323 A3 | 5/2005 |
| WO | WO 2005/016528 A3 | 5/2005 |
| WO | WO 2005/044181 A2 | 5/2005 |
| WO | WO 2005/047289 A1 | 5/2005 |
| WO | WO 2005/061460 A1 | 7/2005 |
| WO | WO 2005/063258 A1 | 7/2005 |
| WO | WO 2005/067901 A2 | 7/2005 |
| WO | WO 2005/074603 A2 | 8/2005 |
| WO | WO 2005/007085 A3 | 9/2005 |
| WO | WO 2005/085248 A1 | 9/2005 |
| WO | WO 2005/097800 A1 | 10/2005 |
| WO | WO 2005/105760 A1 | 11/2005 |
| WO | WO 2005/067901 A3 | 12/2005 |
| WO | WO 2005/112935 A1 | 12/2005 |
| WO | WO 2005/113556 A1 | 12/2005 |
| WO | WO 2005/117889 A1 | 12/2005 |
| WO | WO 2005/120511 A1 | 12/2005 |
| WO | WO 2005/044181 A3 | 3/2006 |
| WO | WO 2006/030032 A1 | 3/2006 |
| WO | WO 2006/038865 A1 | 4/2006 |
| WO | WO 2006/050501 A2 | 5/2006 |
| WO | WO 2006/050946 A1 | 5/2006 |
| WO | WO 2006/068760 A2 | 6/2006 |
| WO | WO 2004/087053 A3 | 8/2006 |
| WO | WO 2006/089106 A2 | 8/2006 |
| WO | WO 2006/108107 A1 | 10/2006 |
| WO | WO 2006/112666 A1 | 10/2006 |
| WO | WO 2005/074603 A3 | 11/2006 |
| WO | WO 2006/114064 A2 | 11/2006 |
| WO | WO 2006/114065 A2 | 11/2006 |
| WO | WO 2006/114180 A1 | 11/2006 |
| WO | WO 2006/068760 A3 | 12/2006 |
| WO | WO 2006/089106 A3 | 12/2006 |
| WO | WO 2007/002293 A2 | 1/2007 |
| WO | WO 2007/006547 A1 | 1/2007 |
| WO | WO 2007/020046 A1 | 2/2007 |
| WO | WO 2007/002293 A3 | 3/2007 |
| WO | WO 2007/023115 A2 | 3/2007 |
| WO | WO 2007/025090 A2 | 3/2007 |
| WO | WO 2007/023115 A3 | 4/2007 |
| WO | WO 2006/050501 A3 | 5/2007 |
| WO | WO 2007/061737 A2 | 5/2007 |
| WO | WO 2006/114064 A3 | 6/2007 |
| WO | WO 2006/114065 A3 | 6/2007 |
| WO | WO 2007/025090 A3 | 6/2007 |
| WO | WO 2007/075554 A2 | 7/2007 |
| WO | WO 2007/079164 A2 | 7/2007 |
| WO | WO 2007/095223 A2 | 8/2007 |
| WO | WO 2007/075554 A3 | 9/2007 |
| WO | WO 2007/103308 A2 | 9/2007 |
| WO | WO 2007/106503 A2 | 9/2007 |
| WO | WO 2007/112005 A2 | 10/2007 |
| WO | WO 2007/114926 A2 | 10/2007 |
| WO | WO 2007/121453 A2 | 10/2007 |
| WO | WO 2007/121920 A2 | 11/2007 |
| WO | WO 2007/121924 A2 | 11/2007 |
| WO | WO 2007/124405 A2 | 11/2007 |
| WO | WO 2007/124854 A1 | 11/2007 |
| WO | WO 2007/125310 A2 | 11/2007 |
| WO | WO 2007/125315 A2 | 11/2007 |
| WO | WO 2007/126841 A2 | 11/2007 |
| WO | WO 2007/134828 A1 | 11/2007 |
| WO | WO 2007/135380 A2 | 11/2007 |
| WO | WO 2007/135398 A1 | 11/2007 |
| WO | WO 2007/061737 A3 | 12/2007 |
| WO | WO 2007/125315 A3 | 12/2007 |
| WO | WO 2007/121920 A3 | 1/2008 |
| WO | WO 2008/012326 A1 | 1/2008 |
| WO | WO 2007/103308 A3 | 2/2008 |
| WO | WO 2007/112005 A3 | 2/2008 |
| WO | WO 2007/125310 A3 | 3/2008 |
| WO | WO 2008/025755 A1 | 3/2008 |
| WO | WO 2008/031594 A1 | 3/2008 |
| WO | WO 2008/037477 A1 | 4/2008 |
| WO | WO 2008/047821 A1 | 4/2008 |
| WO | WO 2007/106503 A3 | 5/2008 |
| WO | WO 2008/063625 A2 | 5/2008 |
| WO | WO 2008/064018 A1 | 5/2008 |
| WO | WO 2007/121453 A3 | 7/2008 |
| WO | WO 2007/135380 A3 | 7/2008 |
| WO | WO 2008/063625 A3 | 7/2008 |
| WO | WO 2008/079028 A1 | 7/2008 |
| WO | WO 2008/082487 A2 | 7/2008 |
| WO | WO 2008/083070 A1 | 7/2008 |
| WO | WO 2008/094737 A2 | 8/2008 |
| WO | WO 2007/121924 A3 | 9/2008 |
| WO | WO 2008/112715 A2 | 9/2008 |
| WO | WO 2007/114926 A3 | 10/2008 |
| WO | WO 2008/118454 A2 | 10/2008 |
| WO | WO 2008/118455 A1 | 10/2008 |
| WO | WO 2008/118468 A1 | 10/2008 |
| WO | WO 2008/125014 A1 | 10/2008 |
| WO | WO 2008/125207 A1 | 10/2008 |
| WO | WO 2008/127226 A2 | 10/2008 |
| WO | WO 2007/126841 A3 | 11/2008 |
| WO | WO 2008/112715 A3 | 11/2008 |
| WO | WO 2008/118454 A3 | 11/2008 |
| WO | WO 2008/136457 A1 | 11/2008 |
| WO | WO 2007/124405 A3 | 12/2008 |

(56) References Cited

FOREIGN PATENT DOCUMENTS

| | | |
|---|---|---|
| WO | WO 2008/082487 A3 | 12/2008 |
| WO | WO 2008/127226 A3 | 12/2008 |
| WO | WO 2009/000412 A1 | 12/2008 |
| WO | WO 2009/004621 A1 | 1/2009 |
| WO | WO 2009/010925 A2 | 1/2009 |
| WO | WO 2009/021990 A1 | 2/2009 |
| WO | WO 2009/023718 A2 | 2/2009 |
| WO | WO 2008/094737 A3 | 3/2009 |
| WO | WO 2009/023718 A3 | 4/2009 |
| WO | WO 2009/044707 A1 | 4/2009 |
| WO | WO 2009/050506 A2 | 4/2009 |
| WO | WO 2009/059304 A2 | 5/2009 |
| WO | WO 2009/064802 A2 | 5/2009 |
| WO | WO 2009/010925 A3 | 7/2009 |
| WO | WO 2009/064802 A3 | 7/2009 |
| WO | WO 2009/088986 A1 | 7/2009 |
| WO | WO 2009/088990 A1 | 7/2009 |
| WO | WO 2009/059304 A3 | 8/2009 |
| WO | WO 2009/100406 A2 | 8/2009 |
| WO | WO 2007/079164 A3 | 9/2009 |
| WO | WO 2009/114874 A2 | 9/2009 |
| WO | WO 2009/117157 A1 | 9/2009 |
| WO | WO 2009/050506 A3 | 11/2009 |
| WO | WO 2009/100406 A3 | 11/2009 |
| WO | WO 2009/114874 A3 | 12/2009 |
| WO | WO 2010/009207 A1 | 1/2010 |
| WO | WO 2010/019210 A2 | 2/2010 |
| WO | WO 2010/036380 A1 | 4/2010 |
| WO | WO 2010/039534 A2 | 4/2010 |
| WO | WO 2010/019210 A3 | 5/2010 |
| WO | WO 2010/051043 A1 | 5/2010 |
| WO | WO 2010/039534 A3 | 8/2010 |
| WO | WO 2010/088050 A2 | 8/2010 |
| WO | WO 2010/099139 A2 | 9/2010 |
| WO | WO 2010/099139 A3 | 10/2010 |
| WO | WO 2010/118367 A2 | 10/2010 |
| WO | WO 2010/088050 A3 | 11/2010 |
| WO | WO 2010/129816 A2 | 11/2010 |
| WO | WO 2010/118367 A3 | 3/2011 |

OTHER PUBLICATIONS

Office action dated Jul. 8, 2013 for U.S. Appl. No. 12/677,098.
Office action dated Oct. 4, 2013 for U.S. Appl. No. 13/002,438.
Richter, et al. "Inhibition of mammalian dihydrofolate reductase by selected 2,4-diaminoquinazolines and related compounds" Journal of Medicinal Chemistry (1974), 17(9), 943-7.
Vopicka, et al. "Quinazolines. III. Interaction of aniline with 2-chloro-4-alkoxyquinazolines and 2-chloro-4-ketodihydroquinazoline" Journal of the American Chemical Society (1932), 54, 1068-1070.
Sam, et al. Benzoxazoles: Potent skeletal muscle relaxants. Pharm Sci. May 1964; 53:538-44.
Office action dated May 6, 2014 for U.S. Appl. No. 13/003,562.
Office action dated Mar. 26, 2014 for U.S. Appl. No. 11/719,722.
West, et al. Activation of the PI3K/Akt pathway and chemotherapeutic resistance. Drug Resist Updat. Dec. 2002;5(6):234-48.
European search report dated Jan. 4, 2013 for EP Application No. 12175019.4.
McMahon, et al. VEGF receptor signaling in tumor angiogenesis. The Oncologist. 2000; 5(suppl 1):3-10.
Office action dated Feb. 8, 2013 for U.S. Appl. No. 12/509,281.
Office action dated Feb. 11, 2013 for U.S. Appl. No. 13/003,562.
Office action dated Feb. 27, 2013 for U.S. Appl. No. 12/920,970.
Office action dated Mar. 14, 2007 for U.S. Appl. No. 10/871,732.
Office action dated Mar. 23, 2006 for U.S. Appl. No. 10/871,732.
Office action dated May 10, 2012 for U.S. Appl. No. 12/586,241.
Office action dated May 10, 2012 for U.S. Appl. No. 12/586,309.
Office action dated May 29, 2012 for U.S. Appl. No. 12/509,281.
Office action dated Jun. 3, 2009 for U.S. Appl. No. 11/732,856.
Office action dated Jun. 20, 2012 for U.S. Appl. No. 11/719,722.
Office action dated Oct. 11, 2011 for U.S. Appl. No. 11/719,722.
Office action dated Oct. 25, 2012 for U.S. Appl. No. 12/586,241.
Office action dated Oct. 25, 2012 for U.S. Appl. No. 12/586,309.
Office action dated Oct. 30, 2006 for U.S. Appl. No. 10/871,732.
Office action dated Nov. 20, 2007 for U.S. Appl. No. 10/871,732.
Office action dated Dec. 24, 2008 for U.S. Appl. No. 11/732,856.
Pinedo, et al. Translational research: the role of VEGF in tumor angiogenesis. The Oncologist. 2000; 5(suppl 1):1-2.
Tseng, et al. Synergistic interactions between imatinib mesylate and the novel phosphoinositide-dependent kinase-1 inhibitor OSU-03012 in overcoming imatinib mesylate resistance. Blood. May 15, 2005;105(10):4021-7. Epub Jan. 21, 2005.
U.S. Appl. No. 13/112,611, filed May 20, 2011, Ren et al.
U.S. Appl. No. 13/289,540, filed Nov. 4, 2011, Ren et al.
Ames et al., "Heterocyclic Synthesis from o-Halogen-acids. Part II. Thienopyridinones and Thienopyranones from 3-bromothiophene-2- and 4-Bromothiophene-3-Carboxylic Acids", Journal of the Chemical Society, Perkin Transactions 1, Jan., 14:1390-1395 (1975).
Basotest®, "Test Kit for the Quantitative Determination of the Degranulation of Basophilic Granulocytes in Heparinized Human Whole Blood", [www.biocarta.com/TDS/10-0500.pdf], Retreived from the Internet Nov. 29, 2011.
Cámpora, et al. Binuclear complexes of nickel bridged by hydrocarbon ligands, Isocyanide insertion chemistry and amide formation by intramolecular coupling of acyl and imidoyl functionalities. Organometallics. Jan. 1992;11(1):11-13.
Cámpora, et al. Isocyanide insertion chemistry. Synthesis and structural characterization of bridging imidoyl complexes of nickel and amide formation by intramolecular coupling of acyl and imidoyl functionalities. Organometallics. Oct. 1993;12(10):4025-31.
Chaisuparat, et al. Dual Inhibition of P13K(alpha) and mTOR as an Alternative Treatment for Kaposi's Sarcoma. Cancer Research. 2008;68:8361.
Chappelow, et al. Neovascular Age-Related Macular Degeneration: Potential Therapies. Drugs. 2008;68(8):1029-1036.
Davis, et al. The Preparation of Substituted 1(2H)-Isoquinolinones from Dilithiated 2-Methyl-N-arylbenzamides, 2-Methyl-N-(arylmethyl)-benzamides, or 2-Methylbenzoic Acid, 2,2-Dimethylhydrazide. Synthetic Communications. Sep. 1997;27(17):2961-9.
Dijksman, et al. 271. 1 : 2-Dihydro-2-thianaphthalene derivatives. Part I. Preparation and reactions of 1 : 2-dihydro-1-keto-2-thianaphthalenes. J. Chem. Soc. 1951:1213-18.
Donati. Emerging Therapies for Neovascular Age-Related Macular Degeneration: State of the Art. Ophthalmologica. 2007;221:366-377.
European search report and search opinion dated Oct. 26, 2011 for Application No. 9700424.6.
European Search Report dated Mar. 1, 2010 for EP Application No. 07873406.8.
Extended European Search Report from corresponding European Application No. 09700784.3 dated Oct. 28, 2011.
Graupera, et al. Angiogenesis selectively requires the p110 isoform of PI3K to control endothelial cell migration. Nature. 2008;453:662-666.
Hellwinkel, et al. Heterocyclensynthesen mit MF/Al2O3-Basensystemen: 2-Arylbenzofurane and 2,3-Diarylisochinolin-1(2H)-one. Synthesis. 1995;1995(9):1135-41.
International Preliminary Report on Patentability from International Application No. PCT/US2009/000042 issued Jul. 6, 2010.
International search report and written opinion dated Aug. 22, 2011 for PCT/US2011/037412.
International search report and written opinion dated Nov. 20, 2009 for PCT/US2009/005380.
International search report dated Nov. 2, 2010 for PCT Application No. US10/02020.
International search report dated Mar. 11, 2009 for PCT Application No. US2009/00038.
International search report dated Mar. 23, 2009 for PCT Application No. US2009/00042.

(56) References Cited

OTHER PUBLICATIONS

Kajita, et al. Nickel-catalyzed decarbonylative addition of phthalimides to alkynes. J Am Chem Soc. May 14, 2008;130(19):6058-9.

Kost et al., "Recyclization of 3-Alkyl- and 1,3-Dialkylisoquinolinium Salts to Naphthylamines", Chemistry of Heterocyclic Compounds, Jan., 16(9):965-970 (1981).

Kumar et al., "Keten Dithioacetals. Part II. Reaction of 3-Cyano-4-Methylthio-2(1H)-pyridones with Hydazine and Guanidine: Synthesis of Novel Substituted and Fused Pyrazolo[4,3-c]pyridone and Pyrido[4,3-d]pyrimidine Derivatives", Journal of the Chemical Society, Perkin Transactions 1, Chemical Society, Letchworth, Jan., 8:857-862 (1978).

Kundu, et al. Palladium-Catalysed Heteroannulation with Terminal Alkynes: a Highly Regio- and Stereoselective Synthesis of (Z)-3-Aryl(alkyl)idene Isoindolin-1-ones1. Tetrahedron. Jun. 30, 2000;56(27):4777-92.

Lee, et al. All roads lead to mTOR: integrating inflammation and tumor angiogenesis . . . Cell Cycle. 2007;6(24):3011-3014.

Majumder, et al. mTOR inhibition reverses Akt-dependent prostate intraepithelial neoplasia through regulation of apoptotic and HIF-1-dependent pathways. Nature Medicine. 2004;10:594-601.

Mellinghoff, et al. TORward AKTually useful mouse models. Nature Medicine. 2004;10:579-580.

Modi, et at. Isoquinolones: Part IV—Synthesis of 3-Methyl, 3-Formyl & Other 3-Substituted N-Arylisoquinolones, Indian J. Chem. 1979; 18B:304-306.

Nemazanyi, et al. 3-Amino-4-aryl-1(2H)-isoquinolones. Chemistry of Heterocyclic Compounds. Mar. 1991;27(3):307-8.

Oda, et al. PIK3CA Cooperates with Other Phosphatidylinositol 3'-Kinase Pathway Mutations to Effect Oncogenic Transformation. Cancer Research. 2008;68:8127.

Ozaki, et al. Studies on 4 (1H)-Quinazolinones. IV. Convenient Syntheses of 12-Methyl-6H-isoquino [2,1-a] quinazolin-6-one and 6-Methyl-13H-quinazolino [3,4-a] quinazolin-13-one. Chem. Pharm. Bull. Jun. 25, 1984;32(6):2160-4.

Ozol, et al. Autoxidative transformations of 2-substituted 3-alkyl-4-hydroxy-1-oxo-1, 2-dihydroisoquinolines. Chemistry of Heterocyclic Compounds. Jun. 1978;14(6):644-8.

Patel, et al. Immunopathological aspects of age-related macular degeneration. Seminars in Immunopathology. 2008;30(2):97-110.

Stanoeva et al. Homophthalic anhydrides and their application to the synthesis of heterocyclic compounds (review). Chemistry of Heterocyclic Compounds. Dec. 1984;20(12);1305-15.

Vasilevsky et al., "Study of the Heterocyclization of vic-Substituted Hydrazides of Acetylenylpyrazolecarboxylic Acids into N-Amino Pyrazolopyridinones", Journal of Heterocyclic Chemistry, Nov., 39(6):1229-1233 (2002).

Vasilevsky et al., "Unexpected results in the heterocyclization of 5-acetylenylpyrazole-4-carboxylic acid hydrazides under the influence of CuCI: formatin of a diazepinone and dehydrodimerization into the corresponding bis(pyrazolo [4,3-d] [1,2] diazepinone)", Tetrahedron Letters, Jan., 46(26): 4457-4459 (2005).

Yaguchi, et al. Antitumor activity of ZSTK474, a new phosphatidylinositol 3-kinase inhibitor. J. Natl. Cancer. Inst. 2006; 98(8): 545-556. Abstract only.

European extended search report and search opinion dated Jan. 31, 2012 for EP Application No. 09795147.9.

U.S. Appl. No. 13/016,957, filed Jan. 28, 2011, Tanaka et al.

Abdel-Mohsen. Synthesis, Reactions and Antimicrobial Activity of 2-Amino-4-(8-quinolinol-5-yI)-1-(p-tolyl)-pyrrole-3-carbonitrile. Bull. Korean Chem. Soc. 2005;26(5):719-728.

Andrews, R.C., et al. "Effects of the 11β-Hydroxysteroid Dehydrogenase Inhibitor Carbenoxolone on Insulin Sensitivity in Men with Type 2 Diabetes", J. Clin. Endocrinol. Metab. (2003) 88(1):285-291.

Apsel, et al. Targeted polypharmacology: discovery of dual inhibitors of tyrosine and phosphoinositide kinases. Nat Chem Biol. Nov. 2008;4(11):691-9.

Arnold, et al. "Pyrrolo[2,3-d]pyrimidines containing an extended 5-substituent as potent and selective inhibitors of lck I", Bioorg. & Med. Chem. Lett (2000) 10:2167-70.

Banker, G.S., et al. Modern Pharmaceutics, 3ed, Marcel Dekker, New York, 1996, pp. 451-596.

Barf, T. et al. "Arylsulfonamidothiazoles as a New Class of Potential Antidiabetic Drugs. Discovery of Potent and Selective Inhibitors of the 11β-Hydroxysteroid Dehydrogenase Type 1", J. Med. Chem. (2002) 45(18):3813-3815.

Barnes, P.J., et al. "Efficacy and Safety of Inhaled Corticosteroids in Asthma", Am Rev. Respir. Dis. (1993) 148:S1-26.

Beeram, et al. Akt-induced endocrine therapy resistance is reversed by inhibition of mTOR signaling. Ann Oncol. Aug. 2007;18(8):1323-8.

Bell, G., et al. "Glucokinase Mutations Insulin Secretion, and Diabetes Mellitus", Annu. Rev. Physiol., (1996) 58:171-186.

Bhat, et al. Pyrazolopyrimidine nucleosides. 12. Synthesis and biological activity of certain pyrazolo[3,4-d]pyrimidine nucleosides related to adenosine. J Med Chem. Oct. 1981;24(10):1165-72.

Bishop, A.C. et al. "Generation of monospecific nanomolar tyrosine kinase inhibitors via a chemical genetic approach", Journal of the American Chemical Society, American Chemical Society, Washington, DC, US, vol. 121, No. 4, 1999, pp. 627-631.

Bohren, K.M., et al. "Expression, Crystallization and Preliminary Crystallographic Analysis of Human Carbonyl Reductase", J. Mol. Biol. (1994) 224:659-664.

Cox, B., et al. "Human Colorectal Cancer Cells Efficiently Conjugate the Cyclopentenone Prostaglandin, Prostaglandin J2 to Glutathione", Biochim. Biophys. Acta (2002) 1584:37-45.

Diederich, S., et al. "In the Search for Specific Inhibitors of Human 11β-Hydroxysteroid-Dehydrogenases (11β-HSDs): Chenodeoxycholic Acid Selectively Inhibits 11β-HSD-I", Eur. J. Endocrinol. (2000) 142:200-207.

Ding, S., et al. "A Combinatorial Scaffold Approach Toward Kinase-Directed Heterocycle Libraries", J. Am. Chem. Soc. (2002) 124(8):1594-1596.

Ding, S., et al. "A Concise and Traceless Linker Strategy Toward Combinatorial Libraries of 2,6,9-Substituted Purines", J. Org. Chem. (2001) 66:8273-8276.

Ding, S., et al. "Resin-Capture and Release Strategy Toward Combinatorial Libraries of 2,6,9-Substituted Purines", J. Comb. Chem.(2002) 4:183-186.

European Examination Report dated Sep. 14, 2011 for EP Application No. 07873406.8, 4 pages.

European search report dated Feb. 4, 2011 for EP Application No. 05857011.0.

European search report dated Feb. 24, 2010 for EP Application No. 07754845.1.

Examination report dated Oct. 27, 2010 for GB Application No. GB0819947.3.

Fajans, S., et al."Maturity Onset Diabetes of the Young (MODY)", Diabet. Med. (1996) 13:S90-S95.

Feinstein, M.B., et al. "Regulation of the Action of Hydrocotisone in Airway Epithelial Cells by 11β-Hydroxysteroid Dehydrogenase", Am. J. Respir. Cell. Mol. Biol. (1999) 21:403-408.

Feldman, et al. Active-site inhibitors of mTOR target rapamycin-resistant outputs of mTORC1 and mTORC2. PLoS Biol. Feb. 10, 2009;7(2):371-383.

Fingl, E., et al. "General Principles", The Pharmacological Basis of Therapeutics, Fifth Edition (1975), Ch. 1, 1-46.

Forrest, G.L., et al. "Carbonyl Reductase", Chem. Biol. Interact. (2000) 129:21-40.

Forrest, G.L., et al. "Induction of a human Carbonyl Reductase Gene Located on Chromosome 21", Biochim. Biophys. Acta. (1990) 1048:149-155.

Franzen, R. "The Suzuki, the Heck, and the Stille reaction—three versative methods for the introduction of new C—C bonds on solid support", Can J. Chem. (2000) 78:957-962.

Funder, J.W., et al. "Mineralocorticoid Action: Target Tissue Specificity Is Enzyme, Not Receptor, Mediated", Science (1998) 242:583-585.

(56) References Cited

OTHER PUBLICATIONS

Garber, M.E., et al. "Diversity of Gene Expression in Adenocarcinoma of the Lung", Proc. Nat. Acad. Sci. USA (2001) 98(24):13784-13789.

Gonzalez, B., et al. "Protection against Daunorubicin Cytotoxicity by Expression of a Cloned Human Carbonyl Reductase cDNA in K562 Leukemia Cells", Cancer Res. (1995) 55:4646-4650.

Haase, A.,et al. "Detection of Viral Nucleic Acids by in Situ Hybridization", Methods in Virology (1984) VII:189-226.

Hanefeld, U., et al. "One-pot Synthesis of Tetrasubstituted Pyrazoles Proof of Regiochemistry", J. Chem. Soc. Perkin Trans. (1996) 1:1545-1552.

International Preliminary Report on Patentability and Written Opinion dated Apr. 19, 2011 for International Application No. PCT/US2009/060985, 6 pages.

International Preliminary Report on Patentability and Written Opinion dated Jan. 1, 2011 for International Application No. PCT/US2009/049969, 7 pages.

International Preliminary Report on Patentability and Written Opinion dated May 22, 2007 for International Application No. PCT/US2005/042524, 12 pages.

International Preliminary Report on Patentability and Written Opinion dated Nov. 4, 2008 for International Application No. PCT/US2007/008355, 7 pages.

International Preliminary Report on Patentability and Written Opinion dated Oct. 8, 2008 for International Application No. PCT/US2007/008395, 6 pages.

International search report and written opinion dated Jan. 15, 2010 for PCT/US2009/064717.

International search report and written opinion dated Jul. 22, 2005 for PCT/US2004/019782.

International search report and written opinion dated Dec. 11, 2008 for PCT Application No. US08/78990.

International search report and written opinion dated Mar. 15, 2010 for PCT Application No. US2009/049969.

International search report dated Feb. 17, 2010 for PCT Application No. US2009/049983.

International search report dated Apr. 5, 2006 for PCT/FR2005/051073.

International search report dated Aug. 27, 2008 for PCT/US2007/008395.

International search report dated Sep. 25, 2008 for PCT/US2007/008355.

International search report dated Jan. 11, 2010 for PCT Application No. US2009/05959.

International search report dated Jan. 12, 2010 for PCT Application No. US2009/05958.

International search report dated Oct. 2, 2006 for PCT/US2005/042524.

International search report dated Dec. 24, 2009 for PCT Application No. US09/37313.

International Search Report dated Jun. 28, 2010 for International Application No. PCT/US2009/060985, 5 pages.

Ishiyama, T., et al. "A Stoichiometric Aromatic C—H Borylation Catalyzed by Iridium(I)/2,2'-Bipyridine Complexes at Room Temperature", Angew. Chem. Int. Ed. (2002) 41(16):3056-3058.

Ishiyama, T., et al. "Mild Iridium-Catalyzed Borylation of Arenes. High Turnover Numbers, Room Temperature Reactions, and Isolation of a Potential Intermediate", J. Am. Chem. Soc. (2002) 124(3):390-391.

Kallberg, et al. Short-Chain Dehydrogenase/Reductase (SDR) Relationships: a Large Family with Eight Clusters Common to Human, Animal, and Plant Genomes. Protein Sci. (2002) 11:636-641.

Kallberg, et al. Short-Chain Dehydrogenases/Reductases (SDRs). Eur. J. Biochem. (2002) 269:4409-4417.

Kim, et al. Activation and function of the mTORC1 pathway in mast cells. J Immunol. 2008 Apr. 1;180(7):4586-95.

Knight, et al. "A Pharmacological Map of the P13-K Family Defines a Role for p110α in Insulin Signaling", Cell (2006) 125:733-747.

Kraybill, B.C. et al. "Inhibitor scaffolds as new allele specific kinase substrates", Journal of the American Chemical Society, American Chemical Society, Washington, DC, US, vol. 124, No. 41, Oct. 16, 2002, pp. 12118-12128.

Kreutzberger, et al. 5-Substituierte 4-Aminopyrimidine durch Aminomethinylierung von Acetonitrilen. Liebigs Ann. Chem. 1977:537-544.

Kwok, B.H., et al. "The Anti-Inflammatory Natural Product Parthenolide from the Medicinal Herb Feverfew Directly Binds to and Inhibits IkB Kinase", Chem. Biol. (2001) 8:759-766.

Mayer, T.U., et al. "Small Molecule Inhibitor of Mitotic Spindle Bipolarity Identified in a Pheontype-Based Screen", Science (1999) 286:971-974.

Miyaura, N., et al., "Palladium-Catalyzed Cross-Coupling Reactions of Organoboron Compounds," Chem. Rev. (1995) 95(7):2457-2483.

Moon, H.S., et al. "A Novel Microtubule Destabilizing Entity from Orthogonal Synthesis of Triazine Library and Zebrafish Embryo Screening", J. Am. Chem. Soc. (2002) 124:11608-11609.

Nakanishi, M., et al. "Cloning and Sequence Analysis of a cDNA Encoding Tetrameric Carbonyl Reductase of Pig Lung", Biochem. Biophys. Acta (1993) 194(3):1311-1316.

Niswender, C.M., et al. "Protein Engineering of Protein Kinase A Catalytic Subunits Results in the Acquisition of Novel Inhibitor Sensitivity", The Journal of Biological Chemistry (2002) 277(32):28916-28922.

Nobel, C.S.I., et al. "Purification of Full-Length Recombinant Human and Rat Type 1 11β-hydroxysteroid Dehydrogenases with Retained Oxidoreductase Activities", Protein Expr. Purif. (2002) 26:349-356.

Oppermann, U.C., et al. "Forms and Functions of Human SDR Enzymes", Chem. Biol. Interact. (2001) 130-132(1-3):699-705.

Persson, C.G. "Glucocorticoids for Asthma—Early Contributions", Pulm. Pharmacol. (1989) 2:163-166.

Petrie, et al. A novel biotinylated adenylate analogue derived from pyrazolo[3,4-d]pyrimidine for labeling DNA probes. Bioconjug Chem. Nov.-Dec. 1991;2(6):441-6.

Pudlo, J.S., et al. "Synthesis, Antiproliferative, and Antiviral Activity of Certain 4-Substituted and 4,5 Disubstituted 7-[1,3-Dihydroxy-2-propoxy)methyl]pyrrolo[2,3-d]pyrimidines", J. Med. Chem. (1990) 33:1984-1992.

Report of the Expert Committee on the Diagnosis and Classification of Diabetes Mellitus, Diabetes Care (1992) 2(Suppl 1):S5-S19.

Robertson, R.P. "Eicosanoids and Human Disease", Harrison's Principles of Internal Medicine, Isselbacher K.J., et al. (eds.), McGraw-Hill, New York City (1994) 1:431-435.

Romero, D.G., et al. "Cloning and Expression of the Bovine 11βhydroxysteroid Dehydrogenase Type-2", J. Steroid Biochm. Mol. Biol. (2000) 72:231-237.

Singer, R.H., et al. "Optimization of in situ Hybridization Using Isotopic and Non-Isotopic Detection Methods", Biotechniques (1986) 4(3):230-250.

Soldan, M., et al. "Induction of Daunorubicin Carbonyl Reducing Enzymes by Daunorubicin in Sensitive and Resistant Pancreas Carcinoma Cells", Biochem. Pharmacol. (1996) 51:117-123.

Supplementary European Examination Report dated Sep. 20, 2011 for EP Application No. 07754845.1, 4 pages.

Takeuchi, et al. Synergistic augmentation of rapamycin-induced autophagy in malignant glioma cells by phosphatidylinositol 3-kinase/protein kinase B inhibitors. Cancer Res. Apr. 15, 2005;65(8):3336-46.

Tanaka, M., et al. "An Unbiased Cell Morphology-Based Screen for New, Biologically Active Small Molecules", PLoS Biology (2005) 3(5):0764-0776.

Ugarkar, B.G., et al. "Adenosine Kinase Inhibitors. 2. Synthesis, Enzyme Inhibition, and Antiseizure Activity of Diaryltubercidin Analogues", J. Med. Chem. (2000) 43:2894-2905.

White, P.C., et al. "11β-Hydroxysteroid Dehydrogenase and the Syndrome of Apparent Mineralocorticoid Excess", Endocr. Rev. (1997) 18(1):135-156.

Widler, L., et al. "7-Alkyl- and 7-Cycloalkyl-5-aryl-pyrrolo[2,3-d]pyrimidines-Potent Inhibitors of the Tyrosine Kinase c-Src," Bioorganic & Medicinal Chemistry Letters (2001) 11(6):849-852.

(56) References Cited

OTHER PUBLICATIONS

Wolff, M. E. Burger's Medicinal Chemistry, 5ed, Part 1, John Wiley & Sons, 1995, pp. 975-977.
Fan, et al. A dual phosphoinositide-3-kinase alpha/mTOR inhibitor cooperates with blockade of epidermal growth factor receptor in PTEN-mutant glioma. Cancer Res. Sep. 1, 2007;67(17):7960-5.
International search report dated Aug. 13, 2010 for PCT Applilcation No. US09/37324.

\* cited by examiner

Pharmacokinetics parameters of compound 4 in Table 5 when tested in CD-1 mice following intravenous or oral administration
NA: Not applicable

| Treatment | AUC$_{(0-t)}$ μg/L*hr | AUC$_{(0-\infty)}$ μg/L*hr | MRT$_{(0-\infty)}$ hr | t$_{1/2z}$ hr | T$_{max}$ hr | Vz L/kg | CLz L/hr/kg | C$_{max}$ μg/L | F % |
|---|---|---|---|---|---|---|---|---|---|
| IV-2mg/kg | 472.68 | 479.72 | 0.82 | 0.65 | 0.08 | 3.89 | 4.17 | 555.05 | |
| PO-10mg/kg | 4845.64 | 4971.20 | 2.86 | 1.62 | 0.50 | NA | NA | 1646.71 | 207.25 |

Figure 1

Absorption Distribution Metabolism and Excretion Data

| Comp ID | Plasma Stability Mean Parent Remaining (%) | Chemical Stability Mean Parent Remaining (%) | Mean Permeability (TC7, PH 7.4/7.4) (10⁻⁶ cm/s) | | Mean of % protein bound | K+ Channel (hERG)% Inhibition of Tail current | | | Solubility (PBS, PH 7.4) | Human Liver Microsome Stability (min) |
|---|---|---|---|---|---|---|---|---|---|---|
| | | | A→B | B→A | | 10 μM | 1 μM | 0.1 μM | | |
| Compound 4 in Table 5 | 101 | 102 | 35.3 | 38.5 | 87.8 | 33.2 | 10.7 | 4.7 | 8.5 | >60 |
| Compound 3 in Table 1 | 95 | | | | | | | | 184.7 | |

Figure 2

Inhibitory effects of Compound 3 and Compound 4 in Table 5 on a variety of kinases

| | Compound 4 in Table 5 | Compound 3 in Table 5 | Compound 3 in Table 5 |
|---|---|---|---|
| Abl(h) | +++ | +++ | ++ |
| Aurora-A(h) | ++ | +++ | +++ |
| Axl(h) | ++ | + | + |
| Bmx(h) | +++ | +++ | +++ |
| BTK(h) | + | ++ | +++ |
| CDK2/cyclinA(h) | ++ | +++ | +++ |
| CDK9/cyclin T1(h) | +++ | +++ | +++ |
| CK1(h) | + | + | + |
| CK2(h) | + | +++ | ++ |
| cKit(h) | + | + | ++ |
| c-RAF(h) | ++ | ++ | ++ |
| cSRC(h) | + | + | + |
| EGFR(h) | + | ++ | ++ |
| EphA4(h) | + | + | + |
| EphB2(h) | + | +++ | ++ |
| FAK(h) | ++ | +++ | +++ |
| Fes(h) | + | ++ | ++ |
| Fms(h) | +++ | +++ | +++ |
| GSK3(h) | + | + | + |
| IGF-1R(h) | ++ | ++ | ++ |
| IKK(h) | + | + | + |
| Itk(h) | ++ | +++ | +++ |
| JAK2(h) | +++ | +++ | +++ |
| KDR(h) | ++ | ++ | ++ |
| Lck(h) | + | + | + |
| MAPK2(h) | ++ | +++ | +++ |
| Met(h) | + | + | + |
| MST1(h) | + | +++ | +++ |
| NEK2(h) | + | + | + |
| p70S6K(h) | ++ | ++ | ++ |
| PAK2(h) | + | +++ | +++ |
| PDGFRa(h) | + | ++ | + |
| PDK1(h) | + | + | + |
| Pim-1(h) | + | +++ | +++ |
| PKA(h) | + | + | ++ |
| PKBa(h) | ++ | + | + |
| PKCθ(h) | +++ | +++ | +++ |
| Plk1(h) | ++ | ++ | ++ |
| Ret(h) | + | + | + |
| Rsk1(h) | ++ | + | + |
| SAPK2a(h) | + | + | + |
| Syk(h) | ++ | +++ | ++ |
| Tie2(h) | + | ++ | + |
| ZAP-70(h) | +++ | + | + |

Figure 3

BENZOTHIAZOLE KINASE INHIBITORS AND METHODS OF USE

This application is a continuation of U.S. application Ser. No. 12/920,966, filed on Jan. 13, 2011, which is a national phase of PCT/US2009/37324, filed on Mar. 16, 2009, published as WO2009/114874, which claims the benefit under 35 USC §119(e) of U.S. Provisional Application Ser. No. 61/069,637, filed on Mar. 14, 2008, which is hereby incorporated by reference in its entirety.

BACKGROUND OF THE INVENTION

Kinases represent a class of important signaling molecules. Kinases can generally be classified into protein kinases and lipid kinases, and certain kinases exhibit dual specificities. Protein kinases are enzymes that phosphorylate other proteins and/or themselves (i.e., autophosphorylation). Protein kinases can be generally classified into three major groups based upon their substrate utilization: tyrosine kinases which predominantly phosphorylate substrates on tyrosine residues (e.g., erb2, PDGF receptor, EGF receptor, VEGF receptor, src, abl), serine/threonine kinases which predominantly phosphorylate substrates on serine and/or threonine residues (e.g., mTorC1, mTorC2, ATM, ATR, DNA-PK), and dual-specificity kinases which phosphorylate substrates on tyrosine, serine and/or threonine residues.

Lipid kinases are enzymes that catalyze the phosphorylation of lipids within cells. These enzymes, and the resulting phosphorylated lipids and lipid derived biologically active organic molecules, play a role in many different physiological processes, including cell proliferation, migration, adhesion, and differentiation. A particular group of lipid kinases comprises membrane lipid kinases, i.e., kinases that catalyze the phosphorylation of lipids contained in or associated with cell membranes. Examples of such enzymes include phosphinositide(s) kinases (such as PI3-kinases, PI4-Kinases), diacylglycerol kinases, and sphingosine kinases.

The phosphoinositide 3-kinases (PI3Ks) signaling pathway is one of the most highly mutated systems in human cancers. PI3K signaling is involved in many other disease states including allergic contact dermatitis, rheumatoid arthritis, osteoarthritis, inflammatory bowel diseases, chronic obstructive pulmonary disorder, psoriasis, multiple sclerosis, asthma, disorders related to diabetic complications, and inflammatory complications of the cardiovascular system such as acute coronary syndrome.

PI3Ks are members of a unique and conserved family of intracellular lipid kinases that phosphorylate the 3'-OH group on phosphatidylinositols or phosphoinositides. The PI3K family comprises 15 kinases with distinct substrate specificities, expression patterns, and modes of regulation (Katso et al., 2001). The class I PI3Ks (p110α, p110β, p110δ, and p110γ) are typically activated by tyrosine kinases or G-protein coupled receptors to generate PIP3, which engages downstream effectors such as those in the pathways of Akt/PDK1, mTor, the Tec family kinases, and the Rho family GTPases. The class II and III PI3Ks play a key role in intracellular trafficking through the synthesis of PI(3)P and PI(3,4)P2.

The production of phosphatidylinositol-3,4,5-trisphosphate initiates potent growth and survival signals. In some epithelial cancers the PI3K pathway is activated by direct genetic mutation. Additionally, the PI3K signaling pathway appears to be a crucial survival and growth signal in a broad spectrum of cancers. As PI3K signaling pathway plays a pivotal role in cell proliferation and differentiation, inhibition of this pathway is believed to be beneficial in hyperproliferative diseases.

Likewise, dysregulation of signaling pathways mediated by many other kinases is a key factor in the development of human diseases. Aberrant or excessive protein kinase activity or expression has been observed in many disease states including benign and malignant proliferative diseases, disorders such as allergic contact dermatitis, rheumatoid arthritis, osteoarthritis, inflammatory bowel diseases, chronic obstructive pulmonary disorder, psoriasis, multiple sclerosis, asthma, disorders related to diabetic complications, and inflammatory complications of the cardiovascular system such as acute coronary syndrome.

Downstream mediators of the PI3K signal transduction pathway include Akt and mammalian target of rapamycin (mTOR). Akt possesses a plckstrin homology (PH) domain that binds PIP3, leading to Akt kinase activation. Akt phosphorylates many substrates and is a central downstream effector of PI3K for diverse cellular responses. One important function of Akt is to augment the activity of mTOR, through phosphorylation of TSC2 and other mechanisms. mTOR is a serine-threonine kinase related to the lipid kinases of the PI3K family. mTOR has been implicated in a wide range of biological processes including cell growth, cell proliferation, cell motility and survival. Disregulation of the mTOR pathway has been reported in various types of cancer. mTOR is a multifunctional kinase that integrates growth factor and nutrient signals to regulate protein translation, nutrient uptake, autophagy, and mitochondrial function.

As such, kinases particularly protein kinases such as mTor and lipid kinases such as PI3Ks are prime targets for drug development. The present invention addresses a need in the art by providing a new class of kinase inhibitors.

SUMMARY OF THE INVENTION

In one aspect, a compound of Formula I or a pharmaceutically acceptable salt thereof, is provided wherein

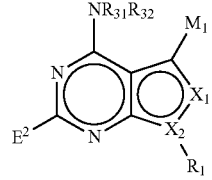

Formula I $M_1$ is benzothiazolyl substituted with —$(W^2)_k$—$R^2$; k is 0 or 1; $R_1$ is —H, -L-alkyl, -L-cycloalkyl, -L-alkyl-cycloalkyl, -L-aryl, -L-heteroaryl, -L-alkylaryl, -L-alkylheteroaryl, -L-alkylheterocylyl, -L-alkenyl, -L-alkynyl, -L-alkenyl-cycloalkyl, -L-alkynyl-cycloalkyl, or -L-heterocyclyl, each of which is unsubstituted or substituted by one or more independent $R^3$ substituents; L is absent, C=O, —C(=O)O—, —C(=O)$NR^{31}$—, —S—, —S(O)—, —S(O)$_2$—, —S(O)$_2$$NR^{31}$—, or —$NR^{31}$—; $X_1$ is N or C-$E^1$ and $X_2$ is N; or $X_1$ is NH or CH-$E^1$ and $X_2$ is C; $E^1$ and $E^2$ are independently —$(W^1)_j$—$R^4$; j, in each instance, is 0 or 1; $W^1$ is —O—, —$NR^6$—, —S(O)$_{0-2}$—, —C(O)—, —C(O)N($R^6$)—, —N($R^6$)C(O)—, —N($R^6$)S(O)—, —N($R^6$)S(O)$_2$—, —C(O)O—, —CH($R^6$)N(C(O)O$R^7$)—, —CH($R^7$)N(C(O) $R^7$)—, —CH($R^6$)N(SO$_2$$R^7$)—, —CH($R^6$)N($R^7$)—, —CH ($R^6$)C(O)N($R^7$)—, —CH($R^6$)N($R^7$)C(O)—, —CH($R^6$)N —(R⁷)S(O)—, or —CH(R⁶)N(R⁷)S(O)₂—; W² is —O—, —NR⁶—, —S(O)₀₋₂—, —C(O)—, —C(O)N(R⁶)—, —N(R⁶)C(O)—, —N(R⁶)S(O)—, —N(R⁶)S(O)₂—, —C(O)O—, —CH(R⁶)N(C(O)OR⁷)—, —CH(R⁷)N(C(O) R⁷)—, —CH(R⁶)N(SO₂R⁷)—, —CH(R⁶)N(R⁷)—, —CH (R⁶)C(O)N(R⁷)—, —CH(R⁶)N(R⁷)C(O)—, —CH(R⁶)N (R⁷)S(O)—, or —CH(R⁶)N(R⁷)S(O)₂—; R³ and R⁴ are independently hydrogen, halogen, aryl, heteroaryl, alkyl, cycloalkyl, -alkyl-cycloalkyl, -alkylheterocyclyl, C₂₋₁₀alkenyl, or C₂₋₁₀alkynyl; R² is hydrogen, bicyclic aryl, substituted monocyclic aryl, hetaryl, alkyl, cycloalkyl, -alkyl-cycloalkyl, -alkyl-monocyclic aryl, -alkylbicycloaryl, -alkylhetaryl, -alkylheterocyclyl, alkenyl, or alkynyl; R⁶ and R⁷ are each independently hydrogen, alkyl, alkenyl, aryl, heteroaryl, heterocyclyl or cycloalkyl, wherein each alkyl, alkenyl, aryl, heteroaryl, heterocyclyl or cycloalkyl is unsubstituted or substituted by one or more independent R⁸ substituents; and R⁸ is halo, —OR³¹, —SH, NH₂, —NR³⁴R³⁵, —NR³¹R³², —CO₂R³¹, —CO₂aryl-C(=O) NR³¹R³², C(=O)NR³⁴R³⁵, —NO₂, —CN, —S(O)₀₋₂ alkyl, —S(O)₀₋₂ aryl, —SO₂NR³⁴R³⁵, —SO₂NR³¹R³², alkyl, alkenyl, or alkynyl; R³¹, R³², and R³³, in each instance, are independently H or alkyl; and R³⁴ and R³⁵ are taken together with the nitrogen atom to which they are attached to form a 3-10 membered ring.

In a second aspect, a compound of Formula I or a pharmaceutically acceptable salt thereof, is provided wherein

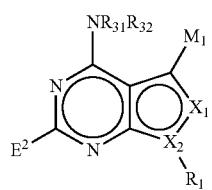

Formula I wherein M₁ is benzothiazolyl substituted with —(W²)ₖ—R²; k is 0 or 1; R₁ is —H, -L-alkyl, -L-cycloalkyl, -L-alkylcycloalkyl, -L-aryl, -L-heteroaryl, -L-alkylaryl, -L-alkylheteroaryl, -L-alkylheterocyclyl, -L-alkenyl, -L-alkynyl, -L-alkenyl-cycloalkyl, -L-alkynyl-cycloalkyl, or -L-heterocyclyl, each of which is unsubstituted or substituted by one or more independent R³ substituents; L is absent, C=O, —C(=O)O—, —C(=O) NR³¹—, —S—, —S(O)—, —S(O)₂—, —S(O)₂NR³¹—, or —NR³¹—; X₁ is N or C-E¹ and X₂ is N; or X₁ is NH or CH-E¹ and X₂ is C; E¹ and E² are independently —(W¹)ⱼ—R⁴; j, in each instance, is 0 or 1; W¹ is —O—, —NR⁶—, —S(O)₀₋₂—, —C(O)—, —C(O) N(R⁶)—, —N(R⁶)C(O)—, —N(R⁶)S(O)—, —N(R⁶) S(O)₂—, —C(O)O—, —CH(R⁶)N(C(O)OR⁷)—, —CH(R⁷) N(C(O)R⁷)—, —CH(R⁶)N(SO₂R⁷)—, —CH(R⁶)N(R⁷)—, —CH(R⁶)C(O)N(R⁷)—, —CH(R⁶)N(R⁷)C(O)—, —CH (R⁶)N(R⁷)S(O)—, or —CH(R⁶)N(R⁷)S(O)₂—; W² is —O—, —NR⁶—, —S(O)₀₋₂—, —C(O)—, —C(O)N (R⁶)—, —N(R⁶)C(O)—, —N(R⁶)S(O)—, —N(R⁶)S(O)₂—, —C(O)O—, —CH(R⁶)N(C(O)OR⁷)—, —CH(R⁷)N(C(O) R⁷)—, —CH(R⁶)N(SO₂R⁷)—, —CH(R⁶)N(R⁷)—, —CH (R⁶)C(O)N(R⁷)—, —CH(R⁶)N(R⁷)C(O)—, —CH(R⁶)N (R⁷)S(O)—, or —CH(R⁶)N(R⁷)S(O)₂—; R³ and R⁴ are independently hydrogen, halogen, aryl, heteroaryl, alkyl, cycloalkyl, -alkyl-cycloalkyl, -alkylheterocyclyl, C₂₋₁₀alkenyl, or C₂₋₁₀alkynyl; R² is hydrogen, bicyclic aryl, substituted monocyclic aryl, hetaryl, alkyl, cycloalkyl, -alkylcycloalkyl, -alkyl-monocyclic aryl, -alkylbicycloaryl, -alkylhetaryl, -alkylheterocyclyl, or alkenyl, alkynyl; R⁶ and R⁷ are each independently hydrogen, alkyl, alkenyl, aryl, heteroaryl, heterocyclyl or cycloalkyl, wherein each alkyl, alkenyl, aryl, heteroaryl, heterocyclyl or cycloalkyl is unsubstituted or substituted by one or more independent R⁸ substituents; R⁸ is halo, —OR³¹, —SH, NH₂, —NR³⁴R³⁵, —NR³¹R³², —CO₂R³¹, —CO₂aryl-C(=O)NR³¹R³², C(=O) NR³⁴R³⁵, —NO₂, —CN, —S(O)₀₋₂ alkyl, —S(O)₀₋₂aryl, —SO₂NR³⁴R³⁵, —SO₂NR³¹R³², alkyl, alkenyl, or alkynyl; R³¹, R³², and R³³, in each instance, are independently H or alkyl; and R³⁴ and R³⁵ are taken together with the nitrogen atom to which they are attached to form a 3-10 membered ring.

In a third aspect of the invention, a compound of Formula I is provided having a structure of Formula II, Formula III, Formula IV, or Formula V, or a pharmaceutically acceptable salt thereof, wherein

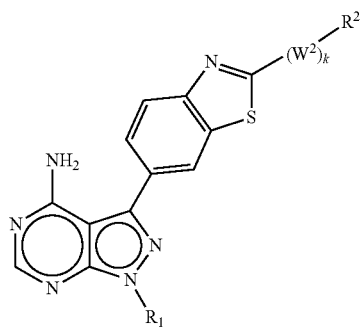

Formula II

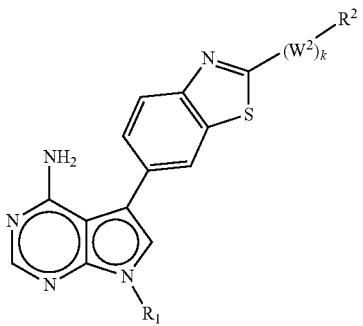

Formula III

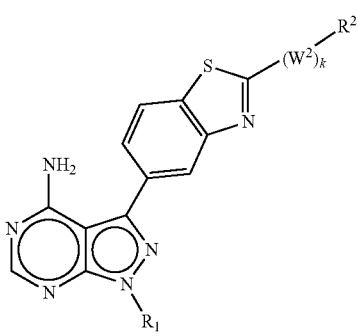

Formula IV

-continued

Formula V

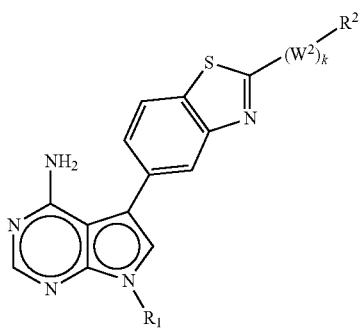

k is 0 or 1; $R_1$ is —H, -L-alkyl, -L-cycloalkyl, -L-alkyl-cycloalkyl, -L-aryl, -L-heteroaryl, -L-alkylaryl, -L-alkylheteroaryl, -L-alkylheterocylyl, -L-alkenyl, -L-alkynyl, -L-alkenyl-cycloalkyl, -L-alkynyl-cycloalkyl, or -L-heterocyclyl, each of which is unsubstituted or substituted by one or more independent $R^3$ substituents; L is absent, C=O, —C(=O)O—, —C(=O) $NR^{31}$—, —S—, —S(O)—, —S(O)$_2$—, —S(O)$_2NR^{31}$—, or —$NR^{31}$; $W^2$ is —O—, —$NR^6$—, —S(O)$_{0-2}$—, —C(O)—, —C(O)N($R^6$)—, —N($R^6$)C(O)—, —N($R^6$)S(O)—, —N($R^6$)S(O)$_2$—, —C(O)O—, —CH($R^6$)N(C(O)O$R^7$)—, —CH($R^7$)N(C(O)$R^7$)—, —CH($R^6$)N(SO$_2R^7$)—, —CH($R^6$)N($R^7$)—, —CH($R^6$)C(O)N($R^7$)—, —CH($R^6$)N($R^7$)C(O)—, —CH($R^6$)N($R^7$)S(O)—, or —CH($R^6$)N($R^7$)S(O)$_2$—; $R^3$ and $R^4$ are independently hydrogen, halogen, aryl, heteroaryl, alkyl, cycloalkyl, -alkyl-cycloalkyl, -alkylheterocyclyl, $C_{2-10}$alkenyl, or $C_{2-10}$alkynyl; $R^2$ is hydrogen, bicyclic aryl, substituted monocyclic aryl, hetaryl, alkyl, cycloalkyl, -alkyl-cycloalkyl, -alkyl-monocyclic aryl, -alkylbicycloaryl, -alkylhetaryl, -alkylheterocyclyl, alkenyl, or alkynyl; $R^6$ and $R^7$ are each independently hydrogen, alkyl, alkenyl, aryl, heteroaryl, heterocyclyl or cycloalkyl, wherein each alkyl, alkenyl, aryl, heteroaryl, heterocyclyl or cycloalkyl is unsubstituted or substituted by one or more independent $R^8$ substituents; and $R^8$ is halo, —$OR^{31}$, —SH, $NH_2$, —$NR^{34}R^{35}$, —$NR^{31}R^{32}$, —$CO_2R^{31}$, —$CO_2$aryl-C(=O)$NR^{31}R^{32}$, C(=O) $NR^{34}R^{35}$, —$NO_2$, —CN, —S(O)$_{0-2}$ alkyl, —S(O)$_{0-2}$aryl, —$SO_2NR^{34}R^{35}$, —$SO_2NR^{31}R^{32}$, alkyl, alkenyl, or alkynyl; $R^{31}$, $R^{32}$, and $R^{33}$, in each instance, are independently H or alkyl; and $R^{34}$ and $R^{35}$ are taken together with the nitrogen atom to which they are attached to form a 3-10 membered ring.

In a fourth aspect of the invention, a compound of Formula I is provided having a structure of Formula II, Formula III, Formula IV, or Formula V, or a pharmaceutically acceptable salt thereof, wherein Formula II

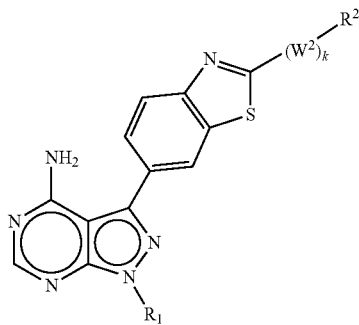

-continued

Formula III

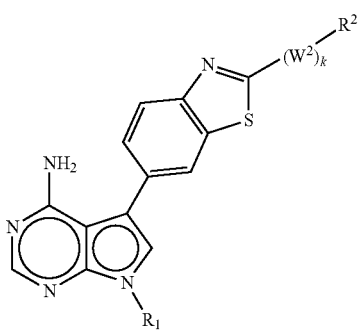

Formula IV

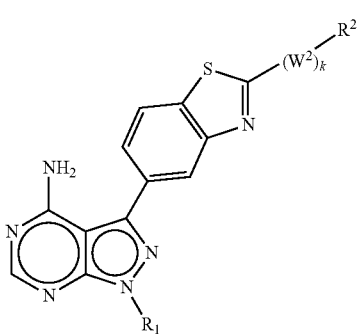

Formula V

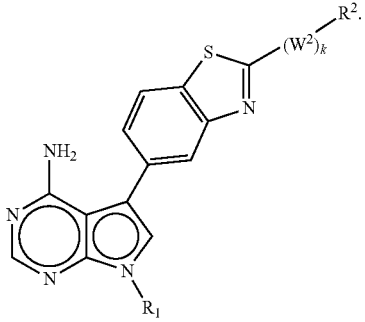

In a fifth aspect of the invention, a compound of Formula II, Formula III, Formula IV, or Formula V, or a pharmaceutically acceptable salt thereof, is provided wherein:

k is 1; $R_1$ is —H, -L-alkyl, -L-cycloalkyl, -L-alkyl-cycloalkyl, -L-aryl, -L-heteroaryl, -L-alkylaryl, -L-alkylheteroaryl, -L-alkylheterocylyl, -L-alkenyl, -L-alkynyl, -L-alkenyl-cycloalkyl, -L-alkynyl-cycloalkyl, or -L-heterocyclyl, each of which is unsubstituted or substituted by one or more independent $R^3$ substituents; L is absent, C=O, —C(=O)O—, —C(=O) $NR^{31}$—, —S—, —S(O)—, —S(O)$_2$—, —S(O)$_2NR^{31}$—, or —$NR^{31}$—; $W^2$ is —$NR^6$—, —N($R^6$)C(O)—N($R^6$)S(O)—, or —N($R^6$)S(O)$_2$—; $R^3$ and $R^4$ are independently hydrogen, halogen, aryl, heteroaryl, alkyl, cycloalkyl, -alkyl-cycloalkyl, -alkylheterocyclyl, $C_{2-10}$alkenyl, or $C_{2-10}$alkynyl; $R^2$ is hydrogen, bicyclic aryl, substituted monocyclic aryl, hetaryl, alkyl, cycloalkyl, -alkyl-cycloalkyl, -alkyl-monocyclic aryl, -alkylbicycloaryl, -alkylhetaryl, -alkylheterocyclyl, alkenyl, or alkynyl; $R^6$ and $R^7$ are each independently hydrogen, alkyl, alkenyl, aryl, heteroaryl, heterocyclyl or cycloalkyl, wherein each alkyl, alkenyl, aryl, heteroaryl, heterocyclyl or cycloalkyl is unsubstituted or substituted by one or more independent $R^8$ substituents; and $R^8$ is halo, —$OR^{31}$, —SH, $NH_2$, —$NR^{34}R^{35}$, —$NR^{31}R^{32}$, —$CO_2R^{31}$, —$CO_2$aryl-C(=O) $NR^{31}R^{32}$, C(=O) $NR^{34}R^{35}$, —$NO_2$, —CN, —S(O)$_{0-2}$ alkyl, —S(O)$_{0-2}$ aryl, —SO$_2$NR$^{34}$R$^{35}$, —SO$_2$NR$^{31}$R$^{32}$, alkyl, alkenyl, or alkynyl; R$^{31}$, R$^{32}$, and R$^{33}$, in each instance, are independently H or alkyl; and R$^{34}$ and R$^{35}$ are taken together with the nitrogen atom to which they are attached to form a 3-10 membered ring.

In some embodiments, the compound of Formula I, Formula II, Formula III, Formula IV, or Formula V, is a compound wherein L is optionally —N(R$^{31}$)C(O)—. In other embodiments, R$^3$ and R$^4$ are optionally alkoxy, heterocyclyl, —OH, —R$^{31}$, —CF$_3$, —OCF$_3$, —OR$^{31}$, —NR$^{31}$R$^{32}$, —NR$^{34}$R$^{35}$, —C(O)R$^{31}$, —CO$_2$R$^{31}$, —(=O)NR$^{31}$R$^{32}$, —C(=O)NNR$^{34}$R$^{35}$, —NO$_2$, —CN, —S(O)$_2$R$^{31}$, —SO$_2$NR$^{31}$R$^{32}$, —SO$_2$NR$^{34}$R$^{35}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_{0-2}$R$^{32}$, —C(=S)OR$^{31}$, —C(=O)SR$^{31}$, —NR$^{31}$C(=NR$^{32}$)NR$^{33}$R$^{32}$, —NR$^{31}$C(=NR$^{32}$)OR$^{33}$, —NR$^{31}$C(=NR$^{32}$)SR$^{33}$, —OC(=O)OR$^{33}$, —OC(=O)NR$^{31}$R$^{32}$, —OC(=O)SR$^{31}$, —SC(=O)OR$^{31}$, —P(O)OR$^{31}$OR$^{32}$, or —SC(=O)NR$^{31}$R$^{32}$.

In yet other embodiments, R$^2$ is optionally-alkyl-substituted monocyclic aryl, heterocyclyl, -cycloalkyl-heterocyclyl, or -heterocyclyl-heterocyclyl. In further embodiments, W$^2$ is optionally —N(R$^6$)C(O)N(R$^7$)—, or —NR$^{34}$R$^{35}$.

In a sixth aspect of the invention, a compound of Formula X, or a pharmaceutically acceptable salt thereof, is provided wherein:

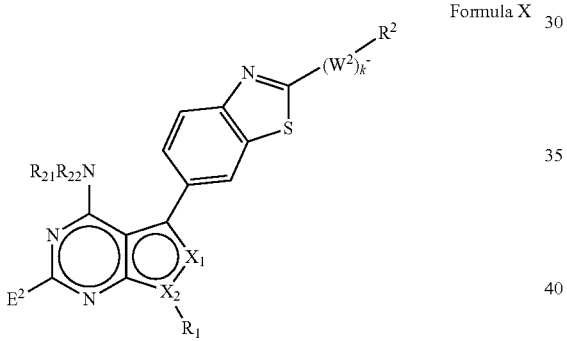

Formula X k is 0 or 1; R$_1$ is —H, -L-alkyl, -L-cycloalkyl, -L-alkylcycloalkyl, -L-aryl, -L-heteroaryl, -L-alkylaryl, -L-alkylheteroaryl, -L-alkylheterocyclyl, -L-alkenyl, -L-alkynyl, -L-alkenyl-cycloalkyl, -L-alkynyl-cycloalkyl, or -L-heterocyclyl, each of which is unsubstituted or substituted by one or more independent R$^3$ substituents; L is absent, C=O, —C(=O)O—, —C(=O) NR$^{31}$—, —S—, —S(O)—, —S(O)$_2$—, —S(O)$_2$NR$^{31}$—, or —NR$^{31}$—; X$_1$ is N or C-E$^1$ and X$_2$ is N; or X$_1$ is NH or CH-E$^1$ and X$_2$ is C; E$^1$ and E$^2$ are independently —(W$^1$)$_j$—R$^4$; j, in each instance, is 0 or 1; W$^1$ is —O—, —NR$^6$—, —S(O)$_{0-2}$—, —C(O)—, —C(O)N(R$^6$)—, —N(R$^6$)C(O)—, —N(R$^6$)S(O)—, —N(R$^6$)S(O)$_2$—, —C(O)O—, —CH(R$^6$)N(C(O)OR$^7$)—, —CH(R$^7$)N(C(O)R$^7$)—, —CH(R$^6$)N(SO$_2$R$^7$)—, —CH(R$^6$)N(R$^7$)—, —CH(R$^6$)C(O)N(R$^7$)—, —CH(R$^6$)N(R$^7$)C(O)—, —CH(R$^6$)N(R$^7$)S(O)—, or —CH(R$^6$)N(R$^7$)S(O)$_2$—; W$^2$ is —O—, —NR$^6$—, —S(O)$_{0-2}$—, —C(O)—, —C(O)N(R$^6$)—, —N(R$^6$)C(O)—, —N(R$^6$)S(O)—, —N(R$^6$)S(O)$_2$—, —C(O)O—, —CH(R$^6$)N(C(O)OR$^7$)—, —CH(R$^6$)N(C(O)R$^7$)—, —CH(R$^6$)N(SO$_2$R$^7$)—, —CH(R$^6$)N(R$^7$)—, —CH(R$^6$)C(O)N(R$^7$)—, —CH(R$^6$)N(R$^7$)C(O)—, —CH(R$^6$)N(R$^7$)S(O)—, or —CH(R$^6$)N(R$^7$)S(O)$_2$—; R$^2$, R$^3$, and R$^4$ are independently hydrogen, halogen, aryl, heteroaryl, alkyl, cycloalkyl, alkenyl, alkynyl, heteroalkyl, heterocyclyl, -alkyl-aryl, -alkyl-cycloalkyl, -alkylheterocyclyl, or -alkynyl-cycloalkyl; R$^6$ and R$^7$ are each independently hydrogen, alkyl, alkenyl, aryl, heteroaryl, heterocyclyl or cycloalkyl, wherein each alkyl, alkenyl, aryl, heteroaryl, heterocyclyl or cycloalkyl is unsubstituted or substituted by one or more independent R$^8$ substituents; R$^8$ is halo, —OR$^{31}$, —SH, NH$_2$, —NR$^{34}$R$^{35}$, —NR$^{31}$R$^{32}$, —CO$_2$R$^{31}$, —CO$_2$aryl-C(=O)NR$^{31}$R$^{32}$, C(=O) NR$^{34}$R$^{35}$, —NO$_2$, —CN, —S(O)$_{0-2}$alkyl, —S(O)$_{0-2}$aryl, —SO$_2$NR$^{34}$R$^{35}$, —SO$_2$NR$^{31}$R$^{32}$, alkyl, alkenyl, or alkynyl; R$^{31}$, R$^{32}$, and R$^{33}$, in each instance, are independently H or alkyl; and R$^{34}$ and R$^{35}$ are taken together with the nitrogen atom to which they are attached to form a 3-10 membered ring.

In a seventh aspect of the invention, a compound of Formula X, or a pharmaceutically acceptable salt thereof, is provided wherein

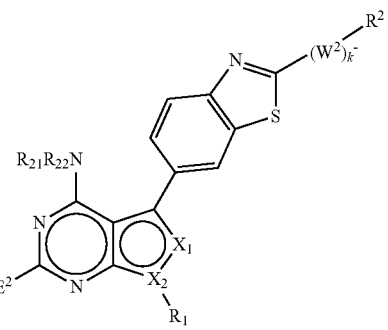

Formula X k is 0 or 1; R$_1$ is —H, -L-alkyl, -L-cycloalkyl, -L-alkylcycloalkyl, -L-aryl, -L-heteroaryl, -L-alkylaryl, -L-alkylheteroaryl, -L-alkylheterocyclyl, -L-alkenyl, -L-alkynyl, -L-alkenyl-cycloalkyl, -L-alkynyl-cycloalkyl, or -L-heterocyclyl, each of which is unsubstituted or substituted by one or more independent R$^3$ substituents; L is absent, C=O, —C(=O)O—, —C(=O) NR$^{31}$—, —S—, —S(O)—, —S(O)$_2$—, —S(O)$_2$NR$^{31}$—, or —NR$^{31}$—; X$_1$ is N or C-E$^1$ and X$_2$ is N; or X$_1$ is NH or CH-E$^1$ and X$_2$ is C; E$^1$ and E$^2$ are independently —(W$^1$)$_j$—R$^4$; j, in each instance, is 0 or 1; W$^1$ is —O—, —NR$^6$—, —S(O)$_{0-2}$—, —C(O)—, —C(O)N(R$^6$)—, —N(R$^6$)C(O)—, —N(R$^6$)S(O)—, —N(R$^6$)S(O)$_2$—, —C(O)O—, —CH(R$^6$)N(C(O)OR$^7$)—, —CH(R$^7$)N(C(O)R$^7$)—, —CH(R$^6$)N(SO$_2$R$^7$)—, —CH(R$^6$)N(R$^7$)—, —CH(R$^6$)C(O)N(R$^7$)—, —CH(R$^6$)N(R$^7$)C(O)—, —CH(R$^6$)N(R$^7$)S(O)—, or —CH(R$^6$)N(R$^7$)S(O)$_2$—; W$^2$ is —O—, —NR$^6$—, —S(O)$_{0-2}$—, —C(O)—, —C(O)N(R$^6$)—, —N(R$^6$)C(O)—, —N(R$^6$)S(O)—, —N(R$^6$)S(O)$_2$—, —C(O)O—, —CH(R$^6$)N(C(O)OR$^7$)—, —CH(R$^6$)N(C(O)R$^7$)—, —CH(R$^6$)N(SO$_2$R$^7$)—, —CH(R$^6$)N(R$^7$)—, —CH(R$^6$)C(O)N(R$^7$)—, —CH(R$^6$)N(R$^7$)C(O)—, —CH(R$^6$)N(R$^7$)S(O)—, or —CH(R$^6$)N(R$^7$)S(O)$_2$—; R$^2$, R$^3$, and R$^4$ are independently hydrogen, halogen, aryl, heteroaryl, alkyl, cycloalkyl, alkenyl, alkynyl, heteroalkyl, heterocyclyl, -alkyl-aryl, -alkyl-cycloalkyl, -alkylheterocyclyl, or -alkynyl-cycloalkyl; R$^6$ and R$^7$ are each independently hydrogen, alkyl, alkenyl, aryl, heteroaryl, heterocyclyl or cycloalkyl, wherein each alkyl, alkenyl, aryl, heteroaryl, heterocyclyl or cycloalkyl is unsubstituted or substituted by one or more independent R$^8$ substituents; R$^8$ is halo, —OR$^{31}$, —SH, NH$_2$, —NR$^{34}$R$^{35}$, —NR$^{31}$R$^{32}$, —CO$_2$R$^{31}$, —CO$_2$aryl-C(=O)NR$^{31}$R$^{32}$, C(=O) NR$^{34}$R$^{35}$, —NO$_2$, —CN, —S(O)$_{0-2}$alkyl, —S(O)$_{0-2}$aryl, —SO$_2$NR$^{34}$R$^{35}$, —SO$_2$NR$^{31}$R$^{32}$, alkyl, alkenyl, or alkynyl; R$^{31}$, R$^{32}$, and R$^{33}$, in each instance, are independently H or alkyl; and $R^{34}$ and $R^{35}$ are taken together with the nitrogen atom to which they are attached to form a 3-10 membered ring.

In a eighth aspect of the invention, a compound of Formula X has a structure of Formula XI or Formula XII:

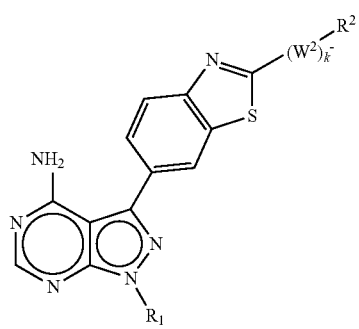

Formula XI

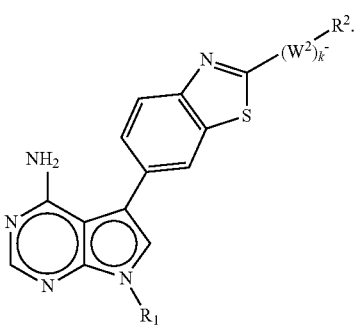

Formula XII

In an ninth aspect of the invention, a compound of Formula XI or Formula XII, or a pharmaceutically acceptable salt thereof, is provided wherein:

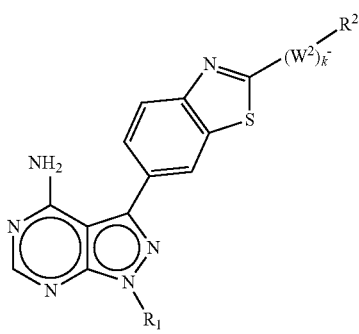

Formula XI

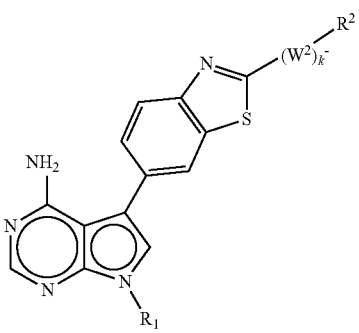

Formula XII k is 1; $R_1$ is H, L-alkyl, -L-cycloalkyl, -L-alkyl-cycloalkyl, -L-aryl, -L-heteroaryl, -L-alkylaryl, -L-alkylheteroaryl, -L-alkylheterocyclyl, -L-alkenyl, -L-alkynyl, -L-alkenyl-cycloalkyl, -L-alkynyl-cycloalkyl, or -L-heterocyclyl, each of which is unsubstituted or substituted by one or more independent $R^3$ substituents; L is absent, C=O, —C(=O) O—, —C(=O) $NR^{31}$—, —S—, —S(O)—, —S(O)$_2$—, —S(O)$_2NR^{31}$—, or —$NR^{31}$—; $W^2$ is $NR^6$, —N($R^6$)C(O)—, —N($R^6$)S(O)—, or —N($R^6$)S(O)$_2$—; $R^2$, $R^3$, and $R^4$ are independently hydrogen, halogen, aryl, heteroaryl, alkyl, cycloalkyl, alkenyl, alkynyl, heteroalkyl, heterocyclyl, -alkyl-aryl, -alkyl-cycloalkyl, -alkylheterocyclyl, or alkynyl-cycloalkyl; $R^6$ and $R^7$ are each independently hydrogen, alkyl, alkenyl, aryl, heteroaryl, heterocyclyl or cycloalkyl, wherein each alkyl, alkenyl, aryl, heteroaryl, heterocyclyl or cycloalkyl is unsubstituted or substituted by one or more independent $R^8$ substituents; $R^8$ is halo, —$OR^{31}$, —SH, —$NH_2$, —$NR^{34}R^{35}$, —$NR^{31}R^{32}$, —$CO_2R^{31}$, —$CO_2$aryl-C(=O)$NR^{31}R^{32}$, C(=O)$NR^{34}R^{35}$, —$NO_2$, —CN, —S(O)$_{0-2}$alkyl, —S(O)$_{0-2}$aryl, —SO$_2NR^{34}R^{35}$, —SO$_2NR^{31}R^{32}$, alkyl, alkenyl, or alkynyl; $R^{31}$, $R^{32}$, and $R^{33}$, in each instance, are independently H or alkyl; and $R^{34}$ and $R^{35}$ are taken together with the nitrogen atom to which they are attached to form a 3-10 membered ring.

In a tenth aspect of the invention, a compound of Formula XI or Formula XII, or a pharmaceutically acceptable salt thereof, is provided wherein:

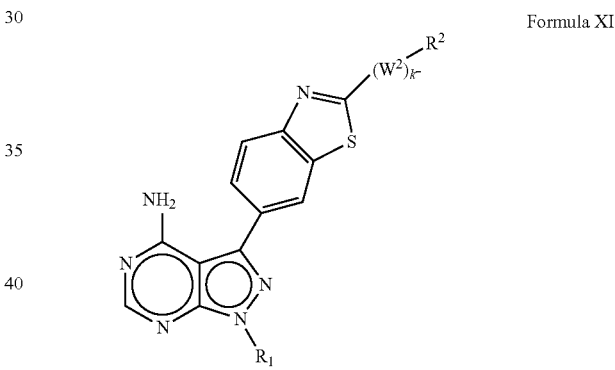

Formula XI

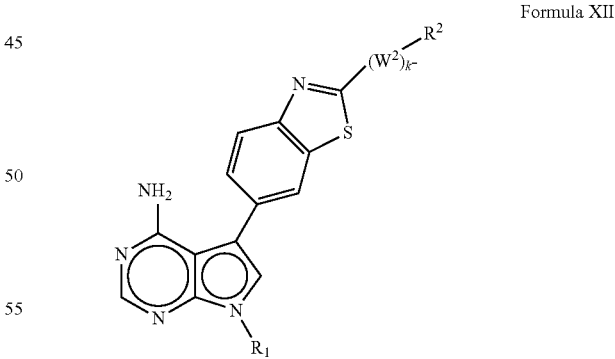

Formula XII k is 1; $R_1$ is H, L-alkyl, -L-cycloalkyl, -L-alkyl-cycloalkyl, -L-aryl, -L-heteroaryl, -L-alkylaryl, -L-alkylheteroaryl, -L-alkylheterocyclyl, -L-alkenyl, -L-alkynyl, -L-alkenyl-cycloalkyl, -L-alkynyl-cycloalkyl, or -L-heterocyclyl, each of which is unsubstituted or substituted by one or more independent $R^3$ substituents; L is absent, C=O, —C(=O) O—, —C(=O) $NR^{31}$—, —S—, —S(O)—, —S(O)$_2$—, —S(O)$_2NR^{31}$—, or —$NR^{31}$—; $W^2$ is $NR^6$ or N($R^6$)C(O); $R^2$, $R^3$, and $R^4$ are independently hydrogen, halogen, aryl, heteroaryl, alkyl, cycloalkyl, alkenyl, alkynyl, heteroalkyl, heterocyclyl, alkyl-aryl, -alkyl-cycloalkyl, -alkylheterocyclyl, or alkynyl-cycloalkyl; $R^6$ and $R^7$ are each independently hydrogen, alkyl, alkenyl, aryl, heteroaryl, heterocyclyl or cycloalkyl, wherein each alkyl, alkenyl, aryl, heteroaryl, heterocyclyl or cycloalkyl is unsubstituted or substituted by one or more independent $R^8$ substituents; $R^8$ is halo, —$OR^{31}$, —SH, $NH_2$, —$NR^{34}R^{35}$, —$NR^{31}R^{32}$, —$CO_2R^{31}$, —$CO_2$aryl-C(=O)$NR^{31}R^{32}$, C(=O) $NR^{34}R^{35}$, —$NO_2$, —CN, —$S(O)_{0-2}$ alkyl, —$S(O)_{0-2}$aryl, —$SO_2NR^{34}R^{35}$, —$SO_2NR^{31}R^{32}$, alkyl, alkenyl, or alkynyl; $R^{31}$, $R^{32}$, and $R^{33}$, in each instance, are independently H or alkyl; and $R^{34}$ and $R^{35}$ are taken together with the nitrogen atom to which they are attached to form a 3-10 membered ring.

In some embodiments of the compound of Formula X, XI, or XII, L is optionally —$N(R^{31})C(O)$—. In other embodiments, $R^3$ and $R^4$ are optionally alkoxy, —OH, —$R^{31}$, —$CF_3$, —$OCF_3$, —$OR^{31}$, —$NR^{31}R^{32}$, —$NR^{34}R^{35}$, —C(O)$R^{31}$, —$CO_2R^{31}$, —C(=O)$NR^{31}R^{32}$, —C(=O)$NNR^{34}R^{35}$, —$NO_2$, —CN, $S(O)_{0-2}R^{31}$, —$SO_2NR^{31}R^{32}$, —$SO_2NR^{34}R^{35}$, —$NR^{31}C(=O)R^{32}$, —$NR^{31}C(=O)OR^{32}$, —$NR^{31}C(=O)NR^{32}R^{33}$, —$NR^{31}S(O)_2R^{32}$, —C(=S)$OR^{31}$, —C(=)$SR^{31}$, —$NR^{31}C(=NR^{32})NR^{33}R^{32}$, —$NR^{31}C(=NR^{32})OR^{33}$, —$NR^{31}C(=NR^{32})SR^{33}$, —OC(=O)$OR^{33}$, —OC(=O)$NR^{31}R^{32}$, —OC(=O)$SR^{31}$, —SC(=O)$OR^{31}$, —P(O)$OR^{31}OR^{32}$, or —SC(=O)$NR^{31}R^{32}$. In some other embodiments, $R^2$ is optionally -cycloalkyl-heterocyclyl, or heterocyclyl-heterocyclyl. Alternatively, $W^2$ is optionally $N(R^6)C(O)N(R^7)$—, $CH(R^7)C(O)$—, or $NR^{34}R^{35}$.

In some embodiments of the invention, a compound having one of the following formulae is provided:

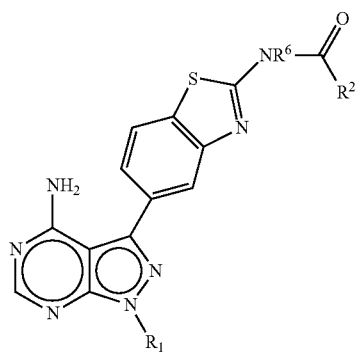

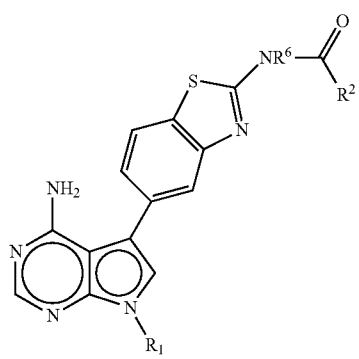

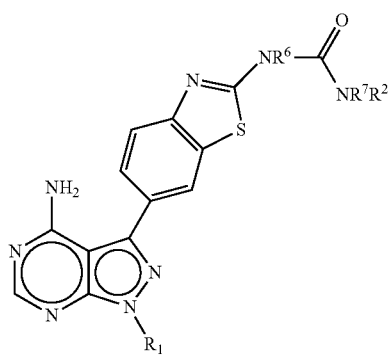

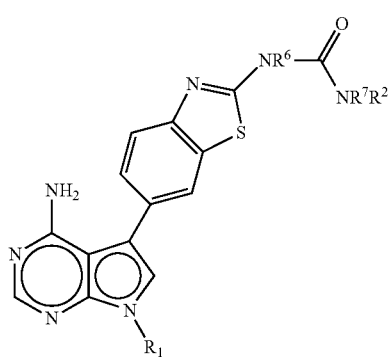

-continued
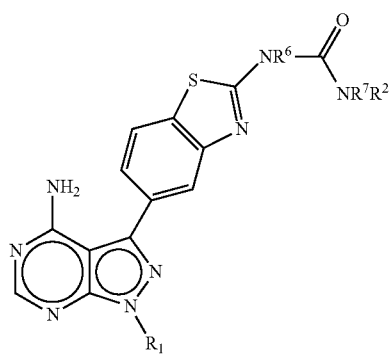
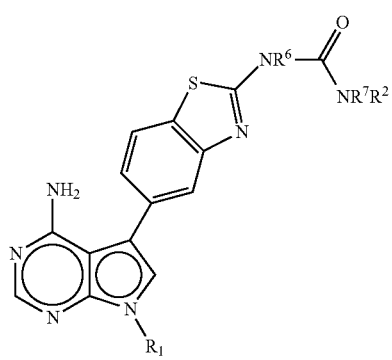
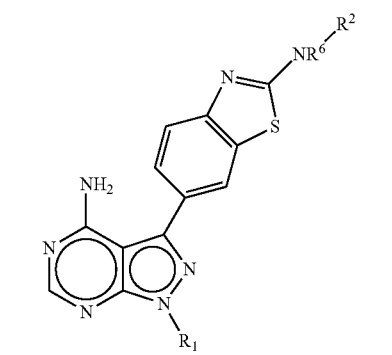
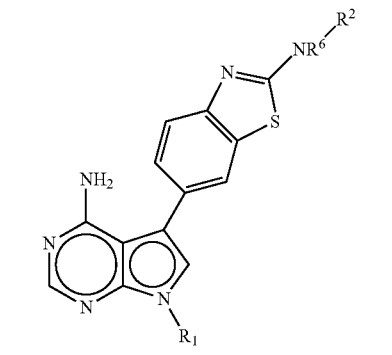
-continued
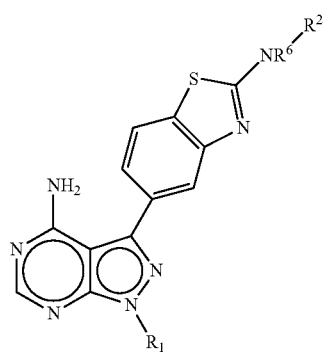
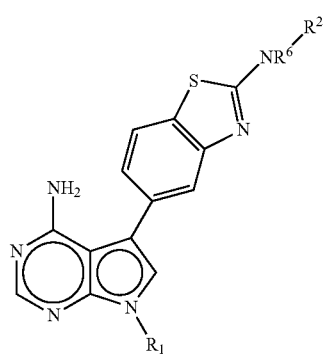
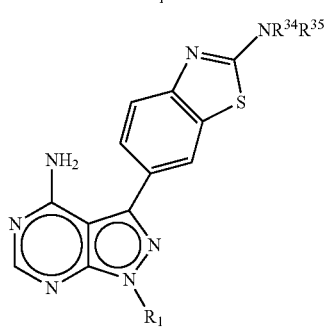
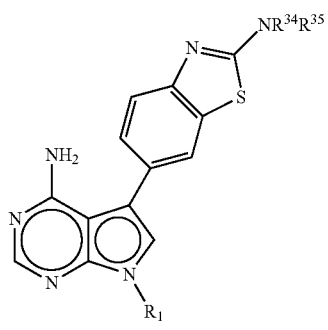
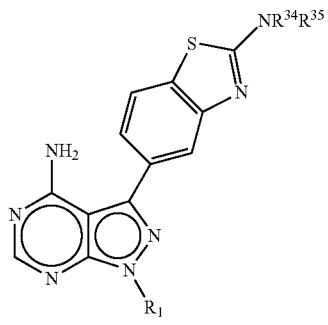

-continued

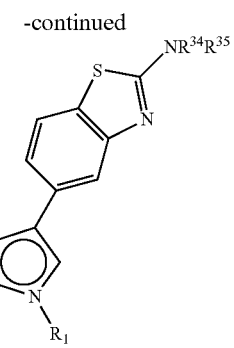

In some embodiments of the invention, $X_1$ is N and $X_2$ is N or $X_1$ is $C-E^1$ and $X_2$ is N.

In some embodiments of the invention, $M_1$ is 5-benzothiazolyl substituted at the 2-position with $(W^2)$ $R^2$. In other embodiments of the invention, $M_1$ is 6-benzothiazolyl substituted at the 2-position with $(W^2)$ $R^2$.

In some embodiments of the invention, $—(W^2)_k—$ is $—NR^7—$, $—N(R^7)C(O)—$ or $—N(R^7)S(O)_2$. In other embodiments of the invention, $R^2$ is —H, alkyl, cycloalkyl, or alkyl-cycloalkyl. In further embodiments, $R_1$ is alkyl, cycloalkyl or heterocyclyl.

In some embodiments, the compound of Formula I, II, III, IV, V, X, XI, or XII inhibits a protein kinase. In some embodiments, the compound of Formula I, II, III, IV, V, X, XI, or XII inhibits a lipid kinase. In some embodiments, the compound of Formula I, II, III, IV, V, X, XI, or XII inhibits a protein kinase and a lipid kinase. In some embodiments, the compound of Formula I, II, III, IV, V, X, XI, or XII inhibits mTorC1 and/or mTorC2.

In a tenth aspect of the invention, a pharmaceutical composition comprising a compound of Formula I, II, III, IV, V, X, XI, or XII and a pharmaceutically acceptable carrier is provided.

In an eleventh aspect of the invention, a method is provided to inhibit activity of a protein kinase and/or a lipid kinase present in a cell, comprising; contacting said cell with an effective amount of a compound of Formula I, II, III, IV, V, X, XI, or XII. In some embodiments of the method, the inhibiting takes place in a subject suffering from a disorder selected from the group consisting of cancer, bone disorder, inflammatory disease, immune disease, nervous system disease, metabolic disease, respiratory disease, and cardiac disease. In some other embodiments, the method further comprises administering a second therapeutic agent.

In a twelfth aspect of the invention, a method is provided to inhibit cell proliferation comprising contacting a cell with a compound of Formula I, II, III, IV, V, X, XI, or XII that selectively inhibits mTorC1 and/or mTorC2 activity relative to one or more type I phosphatidylinositol 3-kinases (PI3-kinase) ascertained by an in vitro kinase assay, wherein the one or more type I PI3-kinase is selected from the group consisting of PI3-kinase α, PI3-kinase β, PI3-kinase γ, and PI3-kinase δ.

In a thirteenth aspect of the invention, a method is provided to ameliorate a medical condition mediated by mTorC1 and/or mTorC2, comprising administering to a subject in need thereof a therapeutically effective amount of a compound of any one of Formula I, II, III, IV, V, X, XI, or XII that selectively inhibits mTorC1 and/or mTorC2 activity relative to one or more type I phosphatidylinositol 3-kinases (PI3-kinase) as ascertained in a cell-based assay or an in vitro kinase assay, wherein the one or more type I PI3-kinase is selected from the group consisting of PI3-kinase α, PI3-kinase β, PI3-kinase γ, and PI3-kinase δ.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

FIG. 1 depicts the pharmacokinetics parameters of compound 4 in Table 5 when tested in CD-1 mice following intravenous or oral administration.

FIG. 2 summaries the absorption distribution metabolism and excretion data of compound 3 and compound 5 in Table 5. The data is obtained by performing the procedures disclosed herein in the Example section.

FIG. 3 summarizes the inhibitory effects of Compound 3 and Compound 4 in Table 5on a variety of kinases. The symbols "+", "++" and "+++" are used to show the effectiveness of Compound 3 and Compound 4 in inhibiting a given kinase in the Table.

DETAILED DESCRIPTION OF THE INVENTION

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the appended claims define the scope of the invention and that methods and structures within the scope of these claims and their equivalents be covered thereby.

Unless defined otherwise, all technical and scientific terms used herein have the same meaning as is commonly understood by one of skill in the art to which this invention belongs. All patents and publications referred to herein are incorporated by reference.

As used in the specification and claims, the singular form "a", "an" and "the" include plural references unless the context clearly dictates otherwise.

The term "effective amount" or "therapeutically effective amount" refers herein to that amount of a compound described herein that is sufficient to effect the intended application including but not limited to disease treatment, as defined below. The therapeutically effective amount may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g. activation of a particular signaling pathway including but not limited to activation of PI3K pathway, reduction of platelet adhesion and/or cell migration, reduction in foci formation and other tumorigenic responses. The specific dose will vary depending on the particular compounds chosen, the dosing regimen to be followed, whether it is administered in combination with other compounds, timing of administration, the tissue to which it is administered, and the physical delivery system in which it is carried.

As used herein, "treatment" or "treating," or "palliating" and "ameliorating" are used interchangeably herein. These terms refers to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "co-administration," "administered in combination with," and their grammatical equivalents, as used herein, encompasses administration of two or more agents to an animal so that both agents and/or their metabolites are present in the animal at the same time. Co-administration includes simultaneous administration in separate compositions, administration at different times in separate compositions, or administration in a composition in which both agents are present.

The term "pharmaceutically acceptable salt" refers herein to salts derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

The terms "antagonist" and "inhibitor" are used interchangeably, and they refer herein to a compound having the ability to inhibit a biological function of a target protein, whether by inhibiting the activity or expression of the target protein. Accordingly, the terms "antagonist" and "inhibitors" are defined in the context of the biological role of the target protein. While preferred antagonists herein specifically interact with (e.g. bind to) the target, compounds that inhibit a biological activity of the target protein by interacting with other members of the signal transduction pathway of which the target protein is a member are also specifically included within this definition. A preferred biological activity inhibited by an antagonist is associated with the development, growth, or spread of a tumor.

The term "agonist" as used herein refers herein to a compound having the ability to initiate or enhance a biological function of a target protein, whether by inhibiting the activity or expression of the target protein. Accordingly, the term "agonist" is defined in the context of the biological role of the target polypeptide. While preferred agonists herein specifically interact with (e.g. bind to) the target, compounds that initiate or enhance a biological activity of the target polypeptide by interacting with other members of the signal transduction pathway of which the target polypeptide is a member are also specifically included within this definition.

As used herein, "agent" or "biologically active agent" refers herein to a biological, pharmaceutical, or chemical compound or other moiety. Non-limiting examples include simple or complex organic or inorganic molecule, a peptide, a protein, an oligonucleotide, an antibody, an antibody derivative, antibody fragment, a vitamin derivative, a carbohydrate, a toxin, or a chemotherapeutic compound. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like. A skilled artisan can readily recognize that there is no limit as to the structural nature of the agents of the present invention.

"Signal transduction" is a process during which stimulatory or inhibitory signals are transmitted into and within a cell to elicit an intracellular response. A modulator of a signal transduction pathway refers to a compound which modulates the activity of one or more cellular proteins mapped to the same specific signal transduction pathway. A modulator may augment (agonist) or suppress (antagonist) the activity of a signaling molecule.

An "anti-cancer agent", "anti-tumor agent" or "chemotherapeutic agent" refers herein to any agent useful in the treatment of a neoplastic condition. One class of anti-cancer agents comprises chemotherapeutic agents. "Chemotherapy" means the administration of one or more chemotherapeutic drugs and/or other agents to a cancer patient by various methods, including intravenous, oral, intramuscular, intraperitoneal, intravesical, subcutaneous, transdermal, buccal, or inhalation or in the form of a suppository.

The term "cell proliferation" refers herein to a phenomenon by which the cell number has changed as a result of division. This term also encompasses cell growth by which the cell morphology has changed (e.g., increased in size) consistent with a proliferative signal.

As used herein, the term "selective inhibition" or "selectively inhibit" as referred to a biologically active agent refers to the agent's ability to preferentially reduce the target signaling activity as compared to off-target signaling activity, via direct or interact interaction with the target.

As used herein, "mTorC1 and/or mTorC2 activity" as applied to a biologically active agent refers to the agent's ability to modulate signal transduction mediated by mTorC1 and/or mTorC2. For example, modulation of mTorC1 and/or mTorC2 activity is evidenced by alteration in signaling output from the PI3K/Akt/mTor pathway.

The term "B-ALL" as used herein refers to B-cell Acute Lymphoblastic Leukemia.

As used herein, "subject" refers to an animal, such as a mammal, for example a human. The methods described herein can be useful in both human therapeutics and veterinary applications. In some embodiments, the patient is a mammal, and in some embodiments, the patient is human.

An "anti-cancer agent", "anti-tumor agent" or "chemotherapeutic agent" refers herein to any agent useful in the treatment of a neoplastic condition. One class of anti-cancer agents comprises chemotherapeutic agents. "Chemotherapy" means the administration of one or more chemotherapeutic drugs and/or other agents to a cancer patient by various methods, including intravenous, oral, intramuscular, intraperitoneal, intravesical, subcutaneous, transdermal, buccal, or inhalation or in the form of a suppository.

"Prodrug" as used herein is meant to indicate a compound that may be converted under physiological conditions or by solvolysis to a biologically active compound described herein. Thus, the term "prodrug" refers to a precursor of a biologically active compound that is pharmaceutically acceptable. A prodrug may be inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam). A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein. The term "prodrug" is also meant to include any covalently bonded carriers, which release the active compound in vivo when such prodrug is administered to a mammalian subject. Prodrugs of an active compound, as described herein, may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like.

The term "in vivo" refers to an event that takes place in a subject's body.

The term "in vitro" refers to an event that takes places outside of a subject's body. For example, an in vitro assay encompasses any assay run outside of a subject assay. In vitro assays encompass cell-based assays in which cells Unless otherwise stated, the connections of compound name moieties are at the rightmost recited moiety. That is, the substituent name starts with a terminal moiety, continues with any bridging moieties, and ends with the connecting moiety. For example, hetarylthio $C_{1-4}$ alkyl has a heteroaryl group connected through a thio sulfur to a $C_{1-4}$ alkyl radical that connects to the chemical species bearing the substituent. This condition does not apply where a formula such as, for example "-L-$C_{1-10}$ alkyl-$C_{3-8}$ cycloalkyl is represented. In such case, the terminal group is a $C_{3-8}$ cycloalkyl group attached to a bridging $C_{1-10}$ alkyl moiety which is attached to an element L.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this invention.

The compounds of the present invention may also contain unnatural proportions of atomic isotopes at one or more of atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are encompassed within the scope of the present invention.

The term "alkyl" as used herein refers to 1-10 carbons, that is 1, 2, 3, 4, 5, 6, 7, 8, 9, 10 in either branched or straight chain configuration. As used herein, for example, "$C_{1-n}$ alkyl" is used to mean an alkyl having 1–n carbons—that is 1 or n carbons in a straight or branched configuration, wherein n is an integer no more than 10. Typical alkyl groups are methyl, ethyl, n-propyl, isopropyl, n-butyl, sec-butyl, isobutyl, tert-butyl, n-pentyl, isopentyl, n-hexyl, n-heptyl, isooctyl, nonyl, decyl, undecyl, dodecyl, tetradecyl, hexadecyl, octadecyl, eicosyl, and the like. Suitable substituents for alkyl group, unless disclosed otherwise specifically in the specification, include halogen, aryl, hetaryl, —$C_{1-10}$ alkyl, —$C_{3-8}$cycloalkyl, —$C_{1-10}$alkylheterocyclyl, —$C_{2-10}$ alkenyl-, —$C_{2-10}$ alkynyl, —OH, —$C_{1-10}$alkyl, —$CF_3$, —O-aryl, —$OCF_3$, —$OC_{1-10}$alkyl, —$NH_2$, —N($C_{1-10}$alkyl)($C_{1-10}$alkyl), —NH($C_{1-10}$alkyl), —NH(aryl), —$NR^{34}R^{35}$, —C(O)($C_{1-10}$alkyl), —C(O)($C_{1-10}$alkyl-aryl), —C(O)(aryl), —$CO_2$—$C_{1-10}$ alkyl, —$CO_2$—$C_{1-10}$alkylaryl, —$CO_2$-aryl, —C(=O)N($C_{1-10}$alkyl)($C_{1-10}$alkyl), —C(=O)NH($C_{1-10}$alkyl), —C(=O)$NR^{34}R^{35}$, —(=O)$NH_2$, —$OCF_3$, —O($C_{1-10}$ alkyl), —O-aryl, —N(aryl)($C_{1-10}$ alkyl), —$NO_2$, —CN, —S(O)$_{0-2}$ $C_{1-10}$alkyl, —S(O)$_{0-2}$ $C_{1-10}$alkylaryl, —S(O)$_{0-2}$ aryl, —$SO_2$N(aryl), —$SO_2$N($C_{1-10}$alkyl)($C_{1-10}$alkyl), —$SO_2$NH($C_{1-10}$alkyl) or —$SO_2NR^{34}R^{35}$ substituents. The term "halo" or "halogen" refers to fluoro, chloro, bromo, or iodo.

The term "haloalkyl" refers to an alkyl group substituted with one or more halo groups, for example chloromethyl, 2-bromoethyl, 3-iodopropyl, trifluoromethyl, perfluoropropyl, 8-chlorononyl, and the like.

The term "acyl" refers to the structure —C(=O)—R, in which R is a general substituent variable such as, for example $R^1$ described above. Examples include, but are not limited to, (bi)(cyclo)alkylketo, (cyclo)alkenylketo, alkynylketo, arylketo, hetarylketo, heterocyclylketo, heterobicycloalkylketo.

As used herein, "cycloalkyl" refers to a 3-8 carbon cyclic aliphatic ring structure, unsubstituted or substituted, such as cyclopropyl, methylcyclopropyl, cyclobutyl, cyclopentyl, 2-hydroxycyclopentyl, cyclohexyl, 4-chlorocyclohexyl, cycloheptyl, cyclooctyl, and the like. Cycloalkyl may be substituted by one or more substituents. Suitable substituents, unless specifically disclosed otherwise in the specification, are: aryl, hetaryl, $C_{1-4}$alkyl, $C_{1-10}$alkyl, $C_{3-8}$cycloalkyl, —$C_{1-10}$alkylheterocyclyl, —$C_{2-10}$alkenyl-, —$C_{2-10}$ alkynyl, —$C_{2-10}$alkynylheterocylyl, halo, —OH, —$R^{31}$, —$CF_3$, —$OCF_3$, —$OR^{31}$, —$NR^{31}R^{32}$, —$NR^{34}R^{35}$, —C(O)$R^{31}$, —$CO_2R^{31}$, —C(=O)$NR^{31}R^{32}$, —C(=O)NN$R^{34}R^{35}$, —$NO_2$, —CN, —S(O)$_{0-2}R^{31}$, —$SO_2NR^{31}R^{32}$, —$SO_2NR^{34}R^{35}$, —$NR^{31}$C(=O)$R^{32}$, —$NR^{31}$C(=O)$OR^{32}$, —$NR^{31}$C(=O)$NR^{32}R^{33}$, —$NR^{31}$S(O)$_{0-2}R^{32}$, —C(=S)$OR^{31}$, —C(=O)$SR^{31}$, —$NR^{31}$C(=$NR^{32}$)$NR^{33}R^{32}$, —$NR^{31}$C(=$NR^{32}$)$OR^{33}$, —$NR^{31}$C(=$NR^{32}$)$SR^{33}$, —OC(=O)$OR^{33}$, —OC(=O)$NR^{31}R^{32}$, —OC(=O)$SR^{31}$, —SC(=O)$OR^{31}$, —P(O)$OR^{31}OR^{32}$, or —SC(=O)$NR^{31}R^{32}$ substituents.

"$C_{1-10}$alkyl-$C_3$-8cycloalkyl" refers herein to an alkyl group, branched or straight chain and containing 1 to 10 carbon atoms, attached to a cycloalkyl group which contains 3 to 8 carbons, for example, 2-methyl cyclopropyl, and 4-(cyclopropyl) but-1yl.

As used herein, the term "heteroatom" or "ring heteroatom" is meant to include oxygen (O), nitrogen (N), sulfur (S), phosphorus (P), and silicon (Si).

As used herein, the term "heteroalkyl," by itself or in combination with another term, means, unless otherwise stated, a stable straight or branched chain, or cyclic hydrocarbon radical, or combinations thereof, consisting of at least one carbon atoms and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, O—$CH_3$, —O—$CH_2$—$CH_3$, and —CN. Up to two heteroatoms may be consecutive, such as, for example, —$CH_2$—NH—$OCH_3$ and —$CH_2$—O—Si($CH_3$)$_3$. As described above, heteroalkyl groups, as used herein, include those groups that are attached to the remainder of the molecule through a heteroatom, such as —C(O)R', —C(O)NR', —NR'R'', —OR', —SR', and/or —$SO_2$R'. Where "heteroalkyl" is recited, followed by recitations of specific heteroalkyl groups, such as —NR'R'' or the like, it will be understood that the terms heteroalkyl and —NR'R'' are not redundant or mutually exclusive. Rather, the specific heteroalkyl groups are recited to add clarity. Heteroalkyl is unsubstituted or substituted by one or more substituents. Suitable substituents, unless specifically disclosed otherwise in the specification, are: aryl, hetaryl, $C_{1-4}$alkyl, $C_{1-10}$alkyl, $C_{3-8}$cycloalkyl, —$C_{1-10}$alkylheterocyclyl, —$C_2$10 alkenyl-, —$C_{2-10}$alkynyl, —$C_{2-10}$alkynylheterocyclyl, halo, —OH, —$R^{31}$, —$CF_3$, —$OCF_3$, —$OR^{31}$, —$NR^{31}R^{32}$, —$NR^{34}R^{35}$, —C(O)$R^{31}$, —$CO_2R^{31}$, —C(=O)$NR^{31}R^{32}$, —C(=O)$NNR^{34}R^{35}$, —$NO_2$, —CN, —S(O)$_{0-2}R^{31}$, —$SO_2NR^{31}R^{32}$, —$SO_2NR^{34}R^{35}$, —$NR^{31}$C(=O)$R^{32}$, —$NR^{31}$C(=O)$OR^{32}$, —$NR^{31}$C(=O)$NR^{32}R^{33}$, —$NR^{31}$S(O)$_{0-2}R^{32}$, —C(=S)$OR^{31}$, —C(=O)$SR^{31}$, —$NR^{31}$C(=$NR^{32}$)$NR^{33}R^{32}$, —$NR^{31}$C(=$NR^{32}$)$OR^{33}$, —$NR^{31}$C(=$NR^{32}$)$SR^{33}$, —OC(=O)$OR^{33}$, —OC(=O)$NR^{31}R^{32}$, —OC(=O)$SR^{31}$, —SC(=O)$OR^{31}$, —P(O)$OR^{31}OR^{32}$, or —SC(=O)$NR^{31}R^{32}$ substituents.

The term "heteroalkylaryl" as used herein, refers to a heteroalkyl group as defined above which is attached to an aryl group, and may be attached at a terminal point or through a branched portion of the heteroalkyl, for example, an benzyloxymethyl moiety or a 3-methoxymethylphenyl moiety.

The term "heteroalkylheteroaryl" as used herein refers likewise to a heteroalkyl group which is attached to a hetaryl moiety, for example, an ethoxymethylpyridyl group.

The term "heteroalkyl-heterocyclyl" as used herein refers to a heteroalkyl group as defined above, which is attached to a heterocyclic group, for example, 4(3-aminopropyl)-N-piperazinyl.

The term "heteroalkyl-$C_{3-8}$cycloalkyl" as used herein refers to a heteroalkyl group as defined above, which is attached to a cyclic alkyl containing 3 to 8 carbons, for example, 1-aminobutyl-4-cyclohexyl.

As used herein, the term "alkenyl" refers to an ethylenically unsaturated hydrocarbon group having 2-10 carbon atoms in, straight or branched configuration, for example vinyl, allyl, 1-butenyl, 2-butenyl, isopropenyl, 2-pentenyl, and the like. The term "$C_{2-10}$ alkenyl" refers to an alkenyl having 2-10 carbon atoms, substituted or unsubstituted. Alkenyl can substituted by one or more substituents. Suitable substituents, unless specifically disclosed otherwise in the specification, are: aryl, hetaryl, $C_{1-4}$alkyl, $C_{1-10}$ alkyl, $C_{3-8}$cycloalkyl, —$C_{1-10}$alkylheterocyclyl, —$C_{2-10}$alkenyl-, —$C_{2-10}$alkynyl, —$C_{2-10}$alkynylheterocyclyl, halo, —OH, —$R^{31}$, —$CF_3$, —$OCF_3$, —$OR^{31}$, —$NR^{31}R^{32}$, —$NR^{34}R^{35}$, —C(O)$R^{31}$, —$CO_2R^{31}$, —C(=O)$NR^{31}R^{32}$, —C(=O)$NNR^{34}R^{35}$, —$SO_2NR^{34}R^{35}$, —$NR^{31}$C(=O)$R^{32}$, —$NR^{31}$C(=O)$OR^{32}$, —$NR^{31}$C(=O)$NR^{32}R^{33}$, —$NR^{31}$S(O)$_{0-2}R^{32}$, —C(=S)$OR^{31}$, —C(=O)$SR^{31}$, —$NR^{31}$C(=$NR^{32}$)$NR^{33}R^{32}$, —$NR^{31}$C(=$NR^{32}$)$OR^{33}$, —$NR^{31}$C(=$NR^{32}$)$SR^{33}$, —OC(=O)$OR^{33}$, —OC(=O)$NR^{31}R^{32}$, —OC(=O)$SR^{31}$, —SC(=O)$OR^{31}$, —P(O)$OR^{31}OR^{32}$, or —SC(=O)$NR^{31}R^{32}$ substituents.

As used herein, the term "$C_{2-10}$ alkenyl-$C_{3-8}$ cycloalkyl" refers to a group containing an alkenyl group, containing 2 to 10 carbons and branched or straight chain, which is attached to a cycloalkyl group containing 3 to 8 carbons, such as, for example 3-prop-3-enyl-cyclopent-1yl, 3-(cyclopentyl)propen-1-yl, and the like.

As used herein, the term "$C_{2-10}$ alkenyl-heteroalkyl" refers to a group having an alkenyl moiety, containing 2 to 10 carbon atoms and is branched or straight chain, which is attached to a heteroalkyl group, such as, for example, allyloxy, and the like.

As used herein, the term "$C_{2-10}$ alkynyl-heteroalkyl" refers to a group having an alkynyl moiety, containing 2 to 10 carbon atoms and is branched or straight chain, which is attached to a heteroalkyl group, such as, for example, 4-but-1-ynoxy, and the like.

Unless otherwise specified, the term "cycloalkenyl" refers to a cyclic aliphatic 3 to 8 membered ring structure, optionally substituted with alkyl, hydroxy and halo, having 1 or 2 ethylenic bonds such as methylcyclopropenyl, trifluoromethylcyclopropenyl, cyclopentenyl, cyclohexenyl, 1,4-cyclohexadienyl, and the like.

As used herein, the term "alkynyl" as used herein refers to an unsaturated hydrocarbon group having 2-10 carbon atoms in straight or branched configuration, having at least one acetylenic bond, for example ethynyl, propargyl, and the like. The term $C_{2-10}$ alkynyl refers to an aklynyl group having 2-10 carbon atoms. Alkynyl can be unsubstituted or substituted by one or more substituents. Suitable substituents, unless specifically disclosed otherwise in the specification, are: aryl, hetaryl, $C_{1-4}$alkyl, $C_{1-10}$alkyl, $C_{3-8}$cycloalkyl, —$C_{1-10}$alkylheterocyclyl, —$C_{2-10}$alkenyl-, —$C_{2-10}$alkynyl, $C_{2-10}$alkynylheterocyclyl, halo, —OH, —$R^{31}$, —$CF_3$, —$OCF_3$, —$OR^{31}$, —$NR^{31}R^{32}$, —$NR^{34}R^{35}$, —C(O)$R^{31}$, —$CO_2R^{31}$, —C(=O)$NR^{31}R^{32}$, —C(=O)$NNR^{34}R^{35}$, —$NO_2$, —CN, —S(O)$_{0-2}R^{31}$, —$SO_2NR^{31}R^{32}$, —$SO_2NR^{34}R^{35}$, —$NR^{31}$C(=O)$R^{32}$, —$NR^{31}$C(=O)$OR^{32}$, —$NR^{31}$C(=O)$NR^{32}R^{33}$, —$NR^{31}$S(O)$_{0-2}R^{32}$, —C(=S)$OR^{31}$, —C(=O)$SR^{31}$, —$NR^{31}$C(=$NR^{32}$)$NR^{33}R^{32}$, —$NR^{31}$C(=$NR^{32}$)$OR^{33}$, —$NR^{31}$C(=$NR^{32}$)$SR^{33}$, —OC(=O)$OR^{33}$, —OC(=O)$NR^{31}R^{32}$, —OC(=O)$SR^{31}$, —SC(=O)$OR^{31}$, —P(O)$OR^{31}OR^{32}$, or —SC(=O)$NR^{31}R^{32}$ substituents.

As used herein, the term "$C_{2-10}$ alkynyl-$C_{3-8}$ cycloalkyl" refers to a group containing an alkynyl group, containing 2 to 10 carbons and branched or straight chain, which is attached to a cycloalkyl group containing 3 to 8 carbons, such as, for example 3-prop-3-ynyl-cyclopent-1yl, and the like.

As used herein, the term "aryl" as used herein refers to phenyl or naphthyl which may be optionally substituted. Examples of aryl include, but are not limited to, phenyl, 4-chlorophenyl, 4-fluorophenyl, 4-bromophenyl, 3-nitrophenyl, 2-methoxyphenyl, 2-methylphenyl, 3-methylphenyl, 4-methylphenyl, 4-ethylphenyl, 2-methyl-3-methoxyphenyl, 2,4-dibromophenyl, 3,5-difluorophenyl, 3,5-dimethylphenyl, 2,4,6-trichlorophenyl, 4-methoxyphenyl, naphthyl, 2-chloronaphthyl, 2,4-dimethoxyphenyl, 4-(trifluoromethyl)phenyl, and 2-iodo-4-methylphenyl. As used herein, the term "monocyclic aryl" as used herein refers to an an aryl moiety which has one ring, such as, for example, phenyl, which may be optionally substituted. Examples of monocyclic aryl include, but are not limited to, phenyl, 4-chlorophenyl, 4-fluorophenyl, 4-bromophenyl, 3-nitrophenyl, 2-methoxyphenyl, 2-methylphenyl, 3-methyphenyl, 4-methylphenyl, 4-ethylphenyl, 2-methyl-3-methoxyphenyl, 2,4-dibromophenyl, 3,5-difluorophenyl, 3,5-dimethylphenyl, 2,4,6-trichlorophenyl, 4-methoxyphenyl, 2,4-dimethoxyphenyl, 4-(trifluoromethyl)phenyl, and 2-iodo-4-methylphenyl. As used herein, the term "bicyclic aryl" refers to an aryl with two fused rings, such as, for example, naphthyl, which may be optionally substituted. Examples of bicyclic aryl include but are not limited to 2-chloronaphthyl, 1-iodonaphthyl, naphthol, and 2-hydroxy-1-naphthoic acid. Aryl is optionally substituted by one or more substituents. Suitable substituents, unless specifically disclosed otherwise in the specification, are: aryl, hetaryl, $C_{1-4}$akyl, $C_{1-10}$alkyl, $C_{3-8}$cycloalkyl, —$C_{1-10}$alkylheterocyclyl, $C_{2-10}$alkenyl-, —$C_{2-10}$alkynyl, —$C_{2-10}$alkynylheterocylyl, halo, —OH, —$R^{31}$, —$CF_3$, —$OCF_3$, —$OR^{31}$, —$NR^{31}R^{32}$, —$NR^{34}R^{35}$, —C(O)$R^{31}$, —$CO_2R^{31}$, —C(=O)$NR^{31}R^{32}$, —C(=O)$NNR^{34}R^{35}$, —$NO_2$, —CN, —S(O)$_{0-2}R^{31}$, —$SO_2NR^{31}R^{32}$, —$SO_2NR^{34}R^{35}$, —$NR^{31}$C(=O)$R^{32}$, —$NR^{31}$C(=O)$OR^{32}$, —$NR^{31}$C(=O)$NR^{32}R^{33}$, —$NR^{31}$S(O)$_{0-2}R^{32}$, —C(=S)$OR^{31}$, —C(=O)$SR^{31}$, —$NR^{31}$C(=$NR^{32}$)$NR^{33}R^{32}$, —$NR^{31}$C(=$NR^{32}$)$OR^{33}$, —$NR^{31}$C(=$NR^{32}$)$SR^{33}$, —OC(=O)$OR^{33}$, —OC(=O)$NR^{31}R^{32}$, —OC(=O)$SR^{31}$, —SC(=O)$OR^{31}$, —P(O)$OR^{31}OR^{32}$, or —SC(=O)$NR^{31}R^{32}$ substituents.

As used herein, the term "heteroaryl" or "hetaryl" or "heteroar-" or "hetar-" refer to a substituted or unsubstituted 5- or 6-membered unsaturated ring containing one, two, three, or four independently selected heteroatoms, preferably one or two heteroatoms independently selected from oxygen, nitrogen, and sulfur or to a bicyclic unsaturated ring system containing up to 10 atoms including at least one heteroatom selected from oxygen, nitrogen, and sulfur. Examples of heteroaryls include, but are not limited to, 2-, 3- or 4-pyridinyl, pyrazinyl, 2-, 4-, or 5-pyrimidinyl, pyridazinyl, triazolyl, tetrazolyl, imidazolyl, 2- or 3-thienyl, 2- or 3-furyl, pyrrolyl, oxazolyl, isoxazolyl, thiazolyl, isothiazolyl, oxadiazolyl, thiadiazolyl, quinolyl, isoquinolyl, benzimidazolyl, benzotriazolyl, benzofuranyl, and benzothienyl. The heteroaryl may be optionally substituted with one or more substituents. Suitable substituents, unless specifically disclosed otherwise in the specification are: aryl, hetaryl, $C_{1-4}$alkyl, $C_{1-10}$alkyl, $C_{3-8}$cycloalkyl, —$C_{1-10}$alkylheterocyclyl, —$C_{2-10}$alkenyl-, —$C_{2-10}$alkynyl, —$C_{2-10}$alkynylheterocylyl, halo, —OH, —$R^{31}$, —$CF_3$, —$OCF_3$, —$OR^{31}$, —$NR^{31}R^{32}$, —$NR^{34}R^{35}$, —C(O)$R^{31}$, —$CO_2R^{31}$, —C(=O)$NR^{31}R^{32}$, —C(=O)$NNR^{34}R^{35}$, —$NO_2$, —CN, —S(O)$_{0-2}R^{31}$, —$SO_2NR^{31}R^{32}$, —$SO_2NR^{34}R^{35}$, —$NR^{31}$C(=O)$R^{32}$, —$NR^{31}$C(=O)$OR^{32}$, —$NR^{31}$C(=O)$NR^{32}R^{33}$, —$NR^{31}$S(O)$_{0-2}R^{32}$, —C(=S)$OR^{31}$, —C(=O)$SR^{31}$, —$NR^{31}$C(=$NR^{32}$)$NR^{33}R^{32}$, —$NR^{31}$C(=$NR^{32}$)$OR^{33}$, —$NR^{31}$C(=$NR^{32}$)$SR^{33}$, —OC(=O)$OR^{33}$, —OC(=O)$NR^{31}R^{32}$, —OC(=O)$SR^{31}$, —SC(=O)$OR^{31}$, —P(O)$OR^{31}OR^{32}$, or —SC(=O)$NR^{31}R^{32}$ substituents. Heteroaryl ring system can be monocyclic, bicyclic, tricyclic, or otherwise polycyclic. Non-liming examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzofuranonyl, benzofurazanyl, benzothiazolyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl).

As used herein, the term "aryl-alkyl" or "arylalkyl" or "aralkyl" is used to describe a group wherein the alkyl chain can be branched or straight chain and is attached to an aryl moiety, as defined above. Examples of aryl-alkyl groups include, but are not limited to, optionally substituted benzyl, phenethyl, phenpropyl and phenbutyl such as 4-chlorobenzyl, 2,4-dibromobenzyl, 2-methylbenzyl, 2-(3-fluorophenyl)ethyl, 2-(4-methylphenyl)ethyl, 2-(4-(trifluoromethyl)phenyl)ethyl, 2-(2-methoxyphenyl)ethyl, 2-(3-nitrophenyl)ethyl, 2-(2,4-dichlorophenyl)ethyl, 2-(3,5-dimethoxyphenyl)ethyl, 3-phenylpropyl, 3-(3-chlorophenyl)propyl, 3-(2-methylphenyl)propyl, 3-(4-methoxyphenyl)propyl, 3-(4-(trifluoromethyl)phenyl)propyl, 3-(2,4-dichlorophenyl)propyl, 4-phenylbutyl, 4-(4-chlorophenyl)butyl, 4-(2-methylphenyl)butyl, 4-(2,4-dichlorophenyl)butyl, 4-(2-methoxphenyl)butyl, and 10-phenyldecyl.

As used herein, the term "$C_{1-10}$alkylaryl" as used herein refers to an alkyl group, as defined above, containing 1 to 10 carbon atoms, branched or unbranched, wherein the aryl group replaces one hydrogen on the alkyl group, for example, 3-phenylpropyl.

As used herein, the term $C_{2-10}$ alkyl monocycloaryl" refers to a group containing a terminal alkyl group, branched or straight chain and containing 2 to 10 atoms attached to a bridging aryl group which has only one ring, such as for example, 2-phenyl ethyl.

As used herein, the term $C_{1-10}$ alkyl bicycloaryl" refers to a group containing a terminal alkyl group, branched or straight chain and containing 2 to 10 atoms attached to a bridging aryl group which is bicyclic, such as for example, 2-(1-naphthyl)-ethyl.

As used herein, the term "aryl-cycloalkyl" or "arylcycloalkyl" is used to describe a group wherein the aryl group is attached to a cycloalkyl group, for example phenylcyclopentyl, 3-(cyclopentyl)phenyl, and the like.

As used herein, the term "hetaryl-$C_{3-8}$cycloalkyl" or "heteroaryl-$C_{3-8}$cycloalkyl" is used to describe a group wherein the hetaryl group is attached to a cycloalkyl group, which contains 3 to 8 carbons, for example pyrid-2-yl-cyclopentyl, 3(cyclopentyl)pyridin-1yl, and the like.

As used herein, the term "hetaryl-heteroalkyl" refers to a group wherein the hetaryl group is attached to a heteroalkyl group, such as for example, pyrid-2-yl methylenoxy, and the like.

As used herein, the term "aryl-alkenyl" or "arylalkenyl" or "aralkenyl" is used to describe a group wherein the alkenyl chain can be branched or straight chain and is attached to an aryl portion, as defined above, for example styryl (2-phenylvinyl), phenpropenyl, and the like. As used herein, the term "aryl-$C_{2-10}$ alkenyl" refers to an arylalkenyl as described above wherein the alkenyl moiety contains 2 to 10 carbon atoms such as for example, styryl (2-phenylvinyl), and the like.

As used herein, the term "$C_{2-10}$alkenyl-aryl" is used to describe a group wherein the alkenyl group, which contains 2 to 10 carbon atoms and can be branched or straight chain, is attached to the aryl, such as for example, 3-propenyl-naphth-1-yl, and the like.

As used herein, the term "aryl-alkynyl" or "arylalkynyl" or "aralkynyl" is used to describe a group wherein the alkynyl chain can be branched or straight chain and is attached to the aryl, as defined above, for example 3-phenyl-1-propynyl, and the like. As used herein, the term "aryl-$C_{2-10}$alkynyl" means an arylalkynyl as described above wherein the alkynyl moiety contains two to ten carbons, such as, for example 3-phenyl-1-propynyl, and the like.

As used herein, the term "$C_{2-10}$ alkynyl-aryl" means a group containing an alkynyl moiety attached to an aryl group, both as defined above, wherein the alkynyl moiety contains two to ten carbons, such as, for example 3-propynyl-naphth-1-yl.

As used herein, the term "aryl-oxy" or "aryloxy" or "aroxy" is used to describe an aryl group attached to a oxygen atom. Typical aryl-oxy groups include phenoxy, 3,4-dichlorophenoxy, and the like.

As used herein, the term "$C_{1-10}$alkoxy-$C_{1-10}$alkyl" refers to a group wherein an alkoxy group, containing 1 to 10 carbon atoms and an oxygen atom within the branching or straight chain, is attached to an alkyl group, branched or straight chain which contains 1 to 10 carbon atoms, such as, for example methoxypropyl, and the like.

As used herein, the term "$C_{1-10}$alkoxy-$C_{2-10}$alkenyl" refers to a group wherein an alkoxy group, containing 1 to 10 carbon atoms and an oxygen atom within the branching or straight chain, is attached to a alkenyl group, branched or straight chain which contains 1 to 10 carbon atoms, such as, for example 3-methoxybut-2-en-1-yl, and the like.

As used herein, the term "$C_{1-10}$alkoxy-$C_{2-10}$alkynyl" refers to a group wherein an alkoxy group, containing 1 to 10 carbon atoms and an oxygen atom within the branching or straight chain, is attached to an alkynyl group, branched or straight chain which contains 1 to 10 carbon atoms, such as, for example 3-methoxybut-2-in-1-yl, and the like.

As used herein, the term "heterocycloalkenyl" refers to a cycloalkenyl structure in which at least one carbon atom is replaced with a heteroatom selected from oxygen, nitrogen, and sulfur.

As used herein, the term "hetaryl-oxy" or "heteroaryl-oxy" or "hetaryloxy" or "heteroaryloxy" or "hetaroxy" or "heteroaroxy" is used to describe a hetaryl group attached to a oxygen atom. Typical hetaryl-oxy groups include 4,6-dimethoxypyrimidin-2-yloxy and the like.

As used herein, the term "hetarylalkyl" or "heteroarylalkyl" or "hetaryl-alkyl" or "heteroaryl-alkyl" or "hetaralkyl" or "heteroaralkyl" is used to describe a group wherein the alkyl chain can be branched or straight chain and is attached to an aryl moiety, as defined above, for example 3-furylmethyl, thienyl, furfuryl, and the like. As used herein, the term "hetaryl-$C_{1-10}$alkyl" is used to describe a hetaryl alkyl group as described above where the alkyl group contains 1 to 10 carbon atoms. As used herein, the term "$C_{1-10}$alkyl-hetaryl" is used to describe an alkyl attached to a hetaryl group as described above where the alkyl group contains 1 to 10 carbon atoms.

As used herein, the term "hetarylalkenyl" or "heteroarylalkenyl" or "hetaryl-alkenyl" or "heteroaryl-alkenyl" or "hetaralkenyl" or "heteroaralkenyl" is used to describe a hetarylalkenyl group wherein the alkenyl chain can be branched or straight chain and is attached to an aryl moiety as defined above, for example 3-(4-pyridyl)-1-propenyl. As used herein, the term "hetaryl-$C_{2-10}$alkenyl" group is used to describe a group as described above wherein the alkenyl group contains 2 to 10 carbon atoms. As used herein, the term "$C_{2-10}$ alkenyl-hetaryl" is used to describe a group containing an alkenyl group, which is branched or straight chain and contains 2 to 10 carbon atoms, and is attached hetaryl group, such as, for example 2-styryl-4-pyridyl, and the like.

As used herein, the term "hetarylalkynyl" or "heteroarylalkynyl" or "hetaryl-alkynyl" or "heteroaryl-alkynyl" or "hetaralkynyl" or "heteroaralkynyl" is used to describe a group wherein the alkynyl chain can be branched or straight chain and is attached to a heteroaryl, as defined above, for example 4-(2-thienyl)-1-butynyl, and the like. As used herein, the term "heteroaryl-$C_{2-10}$alkynyl" is used to describe a hetarylalkynyl group as described above wherein the alkynyl group contains 2 to 10 carbon atoms. The term "$C_{2-10}$alkynyl-hetaryl" is used herein to describe a group containing an alkynyl group which contains 2 to 10 carbon atoms and is branched or straight chain, which is attached to a hetaryl group such as, for example, 4(but-1-ynyl) thien-2-yl, and the like.

The term "heterocyclyl" or "hetcyclyl" refers herein to a substituted or unsubstituted 3-, 4-, 5-, or 6-membered saturated or partially unsaturated ring containing one, two, or three heteroatoms, preferably one or two heteroatoms independently selected from oxygen, nitrogen and sulfur; or to a bicyclic ring system containing up to 10 atoms including at least one heteroatom independently selected from oxygen, nitrogen, and sulfur wherein the ring containing the heteroatom is saturated. Examples of heterocyclyls include, but are not limited to, tetrahydrofuranyl, tetrahydrofuryl, pyrrolidinyl, piperidinyl, 4-pyranyl, tetrahydropyranyl, thiolanyl, morpholinyl, piperazinyl, dioxolanyl, dioxanyl, indolinyl, and 5-methyl-6-chromanyl. Heterocyclyl is unsubstituted or substituted by one or more substituents. Suitable substituents, unless specifically disclosed otherwise in the specification, are: aryl, hetaryl, —$C_{1-4}$alkyl, —$C_{1-10}$alkyl, $C_{3-8}$cycloalkyl, —$C_{1-10}$alkylheterocyclyl, —$C_{2-10}$alkenyl-, —$C_{2-10}$alkynyl, —$C_{2-10}$alkynylheterocylyl, halo, —OH, —$R^{31}$, —$CF_3$, —$OCF_3$, —$OR^{31}$, —$NR^{31}R^{32}$, —$NR^{34}R^{35}$, —$C(O)R^{31}$, —$CO_2R^{31}$, —$C(=O)NR^{31}R^{32}$, —$C(=O)NNR^{34}R^{35}$, —$NO_2$, —CN, —$S(O)_{0-2}R^{31}$, —$SO_2NR^{31}R^{32}$, —$SO_2NR^{34}R^{35}$, —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, —C(=S)OR^{31}, —$C(=O)SR^{31}$, —$NR^{31}C(=NR^{32})NR^{33}R^{32}$, —$NR^{31}C(=NR^{32})OR^{33}$, —$NR^{31}C(=NR^{32})SR^{33}$, —OC (=O)OR$^{33}$, —OC(=O)NR$^{31}$R$^{32}$, —OC(=O)SR$^{31}$, —SC(=O)OR$^{31}$, —P(O)OR$^{31}$OR$^{32}$, or —SC(=O)NR$^{31}$R$^{32}$ substituents.

The term "heterocyclylalkyl" or "heterocyclyl-alkyl" or "hetcyclylalkyl" or "hetcyclyl-alkyl" is used herein to describe a group wherein the alkyl chain can be branched or straight chain and is attached to a heterocyclyl portion, as defined above, for example 3-piperidinylmethyl and the like. The term "heterocycloalkylene" refers to the divalent derivative of heterocycloalkyl. The term "$C_{1-10}$alkyl-heterocycyl" refers herein to a group as defined above where the alkyl moiety contains 1 to 10 carbon atoms. The term "heterocycyl-$C_{1-10}$alkyl" refers herein to a group containing a heterocyclic group attached to a alkyl group which contains 1 to 10 carbons and is branched or straight chain, such as, for example, 4-morpholinyl ethyl, and the like.

The term "heterocyclylalkenyl" or "heterocyclyl-alkenyl" or "hetcyclylalkenyl" or "hetcyclyl-alkenyl" are used herein to describe a group wherein the alkenyl chain can be branched or straight chain and is attached to a heterocyclyl portion, as defined above, for example 2-morpholinyl-1-propenyl and the like. The term "heterocycloalkenylene" refers to the divalent derivative of heterocyclylalkenyl.

The term "heterocycyl-$C_{2-10}$ alkenyl" refers herein to a group as defined above where the alkenyl group contains 2 to 10 carbon atoms and is branched or straight chain, such as, for example, 4-(N-piperazinyl)-but-2-en-1-yl, and the like.

The term "heterocyclylalkynyl" or "heterocyclyl-alkynyl" or "hetcyclylalkynyl" or "hetcyclyl-alkynyl" is used herein to describe a group wherein the alkynyl chain can be branched or straight chain and is attached to a heterocyclylalkynyl moiety with the terminal heterocyclyl portion, as defined above, for example 2-pyrrolidinyl-1-butynyl and the like.

The term "heterocycyl-$C_{2-10}$ alkynyl" refers herein to a group as defined above where the alkynyl group contains 2 to 10 carbon atoms and is branched or straight chain, such as, for example, 4-(N-piperazinyl)-but-2-yn-1-yl, and the like.

The term "aryl-heterocycyl" refers herein to a group containing a aryl group attached to a heterocyclic group, such as, for example, N4-(4-phenyl)-piperazinyl, and the like.

The term "hetaryl-heterocycyl" refers herein to a group containing a hetaryl group attached to a heterocyclic group, such as, for example, N4-(4-pyridyl)-piperazinyl, and the like.

The term "cycloalkylalkyl" or "cycloalkyl-alkyl" refer to a cycloalkyl group as defined above attached to an alkyl group, for example cyclopropylmethyl, cyclohexylethyl, and the like.

The term "cycloalkylalkenyl" or "cycloalkyl-alkenyl" refer to a cycloalkyl group as defined above attached to an alkenyl group, for example cyclohexylvinyl, cycloheptylallyl, and the like.

The term "cycloalkylalkynyl" or "cycloalkyl-alkynyl" refer to a cycloalkyl group as defined above attached to an alkynyl group, for example cyclopropylpropargyl, 4-cyclopentyl-2-butynyl, and the like.

The term "cycloalkenylalkyl" or "cycloalkenyl-alkyl" refer to a cycloalkenyl group as defined above attached to an alkyl group, for example 2-(cyclopenten-1-yl)ethyl and the like.

The term "cycloalkenylalkenyl" or "cycloalkenyl-alkenyl" refer to a cycloalkenyl group as defined above attached to an alkenyl group, for example 1-(cyclohexen-3-yl)allyl and the like.

The term "cycloalkenylalkynyl" or "cycloalkenyl-alkynyl" refer to a cycloalkenyl group as defined above attached to an alkynyl group, for example 1-(cyclohexen-3-yl)propargyl and the like.

The term "alkoxy" includes both branched and straight chain alkyl groups attached to an oxygen atom.

Typical alkoxy groups include methoxy, ethoxy, n-propoxy, isopropoxy, tert-butoxy and the like.

The term "haloalkoxy" refers herein to an alkoxy group substituted with one or more halo groups, for example chloromethoxy, trifluoromethoxy, difluoromethoxy, perfluoroisobutoxy, and the like.

The term "alkylthio" includes both branched and straight chain alkyl groups attached to a bridging sulfur atom, for example methylthio and the like.

The term "alkoxyalkyl" refers herein to an alkyl group substituted with an alkoxy group, for example isopropoxymethyl and the like.

The term "alkoxyalkenyl" refers herein to an alkenyl group substituted with an alkoxy group, for example 3-methoxyallyl and the like.

The term "alkoxyalkynyl" refers herein to an alkynyl group substituted with an alkoxy group, for example 3-methoxypropargyl and the like.

The term "$C_{2-10}$ alkenyl$C_{3-8}$cycloalkyl" refers herein to an alkenyl group as defined above substituted with a three to eight membered cycloalkyl group, for example, 4-(cyclopropyl)-2-butenyl and the like.

The term "$C_{2-10}$alkynyl$C_{3-8}$ cycloalkyl" refers herein to an alkynyl group as defined above substituted with a three to eight membered cycloalkyl group, for example, 4-(cyclopropyl)-2-butynyl and the like.

The term "heterocyclyl-$C_{1-10}$ alkyl" refers herein to a heterocyclic group as defined above substituted with an alkyl group as defined above having 1 to 10 carbons, for example, 4-(N-methyl)-piperazinyl, and the like.

The term "heterocyclyl-$C_{2-10}$alkenyl" refers herein to a heterocyclic group as defined above, substituted with an alkenyl group as defined above, having 2 to 10 carbons, for example, 4-(N-allyl) piperazinyl, and the like. Moieties wherein the heterocyclic group is substituted on a carbon atom with an alkenyl group are also included.

The term "heterocyclyl-$C_{2-10}$alkynyl" refers herein to a heterocyclic group as defined above, substituted with an alkynyl group as defined above, having 2 to 10 carbons, for example, 4-(N-propargyl) piperazinyl, and the like. Moieties wherein the heterocyclic group is substituted on a carbon atom with an alkenyl group are also included.

The term "oxo" refers to an oxygen that is double bonded to a carbon atom. One in the art understands that an "oxo" requires a second bond from the atom to which the oxo is attached. Accordingly, it is understood that oxo cannot be substituted onto an aryl or heteroaryl ring, unless it forms part of the aromatic system as a tautomer.

Compounds described herein can contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof. The above Formula I is shown without a definitive stereochemistry at certain positions. The present invention includes all stereoisomers of Formula I and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

The present invention includes all manner of rotamers and conformationally restricted states of a compound of the invention.

The terms "solvent," "organic solvent," and "inert solvent" each mean a solvent inert under the conditions of the reaction being described in conjunction therewith including, for example, benzene, toluene, acetonitrile, tetrahydrofuran ("THF"), dimethylformamide ("DMF"), chloroform, methylene chloride (or dichloromethane), diethyl ether, methanol, N-methylpyrrolidone ("NMP"), pyridine and the like. Unless specified to the contrary, the solvents used in the reactions described herein are inert organic solvents. Unless specified to the contrary, for each gram of the limiting reagent, one cc (or mL) of solvent constitutes a volume equivalent.

Isolation and purification of the chemical entities and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples hereinbelow. However, other equivalent separation or isolation procedures can also be used.

When desired, the (R)- and (S)-isomers of the compounds of the present invention, if present, may be resolved by methods known to those skilled in the art, for example by formation of diastereoisomeric salts or complexes which may be separated, for example, by crystallization; via formation of diastereoisomeric derivatives which may be separated, for example, by crystallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. Alternatively, a specific enantiomer may be synthesized by asymmetric synthesis using optically active reagents, substrates, catalysts or solvents, or by converting one enantiomer to the other by asymmetric transformation.

The compounds described herein can be optionally contacted with a pharmaceutically acceptable acid to form the corresponding acid addition salts.

A compound of Formula I or a pharmaceutically acceptable salt thereof is provided in this invention, wherein:

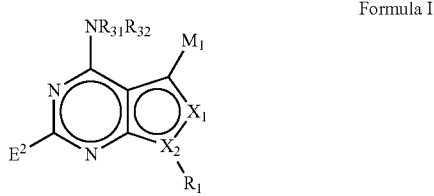

Formula I $X_1$ is N or C-$E^1$ and $X_2$ is N; or $X_1$ is NH or CH-$E^1$ and $X_2$ is C; or $X_1$ is N or C-$E^1$, $X_2$ is S, and $R_1$ is absent; or $X_1$ is N or C-$E^1$, $X_2$ is O, and $R_1$ is absent;

$R_1$ is H, L-$C_{1-10}$alkyl, -L-$C_{3-8}$cycloalkyl, -L-$C_{1-10}$alkyl-$C_{3-8}$ cycloalkyl, -L-aryl, -L-heteroaryl, -L-$C_{1-10}$alkylaryl, -L-$C_{1-10}$alkylhetaryl, -L-$C_{1-10}$alkylheterocylyl, -L-$C_{2-10}$alkenyl, -L-$C_{2-10}$alkynyl, -L-$C_{2-10}$alkenyl-$C_{3-8}$cycloalkyl, -L-$C_{2-10}$alkynyl-$C_{3-8}$cycloalkyl, -L-heteroalkyl, -L-heteroalkylaryl, -L-heteroalkylheteroaryl, -L-heteroalkyl-heterocylyl, -L-heteroalkyl-$C_{3-8}$cycloalkyl, -L-aralkyl, -L-heteroaralkyl, or -L-heterocyclyl, each of which is unsubstituted or substituted by one or more independent $R^3$ substituents;

L is absent, C=O, —C(=O)O—, —C(=O) $NR^{31}$—, —S—, —S(O)—, —S(O)$_2$—, —S(O)$_2NR^{31}$—, —$NR^{31}$—, or $N(R^{31})C(O)$—;

$M_1$ is benzothiazolyl substituted with $(W^2)_k R^2$;

k, in each instance, is 0 or 1;

$E^1$ and $E^2$ are independently $(W^1)_j$—$R^2$;

j, in each instance, is 0 or 1;

$W^1$ is —O—, —$NR^6$—, —$S(O)_{0-2}$—, —C(O)—, —C(O)N($R^6$)—, —N($R^6$)C(O)—, —N($R^6$)S(O)—, —N($R^6$)S(O)$_2$—, —C(O)O—, —CH($R^6$)N(C(O)O$R^7$)—, —CH($R^7$)N(C(O)$R^7$)—, —CH($R^6$)N(SO$_2R^7$), —CH($R^6$)N($R^7$)—, —CH($R^6$)C(O)N($R^7$)—, —CH($R^6$)N($R^7$)C(O)—, —CH($R^6$)N($R^7$)S(O)—, or —CH($R^6$)N($R^7$)S(O)$_2$—;

$W^2$ is —O—, —$NR^6$—, —$S(O)_{0-2}$—, —C(O)—, —C(O)N($R^6$)—, —N($R^6$)C(O)—, —N($R^6$)S(O)—, —N($R^6$)S(O)$_2$—, —C(O)O—, —CH($R^6$)N(C(O)O$R^7$)—, —CH($R^7$)N(C(O)$R^7$)—, —CH($R^6$)N(SO$_2R^7$), —CH($R^6$)N($R^7$)—, —CH($R^6$)C(O)N($R^7$)—, —CH($R^6$)N($R^7$)C(O)—, —CH($R^6$)N($R^7$)S(O)—, —CH($R^6$)N($R^7$)S(O)$_2$—, —N($R^6$)C(O)N($R^7$)—, —CH($R^7$)C(O)—, or —$NR^{34}R^{35}$;

$R^3$ and $R^4$ are independently hydrogen, halogen, aryl, hetaryl, $C_{1-4}$alkyl, $C_{1-10}$alkyl, $C_{3-8}$cycloalkyl, —$C_{1-10}$alkyl-$C_{3-8}$cycloalkyl, —$C_{3-8}$cycloalkyl-$C_{1-10}$alkyl, —$C_{3-8}$cycloalkyl-$C_{2-10}$alkenyl, —$C_{3-8}$cycloalkyl-$C_{2-10}$alkynyl, —$C_{1-10}$alkyl-$C_{2-10}$alkenyl, —$C_{1-10}$ alkyl-$C_{2-10}$alkynyl, —$C_{1-10}$alkylaryl, —$C_{1-10}$alkylhetaryl, —$C_{1-10}$alkylheterocyclyl, —$C_{2-10}$alkenyl, $C_{2-10}$alkynyl, —$C_{2-10}$alkenyl-$C_{1-10}$alkyl, —$C_{2-10}$alkynyl-$C_{1-10}$alkyl, —$C_{2-10}$alkenylaryl, —$C_{2-10}$alkenylhetaryl, —$C_{2-10}$alkenylheteroalkyl, —$C_{2-10}$alkenylheterocyclyl, —$C_{2-10}$alkenyl-$C_{3-8}$cycloalkyl, —$C_{2-10}$alkynyl-$C_{3-8}$cycloalkyl, —$C_{2-10}$alkynylaryl, —$C_{2-10}$alkynylhetaryl, —$C_{2-10}$ alkynylheteroalkyl, —$C_{2-10}$alkynylheterocylyl, —$C_{2-10}$alkynyl-$C_{3-8}$cycloalkenyl, —$C_{1-10}$alkoxy $C_{1-10}$alkyl, —$C_{1-10}$alkoxy-$C_{2-10}$alkenyl, —$C_{1-10}$alkoxy-$C_{2-10}$alkynyl, -heterocyclyl, -heterocyclyl-$C_{1-10}$alkyl, -heterocyclyl-$C_{2-10}$alkenyl, -heterocyclyl-$C_{2-10}$alkynyl, -aryl-$C_{1-10}$alkyl, -aryl-$C_{2-10}$alkenyl, -aryl-$C_{2-10}$alkynyl, -aryl-heterocyclyl, -hetaryl-$C_{1-10}$alkyl, -hetaryl-$C_{2-10}$alkenyl, -hetaryl-$C_{2-10}$alkynyl, -hetaryl-$C_{3-8}$cycloalkyl, -heteroalkyl, -hetaryl-heteroalkyl, -hetaryl-heterocyclyl, or -alkoxy, wherein each of said aryl or heteroaryl moieties is unsubstituted or is substituted with one or more independent halo, —OH, —$R^{31}$, —$CF_3$, —$OCF_3$, —$OR^{31}$, —$NR^{31}R^{32}$, —$NR^{34}R^{35}$, —$C(O)R^{31}$, —$CO_2R^{31}$, —$C(=O)NR^{31}R^{32}$, —$C(=O)NNR^{34}R^{35}$, —$NO_2$, —$CN$, —$S(O)_{0-2}R^{31}$, —$SO_2NR^{31}R^{32}$, —$SO_2NR^{34}R^{35}$, —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, —$C(=S)OR^{31}$, —$C(=O)SR^{31}$, —$NR^{31}C(=NR^{32})NR^{33}R^{32}$, —$NR^{31}C(=NR^{32})OR^{33}$, —$NR^{31}C(=NR^{32})SR^{33}$, —$OC(=O)OR^{33}$, —$OC(=O)NR^{31}R^{32}$, —$OC(=O)SR^{31}$, —$SC(=O)OR^{31}$, —$P(O)OR^{31}OR^{32}$, or —$SC(=O)NR^{31}R^{32}$ substituents, and wherein each of said alkyl, cycloalkyl, heterocyclyl, or heteroalkyl moieties is unsubstituted or substituted with one or more halo, —OH, —R³¹, —CF₃, —OCF₃, —OR³¹, —O-aryl, —NR³¹R³², —NR³⁴R³⁵, —C(O)R³¹, —CO₂R³¹, —C(═O)NNR³⁴R³⁵, —C(═O)NR³¹R³², —SO₂NR³¹R³², or —SO₂NR³⁴R³⁵ substituents; or R³ and R⁴ are independently —OH, —R³¹, —CF₃, —OCF₃, —OR³¹, —NR³¹R³², —NR³⁴R³⁵, —C(O)R³¹, —CO₂R³¹, —C(═O)NR³¹R³², —C(═O)NNR³⁴R³⁵, —NO₂, —CN, —S(O)₀₋₂R³¹, —SO₂NR³¹R³², —SO₂NR³⁴R³⁵, —NR³¹C(═O)R³², —NR³¹C(═O)OR³², —NR³¹C(═O)NR³²R³³, —NR³¹S(O)₀₋₂R³², —C(═S)OR³¹, —C(═O)SR³¹, —NR³¹C(═NR³²)NR³³R³², —NR³¹C(═NR³²)OR³³, —NR³¹C(═NR³²)SR³³, —OC(═O)OR³³, —OC(═O)NR³¹R³², —OC(═O)SR³¹, —SC(═O)OR³¹, —P(O)OR³¹OR³², or —SC(═O)NR³¹R³²;

R² is hydrogen, bicyclic aryl, substituted monocyclic aryl, heteroaryl, C₁₋₄alkyl, C₁₋₁₀ alkyl, C₃₋₈cycloalkyl, —C₁₋₁₀alkyl-C₃₋₈cycloalkyl, —C₃₋₈cycloalkyl-C₁₋₁₀alkyl, —C₃₋₈cycloalkyl-C₂₋₁₀alkenyl, —C₃₋₈cycloalkyl-C₂₋₁₀alkynyl, —C₂₋₁₀alkyl-monocyclic aryl, -monocyclic aryl-C₂₋₁₀alkyl, —C₁₋₁₀alkylbicycloaryl, -bicycloaryl-C₁₋₁₀alkyl, -substituted C₁₋₁₀alkylaryl, -substituted aryl-C₁₋₁₀alkyl, —C₁₋₁₀alkylheteroaryl, —C₁₋₁₀alkylheterocyclyl, —C₂₋₁₀alkenyl, C₂₋₁₀alkynyl, —C₂₋₁₀alkenylaryl, —C₂₋₁₀alkenylhetaryl, —C₂₋₁₀alkenylheteroalkyl, —C₂₋₁₀alkenylheterocyclcyl, —C₂₋₁₀alkynylaryl, —C₂₋₁₀alkynylhetaryl, —C₂₋₁₀alkynylheteroalkyl, —C₂₋₁₀alkynylheterocyclyl, —C₂₋₁₀alkenyl-C₃₋₈cycloalkyl, —C₂₋₁₀alkynyl-C₃₋₈cycloalkenyl, —C₁₋₁₀alkoxy C₁₋₁₀alkyl, —C₁₋₁₀alkoxy C₂₋₁₀alkenyl, —C₁₋₁₀ alkoxyC₂₋₁₀alkynyl, -heterocyclyl, -heteroalkyl, -heterocyclyl C₁₋₁₀alkyl, -heterocyclyl C₂₋₁₀alkenyl, -heterocyclyl-C₂₋₁₀alkynyl, -aryl-C₂₋₁₀alkenyl, -aryl-C₂₋₁₀alkynyl, -aryl-heterocyclyl, -hetaryl-C₁₋₁₀alkyl, -heteroaryl-C₂₋₁₀alkenyl, -heteroaryl-C₂₋₁₀alkynyl, -heteroaryl-C₃₋₈cycloalkyl, -heteroaryl-heteroalkyl, -heteroaryl-heterocyclyl, -alkyl-substituted monocyclic aryl, heterocyclyl, -cycloalkyl-heterocyclyl, or -heterocyclyl-heterocyclyl; wherein each of said bicyclic aryl or heteroaryl moieties is unsubstituted or substituted, and further wherein said substituted monocyclic aryl, substituted bicyclic aryl or substituted heteroaryl is substituted with one or more independent halo, —OH, —R³¹, —CF₃, —OCF₃, —OR³¹, —NR³¹R³², —NR³⁴R³⁵, —C(O)R³¹, —CO₂R³¹, —C(═O)NR³¹R³², —C(═O)NNR³⁴R³⁵, —NO₂, —CN, —S(O)₀₋₂R³¹, —SO₂NR³¹R³², —SO₂NR³⁴R³⁵, —NR³¹C(═O)R³², —NR³¹C(═O)OR³², —NR³¹C(═O)NR³²R³³, —NR³¹S(O)₂R³², —C(═S)OR³¹, —C(═O)SR³¹, —NR³¹C(═NR³²)NR³³R³², —NR³¹C(═NR³²)OR³³, —NR³¹C(═NR³²)SR³³, —OC(═O)OR³³, —OC(═O)NR³¹R³², —OC(═O)SR³¹, —SC(═O)OR³¹, —P(O)OR³¹OR³², or —SC(═O)NR³¹R³² substituents, and wherein each of said alkyl, cycloalkyl, heterocyclyl, or heteroalkyl moieties is unsubstituted or substituted with one or more halo, —OH, —R³¹, —CF₃, —OCF₃, —OR³¹, —O-aryl, —NR³¹R³², —NR³⁴R³⁵, —C(O)R³¹, —CO₂R³¹, —C(═O)NNR³⁴R³⁵, or —C(═O)NR³¹R³² substituents;

R⁶ and R⁷ are each independently hydrogen, C₁₋₁₀alkyl, C₂₋₁₀alkenyl, aryl, heteroaryl, heterocyclyl or C₃₋₁₀cycloalkyl, each of which except for hydrogen is unsubstituted or substituted by one or more independent R⁸ substituents.

R⁸ is halo, —OR³¹, —SH, NH₂, —NR³⁴R³⁵, —NR³¹R³², —CO₂R³¹, —CO₂aryl-C(═O)NR³¹R³², —C(═O)NR³⁴R³⁵, —NO₂, —CN, —S(O)₀₋₂ C₁₋₁₀alkyl, —S(O)₀₋₂ aryl, —SO₂NR³⁴R³⁵, —SO₂NR³¹R³², alkyl, cycloalkyl, alkenyl, or alkynyl; or R⁸ is -aryl-alkyl, -aryl-alkenyl, -aryl-alkynyl, -heteroaryl-alkyl, -heteroaryl-alkenyl, -hetaryl-alkynyl, each of which is unsubstituted or substituted with one or more independent halo, cyano, nitro, —Oalkyl, alkyl, alkenyl, alkynyl, haloalkyl, haloalkenyl, haloalkynyl, —COOH, —C(═O)NR³¹R³², —C(═O)NR³⁴R³⁵, —SO₂NR³⁴R³⁵, —SO₂NR³¹R³², —NR³¹R³², or —NR³⁴R³⁵ substituents;

R³¹, R³², and R³³, in each instance, are H or unsubstituted or substituted C₁₋₁₀alkyl with one or more aryl, heteroalkyl, heterocyclyl, or hetaryl substituents, wherein each of said alkyl, aryl, heteroalkyl, heterocyclyl, or hetaryl groups is unsubstituted or substituted with one or more halo, —OH, —C₁₋₁₀alkyl, —CF₃, —O-aryl, —OCF₃, —OC₁₋₁₀alkyl, —NH₂, —N(C₁₋₁₀alkyl)(C₁₋₁₀alkyl), —NH(C₁₋₁₀alkyl), —NH(aryl), —NR³⁴R³⁵, —C(O)(C₁₋₁₀alkyl), —C(O)(C₁₋₁₀alkyl-aryl), —C(O)(aryl), —CO₂—C₁₋₁₀alkyl, —CO₂—C₁₋₁₀alkylaryl, —CO₂-aryl, —C(═O)N(C₁₋₁₀alkyl)(C₁₋₁₀alkyl), —C(═O)NH(C₁₋₁₀alkyl), —C(═O)NR³⁴R³⁵, —C(═O)NH₂, —OCF₃, —O(C₁₋₁₀alkyl), —O-aryl, —N(aryl)(C₁₋₁₀alkyl), —NO₂, —CN, —S(O)₀₋₂ C₁₋₁₀alkyl, —S(O)₀₋₂ C₁₋₁₀alkylaryl, —S(O)₀₋₂ aryl, —SO₂N(aryl), —SO₂N(C₁₋₁₀alkyl)(C₁₋₁₀alkyl), —SO₂NH(C₁₋₁₀alkyl) or —SO₂NR³⁴R³⁵ substituents;

R³⁴ and R³⁵ in —NR³⁴R³⁵, —C(═O)NNR³⁴R³⁵, or —SO₂NR³⁴R³⁵, are taken together with the nitrogen atom to which they are attached to form a 3-10 membered saturated or unsaturated ring; wherein said ring in each instance is unsubstituted or substituted by one or more —NR³¹R³², hydroxyl, halogen, oxo, aryl, hetaryl, C₁₋₆alkyl, O-aryl, C(O)R³¹, or S(O)₀₋₂R³¹ substituents, and wherein said 3-10 membered saturated or unsaturated ring in each instance includes 0, 1, or 2 more heteroatoms other than the nitrogen.

Some non-limiting examples of the cyclic moiety formed by R³⁴ and R³⁵ in —NR³⁴R³⁵, —C(═O)NNR³⁴R³⁵, or —SO₂NR³⁴R³⁵, being taken together with the nitrogen to which R³⁴ and R³⁵ are attached, include one of the following:

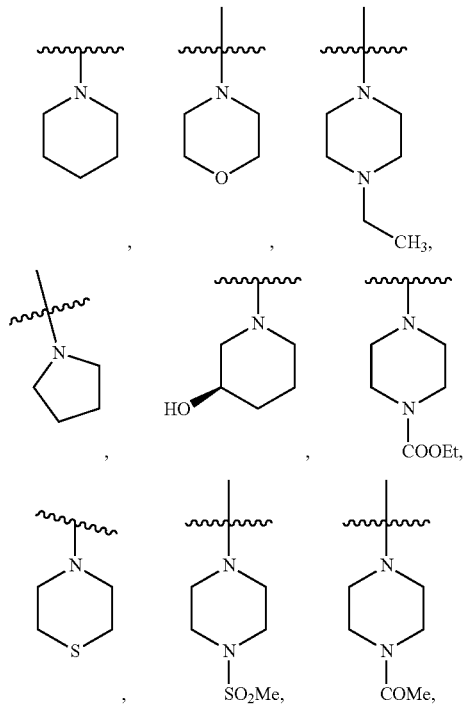

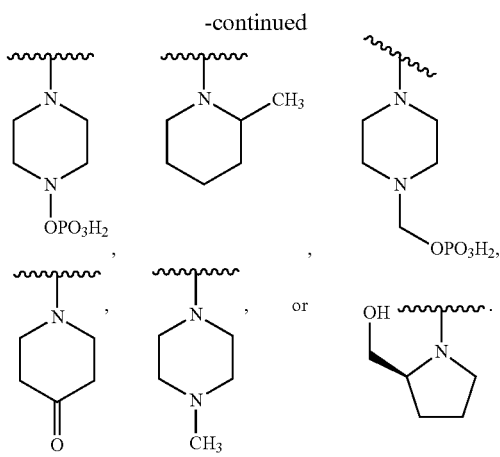

In some embodiments, for the compounds of Formula I, $R_1$ is H or -L- (unsubstituted or -substituted $C_{1-10}$alkyl), wherein alkyl includes but is not limited to $CH_3$, —$CH_2CH_3$, n-propyl, isopropyl, n-butyl, tert-butyl, sec-butyl, pentyl, hexyl, and heptyl. In some embodiments, L- is absent, and $R_1$ includes but is not limited to methyl, trifluoromethyl, isopropyl, tert-butyl, sec-butyl, or 2-(morpholinyl)ethyl. When $R_1$ is —C(O)alkyl, non-limiting exemplary $R_1$ include acetyl, propionyl, and 3-(piperazinyl)propionyl. In other embodiments, $R_1$ is —C(O)O-alkyl, including but not limited to —COOCH3, —COOCH$_2$C$_6$H$_6$, and —COO-t-butyl. $R_1$ is also —C(O)NR$^{31}$-alkyl, including but not limited to —C(O)NHMe, —C(O)N(Et)$_2$-C(O)NH(isopropyl), and —C(O)NH(ethyl). In other embodiments, $R_1$ is —S-alkyl (including but not limited to —S(ethyl), —S(isopropyl), —S(iso-butyl) and —S(n-pentyl)), —S(O)alkyl (including but not limited to —S(O)-ethyl and —S(O)-methyl), and —S(O)$_2$-alkyl (including but not limited to methyl sulfonyl, n-butylsulfonyl, and ethylsulfonyl. Alternatively, $R_1$ is —S(O)$_2$NR$^{31}$-(alkyl), wherein non limiting examples are —S(O)$_2$NHMe., —S(O)$_2$N(Me)(butyl), and —S(O)$_2$N(iso-propyl)(ethyl). The invention also provides compounds wherein $R_1$ is —N(R$^{31}$)C(O)-alkyl (including but not limited to —NHC(O)CH$_2$(morpholinyl), —NHC(O)CH$_2$(piperidin-1-yl), and —NHC(O)CH$_2$CH$_2$(cyclopropyl)) or —NR$^{31}$-alkyl (including —NHCH$_2$CH$_2$ (4-N-methyl-piperazinyl), —NHCH$_2$CH$_2$(morpholinyl), and —NHCH$_2$CH$_2$CH(CH$_3$)$_2$ Other compounds are provided wherein $R_1$ is -L- (unsubstituted or substituted $C_3$-$C_8$cycloalkyl) (which includes but is not limited to cyclopropyl, cyclobutyl, cyclopentyl, and cyclohexyl). In some embodiments, L is absent and $R_1$ includes but is not limited to cyclopropyl, cyclobutyl, 3-hydroxy cyclobut-1-yl, and 4-morpholinyl cyclohex-1yl). In other embodiments, $R_1$ is —C(O)-cycloalkyl, which includes but is not limited to —C(O)— cyclopropyl, —C(O)-cyclopentyl, and —C(O)-(4-diethylamino)cyclohexyl. $R_1$ may also be —C(O)O-cycloalkyl (including but not limited to —COO-cyclopropyl, —COO-tert-butyl, and —COO-cyclohexyl) or —C(O) NR$^{31}$ (including but not limited to —C(O)NH-cyclopropyl, —C(O)N(Me)-cyclobutyl, and —C(O)N(Et)-(4-morpholinyl)cyclohexyl. In some other embodiments, $R_1$ is —S-cycloalkyl (including but not limited to —S-cyclobutyl, —S-(3-methyl)cyclopentyl, and —S-(4-(4'N-Me)piperazinyl)cyclohexyl), —S—(O)cyclalkyl (including but not limited to —S(O)-cyclobutyl and —S(O)-cyclopentyl), or —S(O)$_2$-cycloalkyl (including but not limited to —S(O)$_2$-cyclobutyl, —S(O)$_2$— (3-Cl)cyclopentyl, —S(O)$_2$— (4-imidazolyl)cyclohexyl. Alternatively, $R_1$ is —S(O)$_2$NR$^{31}$-cycloalkyl, wherein nonlimiting examples include —S(O)$_2$NH-cyclopropyl, —S(O)$_2$N(Me)-(3-azetidinyl)cyclobut-1-yl, and —S(O)$_2$NH— (2-methyl) cyclohex-1yl. The invention also provides compounds wherein $R_1$ is N(R$^{31}$)C(O)-cycloalkyl (including but not limited to —N(H)C(O)-cyclobutyl, —N(Me)C(O)-cyclopentyl, and N(H)C(O)-(4-methoxy cyclohex-1-yl) or —NR$^{31}$-cycloalkyl (exemplary nonlimiting —NR$^{31}$-cycloalkyl include —NHcyclopropyl, N(Me)-cyclobutyl, and NH-(3-Cl-cyclopent-1-yl.

Additionally, $R_1$ can be -L-$C_{1-10}$ alkyl-$C_3$-$C_8$cycloalkyl, wherein $C_{1-10}$alkyl is unsubstituted or -substituted $C_{1-10}$ alkyl. Alkyl includes but is not limited to $CH_3$, —$CH_2CH_3$, n-propyl, isopropyl, n-butyl, tert-butyl, sec-butyl, pentyl, hexyl, and heptyl. $C_3$-$C_8$cycloalkyl is unsubstituted or substituted $C_3$-$C_8$cycloalkyl, wherein $C_3$-$C_8$cycloalkyl includes but is not limited to cyclopropyl, cyclobutyl, cyclopentyl, and cyclohexyl. In some embodiments, $R_1$ is $C_{1-10}$alkyl-$C_3$-$C_8$cycloalkyl, Non-limiting examples of $R_1C_{1-10}$alkyl-$C_3$-$C_8$cycloalkyl include —CH$_2$cyclopropyl, -(3-cyclopentyl)prop-1-yl, and -(4-(3-Cl-cyclohex-1-yl)butyl. $R_1$ is also —C(O)-alkylcycloalkyl (non-limiting examples include —C(O)methylcyclobutyl, —C(O)ethylcyclopropyl, and —C(O)(3-(4-morpholinyl)cyclohex-1yl)propyl) or —C(O) O-cycloalkyl (including but not limited to —C(O)Ocyclobutyl, —C(O)O(3,5-dimethyl)cyclohexyl, and —C(O)O(3-Cl)-cyclopentyl. In some other embodiments, $R_1$ is —C(O) NR$^{31}$-alkyl-cycloalkyl, wherein nonlimiting examples include —C(O) NH—CH$_2$-cyclobutyl, —C(O)NH— (2-(cyclopent-1-yl)ethyl), and —C(O)NH-(3-(4-diethylaminocyclohex-1-yl)propyl. In yet other embodiments, $R_1$ is —S-alkyl-cycloalkyl (including but not limited to —SCH$_2$cyclopropyl, —SCH$_2$CH$_2$(3-morpholinyl)cyclobutyl, and —SCH$_2$CH$_2$-(4-methoxyl)cyclohexyl), —S(O)-alkyl-cycloalkyl (non-limiting examples including —S(O)CH$_2$cyclobutyl and —S(O)CH$_2$cyclohexyl), or —S(O)$_2$alkyl-cycloalkyl (including but not limited to —S(O)$_2$CH$_2$cyclopropyl, —S(O)$_2$CH$_2$CH$_2$(4-(4'-N Me piperazinyl cyclohex-1yl). Alternatively, $R_1$ is —N(R$^{31}$)C(O)-alkyl-cycloalkyl (including but not limited to —N(Me)C(O)— CH$_2$cyclopropyl, —NHC(O)CH$_2$CH$_2$— (3-CN)cyclopent-1-yl, and —N(H)C(O)—CH$_2$(4-(4N-piperidinyl) cyclohexyl) or —NR$^{31}$alkyl-cycloalkyl (nonlimiting examples include —NHCH$_2$ cyclopropyl, —N(Me) CH$_2$cyclopentyl, and —NHCH$_2$CH$_2$(4-morpholinylcyclhex-1yl).

In other embodiments, $R_1$ is -L- (unsubstituted or substituted aryl), including but not limited to monocyclic or bicyclic aryl. When L is absent, $R_1$ is -aryl, wherein nonlimiting examples include -phenyl, 3-methoxyphenyl, and 3-(4-N-Me piperazinyl)phenyl. In other embodiments, $R_1$ is —C(O)-aryl (including benzoyl, 3-(2-morpholinyl methyl) phenyl, and 4-diethylaminomethyl phenyl) or —C(O)O-aryl (including carboxyphenyl). $R_1$ is also —C(O)NR$^{31}$-aryl, including but not limited to —C(O)NH-phenyl, —C(O) NH(3-(4-N-Me piperazinyl))phenyl, and —C(O)NMe 3,5-dimethoxyphenyl. In some other embodiments, $R_1$ is —S-aryl (including but not limited to —S— phenyl), —S(O)-aryl (including but not limited to —S(O)-phenyl), or —S(O)$_2$-aryl(including but not limited to —S(O)$_2$-phenyl, —S(O)$_2$— ((3-(4-N-Me piperazinyl))phenyl, and —S(O)$_2$— (4-chloro)phenyl.

The invention also provides compounds wherein $R_1$ is -L- (unsubstituted or substituted heteroaryl), wherein heteroaryl includes but is not limited to monocyclic and bicyclic heteroaryl. Monocyclic heteroaryl $R_1$ includes but is not limited to pyrrolyl, thienyl, furyl, pyridinyl, pyranyl, imidazolyl, thiazolyl, pyrazolyl, and oxazolyl. Bicyclic heteroaryl $R_1$ includes but is not limited to benzothiophenyl, benzofuryl, indolyl, quinolinyl, isoquinolinyl, benzimidazolyl, benzoxazolyl, benzothiazolyl, quinazolinyl, azaindolyl, pyrazolopyrimidinyl, and purinyl. In some embodiments, -L is absent, and $R_1$ is heteroaryl (including but not limited to thiazolyl, oxazolyl, imidazolyl, thiazolyl, pyridinyl, pyrimidinyl, pyrrolyl, and 4-morpholinylmethyl-pyridin-2-yl, and 3-(4N-Me piperazinyl)pyridin-2-yl). In other embodiments, $R_1$ is —C(O)-heteroaryl (including but not limited to —C(O)-pyridinyl, —C(O)-thiazolyl, and —C(O) 3-(4N-Me piperazinyl)pyridin-2-yl) or —C(O)O-heteroaryl (including but not limited to —COO-pyridinyl). $R_1$ may also be —C(O)$NR^{31}$-heteroaryl, non-limiting examples including —C(O) NH— (4-morpholinylmethyl)-pyridin-2-yl, —C(O)N(Me)-thiazolyl, and —C(O)NH— (3-(4N-Me piperazinyl)pyridin-2-yl)). In yet other embodiments, $R_1$ is —S-heteroaryl (including but not limited to —S-pyridinyl), —S(O)-heteroaryl (including but not limited to —S(O)-pyrimidinyl), or —S(O)$_2$-heteroaryl (exemplary $R_1$ include, without limitation, —S(O)$_2$-pyridinyl, —S(O)$_2$-imidazolyl, and S(O)$_2$— (3-(4N-Me piperazinyl)pyridin-2-yl))). In some other embodiments, $R_1$ is —S(O)$_2NR^{31}$-heteroaryl (including but not limited to —S(O)$_2$NH-pyridinyl, —S(O)$_2$N(Me)-thiazolyl, and —S(O)$_2$NH— (3-(4N-Me piperazinyl)pyridin-2-yl))). Alternatively, $R_1$ is —N($R^{31}$)C(O)-heteroaryl (including but not limited to —N(H)C(O)-pyridinyl, —N(Me)C(O)-oxazolyl, and —N($R^{31}$)C(O)-(3-(4N-Me piperazinyl)pyridin-2-yl))), or —$NR^{31}$-heteroaryl (including but not limited to —NH-pyridinyl, —N(Me)-thiazolyl, and —NH— (3-(4N-Me piperazinyl)pyridin-2-yl))).

In yet other embodiments, $R_1$ is -L-alkylaryl, -L-alkylheteroaryl, or -L-alkylheterocylyl, wherein alkyl, aryl, heteroaryl and heterocyclyl are as described herein. Each of alkyl, aryl, heteroaryl and heterocyclyl is unsubstituted or substituted. In some embodiments L is absent and $R_1$ is -alkylaryl (including but not limited to benzyl, ethylphenyl, and (3-(4N-Me piperazinyl)phenyl), -alkylheteroaryl (including but not limited to —$CH_2$pyridin-2-yl, —$CH_2$pyrrolyl, and —$CH_2$(3-(4N-Me piperazinyl)pyridinyl), or -alkylheterocylyl (including but not limited to —$CH_2CH_2$morpholinyl, —$CH_2CH_2$-(4N-Me) piperazinyl, —$CH_2$morpholinyl, and —$CH_2CH_2$azetidinyl). In other embodiments, $R_1$ is —C(O)-aryl (including but not limited to —C(O)-benzyl and —C(O)— (3-(4N-Me piperazinyl) phenyl), —C(O)-alkylheteroaryl (including but not limited to —C(O)$CH_2$-pyridin-2-yl, and —C(O)$CH_2$-pyrrolyl), or —C(O)-alkylheterocyly (including but not limited to —C(O)—$CH_2CH_2$morpholinyl, —C(O)—$CH_2CH_2$(4N-Me) piperazinyl, —C(O)—$CH_2$-morpholinyl, and —C(O)—$CH_2CH_2$-azetidinyl). Additionally, $R_1$ is —C(O) O-alkylaryl (including but not limited to —C(O)O— $CH_2C_6H_6$), —C(O)O-alkylheteroaryl (including but not limited to —$CH_2$-pyridin-2-yl), or —C(O)O-alkylheterocylyl (including but not limited to —C(O)O$CH_2CH_2$— (4N-Me) piperazinyl). In some other embodiments, $R_1$ is —C(O) $NR^{31}$-alkylaryl (including but not limited to C(O) NH$CH_2C_6H_6$), —C(O)$NR^{31}$-alkylheteroaryl (including but not limited to —C(O)NH$CH_2$-pyridin-2-yl, —C(O)NH$CH_2$-pyrrolyl, and —C(O)NH$CH_2$— (3-(4N-Me piperazinyl) pyridinyl), or —C(O)$NR^{31}$-alkylheterocylyl (not limiting examples include —C(O)NH$CH_2CH_2$-morpholinyl, —C(O) NH$CH_2CH_2$— (4N-Me) piperazinyl, —C(O)NH$CH_2$— (4N—$SO_2$Me) piperazinyl-C(O)NH$CH_2$-morpholinyl, and —C(O)NH$CH_2CH_2$-azetidinyl). $R_1$ may also be —S-alkylaryl (including but not limited to —S—$CH_2C_6H_6$), —S-alkylheteroaryl (including but not limited to —S$CH_2$pyridin-2-yl), or —Salkylheterocylyl (including but not limited to —S$CH_2CH_2$-morpholinyl, —S$CH_2CH_2$— (4N-Me) piperazinyl, and —S$CH_2$— (4N—$SO_2$Me) piperazinyl). In a different embodiment, $R_1$ is —S(O)-alkylaryl (including but not limited to —S(O)$CH_2C_6H_6$), —S(O)-alkylheteroaryl (including but not limited to —S(O)$CH_2$-pyridin-2-yl), or —S(O)-alkylheterocylyl (including but not limited to —S(O)$CH_2CH_2$-morpholinyl, —S(O)$CH_2CH_2$— (4N-Me) piperazinyl, and —S(O)$CH_2$— (4N—$SO_2$Me) piperazinyl). In a further embodiment, $R_1$ is —S(O)$_2$-alkylaryl (including but not limited to —S(O)$_2CH_2C_6H_6$, and —S(O)$_2$— (3-(4N-Me) piperazinyl)$CH_2$)$C_6H_6$), —S(O)$_2$-alkylheteroaryl (including but not limited to —S(O)$_2$$CH_2CH_2$-morpholinyl, —S(O)$_2CH_2CH_2$— (4N-Me) piperazinyl, and —S(O)$_2CH_2$— (4N—$SO_2$Me) piperazinyl), or —S(O)$_2$-alkylheterocylyl (including but not limited to —S(O)$_2CH_2CH_2$-morpholinyl, —S(O)$_2CH_2CH_2$— (4N-Me) piperazinyl, and —S(O)$_2CH_2$— (4N—$SO_2$Me) piperazinyl). Alternatively, $R_1$ is —S(O)$_2NR^{31}$-alkylaryl (including but not limited to —S(O)$_2$NH$CH_2C_6H_6$), —S(O)$_2NR^{31}$-alkylheteroaryl (including but not limited to —S(O)$_2$ NH$CH_2$-pyridin-2-yl), or —S(O)$_2NR^{31}$-alkylheterocylyl (including but not limited to —S(O)$_2$NH$CH_2CH_2$-morpholinyl, —S(O)$_2$NH$CH_2CH_2$— (4N-Me) piperazinyl, and —S(O)$_2$NH$CH_2$— (4N—$SO_2$Me) piperazinyl). In some other embodiments, $R_1$ is —N($R^{31}$)C(O)-alkylaryl (including but not limited to —N(Me)C(O)$CH_2C_6H_6$, and —NHC (O)— (3-(4N-Me) piperazinyl)$CH_2$)$C_6H_6$), —N($R^{31}$)C(O)-alkylheteroaryl (including but not limited to NHC(O)$CH_2$-pyridin-2-yl), or —N($R^{31}$)C(O)-alkylheterocylyl (non-limiting examples include —N(HC(O)$CH_2CH_2$-morpholinyl, —N(HC(O)$CH_2CH_2$— (4N-Me) piperazinyl, and —N(HC(O)$CH_2$— (4N—$SO_2$Me) piperazinyl). In addition, the invention provides for compounds wherein $R_1$ is —$NR^{31}$-alkylaryl (including but not limited to —NMe$CH_2C_6H_6$), —$NR^{31}$-alkylheteroaryl (non-limiting examples include —NH$CH_2$-pyridin-2-yl), or —$NR^{31}$-alkylheterocylyl (including but not limited to —NH$CH_2CH_2$-morpholinyl, —NMe$CH_2CH_2$— (4N-Me) piperazinyl, and —NH$CH_2$— (4N—$SO_2$Me) piperazinyl).

$R_1$ can also be -L- (unsubstituted or substituted alkenyl) or -L- (unsubstituted or substituted alkynyl). $C_2$-$C_{10}$alkenyl includes but is not limited to for example, vinyl, allyl, 1-methyl propen-1-yl, butenyl, or pentenyl, and $C_2$-$C_{10}$alkynyl includes but is not limited to acetylenyl, propargyl, butynyl, or pentynyl). In some embodiments, L is absent and $R_1$ is alkenyl (including but not limited to vinyl, allyl, 1-methyl propen-1-yl, butenyl, or pentenyl) or alkynyl (including but not limited to acetylenyl, 3-cyclopropyl proparg-1-yl, butynyl, or pentynyl). In other embodiments, $R_1$ is —C(O)-alkenyl (including but not limited to —C(O) $CH_2$CH($CH_3$)CH=$CH_2$), or —C(O)alkynyl (including but not limited to —C(O)$CH_2$C≡CH and —C(O)$CH_2$CH($CH_3$)C≡CH). $R_1$ may also be —C(O)O-alkenyl (including but not limited to —C(O)O$CH_2$CH($CH_3$)CH=$CH_2$), or —C(O) O-alkynyl (including but not limited to —C(O) O$CH_2$C≡CH and —C(O)O$CH_2$CH($CH_3$)C≡CH). In some other embodiments, $R_1$ is C(O)$NR^{31}$-alkenyl (including but not limited to —C(O)NH$CH_2$CH($CH_3$)CH=$CH_2$), or C(O) $NR^{31}$-alkynyl (including but not limited to —C(O) NH$CH_2$C≡CH and —C(O)NH$CH_2$CH($CH_3$)C≡CH). Additionally, $R_1$ is —S-alkenyl (including but not limited to —S$CH_2$CH($CH_3$)CH=$CH_2$), —S(O)-alkenyl (including but not limited to —S(O)$CH_2$CH($CH_3$)CH=$CH_2$), —S(O)$_2$-alkenyl (including but not limited to —S(O)$_2$ CH$_2$CH(CH$_3$)CH=CH$_2$), —S— alkynyl (including but not limited to —SCH$_2$C≡CH and —SCH$_2$CH(CH$_3$)C≡CH), —S(O)-alkynyl (including but not limited to —S(O) CH$_2$C≡CH and —S(O)CH$_2$CH(CH$_3$)C≡CH), or —S(O)$_2$-alkynyl (including but not limited to —S(O)$_2$CH$_2$C≡CH and —S(O)$_2$CH$_2$CH(CH$_3$)C≡CH). In yet other embodiments, R$_1$ is —S(O)$_2$NR$^{31}$-alkenyl (including but not limited to —S(O)$_2$NHCH$_2$CH(CH$_3$)CH=CH$_2$), or —S(O)$_2$NR$^{31}$-alkynyl (including but not limited to —S(O)$_2$ NHCH$_2$C≡CH and —S(O)$_2$NHCH$_2$CH(CH$_3$)C≡CH). R$_1$ may also be —N(R$^{31}$)C(O)-alkenyl (including but not limited to —N(Me)C(O) CH$_2$CH(CH$_3$)CH=CH$_2$), —NR$^{31}$-alkenyl (including but not limited to —NHCH$_2$CH(CH$_3$) CH=CH$_2$), N(R$^{31}$)C(O)-alkynyl (including but not limited to -(including but not limited to —N(Me)C(O)CH$_2$C≡CH and —NHC(O) CH$_2$CH(CH$_3$)C≡CH), or —NR$^{31}$-alkynyl (including but not limited to —NHCH$_2$C≡CH and —NHCH$_2$CH(CH$_3$)C≡CH).

R$_1$ can also be -L-alkenyl-cycloalkyl or -L-alkynyl-cycloalkyl, wherein alkenyl, alkynyl, and cycloalkyl are as described herein. In some embodiments, L is absent and R$_1$ is -alkenyl-cycloalkyl (including but not limited to CH$_2$CH=CH(cyclopropyl)) or -alkynyl-cycloalkyl (nonlimiting examples include —CH$_2$C≡C(cyclopropyl), —CH$_2$C≡C(cyclobutyl), and —CH$_2$C≡C(3-(4N-Me) piperazinylcyclobutyl)). In other embodiments, R$_1$ is —C(O)-alkenyl-cycloalkyl (including but not limited to —C(O) CH$_2$CH=CH(cyclopropyl)) or C(O)-alkynyl-cycloalkyl (nonlimiting examples include —C(O)CH$_2$C≡C(cyclopropyl), —C(O)CH$_2$C≡C— (cyclobutyl), and —C(O) CH$_2$≡C— (3-(4N-Me) piperazinylcyclobutyl)). In some other embodiments, R$_1$ is —C(O)O-alkenyl-cycloalkyl (including but not limited to —C(O)OCH$_2$CH=CH— (cyclopropyl)) or C(O)O-alkynyl-cycloalkyl (nonlimiting examples include —C(O)OCH$_2$C≡C— (cyclopropyl), —C(O)OCH$_2$C≡C— (cyclobutyl), and —C(OO) CH$_2$C≡C— (3-(4N-Me) piperazinylcyclobutyl)). In yet other embodiments, R$_1$ is —C(O) NR$^{31}$-alkenyl-cycloalkyl (including but not limited to —C(O)NHCH$_2$CH=CH— (cyclopropyl)) or —C(O) NR$^{31}$-alkynyl-cycloalkyl (nonlimiting examples include —C(O) NHCH$_2$C≡C— (cyclopropyl), —C(O)NMeCH$_2$C≡C— (cyclobutyl), and —C(O) NHCH$_2$C≡C-3-(4N-Me) piperazinylcyclobutyl)). In other embodiments, R$_1$ is —S-alkenyl-cycloalkyl (including but not limited to —SCH$_2$CH=CH(cyclopropyl)), —S(O)-alkenyl-cycloalkyl (including but not limited to —S(O) CH$_2$CH=CH(cyclopropyl)), —S(O)$_2$-alkenyl-cycloalkyl (including but not limited to —S(O)$_2$CH$_2$CH=CH(cyclopropyl)), —S-alkynyl-cycloalkyl (nonlimiting examples include —SCH$_2$C≡C(cyclopropyl), —SCH$_2$C≡C(cyclobutyl), and —SCH$_2$C≡C(3-(4N-Me) piperazinylcyclobutyl)), —S(O)-alkynyl-cycloalkyl (nonlimiting examples include —S(O)CH$_2$C≡C(cyclopropyl), —S(O) CH$_2$C≡C(cyclobutyl), and —S(O)CH$_2$C≡C(3-(4N-Me) piperazinylcyclobutyl)), or —S(O)$_2$-alkynyl-cycloalkyl (nonlimiting examples include —S(O)$_2$CH$_2$C≡C(cyclopropyl), —S(O)$_2$MeCH$_2$C≡C(cyclobutyl), and —S(O)$_2$ CH$_2$C≡C(3-(4N-Me) piperazinylcyclobutyl))). Alternatively, R$_1$ is —S(O)$_2$NR$^{31}$-alkenyl-cycloalkyl (including but not limited to —S(O)$_2$NHCH$_2$CH=CH— (cyclopropyl)), or —S(O)$_2$NR$^3$-alkynyl-cycloalkyl (nonlimiting examples include —S(O)$_2$NHCH$_2$C≡C(cyclopropyl), —S(O)$_2$ NHCH$_2$C≡C(cyclobutyl), and —S(O)$_2$NHCH$_2$C≡C(3-(4N-Me) piperazinylcyclobutyl)). In other embodiments, R$_1$ is —N(R$^{31}$)C(O)-alkenyl-cycloalkyl (including but not limited to —NHC(O)CH$_2$CH=CH— (cyclopropyl)), —NR$^{31}$-alkenyl-cycloalkyl (including but not limited to —NHCH$_2$CH=CH— (cyclopropyl)), —N(R$^{31}$)C(O)-alkynyl-cycloalkyl (nonlimiting examples include —NHC(O) CH$_2$C≡C(cyclopropyl), —NHC(O)CH$_2$C≡C(cyclobutyl), and NHC(O)CH$_2$C≡C(3-(4N-Me) piperazinylcyclobutyl)), or —NR$^{31}$-alkynyl-cycloalkyl (nonlimiting examples include —NHCH$_2$C≡C— (cyclopropyl), —NMeCH$_2$C≡C— (cyclobutyl), and —NHCH$_2$C≡C— (3-(4N-Me)piperazinylcyclobutyl)).

Additionally, R$_1$ can be -L- (unsubstituted or substituted heteroalkyl), wherein heteroalkyl includes but is not limited to (non-limiting examples include ethoxymethyl, methoxymethyl, and diethylaminomethyl. In some embodiments, L is absent and R$_1$ is —C(O)heteroalkyl (including but not limited to —C(O)CH$_2$OCH$_3$), —C(O)Oheteroalkyl (including but not limited to —C(O)OCH$_2$CH$_2$OCH$_3$), —C(O)NR$^{31}$heteroalkyl (including but not limited to —C(O)NHCH$_2$CH$_2$OCH$_3$), —S-heteroalkyl (including but not limited to —SCH$_2$CH$_2$OCH$_3$), —S(O)— heteroalkyl (including but not limited to —S(O)CH$_2$CH$_2$OCH$_3$), —S(O)$_2$-heteroalkyl (including but not limited to —S(O)$_2$ CH$_2$CH$_2$OCH$_3$), —S(O)$_2$NR$^{31}$-heteroalkyl (including but not limited to —S(O)$_2$NHCH$_2$CH$_2$OCH$_3$), —N(R$^{31}$)C(O)-heteroalkyl (including but not limited to —NHC(O) CH$_2$CH$_2$OCH$_3$) or —NR$^{31}$-heteroalkyl (including but not limited to —N(Me)CH$_2$CH$_2$OCH$_3$).

The invention also provides compounds wherein R$_1$ is -L-heteroalkyl-aryl, -L-heteroalkylheteroaryl, -L-heteroalkyl-heterocyclyl, or -L-heteroalkyl-cycloalkyl, wherein heteroalkyl, aryl, heteroaryl, heterocyclyl, and cycloalkyl are as described herein. In some embodiments, L is absent and R$_1$ is -heteroalkylaryl (including but not limited to —CH$_2$CH$_2$OCH$_2$C$_6$H$_6$), -heteroalkylheteroaryl (including but not limited to —CH$_2$CH$_2$OCH$_2$-pyridinyl), -heteroalkyl-heterocylyl (including but not limited to —CH$_2$CH$_2$OCH$_2$-piperidin-1yl, —CH$_2$CH$_2$OCH$_2$-morpholinyl, and —CH$_2$CH$_2$OCH$_2$— (4N-Me-piperazinyl), or -heteroalkyl-cycloalkyl (including —CH$_2$CH$_2$OCH$_2$(cyclobutyl)). In other embodiments, R$_1$ is —C(O)-heteroalkylaryl (including but not limited to —C(O)CH$_2$CH$_2$OCH$_2$C$_6$H$_6$), —C(O)-heteroalkylheteroaryl (including but not limited to —C(O) CH$_2$CH$_2$OCH$_2$-pyridinyl), —C(O)heteroalkyl-heterocylyl (including but not limited to —C(O)CH$_2$CH$_2$OCH$_2$-piperidin-1yl, —C(O)CH$_2$CH$_2$OCH$_2$-morpholinyl, and —C(O) CH$_2$CH$_2$OCH$_2$— (4N-Me-piperazinyl), or —C(O)-heteroalkyl-cycloalkyl (including —C(O)CH$_2$CH$_2$OCH$_2$— (cyclobutyl)). In other embodiments, R$_1$ is —C(O)O-heteroalkylaryl (including but not limited to —C(O) OCH$_2$CH$_2$OCH$_2$C$_6$H$_6$), —C(O)O-heteroalkylheteroaryl (including but not limited to —C(O)OCH$_2$CH$_2$OCH$_2$-pyridinyl), —C(O)O-heteroalkyl-heterocylyl (including but not limited to —C(O)OCH$_2$CH$_2$OCH$_2$-piperidin-1yl, —C(O)OCH$_2$CH$_2$OCH$_2$-morpholinyl, and —C(O) OCH$_2$CH$_2$OCH$_2$— (4N-Me-piperazinyl), or —C(O)O-heteroalkyl-cycloalkyl (including —C(O)OCH$_2$CH$_2$OCH$_2$(cyclobutyl)). Alternatively, R$_1$ is —C(O) NR$^{31}$-heteroalkylaryl (including but not limited to —C(O) NHCH$_2$CH$_2$OCH$_2$C$_6$H$_6$), —C(O)NH-heteroalkylheteroaryl (including but not limited to —C(O)NHCH$_2$CH$_2$OCH$_2$-pyridinyl), —C(O)NH-heteroalkyl-heterocylyl (including but not limited to —C(O)NHCH$_2$CH$_2$OCH$_2$-piperidin-1yl, —C(O)NHCH$_2$CH$_2$OCH$_2$-morpholinyl, and —C(O) NHCH$_2$CH$_2$OCH$_2$— (4N-Me-piperazinyl), or —C(O)NH-heteroalkyl-cycloalkyl (including —C(O) NHCH$_2$CH$_2$OCH$_2$— (cyclobutyl)). In other embodiments, R$_1$ is —S-heteroalkylaryl (including but not limited to —SCH$_2$CH$_2$OCH$_2$C$_6$H$_6$), —S— heteroalkylheteroaryl (including but not limited to —SCH$_2$CH$_2$OCH$_2$pyridinyl), —S-heteroalkyl-heterocylyl (including but not limited to —SCH$_2$CH$_2$OCH$_2$piperidin-1yl, —SCH$_2$CH$_2$OCH$_2$morpholinyl, and —SCH$_2$CH$_2$OCH$_2$ (4N-Me-piperazinyl), or —S-heteroalkyl-cycloalkyl (including —SCH$_2$CH$_2$OCH$_2$— (cyclobutyl)). In some other embodiments, R$_1$ is —S(O)-heteroalkylaryl (including but not limited to —S(O)CH$_2$CH$_2$OCH$_2$C$_6$H$_6$), —S(O)-heteroalkylheteroaryl (including but not limited to —S(O)CH$_2$CH$_2$OCH$_2$-pyridinyl), —S(O)-heteroalkyl-heterocylyl (including but not limited to —S(O)CH$_2$CH$_2$OCH$_2$-piperidin-1yl, —S(O)CH$_2$CH$_2$OCH$_2$-morpholinyl, and —S(O)CH$_2$CH$_2$OCH$_2$— (4N-Me-piperazinyl), or —S(O)-heteroalkyl-cycloalkyl (including —S(O)CH$_2$CH$_2$OCH$_2$— (cyclobutyl)). In yet other embodiments, R$_1$ is —S(O)$_2$-heteroalkylaryl (including but not limited to —S(O)$_2$CH$_2$CH$_2$OCH$_2$C$_6$H$_6$), —S(O)$_2$-heteroalkylheteroaryl (including but not limited to —S(O)$_2$CH$_2$CH$_2$OCH$_2$-pyridinyl), —S(O)$_2$-heteroalkyl-heterocylyl (including but not limited to —S(O)$_2$CH$_2$CH$_2$OCH$_2$-piperidin-1yl, —S(O)$_2$CH$_2$CH$_2$OCH$_2$-morpholinyl, and —S(O)$_2$CH$_2$CH$_2$OCH$_2$— (4N-Me-piperazinyl), or —S(O)$_2$-heteroalkyl-cycloalkyl (including —S(O)$_2$CH$_2$CH$_2$OCH$_2$— (cyclobutyl)). Additionally, R$_1$ is —S(O)$_2$NR$^{31}$-heteroalkylaryl (including but not limited to —S(O)$_2$NHCH$_2$CH$_2$OCH$_2$C$_6$H$_6$), —S(O)$_2$NR$^{31}$-heteroalkylheteroaryl (including but not limited to —S(O)$_2$NHCH$_2$CH$_2$OCH$_2$pyridinyl), —S(O)$_2$NR$^{31}$ heteroalkyl-heterocylyl (including but not limited to —S(O)$_2$NH—CH$_2$CH$_2$OCH$_2$piperidin-1yl, —S(O)$_2$NHCH$_2$CH$_2$OCH$_2$morpholinyl, and —S(O)$_2$NHCH$_2$CH$_2$OCH$_2$(4N-Me-piperazinyl), or —S(O)$_2$NR$^{31}$-heteroalkyl-cycloalkyl (including —S(O)$_2$NH—CH$_2$CH$_2$OCH$_2$— (cyclobutyl)). In other embodiments, R$_1$ is —N(R$^{31}$)C(O)-heteroalkylaryl (including but not limited to —NHC(O)CH$_2$CH$_2$OCH$_2$C$_6$H$_6$), —N(R$^{31}$)C(O)-heteroalkylheteroaryl (including but not limited to —NHC(O)CH$_2$CH$_2$OCH$_2$-pyridinyl), —N(R$^{31}$)C(O)-heteroalkyl-heterocylyl (including but not limited to —NHC(O)CH$_2$CH$_2$OCH$_2$-piperidin-1yl, —NHC(O)CH$_2$CH$_2$OCH$_2$-morpholinyl, and —NHC(O)CH$_2$CH$_2$OCH$_2$— (4N-Me-piperazinyl), or N(R$^{31}$)C(O)-heteroalkyl-cycloalkyl (including —NHC(O)CH$_2$CH$_2$OCH$_2$— (cyclobutyl)). In yet other embodiments, R$_1$ is —NR$^{31}$-heteroalkylaryl (including but not limited to —NHCH$_2$CH$_2$OCH$_2$C$_6$H$_6$), —NR$^3$-heteroalkylheteroaryl (including but not limited to —N(Me)CH$_2$CH$_2$OCH$_2$-pyridinyl), —NR$^{31}$-heteroalkyl-heterocylyl (including but not limited to —NHCH$_2$CH$_2$OCH$_2$-piperidin-1yl, —NHCH$_2$CH$_2$OCH$_2$-morpholinyl, and —NHCH$_2$CH$_2$OCH$_2$— (4N-Me-piperazinyl), or NR$^{31}$-heteroalkyl-cycloalkyl (including —NHCH$_2$CH$_2$OCH$_2$— (cyclobutyl)).

The invention also provides compounds wherein R$_1$ is -L-arylalkyl or -L-heteroarylalkyl, wherein aryl, alkyl and heteroaryl are as described herein. In some embodiments, L is absent and R$_1$ is -arylalkyl (including but not limited to -(3-methyl) phen-1yl, and -(4-ethyl)phenyl) or -L-heteroarylalkyl (including but not limited to -(4-(2-morpholinyl)ethyl)pyridin-2-yl and -(5-(2-morpholinyl)ethyl)pyridin-2-yl). In other embodiments, R$_1$ is —C(O)-arylalkyl (including but not limited to —C(O)— (3-methyl) phen-1yl, and —C(O)— (4-ethyl)phenyl) or —C(O)-heteroarylalkyl (including but not limited to —C(O)— (4-(2-morpholinyl)ethyl)pyridin-2-yl and C(O—)(5-(2-morpholinyl)ethyl)pyridin-2-yl). In other embodiments, R$_1$ is —C(O)O-arylalkyl (including but not limited to C(O)O— (3-methyl) phen-1yl, and —C(O)O— (4-ethyl)phenyl) or —C(O)O-heteroarylalkyl (including but not limited to to —C(O)O(-4-(2-morpholinyl)ethyl)pyridin-2-yl and —C(O)O— (5-(2-morpholinyl)ethyl)pyridin-2-yl). In other embodiments, R$_1$ is —C(O)O-arylalkyl (including but not limited to —C(O)O— (3-methyl) phen-1yl, and —C(O)O— (4-ethyl)phenyl) or —C(O)O-heteroarylalkyl (including but not limited to —C(O)O— (4-(2-morpholinyl)ethyl)pyridin-2-yl and —C(O)O— (5-(2-morpholinyl)ethyl)pyridin-2-yl). In some other embodiments, R$_1$ is —C(O) NR$^{31}$-arylalkyl (including but not limited to —C(O)NH— (3-methyl) phen-1yl, and —C(O)NH— (4-ethyl)phenyl) or —C(O)NR$^{31}$-heteroarylalkyl (including but not limited to —C(O)NH— (4-(2-morpholinyl)ethyl)pyridin-2-yl and —C(O)NH— (5-(2-morpholinyl)ethyl)pyridin-2-yl). R$_1$ may also be —S-arylalkyl (including but not limited to —S-(3-methyl) phen-1yl, and —S-(4-ethyl)phenyl) or —S-heteroarylalkyl (including but not limited to —S-(4-(2-morpholinyl)ethyl)pyridin-2-yl and —S-(5-(2-morpholinyl)ethyl)pyridin-2-yl). In other embodiments, R$_1$ is —S(O)-arylalkyl (including but not limited to —S(O)-(3-methyl) phen-1yl, and —S(O)-(4-ethyl)phenyl) or —S(O)-heteroarylalkyl (including but not limited to —S(O)-(4-(2-morpholinyl)ethyl)pyridin-2-yl and —S(O)-(5-(2-morpholinyl)ethyl)pyridin-2-yl). In yet other embodiments, R$_1$ is —S(O)$_2$-arylalkyl (including but not limited to —S(O)$_2$-(3-methyl) phen-1yl, and —S(O)$_2$-(4-ethyl)phenyl) or —S(O)$_2$-heteroarylalkyl (including but not limited to —S(O)$_2$-(4-(2-morpholinyl)ethyl)pyridin-2-yl and —S(O)$_2$-(5-(2-morpholinyl)ethyl)pyridin-2-yl). Alternatively, R$_1$ is —S(O)$_2$NR$^{31}$-arylalkyl (including but not limited to —S(O)$_2$NH— (3-methyl) phen-1yl, and —S(O)$_2$NH— (4-ethyl)phenyl) or —S(O)$_2$NR$^{31}$-heteroarylalkyl (including but not limited to —S(O)$_2$NH— (4-(2-morpholinyl)ethyl)pyridin-2-yl and —S(O)$_2$NH— (5-(2-morpholinyl)ethyl)pyridin-2-yl). In other embodiments, R$_1$ is —N(R$^{31}$)C(O)-arylalkyl (including but not limited to —N(Me)C(O)-(3-methyl) phen-1yl, and —NHC(O)-(4-ethyl)phenyl) or —N(R$^{31}$)C(O)-heteroarylalkyl (including but not limited to —N(Me)C(O)— (4-(2-morpholinyl)ethyl) pyridin-2-yl and —NHC(O)— (5-(2-morpholinyl)ethyl) pyridin-2-yl). Additionally, R$_1$ is —NR$^{31}$-arylalkyl (including but not limited to —N(Me)-(3-methyl) phen-1yl, and —NH— (4-ethyl)phenyl) or —N(R$^{31}$)-heteroarylalkyl (including but not limited to N(Me)(4-(2-morpholinyl)ethyl) pyridin-2-yl and —NH(5-(2-morpholinyl)ethyl)pyridin-2-yl).

In some embodiments, R$_1$ is -L- (unsubstituted or substituted heterocyclyl) wherein heterocyclyl includes but is not limited to azetidinyl, pyrrolidinyl, tetrahydrofuranyl, piperidinyl, tetrahydropyranyl, thiazolidinyl, imidazolidinyl, morpholinyl, and piperazinyl. In some embodiments, L is absent and R$_1$ is heterocyclyl (including but not limited to morpholinyl, thiomorpholinyl, azetidinyl, pyrrolidinyl, tetrahydropyranyl, piperazinyl, and 4-NMe-piperazinyl). In some embodiments, R$_1$ is —C(O)-heterocyclyl (including but not limited to —C(O)-morpholinyl, —C(O)-thiomorpholinyl, —C(O)-azetidinyl, —C(O)-pyrrolidin-1-yl, —C(O)-etrahydropyran-4-yl, —C(O)-piperazin-1-yl, and —C(O)— (4-NMe-piperazin-1-yl)). In some other embodiments, R$_1$ is —C(O)O-heterocyclyl (including but not limited to —C(O)O-azetidinyl, —C(O)O-pyrrolidin-3-yl, —C(O)O-tetrahydropyran-4-yl, —C(O)O-piperazin-3-yl, and —C(O)O(4-NMe-piperazin-3-yl)). In yet other embodiments, R$_1$ is C(O)NR$^{31}$-heterocyclyl (including but not limited to —C(O)NH-azetidinyl, —C(O)NH-pyrrolidin-3-yl, C(O)NH-tetrahydropyran-4-yl, —C(O)NH-piperazin-3-yl, and —C(O)NH(4-NMe-piperazin-3-yl)). R$_1$ may also be —S-heterocyclyl (including but not limited to —S-azetidinyl, —S-pyrrolidin-3-yl, S-tetrahydropyran-4-yl, —S-piperazin-3-yl, and —S(4-NMe-)piperazin-3-yl). The invention also provides compounds wherein $R_1$ is —S(O)-heterocyclyl (including but not limited to —S(O)-azetidinyl, —S(O)-pyrrolidin-3-yl, S(O)-tetrahydropyran-4-yl, —S(O)-piperazin-3-yl, and —S(O)—(4-NMe-)piperazin-3-yl). In other embodiments, $R_1$ is —S(O)$_2$-heterocyclyl (including but not limited to —S(O)$_2$-azetidinyl, —S(O)$_2$-pyrrolidin-3-yl, S(O)$_2$-tetrahydropyran-4-yl, —S(O)$_2$-piperazin-3-yl, and —S(O)$_2$ (4-NMe-)piperazin-3-yl). In some other embodiments, $R_1$ is —S(O)$_2$NR$^{31}$-heterocyclyl (including but not limited to —S(O)$_2$NH-azetidinyl, —S(O)$_2$NH-pyrrolidin-3-yl, S(O)$_2$NH-tetrahydropyran-4-yl, —S(O)$_2$NH-piperazin-3-yl, and —S(O)$_2$NH (4-NMe-)piperazin-3-yl). Alternatively, $R_1$ is —N(R$^{31}$)C(O)-heterocyclyl (including but not limited to —N(Me)C(O)-azetidinyl, —N(Me)C(O)-pyrrolidin-3-yl, —N(Me)C(O)-tetrahydropyran-4-yl, —N(Me)C(O)-piperazin-3-yl, and —N(Me)C(O)-(4-NMe-)piperazin-3-yl). In yet other embodiments, $R_1$ is —NR$^{31}$-heterocyclyl (including but not limited to —N(Me)-azetidinyl, —NH-pyrrolidin-3-yl, —N(Me)-tetrahydropyran-4-yl, —N(Me)piperazin-3-yl, and —NH-(4-NMe-)piperazin-3-yl).

In some embodiments, each alkyl, cycloalkyl, aryl, heteroaryl, heterocyclyl, alkenyl, alkynyl, heteroalkyl, forming all or part of $R_1$ may be substituted by one or more $R^3$. $R^3$ is hydrogen or halogen, such as chloro, bromo, fluoro or iodo. In other embodiments, $R^3$ is unsubstituted or substituted aryl (including but not limited to monocyclic or bicyclic aryl) or unsubstituted or substituted heteroaryl, including but not limited to monocyclic and bicyclic heteroaryl. Monocyclic heteroaryl $R^3$ includes but is not limited to pyrrolyl, thienyl, furyl, pyridinyl, pyranyl, imidazolyl, thiazolyl, pyrazolyl, and oxazolyl. Bicyclic heteroaryl $R^3$ includes but is not limited to benzothiophenyl, benzofuryl, indolyl, quinolinyl, isoquinolinyl, benzimidazolyl, benzoxazolyl, benzothiazolyl, quinazolinyl, azaindolyl, pyrazolopyrimidinyl, and purinyl $R^3$ is also unsubstituted or substituted $C_{1-10}$alkyl (including but not limited to CH$_3$, —CH$_2$CH$_3$, n-propyl, isopropyl, n-butyl, tert-butyl, sec-butyl, pentyl, hexyl, and heptyl) or unsubstituted or substituted $C_{3-8}$cycloalkyl (including but not limited to cyclopropyl, cyclobutyl, and cyclopentyl. In other embodiments, $R^3$ is -alkylaryl, -alkyl heteroaryl, or -alkylheterocyclyl. Alkyl, aryl, and heteroaryl are as described herein and the heterocyclyl is unsubstituted or substituted (non-limiting examples include pyrrolidinyl, tetrahydrofuranyl, piperidinyl, tetrahydropyranyl, thiazolidinyl, imidazolidinyl, morpholinyl, and piperazinyl) For $R^3$-alkylaryl, -alkyl heteroaryl, or -alkylheterocyclyl, connection to $R_1$ is through the alkyl portion of the moiety. In yet other embodiments, $R^3$ is unsubstituted or substituted alkenyl (including but not limited to unsubstituted or substituted $C_2$-$C_{10}$alkenyl such as, for example, vinyl, allyl, 1-methyl propen-1-yl, butenyl, or pentenyl) or unsubstituted or substituted alkynyl (including but not limited to unsubstituted or substituted $C_2$-$C_{10}$alkynyl such as acetylenyl, propargyl, butynyl, or pentynyl). Other compounds are provided by the invention, wherein $R^3$ is -alkenylaryl, -alkenylheteroaryl, -alkenylheteroalkyl, or -alkenylheterocylcyl, wherein the alkenyl, aryl, heteroaryl, heteroalkyl, and heterocyclyl are as described herein. The $R^3$-alkenylaryl, -alkenylheteroaryl, -alkenylheteroalkyl, or -alkenylheterocylcyl moiety is attached to $R_1$ through the alkenyl portion of the moiety. In other embodiments, $R^3$ is -alkynylaryl, -alkynyl heteroaryl, -alkynylheteroalkyl, -alkynylheterocylyl, -alkynylcycloalkyl, or -alkynylcycloalkenyl, wherein alkynyl, aryl, heteroaryl, heteroalkyl, heterocyclyl, cycloalkyl are as described herein.

A $R^3$-cycloalkenyl moiety is unsubstituted or substituted $C_3$-$C_8$cycloalkenyl (including but not limited to cyclopentenyl and cyclohexenyl). The $R^3$-alkynylaryl, -alkynyl heteroaryl, -alkynylheteroalkyl, -alkynylheterocylyl, -alkynylcycloalkyl, or -alkynylcycloalkenyl is attached to $R_1$ through the alkynyl portion of the moiety. Some nonlimiting examples include 2-cyclopropylacetylenyl and 3-(morpholinyl)proparg-1-yl. In some other embodiments, $R^3$ is -alkoxy alkyl, -alkoxyalkenyl, or -alkoxyalkynyl, wherein alkoxy, alkyl, alkenyl, and alkynyl are as described herien. The $R^3$-alkoxy alkyl, -alkoxyalkenyl, or -alkoxyalkynyl is attached to $R_1$ through the alkoxy portion of the moiety. In yet other embodiments, $R^3$ is -arylalkenyl, -arylalkynyl, or aryl-heterocyclyl, wherein aryl, alkenyl, alkynyl or heterocyclyl is as described herein. The $R^3$-arylalkenyl, -arylalkynyl, or aryl-heterocyclyl is attached to $R_1$ through the aryl portion of the moiety. Nonlimiting examples include 4-allylphen-1-yl, 2(morpholinyl)phenyl and 4-(piperidinyl)phenyl Alternatively, $R^3$ is -heteroaryl-alkyl, -heteroaryl-alkenyl, -heteroaryl-alkynyl, -heteroaryl-cycloalkyl, -heteroaryl-heteroalkyl, or -heteroaryl-heterocyclyl, wherein heteroaryl, alkyl, alkenyl, alkynyl, cycloalkyl, heteroalkyl, and heterocyclyl are as described herein. The $R^3$ heteroaryl-alkyl, heteroaryl-alkenyl, heteroaryl-alkynyl, heteroaryl-cycloalkyl, heteroaryl-heteroalkyl, or heteroaryl-heterocyclyl is attached to $R_1$ through the heteroaryl portion of the moiety.

In some other embodiments, each aryl or heteroaryl that forms part or all of $R^3$ is unsubstituted or is substituted with one or more independent halo, —OH, —R$^{31}$, —CF$_3$, —OCF$_3$, —OR$^{31}$, —NR$^{31}$R$^{32}$, —NR$^{34}$R$^{35}$, —C(O)R$^{31}$, CO$_2$R$^{31}$, —C(=O)NR$^{31}$R$^{32}$, —C(=O)NNR$^{34}$R$^{35}$, —NO$_2$, —CN, —S(O)$_{0-2}$R$^{31}$, —SO$_2$NR$^{31}$R$^{32}$, —SO$_2$NR$^{34}$R$^{35}$, —NR$^{31}$C(=O)R$^{32}$, NR$^{31}$C(=O)OR$^{32}$, —NR$^{31}$C(=O)NR$^{32}$R$^{33}$, —NR$^{31}$S(O)$_{0-2}$R$^{32}$, —C(=S)OR$^{31}$, —C(=O)SR$^{31}$, —NR$^{31}$C(=NR$^{32}$)NR$^{33}$R$^{32}$, —NR$^{31}$C(=NR$^{32}$)OR$^{33}$, —NR$^{31}$C(=NR$^{32}$)SR$^{33}$, —OC(=O)OR$^{33}$, —OC(=O)NR$^{31}$R$^{32}$, —OC(=O)SR$^{31}$, —SC(=O)OR$^{31}$, —P(O)OR$^{31}$R$^{32}$, or —SC(=O)NR$^{31}$R$^{32}$ substituents.

In yet other embodiments, each alkyl, cycloalkyl, heterocyclyl, or heteroalkyl forming all or part of $R^3$ is unsubstituted or substituted with one or more halo, —OH, —R$^{31}$, —CF$_3$, —OCF$_3$, —OR$^{31}$, —O-aryl, —NR$^{31}$R$^{32}$, —NR$^{34}$R$^{35}$, —C(O)R$^{31}$, —CO$_2$R$^{31}$, —C(=O)NNR$^{34}$R$^{35}$, —C(=O)NR$^{31}$R$^{32}$, —SO$_2$NR$^{31}$R$^{32}$, or —SO$_2$NR$^{34}$R$^{35}$ substituents.

Alternatively, each alkyl, cycloalkyl, aryl, heteroaryl, heterocyclyl, alkenyl, alkynyl, heteroalkyl, forming all or part of $R_1$ may be substituted by one or more $R^3$ wherein $R^3$ is, each $R^3$ is —OH, —R$^{31}$, —CF$_3$, —OCF$_3$, —OR$^{31}$, NR$^{31}$R$^{32}$, —NR$^{34}$R$^{35}$, —C(O)R$^{31}$, —CO$_2$R$^{31}$, —C(=O)NR$^{31}$R$^{32}$, —C(=O)NNR$^{34}$R$^{35}$, —NO$_2$, —CN, —S(O)$_2$R$^{31}$, —SO$_2$NR$^{31}$R$^{32}$, —SO$_2$NR$^{34}$R$^{35}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_{0-2}$R$^{32}$, —C(=S)OR$^{31}$, —C(=O)SR$^{31}$, —NR$^{31}$C(=NR$^{32}$)NR$^{33}$R$^{32}$, —NR$^{31}$C(=NR$^{32}$)OR$^{33}$, —NR$^{31}$C(=NR$^{32}$)SR$^{33}$, —OC(=O)OR$^{33}$, —OC(=O)NR$^{31}$R$^{32}$, —OC(=O)SR$^{31}$, —SC(=O)OR$^{31}$, —P(O)OR$^{31}$OR$^{32}$, or —SC(=O)NR$^{31}$R$^{32}$ substituents, Nonlimiting exemplary R$_1$ are described in Table 1.

In various embodiments of Formula I, M$_1$ is:

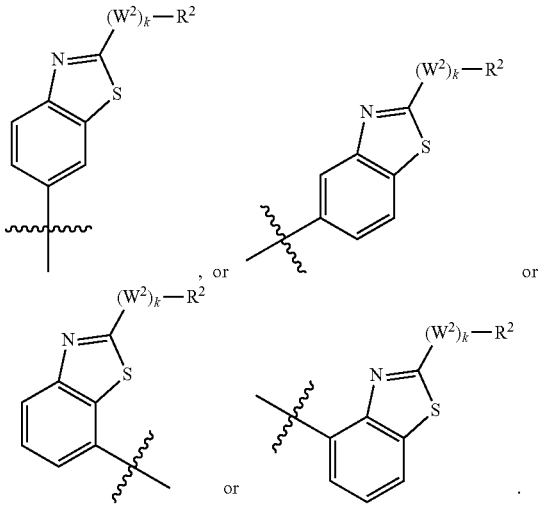

In some embodiments of the invention, M$_1$ is benzothiazolyl substituted with —(W$^2$)$_k$—R$^2$. W$^2$ can be —O—, —S(O)$_{0-2}$— (including but not limited to —S—, —S(O)—, and —S(O)$_2$—), —C(O)—, or —C(O)O—. In other embodiments, W$^1$ is —NR$^6$— or —CH(R$^6$)N(R$^7$)—, wherein R$^6$ and R$^7$ are each independently hydrogen, unsubstituted or substituted C$_1$-C$_{10}$alkyl (which includes but is not limited to —CH$_3$, —CH$_2$CH$_3$, n-propyl, isopropyl, n-butyl, tert-butyl, sec-butyl, pentyl, hexyl, and heptyl), unsubstituted or substituted C$_2$-C$_{10}$ alkenyl (including but not limited to alkenyl such as, for example, vinyl, allyl, 1-methyl propen-1-yl, butenyl, or pentenyl). Additionally when W$^2$ is —NR$^6$— or —CH(R$^6$)N(R$^7$)—, R$^6$ and R$^7$ are each independently unsubstituted or substituted aryl (including phenyl and naphthtyl). In yet other embodiments, when W$^2$ is —NR$^6$— or —CH(R$^6$)N(R$^7$)—, R$^6$ and R$^7$ are each independently heteroaryl, wherein the heteroaryl is unsubstituted or substituted. R$^6$ and R$^7$ heteroaryl is monocyclic heteroaryl, and includes but is not limited to imidazolyl, pyrrolyl, oxazolyl, thiazolyl, and pyridinyl. In some other embodiments, when W$^2$ is NR$^6$ or —CH(R$^6$)N(R$^7$)—, R$^6$ and R$^7$ are each independently unsubstituted or substituted heterocyclyl (which includes but is not limited to pyrrolidinyl, tetrahydrofuranyl, piperidinyl, tetrahydropyranyl, thiazolidinyl, imidazolidinyl, morpholinyl, and piperazinyl) or unsubstituted or substituted C$_{3-8}$cycloalkyl (including but not limited to cyclopropyl, cyclobutyl, and cyclopentyl). Non limiting exemplary W$^2$ include —NH—, —N(cyclopropyl), and —N(4-N-piperidinyl).

W$^2$ may also be —C(O)N(R$^6$)—, —N(R$^6$)C(O)—, —N(R$^6$)S(O)—, —N(R$^6$)S(O)$_2$—CH(R$^6$)N(C(O)OR$^7$)—, CH(R$^7$)N(C(O)R$^7$)—, —CH(R$^6$)N(SO$_2$R$^7$)—, —CH(R$^6$)C(O)N(R$^7$)—, —CH(R$^6$)N(R$^7$)C(O)—, —CH(R$^6$)N(R$^7$)S(O)—, or CH(R$^6$)N(R$^7$)S(O)$_2$—; wherein R$^6$ and R$^7$ are each independently hydrogen, unsubstituted or substituted C$_1$-C$_{10}$alkyl (which includes but is not limited to —CH$_3$, —CH$_2$CH$_3$, n-propyl, isopropyl, n-butyl, tert-butyl, sec-butyl, pentyl, hexyl, and heptyl) or unsubstituted or substituted C$_2$-C$_{10}$alkenyl (including but not limited to alkenyl such as, for example, vinyl, allyl, 1-methyl propen-1-yl, butenyl, or pentenyl). Additionally when W$^2$ is —C(O)N (R$^6$), N(R$^6$)C(O)—, —N(R$^6$)S(O)—, —N(R$^6$)S(O)$_2$—CH (R$^6$)N(C(O)OR$^7$)—, —CH(R$^7$)N(C(O)R$^7$)—, —CH(R$^6$)N (SO$_2$R$^7$), CH(R$^6$)C(O)N(R$^7$)—, —CH(R$^6$)N(R$^7$)C(O)—, —CH(R$^6$)N(R$^7$)S(O)—, or —CH(R$^6$)N(R$^7$)S(O)$_2$—, R$^6$ and R$^7$ are each independently unsubstituted or substituted aryl (including phenyl and naphthtyl). In yet other embodiments, when W$^2$ is —C(O)N(R$^6$)—, —N(R$^6$)C(O)—, —N(R$^6$)S (O)—, —N(R$^6$)S(O)$_2$—CH(R$^6$)N(C(O)OR$^7$)—, —CH(R$^7$) N(C(O)R$^7$), CH(R$^6$)N(SO$_2$R$^7$)—, —CH(R$^6$)C(O)N(R$^7$)—, —CH(R$^6$)N(R$^7$)C(O)—, —CH(R$^6$)N(R$^7$)S(O)—, or —CH (R$^6$)N(R$^7$)S(O)$_2$—, R$^6$ and R$^7$ are each independently heteroaryl, wherein the heteroaryl is unsubstituted or substituted. R$^6$ and R$^7$ heteroaryl is monocyclic heteroaryl, and includes but is not limited to imidazolyl, pyrrolyl, oxazolyl, thiazolyl, and pyridinyl. In some other embodiments, when W$^2$ is —C(O)N(R$^6$)—, —N(R$^6$)C(O)—, —N(R$^6$)S(O)—, —N(R$^6$)S(O)$_2$—CH(R$^6$)N(C(O)OR$^7$)—, —CH(R$^7$)N(C(O) R$^7$)—, —CH(R$^6$)N(SO$_2$R$^7$)—, —CH(R$^6$)C(O)N(R$^7$)—, —CH(R$^6$)N(R$^7$)C(O)—, —CH(R$^6$)N(R$^7$)S(O)—, or —CH (R$^6$)N(R$^7$)S(O)$_2$—, R$^6$ and R$^7$ are each independently unsubstituted or substituted heterocyclyl (which includes but is not limited to pyrrolidinyl, tetrahydrofuranyl, piperidinyl, tetrahydropyranyl, thiazolidinyl, imidazolidinyl, morpholinyl, and piperazinyl) or unsubstituted or substituted C$_{3-8}$cycloalkyl ((including but not limited to cyclopropyl, cyclobutyl, and cyclopentyl). Non limiting exemplary W$^2$ are —C(CO)NH—, —N(Me)C(O)—, —NHC(O)—, N(Me)S(O)—, —NHS(O)$_2$—, —CH(Me)N(C(O)Ophenyl)-, —CH(Me)N(SO$_2$Me)-, —CH$_2$C(O)N(cyclopropyl)-, —CH$_2$N(allyl)C(O)—, —CH(Me)NHS(O)—, or —CH (Me)NHS(O)$_2$—.

In other embodiments, W$^2$ may also be —N(R$^6$)C(O)N (R$^7$)— or —CH(R$^7$)C(O)—, wherein R$^6$ and R$^7$ are each independently hydrogen, unsubstituted or substituted C$_1$-C$_{10}$alkyl (which includes but is not limited to —CH$_3$, —CH$_2$CH$_3$, n-propyl, isopropyl, n-butyl, tert-butyl, sec-butyl, pentyl, hexyl, and heptyl) or unsubstituted or substituted C$_2$-C$_{10}$alkenyl (including but not limited to alkenyl such as, for example, vinyl, allyl, 1-methyl propen-1-yl, butenyl, or pentenyl). Additionally when W$^2$ is —N(R$^6$)C (O)N(R$^7$)— or —CH(R$^7$)C(O)—, R$^6$ and R$^7$ are each independently unsubstituted or substituted aryl (including phenyl and naphthtyl). In yet other embodiments, W$^2$ is —N(R$^6$)C(O)N(R$^7$)— or —CH(R$^7$)C(O)—, R$^6$ and R$^7$ are each independently heteroaryl, wherein the heteroaryl is unsubstituted or substituted. R$^6$ and R$^7$ heteroaryl is monocyclic heteroaryl, and includes but is not limited to imidazolyl, pyrrolyl, oxazolyl, thiazolyl, and pyridinyl. In some other embodiments, W$^2$ is —N(R$^6$)C(O)N(R$^7$)— or —CH (R$^7$)C(O)—, R$^6$ and R$^7$ are each independently unsubstituted or substituted heterocyclyl (which includes but is not limited to pyrrolidinyl, tetrahydrofuranyl, piperidinyl, tetrahydropyranyl, thiazolidinyl, imidazolidinyl, morpholinyl, and piperazinyl) or unsubstituted or substituted C$_{3-8}$cycloalkyl ((including but not limited to cyclopropyl, cyclobutyl, and cyclopentyl). Non limiting examples of —N(R$^6$)C(O)N (R$^7$)— or —CH(R$^7$)C(O)— include —NHC(O)NH—, NHC (O)N(Me)-, and —CH$_2$C(O)—.

In other embodiments, W$^2$ is —NR$^{34}$R$^{35}$, wherein —NR$^{34}$R$^{35}$ is as described above.

In other embodiments wherein W$^2$ comprises R$^6$ and/or R$^7$ alkyl, alkenyl, aryl, heteroaryl, heterocyclyl or cycloalkyl, each R$^6$ and/or R$^7$ alkyl, alkenyl, aryl, heteroaryl, heterocyclyl or cycloalkyl is unsubstituted or substituted by one or more independent R$^8$ substituents. In some embodiments, the R$^6$ and/or R$^7$ alkyl, alkenyl, aryl, heteroaryl, heterocyclyl or cycloalkyl is substituted by one or more halo, —SH, NH$_2$, —NO$_2$, or —CN. In other embodiments, R$^6$ and/or R$^7$ alkyl, alkenyl, aryl, heteroaryl, heterocyclyl or cycloalkyl is substituted by one or more —OR$^{31}$, —NR$^{31}$R$^{32}$, —CO$_2$R$^{31}$, or —C(=O)NR$^{31}$R$^{32}$. Nonlimiting exemplary substituted R$^6$ and/or R$^7$ alkyl, alkenyl, aryl, heteroaryl, heterocyclyl or cycloalkyl include 1-(3-hydroxyl)propyl, 3-diethylaminophenyl, 3-carboxymethyl pyridinyl, and 4-(carboxamido)piperazinyl.

Alternatively, wherein W$^2$ comprises R$^6$ and/or R$^7$alkyl, alkenyl, aryl, heteroaryl, heterocyclyl or cycloalkyl, the R$^6$ and/or R$^7$alkyl, alkenyl, aryl, heteroaryl, heterocyclyl or cycloalkyl is substituted by one or more R$^8$ substituents wherein R$^8$ is —SO$_2$NR$^{34}$R$^{35}$, —NR$^{34}$R$^{35}$, —SO$_2$NR$^{31}$R$^{32}$, or —C(=O) NR$^{34}$R$^{35}$, wherein the R$^{34}$ and R$^{35}$ of NR$^{31}$R$^{32}$ are taken together to form a cyclic moiety as described herein. Non-limiting exemplary substituted R$^6$ and/or R$^7$ alkyl, alkenyl, aryl, heteroaryl, heterocyclyl or cycloalkyl include -ethylSO$_2$(piperazinyl), iso(-3-azetidinyl)buten-1-yl, and (4-morpholinyl)-piperazinyl. In yet other embodiments, R$^6$ and/or R$^7$ alkyl, alkenyl, aryl, heteroaryl, heterocyclyl or cycloalkyl is substituted by one or more —CO$_2$aryl, —S(O)$_{0-2}$aryl, —S(O)$_{0-2}$ alkyl, alkyl, cycloalkyl, alkenyl, or alkynyl, wherein the aryl, alkyl, cycloalkyl, alkenyl or alkenyl are as described herein. Non-limiting exemplary substituted R$^6$ and/or R$^7$ alkyl, alkenyl, aryl, heteroaryl, heterocyclyl or cycloalkyl include (2-phenylsulfonyl)ethyl, (4-methylsulfonyl)cyclohexyl, and (3-phenylsulfonyl)propargyl.

In other embodiments, wherein W$^2$ comprises R$^6$ and/or R$^7$ alkyl, alkenyl, aryl, heteroaryl, heterocyclyl or cycloalkyl, the R$^6$ and/or R$^7$ alkyl, alkenyl, aryl, heteroaryl, heterocyclyl or cycloalkyl is substituted by one or more R$^8$ wherein R$^8$ is -aryl-alkyl, -aryl-alkenyl, -aryl-alkynyl, -heteroaryl-alkyl, -heteroaryl-alkenyl, or -heteroaryl-alkynyl. When R$^8$ is -aryl-alkyl, -aryl-alkenyl, or -aryl-alkynyl, each aryl, alkyl, alkenyl, and alkynyl is as described herein and connection to R$^6$ and/or R$^7$ is made through the aryl portion of each moiety. Each R$^8$-aryl-alkyl, -aryl-alkenyl, and -aryl-alkynyl is unsubstituted or substituted with one or more independent halo, cyano, nitro, —O-alkyl, alkyl, alkenyl, alkynyl, haloalkyl, haloalkenyl, haloalkynyl, —COOH, —C(=O)NR$^{31}$R$^{32}$, —C(=O) NR$^{34}$R$^{35}$, SO$_2$NR$^{34}$R$^{35}$, —SO$_2$NR$^{31}$R$^{32}$, —NR$^{31}$R$^{32}$, or —NR$^{34}$R$^{35}$ substituents. Alternatively, R$^8$ is -heteroaryl-alkyl, -heteroaryl-alkenyl, or -heteroaryl-alkynyl, wherein heteroaryl, alkyl, alkenyl and alkynyl are as described herein and connection to R$^6$ and/or R$^7$ is made through the heteroaryl portion of each moiety. Each R$^8$-heteroaryl-alkyl, -heteroaryl-alkenyl, and -heteroaryl-alkynyl is unsubstituted or substituted with one or more independent halo, cyano, nitro, —O-alkyl, alkyl, alkenyl, alkynyl, haloalkyl, haloalkenyl, haloalkynyl, —COOH, —C(=O)NR$^{31}$R$^{32}$C(=O) NR$^{34}$R$^{35}$, —SO$_2$NR$^{34}$R$^{35}$, —SO$_2$NR$^{31}$R$^{32}$, —NR$^{31}$R$^{32}$, or —NR$^{34}$R$^{35}$ substituents.

In some of the embodiments of the compounds of the invention, R$^2$ of (W$^2$)$_k$—R$^2$, is hydrogen or halogen, such as chloro, bromo, fluoro or iodo. In other embodiments, R$^2$ is substituted monocyclic aryl (including for example, 3-bromophenyl, 4-methyoxyphenyl, and 3-cyanophenyl) or bicyclic aryl. R$^2$ bicyclic aryl is unsubstituted or substituted (including naphthyl and fluorenyl). In other embodiments, R$^2$ is unsubstituted or substituted heteroaryl, including but not limited to monocyclic and bicyclic heteroaryl. Monocyclic heteroaryl R$^2$ includes but is not limited to pyrrolyl, thienyl, furyl, pyridinyl, pyranyl, imidazolyl, thiazolyl, pyrazolyl, and oxazolyl. Bicyclic heteroaryl R$^2$ includes but is not limited to benzothiophenyl, benzofuryl, indolyl, quinolinyl, isoquinolinyl, benzimidazolyl, benzoxazolyl, benzothiazolyl, quinazolinyl, azaindolyl, pyrazolopyrimidinyl, and purinyl R$^2$ is also unsubstituted or substituted C$_{1-10}$alkyl (including but not limited to CH$_3$, —CH$_2$CH$_3$, n-propyl, isopropyl, n-butyl, tert-butyl, sec-butyl, pentyl, hexyl, and heptyl) or unsubstituted or substituted C$_{3-8}$cycloalkyl (including but not limited to cyclopropyl, cyclobutyl, and cyclopentyl. In other embodiments, R$^2$ is -alkyl-substituted monocyclic aryl, -alkyl heteroaryl, or -alkylheterocyclyl. Alkyl, monaryl, and heteroaryl are as described herein and the heterocyclyl is unsubstituted or substituted (non-limiting examples include pyrrolidinyl, tetrahydrofuranyl, piperidinyl, tetrahydropyranyl, thiazolidinyl, imidazolidinyl, morpholinyl, and piperazinyl) For R$^2$-alkyl-substituted monocyclic aryl, -alkyl heteroaryl, or -alkylheterocyclyl, connection to W$^2$ or to the compound of Formula I is through the alkyl portion of the moiety. In yet other embodiments, R$^2$ is unsubstituted or substituted alkenyl (C$_2$-C$_{10}$alkenyl includes but not limited to vinyl, allyl, 1-methyl propen-1-yl, butenyl, or pentenyl) or unsubstituted or substituted alkynyl (C$_2$-C$_{10}$alkynyl includes but is not limited to acetylenyl, propargyl, butynyl, or pentynyl). Other compounds are provided by the invention, wherein R$^2$ is -alkenylaryl, -alkenylheteroaryl, -alkenylheteroalkyl, or -alkenylheterocyclcyl, wherein the alkenyl, aryl, heteroaryl, heteroalkyl, and heterocyclyl are as described herein. The R$^2$-alkenylaryl, -alkenylheteroaryl, -alkenylheteroalkyl, or -alkenylheterocyclcyl moiety is attached to W$^2$ or to the compound of Formula I through the alkenyl portion of the moiety. In other embodiments, R$^2$ is -alkynylaryl, -alkynyl heteroaryl, -alkynylheteroalkyl, -alkynylheterocylyl, -alkynylcycloalkyl, or -alkynylcycloalkenyl, wherein alkynyl, aryl, heteroaryl, heteroalkyl, heterocyclyl, cycloalkyl are as described herein.

A R$^2$-cycloalkenyl moiety is unsubstituted or substituted C$_3$-C$_8$cycloalkenyl (including but not limited to cyclopentenyl and cyclohexenyl). The R$^2$-alkynylaryl, -alkynyl heteroaryl, -alkynylheteroalkyl, -alkynylheterocylyl, -alkynylcycloalkyl, or -alkynylcycloalkenyl is attached to W$^2$ or to the compound of Formula I through the alkynyl portion of the moiety. Some nonlimiting examples include 2-cyclopropylacetylenyl and 3-(morpholinyl)proparg-1-yl. In some other embodiments, R$^2$ is -alkoxy alkyl, -alkoxyalkenyl, or -alkoxyalkynyl, wherein alkoxy, alkyl, alkenyl, and alkynyl are as described herien. The R$^2$-alkoxy alkyl, -alkoxyalkenyl, or -alkoxyalkynyl is attached to W$^2$ or to the compound of Formula I through the alkoxy portion of the moiety. In yet other embodiments, R$^2$ is -arylalkenyl, -arylalkynyl, or -aryl-heterocyclyl, wherein aryl, alkenyl, alkynyl or heterocyclyl is as described herein. The R$^2$-arylalkenyl, -arylalkynyl, or aryl-heterocyclyl is attached to W$^2$ or to the compound of Formula I through the aryl portion of the moiety. Nonlimiting examples include 4-allylphen-1-yl, 2(morpholinyl)phenyl and 4-(piperidinyl)phenyl Alternatively, R$^2$ is -heteroaryl-alkyl, heteroaryl-alkenyl, -heteroaryl-alkynyl, -heteroaryl-cycloalkyl, -heteroaryl-heteroalkyl, or -heteroaryl-heterocyclyl, wherein heteroaryl, alkyl, alkenyl, alkynyl, cycloalkyl, heteroalkyl, and heterocyclyl are as described herein. The R$^2$-heteroaryl-alkyl, -heteroaryl-alkenyl, -heteroaryl-alkynyl, -heteroaryl-cycloalkyl, -heteroaryl-heteroalkyl, or -heteroaryl-heterocyclyl is attached to W$^2$ or to the compound of Formula I through the heteroaryl portion of the moiety. Other compounds are provided by the invention, wherein $R^2$ is -(unsubstituted or substituted heterocyclyl) wherein heterocyclyl includes but is not limited to azetidinyl, pyrrolidinyl, tetrahydrofuranyl, piperidinyl, tetrahydropyranyl, thiazolidinyl, imidazolidinyl, morpholinyl, and piperazinyl. In other embodiments, $R^2$ is -heterocyclyl-heterocyclyl, and include without being limited to -(1-(N4-Me piperazinyl)piperidin-4-yl. In yet other embodiments, $R^2$ is -cycloalkyl-heterocyclyl wherein cycloalkyl and heterocyclyl are as described herein and is connected to $W^2$ or to the compound of Formula I through the cycloalkyl portion of the moiety. $R^2$-cycloalkyl-heterocyclyl include without limitation -(3-morpholinyl)cyclobut-1-yl, and -4-(morpholinyl)cyclohex-1-yl.

In some embodiments, each aryl or heteroaryl that forms part or all of $R^2$ is unsubstituted or is substituted with one or more independent halo, —OH, —$R^{31}$, —$CF_3$, —$OCF_3$, —$OR^{31}$, —$NR^{31}R^{32}$, —$NR^{34}R^{35}$, —$C(O)R^{31}$, —$CO_2R^{31}$, —$C(=O)NR^{31}R^{32}$, —$C(=O)NNR^{34}R^{35}$, —$NO_2$, CN, —$S(O)_{0-2}R^{31}$, $SO_2NR^{31}R^{32}$, $SO_2NR^{34}R^{35}$, —$NR^{31}C(=O)R^{32}$, —$NR^{31}C(=O)OR^{32}$—$NR^{31}C(=O)NR^{32}R^{33}$, —$NR^{31}S(O)_{0-2}R^{32}$, —$C(=S)OR^{31}$, $C(=O)SR^{31}$, —$NR^{31}C(=NR^{32})NR^{33}R^{32}$, —$NR^{31}C(=NR^{32})OR^{33}$, —$NR^{31}C(=NR^{32})SR^{33}$, —$OC(=O)OR^{33}$, —$OC(=O)NR^{31}R^{32}$, —$OC(=O)SR^{31}$, —$SC(=O)OR^{31}$, —$P(O)OR^{31}OR^{32}$, or —$SC(=O)NR^{31}R^{32}$ substituents.

In other embodiments, each alkyl, cycloalkyl, heterocyclyl, or heteroalkyl forming all or part of $R^2$ is unsubstituted or substituted with one or more halo, —OH, —$R^{31}$, —$CF_3$, —$OCF_3$, —$OR^{31}$, —O-aryl, —$NR^{31}R^{32}$, —$NR^{34}R^{35}$, —$C(O)R^{31}$, —$CO_2R^{31}$, —$C(=O)NNR^{34}R^{35}$, or —$C(=O)NR^{31}R^{32}$ substituents. In some embodiments, each alkyl, cycloalkyl, heterocyclyl, or heteroalkyl forming all or part of $R^2$ is unsubstituted or substituted with one or more —$C(=O)NNR^{34}R^{35}$, —$NO_2$, —CN, —$S(O)_{0-2}R^{31}$, —$SO_2NR^{31}R^{32}$, —$SO_2NR^{34}R^{35}$, —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, —$C(=S)OR^{31}$, —$C(=O)SR^{31}$, —$NR^{31}C(=NR^{32})NR^{33}R^{32}$, —$NR^{31}C(=NR^{32})OR^{33}$, —$NR^{31}C(=NR^{32})SR^{33}$, —$OC(=O)OR^{33}$, —$OC(=O)NR^{31}R^{32}$, —$OC(=O)SR^{31}$, —$SC(=O)OR^{31}$, —$P(O)OR^{31}OR^{32}$, or —$SC(=O)NR^{31}R^{32}$ substituents.

Additional, non-limiting exemplary —$(W^2)_k$—$R^2$ are described in Table 2.

The invention provides compounds of Formula I having a structure of one of the following formulae:

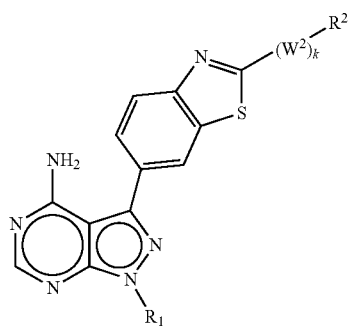

Formula II

-continued

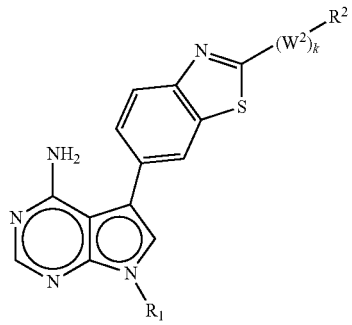

Formula III

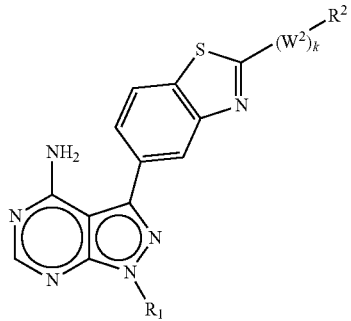

Formula IV

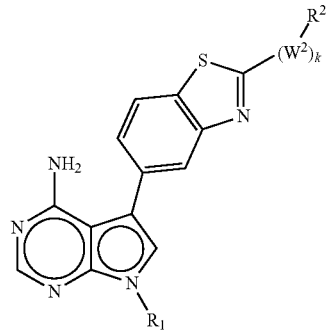

Formula V

In some further embodiments of the invention, the compound of Formulae I-V is a compound of one of the following formualae:

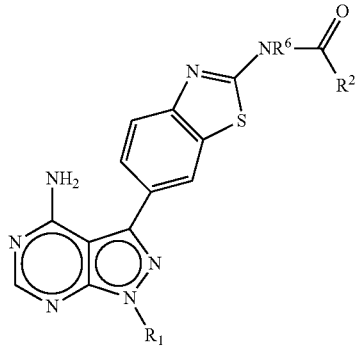

Formula II-1

Formula III-1
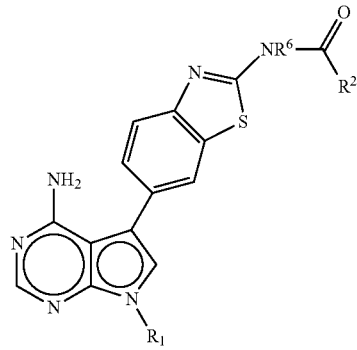
Formula III-2
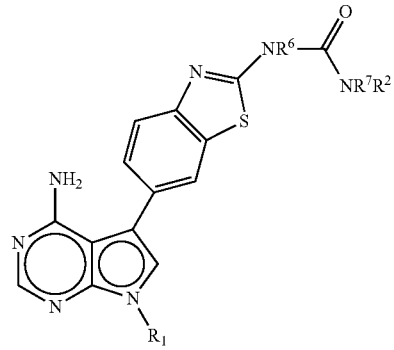
Formula IV-1
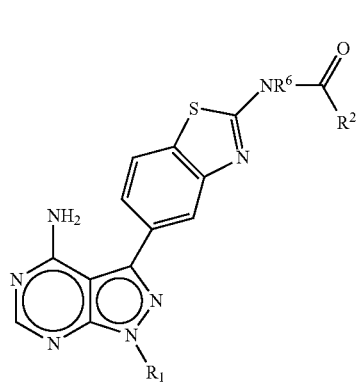
Formula IV-2
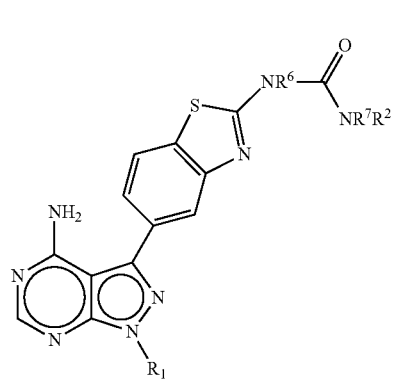
Formula V-1
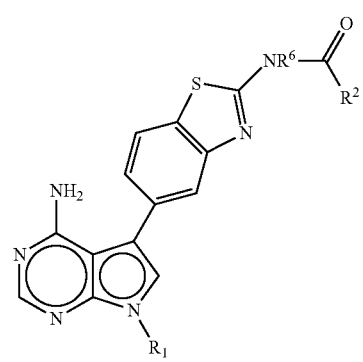
Formula V-2
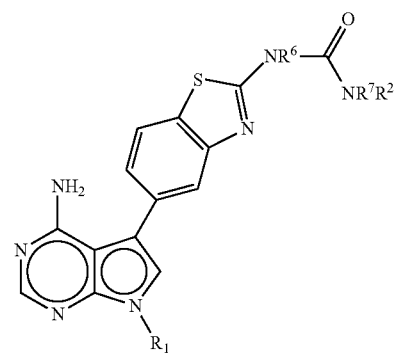
Formula II-2
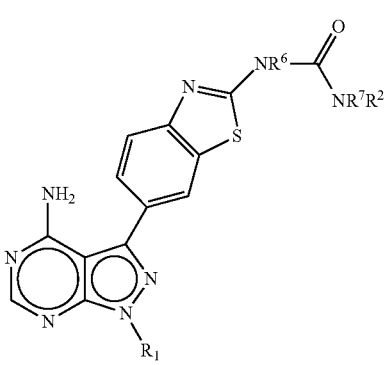
Formula II-3
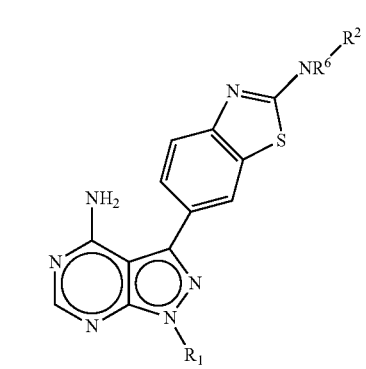

Formula III-3
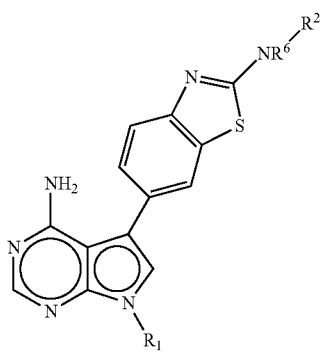

Formula IV-3
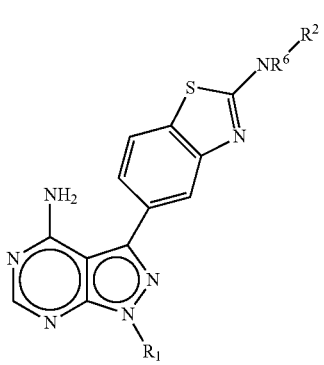

Formula V-3
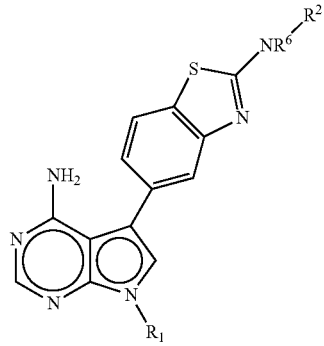

Formula II-4
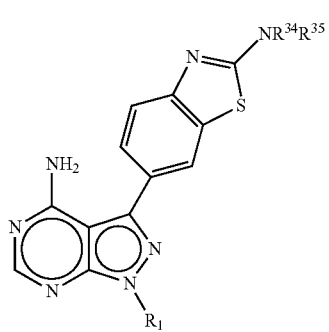

Formula III-4
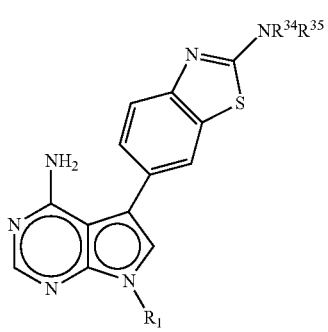

Formula IV-4
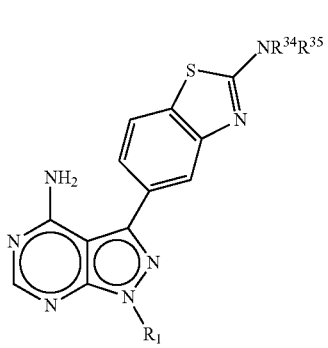

Formula V-4
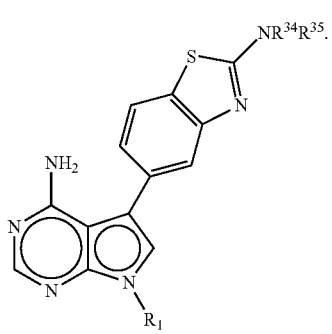

In some of the embodiments of the compounds of Formula II-3, III-3, IV-3, or V-3, when $R^6$ or $R^2$ is phenyl, then the phenyl is a substituted phenyl. In other embodiments, when $R^6$ and/or $R^2$ is alkyl, then $R^6$ and/or $R^2$ is unsubstituted or substituted with one or more halo, OH, —$CF_3$, —$OCF_3$, —$OR^{31}$, —O-aryl, —$NR^{31}R^{32}$, —$NR^{34}R^{35}$, —$C(O)R^{31}$, —$CO_2R^{31}$, —$C(=O)NNR^{34}R^{35}$, —$NO_2$, —CN, —$S(O)_{0-2}R^{31}$, —$SO_2NR^{31}R^{32}$, —$SO_2NR^{34}R^{35}$, —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, —$C(=S)OR^{31}$, —$C(=O)SR^{31}$, —$NR^{31}C(=NR^{32})NR^{33}R^{32}$, —$NR^{31}C(=NR^{32})OR^{33}$, —$NR^{31}C(=NR^{32})SR^{33}$, —$OC(=O)OR^{33}$, —$OC(=O)NR^{31}R^{32}$, —$OC(=O)SR^{31}$, —$SC(=O)OR^{31}$, —$P(O)OR^{31}OR^{32}$, or —$SC(=O)NR^{31}R^{32}$ substituents. In other embodiments, when $R^6$ and/or $R^2$ is alkyl, then $R^6$ and/or $R^2$ is substituted by cycloalkyl or heterocyclyl. In other embodiments, $R^6$ is hydrogen and $R^2$ is unsubstituted alkyl or hydrogen. In some embodiments, $R^6$ and $R^2$ are hydrogen.

In other embodiments of the invention, the compound of Formula I is a compound of Formula VI, VII, VIII, or IX:

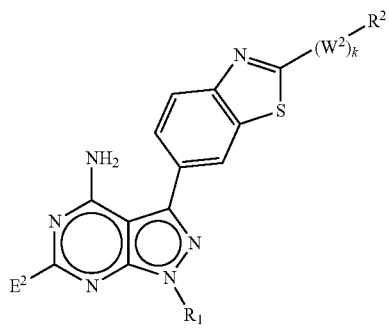

Formula VI

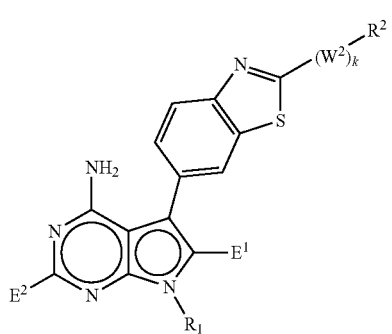

Formula VII

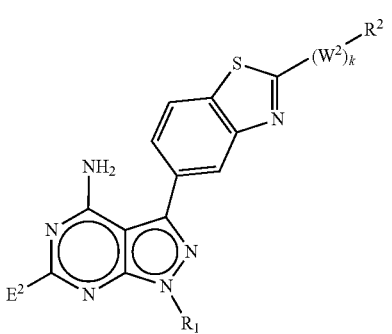

Formula VIII

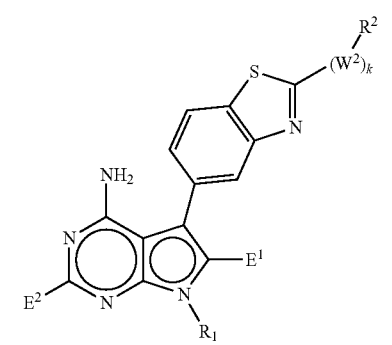

Formula IX wherein $E^1$ and $E^2$ are independently -$(W^1)_j$—$R^4$ and j, in each instance, is 0 or 1.

In some embodiments of a compound of Formulae VI-IX, $W^1$ is —O—, $S(O)_{0-2}$ - (including but not limited to —S—, —S(O)—, and —S(O)$_2$—), —C(O)—, or-, —C(O)O—. In other embodiments, $W^1$ is —$NR^6$— or —CH($R^6$)N($R^7$)—, wherein $R^6$ and $R^7$ are each independently hydrogen, unsubstituted or substituted $C_1$-$C_{10}$alkyl (which includes but is not limited to —CH$_3$, —CH$_2$CH$_3$, n-propyl, isopropyl, n-butyl, tert-butyl, sec-butyl, pentyl, hexyl, and heptyl), unsubstituted or substituted $C_2$-$C_{10}$ alkenyl (including but not limited to alkenyl such as, for example, vinyl, allyl, 1-methyl propen-1-yl, butenyl, or pentenyl). Additionally when $W^1$ is $NR^6$ or —CH($R^6$)N($R^7$)—, $R^6$ and $R^7$ are each independently unsubstituted or substituted aryl (including phenyl and naphthtyl). In yet other embodiments, when $W^1$ is $NR^6$ or —CH($R^6$)N($R^7$)—, $R^6$ and $R^7$ are each independently heteroaryl, wherein the heteroaryl is unsubstituted or substituted. $R^6$ and $R^7$ heteroaryl is monocyclic heteroaryl, and includes but is not limited to imidazolyl, pyrrolyl, oxazolyl, thiazolyl, and pyridinyl. In some other embodiments, when $W^1$ is $NR^6$ or —CH($R^6$)N($R^7$)—, $R^6$ and $R^7$ are each independently unsubstituted or substituted heterocyclyl (which includes but is not limited to pyrrolidinyl, tetrahydrofuranyl, piperidinyl, tetrahydropyranyl, thiazolidinyl, imidazolidinyl, morpholinyl, and piperazinyl) or unsubstituted or substituted $C_{3-8}$cycloalkyl ((including but not limited to cyclopropyl, cyclobutyl, and cyclopentyl). Non limiting exemplary $W^1$ include —NH—, —N(cyclopropyl), and —N(4-N-piperidinyl).

$W^1$ may also be —C(O)N($R^6$)—, —N($R^6$)C(O)—, —N($R^6$)S(O)—, —N($R^6$)S(O)$_2$—CH($R^6$)N(C(O)O$R^7$)—, —CH($R^7$)N(C(O)$R^7$)—, —CH($R^6$)N(SO$_2$$R^7$)—, —CH($R^6$)C(O)N($R^7$)—, —CH($R^6$)N($R^7$)C(O)—, —CH($R^6$)N($R^7$)S(O)—, or —CH($R^6$)N($R^7$)S(O)$_2$—; wherein $R^6$ and $R^7$ are each independently hydrogen, unsubstituted or substituted $C_1$-$C_{10}$alkyl (which includes but is not limited to —CH$_3$, —CH$_2$CH$_3$, n-propyl, isopropyl, n-butyl, tert-butyl, sec-butyl, pentyl, hexyl, and heptyl) or unsubstituted or substituted $C_2$-$C_{10}$alkenyl (including but not limited to alkenyl such as, for example, vinyl, allyl, 1-methyl propen-1-yl, butenyl, or pentenyl). Additionally when $W^1$ is —C(O)N($R^6$)—, —N($R^6$)C(O)—, —N($R^6$)S(O)—, —N($R^6$)S(O)$_2$—CH($R^6$)N(C(O)O$R^7$)—, —CH($R^7$)N(C(O)$R^7$)—, —CH($R^6$)N(SO$_2$$R^7$)—, —CH($R^6$)C(O)N($R^7$)—, —CH($R^6$)N($R^7$)C(O)—, —CH($R^6$)N($R^7$)S(O)—, or —CH($R^6$)N($R^7$)S(O)$_2$—, $R^6$ and $R^7$ are each independently unsubstituted or substituted aryl (including phenyl and naphthtyl). In yet other embodiments, when —C(O)N($R^6$)—, —N($R^6$)C(O)—, —N($R^6$)S(O)—, —N($R^6$)S(O)$_2$—CH($R^6$)N(C(O)O$R^7$)—, —CH($R^7$)N(C(O)$R^7$)—, —CH($R^6$)N(SO$_2$$R^7$)—, —CH($R^6$)C(O)N($R^7$)—, —CH($R^6$)N($R^7$)C(O)—, —CH($R^6$)N($R^7$)S(O)—, or —CH($R^6$)N($R^7$)S(O)$_2$—, $R^6$ and $R^7$ are each independently heteroaryl, wherein the heteroaryl is unsubstituted or substituted. $R^6$ and $R^7$ heteroaryl is monocyclic heteroaryl, and includes but is not limited to imidazolyl, pyrrolyl, oxazolyl, thiazolyl, and pyridinyl. In some other embodiments, when —C(O)N($R^6$)—, —N($R^6$)C(O)—, —N($R^6$)S(O)—, —N($R^6$)S(O)$_2$—CH($R^6$)N(C(O)O$R^7$)—, —CH($R^7$)N(C(O)$R^7$)—, —CH($R^6$)N(SO$_2$$R^7$)—, —CH($R^6$)C(O)N($R^7$)—, —CH($R^6$)N($R^7$)C(O)—, —CH($R^6$)N($R^7$)S(O)—, or —CH($R^6$)N($R^7$)S(O)$_2$—, $R^6$ and $R^7$ are each independently unsubstituted or substituted heterocyclyl (which includes but is not limited to pyrrolidinyl, tetrahydrofuranyl, piperidinyl, tetrahydropyranyl, thiazolidinyl, imidazolidinyl, morpholinyl, and piperazinyl) or unsubstituted or substituted $C_{3-8}$cycloalkyl ((including but not limited to cyclopropyl, cyclobutyl, and cyclopentyl). Non limiting exemplary $W^1$ are —C(CO)NH—, —N(Me)C(O)—, —NHC(O)—, —N(Me)S(O)—, —NHS(O)$_2$—, —CH(Me)N(C(O)Ophenyl)-, —CH(Me)N(SO$_2$Me)-, —CH$_2$C(O)N(cyclopropyl)-, —CH$_2$N(allyl)C(O)—, —CH(Me)NHS(O)—, or —CH(Me)NHS(O)$_2$—.

In other embodiments of a compound of Formulae VI-IX, wherein $E^1$ and/or $E^2$ is —$W^1$—$R^4$, and $W^1$ comprises $R^6$ and/or $R^7$ alkyl, alkenyl, aryl, heteroaryl, heterocyclyl or cycloalkyl, each $R^6$ and/or $R^7$ alkyl, alkenyl, aryl, heteroaryl, heterocyclyl or cycloalkyl is unsubstituted or substituted by one or more independent $R^8$ substituents. In some embodiments, the $R^6$ and/or $R^7$ alkyl, alkenyl, aryl, heteroaryl, heterocyclyl or cycloalkyl is substituted by one or more halo, —SH, $NH_2$, —$NO_2$, or —CN. In other embodiments, $R^6$ and/or $R^7$ alkyl, alkenyl, aryl, heteroaryl, heterocyclyl or cycloalkyl is substituted by one or more —$OR^{31}$, —$NR^{31}R^{32}$, —$CO_2R^{31}$, or $C(=O)NR^{31}R^{32}$. Nonlimiting exemplary substituted $R^6$ and/or $R^7$ alkyl, alkenyl, aryl, heteroaryl, heterocyclyl or cycloalkyl include 1-(3-hydroxyl)propyl, 3-diethylaminophenyl, 3-carboxymethyl pyridinyl, and 4-(carboxamido)piperazinyl.

Alternatively, wherein $E^1$ and/or $E^2$ is —$W^1$—$R^4$, and $W^1$ comprises $R^6$ and/or $R^7$alkyl, alkenyl, aryl, heteroaryl, heterocyclyl or cycloalkyl, the $R^6$ and/or $R^7$alkyl, alkenyl, aryl, heteroaryl, heterocyclyl or cycloalkyl is substituted by one or more $R^8$ substituents wherein $R^8$ is —$SO_2NR^{34}R^{35}$, —$NR^{34}R^{35}$, —$SO_2NR^{31}R^{32}$, or —$C(=O)$ $NR^{34}R^{35}$, wherein the $R^{34}$ and $R^{35}$ of $NR^{31}R^{32}$ are taken together to form a cyclic moiety as described herein. Non-limiting exemplary substituted $R^6$ and/or $R^7$ alkyl, alkenyl, aryl, heteroaryl, heterocyclyl or cycloalkyl include -ethyl$SO_2$ (piperazinyl), iso(-3-azetidinyl)buten-1-yl, and (4-morpholinyl)-piperazinyl. In yet other embodiments, $R^6$ and/or $R^7$ alkyl, alkenyl, aryl, heteroaryl, heterocyclyl or cycloalkyl is substituted by one or more —$CO_2$aryl, —$S(O)_{0-2}$aryl, —$S(O)_{0-2}$alkyl, alkyl, cycloalkyl, alkenyl, or alkynyl, wherein the aryl, alkyl, cycloalkyl, alkenyl or alkenyl are as described herein. Non-limiting exemplary substituted $R^6$ and/or $R^7$ alkyl, alkenyl, aryl, heteroaryl, heterocyclyl or cycloalkyl include (2-phenylsulfonyl)ethyl, (4-methylsulfonyl)cyclohexyl, and (3-phenylsulfonyl)propargyl.

In other embodiments a compound of Formulae VI-IX, wherein $E^1$ and/or $E^2$ is —$W^1$—$R^4$, and W comprises $R^6$ and/or $R^7$ alkyl, alkenyl, aryl, heteroaryl, heterocyclyl or cycloalkyl, the $R^6$ and/or $R^7$ alkyl, alkenyl, aryl, heteroaryl, heterocyclyl or cycloalkyl is substituted by one or more $R^8$ wherein $R^8$ is -aryl-alkyl, -aryl-alkenyl, -aryl-alkynyl, -heteroaryl-alkyl, -heteroaryl-alkenyl, or -heteroaryl-alkynyl. When $R^8$ is -aryl-alkyl, -aryl-alkenyl, or -aryl-alkynyl, each aryl, alkyl, alkenyl, and alkynyl is as described herein and connection to $R^6$ and/or $R^7$ is made through the aryl portion of each moiety. Each $R^8$-aryl-alkyl, -aryl-alkenyl, and -aryl-alkynyl is unsubstituted or substituted with one or more independent halo, cyano, nitro, —Oalkyl, alkyl, alkenyl, alkynyl, haloalkyl, haloalkenyl, haloalkynyl, —COOH, —$C(=O)NR^{31}R^{32}$, —$C(=O)$ $NR^{34}R^{35}$, —$SO_2NR^{34}R^{35}$, —$SO_2NR^{31}R^{32}$, —$NR^{31}R^{32}$, or —$NR^{34}R^{35}$ substituents. Alternatively, $R^8$ is -heteroaryl-alkyl, -heteroaryl-alkenyl, or -heteroaryl-alkynyl, wherein heteroaryl, alkyl, alkenyl and alkynyl are as described herein and connection to $R^6$ and/or $R^7$ is made through the heteroaryl portion of each moiety. Each $R^8$-heteroaryl-alkyl, -heteroaryl-alkenyl, and -heteroaryl-alkynyl is unsubstituted or substituted with one or more independent halo, cyano, nitro, —Oalkyl, alkyl, alkenyl, alkynyl, haloalkyl, haloalkenyl, haloalkynyl, —COOH, —$C(=O)NR^{31}R^{32}$, —$C(=O)$ $NR^{34}R^{35}$, —$SO_2NR^{34}R^{35}$, —$SO_2NR^{31}R^{32}$, —$NR^{31}R^{32}$, or —$NR^{34}R^{35}$ substituents.

In other embodiments of a compound of Formulae VI-IX, $R^{31}$, $R^{32}$, and $R^{33}$ are moieties forming part of $R^1$, $R^2$, $R^3$, $R^4$, $R^5$, and $R^8$. $R^{31}$, $R^{32}$, and $R^{33}$, in each instance, are H or unsubstituted or substituted $C_{1-10}$alkyl (which includes but is not limited to —$CH_3$, —$CH_2CH_3$, n-propyl, isopropyl, n-butyl, tert-butyl, sec-butyl, pentyl, hexyl, and heptyl). When $R^{31}$, $R^{32}$, and/or $R^{33}$ alkyl is substituted, the alkyl is substituted with one or more aryl ((which includes but is not limited to —$CH_3$, —$CH_2CH_3$, n-propyl, isopropyl, n-butyl, tert-butyl, sec-butyl, pentyl, hexyl, and heptyl), heteroalkyl (which includes but is not limited to methoxyethoxy and 3-diethylamino propyl), heterocyclyl (including but not limited to azetidinyl, morpholinyl, or piperazinyl), or heteroaryl (including but not limited to imidazolyl, thiazolyl, or oxazolyl) substituents, wherein each of said alkyl, aryl, heteroalkyl, heterocyclyl, or heteroaryl groups is unsubstituted or substituted with one or more halo, —OH, -alkyl, —$F_3$, —O-aryl, —$OCF_3$, —Oalkyl, —$NH_2$, —N(alkyl)$_2$, —NH(alkyl), —NH(aryl), —$NR^{34}R^{35}$, —C(O)(alkyl), —C(O)(alkyl-aryl), —C(O)(aryl), $CO_2$alkyl, —$CO_2$-alkylaryl, —$CO_2$-aryl, —$C(=O)N$(alkyl)$_2$, —$C(=O)NH$(alkyl), —$C(=O)NR^{34}R^{35}$, —$C(=O)NH_2$, —$OCF_3$, O(alkyl), —O-aryl, —N(aryl)(alkyl), —$NO_2$, —CN, —$S(O)_{0-2}$ alkyl, —$S(O)_{0-2}$alkylaryl, —$S(O)_{0-2}$ aryl, —$SO_2N$(aryl), —$SO_2N$(alkyl)$_2$, —$SO_2NH$(alkyl) or —$SO_2NR^{34}R^{35}$ substituents.

$R^{34}$ and $R^{35}$ may also form part of $R^1$, $R^2$, $R^3$, $R^4$, $R^5$, and $R^8$. $R^{34}$ and $R^{35}$ in —$NR^{34}R^{35}$, —$C(=O)NNR^{34}R^{35}$ or —$SO_2NR^{34}R^{35}$, are taken together with the nitrogen atom to which they are attached to form a 3, 4, 5, 6, 7, 8, 9, or 10 membered saturated or unsaturated ring; wherein said ring in each instance is unsubstituted or substituted by one or more —$NR^{31}R^{32}$, hydroxyl, halogen, oxo, aryl, hetaryl, alkyl, O-aryl, —$C(O)R^{31}$, or —$SO_2R^{31}$ substituents, and wherein said 3-10 membered saturated or unsaturated ring in each instance includes 0, 1, or 2 more heteroatoms other than the nitrogen.

The invention provides compounds of Formulae VI-IX, wherein E and/or $E^2$ is $R^4$ or is —$W^1R^4$. $R^4$ is hydrogen or halogen, such as chloro, bromo, fluoro or iodo. In other embodiments, $R^4$ is unsubstituted or substituted aryl (including but not limited to monocyclic or bicyclic aryl) or unsubstituted or substituted heteroaryl, including but not limited to monocyclic and bicyclic heteroaryl. Monocyclic heteroaryl $R^4$ includes but is not limited to pyrrolyl, thienyl, furyl, pyridinyl, pyranyl, imidazolyl, thiazolyl, pyrazolyl, and oxazolyl. Bicyclic heteroaryl $R^4$ includes but is not limited to benzothiophenyl, benzofuryl, indolyl, quinolinyl, isoquinolinyl, benzimidazolyl, benzoxazolyl, benzothiazolyl, quinazolinyl, azaindolyl, pyrazolopyrimidinyl, and purinyl $R^4$ is also unsubstituted or substituted $C_{1-10}$alkyl (including but not limited to $CH_3$, —$CH_2CH_3$, n-propyl, isopropyl, n-butyl, tert-butyl, sec-butyl, pentyl, hexyl, and heptyl) or unsubstituted or substituted $C_{3-8}$cycloalkyl (including but not limited to cyclopropyl, cyclobutyl, and cyclopentyl. In other embodiments, $R^4$ is -alkylaryl, -alkyl heteroaryl, or -alkylheterocyclyl. Alkyl, aryl, and heteroaryl are as described herein and the heterocyclyl is unsubstituted or substituted (non-limiting examples include pyrrolidinyl, tetrahydrofuranyl, piperidinyl, tetrahydropyranyl, thiazolidinyl, imidazolidinyl, morpholinyl, and piperazinyl) For $R^4$-alkylaryl, -alkyl heteroaryl, or -alkylheterocyclyl, connection to $W^1$ or to the compound of Formula I is through the alkyl portion of the moiety. In yet other embodiments, $R^4$ is unsubstituted or substituted alkenyl (including but not limited to unsubstituted or substituted $C_2$-$C_{10}$alkenyl such as, for example, vinyl, allyl, 1-methyl propen-1-yl, butenyl, or pentenyl) or unsubstituted or substituted alkynyl (including but not limited to unsubstituted or substituted $C_2$-$C_{10}$alkynyl such as acetylenyl, propargyl, butynyl, or pentynyl). Other compounds are provided by the invention, wherein $R^4$ is -alkenylaryl, alkenylheteroaryl, -alkenylheteroalkyl, or -alkenylheterocyclyl, wherein the alkenyl, aryl, heteroalkyl, heteroaryl, and heterocyclyl are as described herein. The $R^4$-alkenylaryl, -alkenylheteroaryl, -alkenylheteroalkyl, or -alkenylheterocyclyl moiety is attached to $W^1$ or to the compound of Formula I through the alkenyl portion of the moiety. In other embodiments, $R^4$ is -alkynylaryl, -alkynyl heteroaryl, -alkynylheteroalkyl, -alkynylheterocylyl, -alkynylcycloalkyl, or -alkynylcycloalkenyl, wherein alkynyl, aryl, heteroaryl, heteroalkyl, heterocyclyl, cycloalkyl are as described herein. A $R^4$-cycloalkenyl moiety is unsubstituted or substituted $C_3$-$C_8$cycloalkenyl (including but not limited to cyclopentenyl and cyclohexenyl). The $R^4$-alkynylaryl, -alkynyl heteroaryl, -alkynylheteroalkyl, -alkynylheterocylyl, -alkynylcycloalkyl, or -alkynylcycloalkenyl is attached to $W^1$ or to the compound of Formula I through the alkynyl portion of the moiety. Some nonlimiting examples include 2-cyclopropylacetylenyl and 3-(morpholinyl)proparg-1-yl. In some other embodiments, $R^4$ is -alkoxy alkyl, -alkoxyalkenyl, or -alkoxyalkynyl, wherein alkoxy, alkyl, alkenyl, and alkynyl are as described herein. The $R^4$ alkoxy alkyl, -alkoxyalkenyl, or -alkoxyalkynyl is attached to $W^1$ or to the compound of Formula I through the alkoxy portion of the moiety. In yet other embodiments, $R^4$ is -arylalkenyl, -arylalkynyl, or aryl-heterocyclyl, wherein aryl, alkenyl, alkynyl or heterocyclyl is as described herein. The $R^4$-arylalkenyl, -arylalkynyl, or aryl-heterocyclyl is attached to $W^1$ or to the compound of Formula I through the aryl portion of the moiety.

Nonlimiting examples include 4-allylphen-1-yl, 2(morpholinyl)phenyl and 4-(piperidinyl)phenyl Alternatively, $R^4$ is heteroaryl-alkyl, heteroaryl-alkenyl, heteroaryl-alkynyl, heteroaryl-cycloalkyl, heteroaryl-heteroalkyl, or heteroaryl-heterocyclyl, wherein heteroaryl, alkyl, alkenyl, alkynyl, cycloalkyl, heteroalkyl, and heterocyclyl are as described herein. The $R^4$-heteroaryl-alkyl, heteroaryl-alkenyl, heteroaryl-alkynyl, -heteroaryl-cycloalkyl, -heteroaryl-heteroalkyl, or -heteroaryl-heterocyclyl is attached to $W^1$ or to the compound of Formula I through the heteroaryl portion of the moiety.

For a compound of Formulae VI-IX, in some embodiments, each aryl or heteroaryl that forms part or all of $R^4$ is unsubstituted or is substituted with one or more independent halo, —OH, —$R^{31}$, —$CF_3$, —$OCF_3$, —$OR^{31}$, —$NR^{31}R^{32}$, —$NR^{34}R^{35}$, —$C(O)R^{31}$, —$CO_2R^{31}$, —$C(=O)NR^{31}R^{32}$, —$C(=O)NNR^{34}R^{35}$, —$NO_2$, —$CN$, —$S(O)_{0-2}R^{31}$, —$SO_2NR^{31}R^{32}$, $SO_2NR^{34}R^{35}$, —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, $C(=S)OR^{31}$, —$C(=O)SR^{31}$, —$NR^{31}C(=NR^{32})NR^{33}R^{32}$, —$NR^{31}C(=NR^{32})OR^{33}$, —$NR^{31}C(=NR^{32})SR^{33}$, —$OC(=O)OR^{33}$, —$OC(=O)NR^{31}R^{32}$, —$OC(=O)SR^{31}$, —$SC(=O)OR^{31}$, —$P(O)OR^{31}OR^{32}$, or —$SC(=O)NR^{31}R^{32}$ substituents.

Each alkyl, cycloalkyl, heterocyclyl, or heteroalkyl forming all or part of $R^4$ is unsubstituted or substituted with one or more halo, —OH, —$R^{31}$, —$CF_3$, —$OCF_3$, —$OR^{31}$, —O-aryl, —$NR^{31}R^{32}$, —$NR^{34}R^{35}$, —$C(O)R^{31}$, —$CO_2R^{31}$, —$C(=O)NNR^{34}R^{35}$, or —$C(=O)NR^{31}R^{32}$ substituents.

In various embodiments, $X_1$ is $C$—$(W)_j$—$R^4$. In some embodiments, $X_1$ is $C$—$R^4$. In some embodiments, $X_1$ is —$OR^4$. In other embodiments, $X_1$ is —$NR^7R^4$ (including but not limited to —$NHR^4$. $X_1$ is also $S(O)_{0-2}R^4$. In other embodiments, $X_1$ is —$C(O)R^4$. Additionally, $X_1$ is —$C(O)N(R^7)R^4$. In some other embodiments, $X_1$ is —$N(R^7)C(O)R^4$. In yet other embodiments, $X_1$ is —$N(R^7)S(O)R^4$. In various embodiments, $X_1$ is $N(R^7)S(O)_2R^4$. In some embodiments, $X_1$ is —$C(O)OR^4$. Alternatively, $X_1$ is $CH(R^7)N(C(O)OR^8)R^4$. In some embodiments, $X_1$ is $CH(R^7)N(C(O)R^8)R^4$. In other embodiments, $X_1$ is —$CH(R^7)N(SO_2R^8)R^4$. $X_1$ may also be —$CH(R^7)N(R^8)R^4$. In other embodiments, $X_1$ is —$CH(R^7)C(O)N(R^8)R^4$. In yet other embodiments, $X_1$ is —$CH(R^7)N(R^8)C(O)R^4$. Additionally, $X_1$ is —$CH(R^7)N(R^8)S(O)R^4$. In some other embodiments, $X_1$ is —$CH(R^7)N(R^8)S(O)_2R^4$.

In one embodiment, $X_1$ is CH.

In various embodiments, $X_2$ is $C$—$(W^1)_j$—$R^4$. In some embodiments, $X_2$ is $C$—$R^4$. In some embodiments, $X_2$ is —$OR^4$. In other embodiments, $X_2$ is —$NR^7R^4$ (including but not limited to —$NHR^4$. $X_2$ is also $S(O)_{0-2}R^4$. In other embodiments, $X_2$ is —$C(O)R^4$. Additionally, $X_2$ is —$C(O)N(R^7)R^4$. In some other embodiments, $X_2$ is $N(R^7)C(O)R^4$. In yet other embodiments, $X_2$ is —$N(R^7)S(O)R^4$. In various embodiments, $X_2$ is $N(R^7)S(O)_2R^4$. In some embodiments, $X_2$ is —$C(O)OR^4$. Alternatively, $X_2$ is $CH(R^7)N(C(O)OR^8)R^4$. In some embodiments, $X_2$ is —$CH(R^7)N(C(O)R^8)R^4$. In other embodiments, $X_2$ is —$CH(R^7)N(SO_2R^8)R^4$. $X_2$ may also be —$CH(R^7)N(R^8)R^4$. In other embodiments, $X_2$ is —$CH(R^7)C(O)N(R^8)R^4$. In yet other embodiments, $X_2$ is —$CH(R^7)N(R^8)C(O)R^4$. Additionally, $X_2$ is —$CH(R^7)N(R^8)S(O)R^4$. In some other embodiments, $X_2$ is —$CH(R^7)N(R^8)S(O)_2R^4$.

In one embodiment, $X_2$ is CH. In one embodiment, $X_2$ is $CR^4$, wherein $R^4$ is alkyl, cycloalkyl or heterocyclyl.

In another embodiment, $X_1$ is $C$—$NH_2$.

In various embodiments, $X_1$ is $C$—NH—$R^4$, where —NH—$R^4$ is:

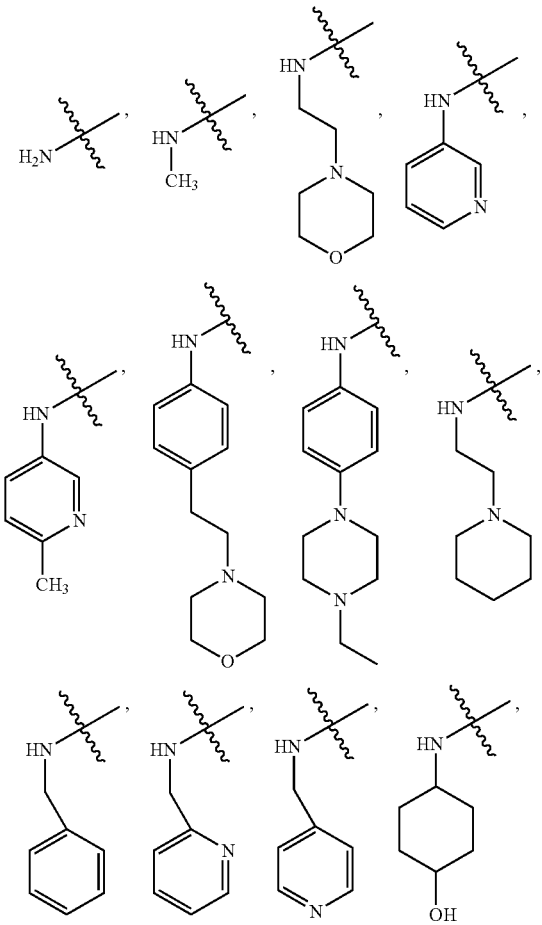

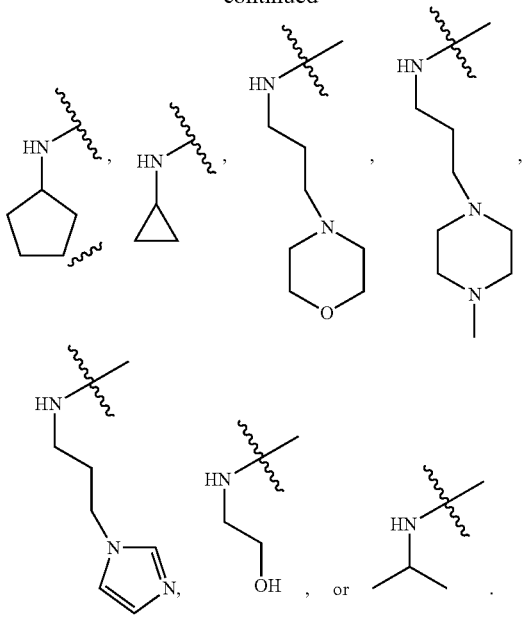

Additional embodiments of E and E² are found in Table 3.

In another aspect of the invention, a compound of Formula X or a pharmaceutically acceptable salt thereof is provided in this invention, wherein

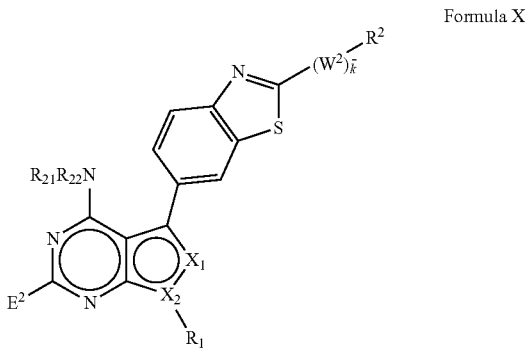

Formula X $X_1$, $X_2$, $R_1E^1$, $E^2$, j, $W^1$, $W^2$, k, $R^6$, $R^7$, $R^8$, $R^{31}$, $R^{32}$, $R^{33}$, $R^{34}$ and $R^{35}$ are defined as for Formula I; and $R^2$, $R^3$ and $R^4$ are independently hydrogen, halogen, aryl, heteroaryl, $C_{1-4}$alkyl, $C_{1-10}$alkyl, $C_{3-8}$cycloalkyl, —$C_{1-10}$alkyl-$C_{3-8}$cycloalkyl, —$C_{3-8}$cycloalkyl-$C_{1-10}$alkyl, —$C_{3-8}$cycloalkyl-$C_{2-10}$alkenyl, —$C_{3-8}$cycloalkyl-$C_{2-10}$alkynyl, —$C_{1-10}$ alkyl-$C_{2-10}$alkenyl, —$C_{1-10}$alkyl-$C_{2-10}$alkynyl, —$C_{1-10}$alkylaryl, —$C_{1-10}$alkyl heteroaryl, —$C_{1-10}$alkylheterocyclyl, —$C_{2-10}$alkenyl, —$C_{2-10}$alkynyl, —$C_{2-10}$alkenyl-$C_{1-10}$alkyl, —$C_{2-10}$alkynyl-$C_{1-10}$alkyl, —$C_{2-10}$alkenylaryl, —$C_{2-10}$alkenylheteroaryl, —$C_{2-10}$alkenylheteroalkyl, —$C_{2-10}$alkenylheterocyclcyl, —$C_{2-10}$alkenyl-$C_{3-8}$cycloalkyl, —$C_{2-10}$alkynylaryl, —$C_{2-10}$alkynyl-heteroaryl, —$C_{2-10}$ alkynylheteroalkyl, —$C_{2-10}$ alkynylheterocylyl, —$C_{2-10}$alkynyl-$C_{3-8}$cycloalkenyl, —$C_{1-10}$alkoxy $C_{1-10}$alkyl, —$C_{1-10}$alkoxy-$C_{2-10}$alkenyl, —$C_{1-10}$alkoxy-$C_{2-10}$alkynyl, -heterocyclyl-$C_{1-10}$alkyl, -heterocyclyl-$C_{2-10}$alkenyl, -heterocyclyl-$C_{2-10}$alkynyl, -aryl-$C_{1-10}$alkyl, -aryl-$C_{2-10}$alkenyl, -aryl-$C_{2-10}$ alkynyl, -aryl-heterocyclyl, -hetarylC$_{1-10}$alkyl, -heteroaryl-$C_{2-10}$alkenyl, -heteroaryl-$C_{2-10}$alkynyl, -hetarylC$_{3-8}$cycloalkyl, -heteroaryl heteroalkyl, or -heteroaryl-heterocyclyl, wherein each of said aryl or heteroaryl moieties is unsubstituted or is substituted with one or more independent halo, —OH, —$R^{31}$, —$CF_3$, —$OCF_3$, —$OR^{31}$, —$NR^{31}R^{32}$, —$NR^{34}R^{35}$, —$C(O)R^{31}$, —$CO_2R^{31}$, —$C(=O)NR^{31}R^{32}$, —$C(=O)NNR^{34}R^{35}$, —$NO_2$, —CN, —$S(O)_{0-2}R^{31}$, —$SO_2NR^{31}R^{32}$, —$SO_2NR^{34}R^{35}$, —$NR^{31}C(=O)R^{32}$, —$NR^{31}C(=)OR^{32}$, —$NR^{31}C(=O)NR^{32}R^{33}$, —$NR^{31}S(O)_{0-2}R^{32}$, —$C(=S)OR^{31}$, —$C(=O)SR^{31}$, —$NR^{31}C(=NR^{32})NR^{33}R^{32}$, —$NR^{31}C(=NR^{32})OR^{33}$, —$NR^{31}C(=NR^{32})SR^{33}$, —OC(=O)OR^{33}$, —OC(=O)NR^{31}R^{32}$, —OC(=O)SR^{31}$, —SC(=O)OR^{31}$, —P(O)OR^{31}OR^{32}$, or —SC(=O)NR^{31}R^{32}$ substituents, and wherein each of said alkyl, cycloalkyl, heterocyclyl, or heteroalkyl moieties is unsubstituted or substituted with one or more halo, —OH, —$R^{31}$, —$CF_3$, —$OCF_3$, —$OR^{31}$, —O-aryl, —$NR^{31}R^{32}$, —$NR^{34}R^{35}$, —$C(O)R^{31}$, —$CO_2R^{31}$, —$C(=O)NNR^{34}R^{35}$, or —$C(=O)NR^{31}R^{32}$ substituents.

In some embodiemnts, for a compound of Formula X, $R^2$ is hydrogen or halogen, such as chloro, bromo, fluoro or iodo. In other embodiments, $R^2$ is unsubstituted or substituted aryl (including but not limited to monocyclic or bicyclic aryl) or unsubstituted or substituted heteroaryl, including but not limited to monocyclic and bicyclic heteroaryl. Monocyclic heteroaryl $R^2$ includes but is not limited to pyrrolyl, thienyl, furyl, pyridinyl, pyranyl, imidazolyl, thiazolyl, pyrazolyl, and oxazolyl. Bicyclic heteroaryl $R^2$ includes but is not limited to benzothiophenyl, benzofuryl, indolyl, quinolinyl, isoquinolinyl, benzimidazolyl, benzoxazolyl, benzothiazolyl, quinazolinyl, azaindolyl, pyrazolopyrimidinyl, and purinyl $R^2$ is also unsubstituted or substituted $C_{1-10}$alkyl (including but not limited to $CH_3$, —$CH_2CH_3$, n-propyl, isopropyl, n-butyl, tert-butyl, sec-butyl, pentyl, hexyl, and heptyl) or unsubstituted or substituted $C_{3-8}$cycloalkyl (including but not limited to cyclopropyl, cyclobutyl, and cyclopentyl. In other embodiments, $R^2$ is -alkylcycloalkyl, -alkylaryl, -alkyl heteroaryl, or -alkylheterocyclyl. Alkyl, aryl, cycloalkyl, and heteroaryl are as described herein and the heterocyclyl is unsubstituted or substituted (non-limiting examples include pyrrolidinyl, tetrahydrofuranyl, piperidinyl, tetrahydropyranyl, thiazolidinyl, imidazolidinyl, morpholinyl, and piperazinyl) For $R^2$-alkylcycloalkyl, -alkylaryl, -alkyl heteroaryl, or -alkylheterocyclyl, connection to $W^2$ or to the compound of Formula I is through the alkyl portion of the moiety. In yet other embodiments, $R^2$ is unsubstituted or substituted alkenyl (including but not limited to unsubstituted or substituted $C_2$-$C_{10}$ alkenyl such as, for example, vinyl, allyl, 1-methyl propen-1-yl, butenyl, or pentenyl) or unsubstituted or substituted alkynyl (including but not limited to unsubstituted or substituted $C_2$-$C_{10}$alkynyl such as acetylenyl, propargyl, butynyl, or pentynyl). Other compounds are provided by the invention, wherein $R^2$ is -alkenylaryl, alkenylheteroaryl, -alkenylheteroalkyl, -alkenylheterocyclcyl or -alkenylcycloalkyl, wherein alkenyl, aryl, heteroaryl, heteroalkyl, heterocyclyl, and cycloalkyl are as described herein. The $R^2$-alkenylaryl, -alkenylheteroaryl, -alkenylheteroalkyl, -alkenylheterocyclcyl, or -alkenylcycloalkyl moiety is attached to $W^2$ or to the compound of Formula I through the alkenyl portion of the moiety. In other embodiments, $R^2$ is -alkynylaryl, -alkynyl heteroaryl, -alkynylheteroalkyl, -alkynylheterocylyl, -alkynylcycloalkyl, or -alkynylcycloalkenyl, wherein alkynyl, aryl, heteroaryl, heteroalkyl, heterocyclyl, cycloalkyl are as described herein. A $R^2$-cycloalkenyl moiety is unsubstituted or substituted $C_3$-$C_8$cycloalkenyl (including but not limited to cyclopentenyl and cyclohexenyl). The $R^2$-alkynylaryl, -alkynyl heteroaryl, -alkynylheteroalkyl, -alkynylheterocylyl, -alkynylcycloalkyl, or -alkynylcycloalkenyl is attached to $W^2$ or to the compound of Formula I through the alkynyl portion of the moiety. Some nonlimiting examples include 2-cyclopropylacetylenyl and 3-(morpholinyl)proparg-1-yl. Alternatively, $R^2$ is -cycloalkyl-heterocyclyl, -cycloalkyl-alkyl, -cycloalkylalkynyl, or -cycloalkylalkenyl, wherein heterocyclyl, cycloalkyl, alkyl, alkenyl, and alkynyl are as described herein. The $R^2$-cycloalkyl-heterocyclyl, -cycloalkyl-alkyl, -cycloalkylalkynyl, or -cycloalkylalkenyl is attached to $W^2$ or to the compound of Formula I through the cycloalkyl portion of the moiety. In some other embodiments, $R^2$ is -alkoxyalkyl, -alkoxyalkenyl, or -alkoxyalkynyl, wherein alkoxy, alkyl, alkenyl, and alkynyl are as described herien. The $R^2$ alkoxy alkyl, -alkoxyalkenyl, or -alkoxyalkynyl is attached to $W^2$ or to the compound of Formula I through the alkoxy portion of the moiety. Alternatively, $R^2$ is (unsubstituted or substituted heterocyclyl) wherein heterocyclyl includes but is not limited to azetidinyl, pyrrolidinyl, tetrahydrofuranyl, piperidinyl, tetrahydropyranyl, thiazolidinyl, imidazolidinyl, morpholinyl, and piperazinyl. Heterocyclyl includes but is not limited to morpholinyl, thiomorpholinyl, azetidinyl, pyrrolidinyl, tetrahydropyranyl, piperazinyl, and 4-NMe-piperazinyl. In some other embodiments, $R^2$ is -heterocyclylalkyl, -heterocyclylalkenyl, -heterocyclyl-alkynyl, -heterocyclylcycloalkyl or -heterocyclylheterocylyl wherein heterocyclyl, alkyl, alkenyl, cycloalkyl, and alkynyl are as described herein. The $R^2$-heterocyclylalkyl, -heterocyclylalkenyl, -heterocyclyl-alkynyl, -heterocyclylcycloalkyl or -heterocylylheterocylyl is connected to $W^2$ or to the compound of Formula I through the heterocylyl portion of the moiety. In yet other embodiments, $R^2$ is -arylalkenyl, -arylalkynyl, or aryl-heterocyclyl, wherein aryl, alkenyl, alkynyl or heterocyclyl is as described herein. The $R^2$-arylalkenyl, -arylalkynyl, or -aryl-heterocyclyl is attached to to $W^2$ or to the compound of Formula I through the aryl portion of the moiety. Nonlimiting examples include 4-allylphen-1-yl, 2(morpholinyl)phenyl and 4-(piperidinyl)phenyl Alternatively, $R^2$ is -heteroaryl-alkyl, -heteroaryl-alkenyl, -heteroaryl-alkynyl, -heteroaryl-cycloalkyl, -heteroaryl-heteroalkyl, or -heteroaryl-heterocyclyl, wherein heteroaryl, alkyl, alkenyl, alkynyl, cycloalkyl, heteroalkyl, and heterocyclyl are as described herein. The $R^2$-heteroaryl-alkyl, -heteroaryl-alkenyl, -heteroaryl-alkynyl, -heteroaryl-cycloalkyl, -heteroaryl-heteroalkyl, or -heteroaryl-heterocyclyl is attached to $W^2$ or to the compound of Formula I through the heteroaryl portion of the moiety.

For a compound of Formula X, each aryl or heteroaryl that forms part or all of $R^2$ is unsubstituted or is substituted with one or more independent halo, —OH, —$R^{31}$, —$CF_3$, —$OCF_3$, —$OR^{31}$, —$NR^{31}R^{32}$, —$NR^{34}R^{35}$, —$C(O)R^{31}$, —$CO_2R^{31}$, —$C(=O)NR^{31}R^{32}$, —$C(=O)NNR^{34}R^{35}$, —$NO_2$, —CN, —$S(O)_{0-2}R^{31}$, —$SO_2NR^{31}R^{32}$, —$SO_2NR^{34}R^{35}$, —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, —$C(=S)OR^{31}$, —$C(=O)SR^{31}$, —$NR^{31}C(=NR^{32})NR^{33}R^{32}$, —$NR^{31}C(=NR^{32})OR^{33}$, —$NR^{31}C(=NR^{32})SR^{33}$, —$OC(=O)OR^{33}$, —$OC(=O)NR^{31}R^{31}R^{32}$, —$OC(=O)SR^{31}$, —$SC(=O)OR^{31}$, —$P(O)OR^{31}OR^{32}$, or —$SC(=O)NR^{31}R^{32}$ substituents.

In some embodiments, each alkyl, cycloalkyl, heterocyclyl, or heteroalkyl forming all or part of $R^2$ is unsubstituted or substituted with one or more halo, —OH, —$R^{31}$, —$CF_3$, —$OCF_3$, —$OR^{31}$, —O-aryl, —$NR^{31}R^{32}$, —$NR^{34}R^{35}$, —$C(O)R^{31}$, —$CO_2R^{31}$, —$C(=O)NNR^{34}R^{35}$, —$C(=O)NR^{31}R^{32}$, $SO_2NR^{31}R^{32}$, or —$SO_2NR^{34}R^{35}$ substituents.

In some embodiments for a compound of Formula X, $R^3$ is hydrogen or halogen, such as chloro, bromo, fluoro or iodo. In other embodiments, $R^3$ is unsubstituted or substituted aryl (including but not limited to monocyclic or bicyclic aryl) or unsubstituted or substituted heteroaryl, including but not limited to monocyclic and bicyclic heteroaryl. Monocyclic heteroaryl $R^3$ includes but is not limited to pyrrolyl, thienyl, furyl, pyridinyl, pyranyl, imidazolyl, thiazolyl, pyrazolyl, and oxazolyl. Bicyclic heteroaryl $R^3$ includes but is not limited to benzothiophenyl, benzofuryl, indolyl, quinolinyl, isoquinolinyl, benzimidazolyl, benzoxazolyl, benzothiazolyl, quinazolinyl, azaindolyl, pyrazolopyrimidinyl, and purinyl $R^2$ is also unsubstituted or substituted $C_{1-10}$alkyl (including but not limited to $CH_3$, —$CH_2CH_3$, n-propyl, isopropyl, n-butyl, tert-butyl, sec-butyl, pentyl, hexyl, and heptyl) or unsubstituted or substituted $C_{3-8}$cycloalkyl (including but not limited to cyclopropyl, cyclobutyl, and cyclopentyl. In other embodiments, $R^3$ is -alkylcycloalkyl, -alkylaryl, -alkyl heteroaryl, or -alkylheterocyclyl. Alkyl, aryl, cycloalkyl, and heteroaryl are as described herein and the heterocyclyl is unsubstituted or substituted (non-limiting examples include pyrrolidinyl, tetrahydrofuranyl, piperidinyl, tetrahydropyranyl, thiazolidinyl, imidazolidinyl, morpholinyl, and piperazinyl) For $R^3$-alkylcycloalkyl, -alkylaryl, -alkyl heteroaryl, or -alkylheterocyclyl, connection to $R_1$ is through the alkyl portion of the moiety. In yet other embodiments, $R^3$ is unsubstituted or substituted alkenyl (including but not limited to unsubstituted or substituted $C_2$-$C_{10}$ alkenyl such as, for example, vinyl, allyl, 1-methyl propen-1-yl, butenyl, or pentenyl) or unsubstituted or substituted alkynyl (including but not limited to unsubstituted or substituted $C_2$-$C_{10}$ alkynyl such as acetylenyl, propargyl, butynyl, or pentynyl).

Other compounds of Formula X are provided by the invention, wherein $R^3$ is -alkenylaryl, -alkenylheteroaryl, -alkenylheteroalkyl, -alkenylheterocyclcyl or -alkenylcycloalkyl, wherein alkenyl, aryl, heteroaryl, heteroalkyl, heterocyclyl, and cycloalkyl are as described herein. The $R^3$-alkenylaryl, -alkenylheteroaryl, -alkenylheteroalkyl, -alkenylheterocyclcyl, or -alkenylcycloalkyl moiety is attached to $R_1$ through the alkenyl portion of the moiety.

In other embodiments, $R^3$ is -alkynylaryl, -alkynyl heteroaryl, -alkynylheteroalkyl, -alkynylheterocylyl, alkynylcycloalkyl, or -alkynylcycloalkenyl, wherein alkynyl, aryl, heteroaryl, heteroalkyl, heterocyclyl, cycloalkyl are as described herein. A $R^3$-cycloalkenyl moiety is unsubstituted or substituted $C_3$-$C_8$cycloalkenyl (including but not limited to cyclopentenyl and cyclohexenyl). The $R^3$-alkynylaryl, -alkynyl heteroaryl, -alkynylheteroalkyl, -alkynylheterocylyl, -alkynylcycloalkyl, or -alkynylcycloalkenyl is attached to $R_1$ through the alkynyl portion of the moiety. Some nonlimiting examples include 2-cyclopropylacetylenyl and 3-(morpholinyl)proparg-1-yl. Alternatively, $R^3$ is -cycloalkyl-alkyl, -cycloalkylalkynyl, or -cycloalkylalkenyl, wherein cycloalkyl, alkyl, alkenyl, and alkynyl are as described herein. The $R^3$-cycloalkyl-alkyl, -cycloalkylalkynyl, or -cycloalkylalkenyl is attached to $R_1$ through the cycloalkyl portion of the moiety. In some other embodiments, $R^3$ is -alkoxy alkyl, -alkoxyalkenyl, or -alkoxyalkynyl, wherein alkoxy, alkyl, alkenyl, and alkynyl are as described herien. The $R^3$-alkoxy alkyl, -alkoxyalkenyl, or -alkoxyalkynyl is attached to $R_1$ through the alkoxy portion of the moiety. Alternatively, $R^3$ is (unsubstituted or substituted heterocyclyl) wherein heterocyclyl includes but is not limited to azetidinyl, pyrrolidinyl, tetrahydrofuranyl, piperidinyl, tetrahydropyranyl, thiazolidinyl, imidazolidinyl, morpholinyl, and piperazinyl. Heterocyclyl includes but is not not limited to morpholinyl, thiomorpholinyl, azetidinyl, pyrrolidinyl, tetrahydropyranyl, piperazinyl, and 4-NMe-piperazinyl. In some other embodiments, $R^3$ is -heterocyclylalkyl, -heterocyclylalkenyl, -heterocyclyl-alkynyl, -heterocyclylcycloalkyl or -heterocyclylheterocylyl wherein heterocyclyl, alkyl, alkenyl, cycloalkyl, and alkynyl are as described herein. The $R^3$-heterocyclylalkyl, -heterocyclylalkenyl, -heterocyclyl-alkynyl, -heterocyclylcycloalkyl or -heterocyclylheterocylyl is connected to $R_1$ through the heterocylyl portion of the moiety. In yet other embodiments, $R^3$ is -arylalkenyl, -arylalkynyl, or -aryl-heterocyclyl, wherein aryl, alkenyl, alkynyl or heterocyclyl is as described herein. The $R^3$-arylalkenyl, -arylalkynyl, or -aryl-heterocyclyl is attached to $R_1$ through the aryl portion of the moiety. Nonlimiting examples include 4-allylphen-1-yl, 2(morpholinyl)phenyl and 4-(piperidinyl)phenyl Alternatively, $R^3$ is -heteroaryl-alkyl, -heteroaryl-alkenyl, -heteroaryl-alkynyl, -heteroaryl-cycloalkyl, -heteroaryl-heteroalkyl, or -heteroaryl-heterocyclyl, wherein heteroaryl, alkyl, alkenyl, alkynyl, cycloalkyl, heteroalkyl, and heterocyclyl are as described herein. The $R^3$-heteroaryl-alkyl, -heteroaryl-alkenyl, -heteroaryl-alkynyl, -heteroaryl-cycloalkyl, -heteroaryl-heteroalkyl, or -heteroaryl-heterocyclyl is attached to $R_1$ through the heteroaryl portion of the moiety.

In some embodiments for a compound of Formula X, each aryl or heteroaryl that forms part or all of $R^3$ is unsubstituted or is substituted with one or more independent halo, —OH, —$R^{31}$, —$CF_3$, —$OCF_3$, —$OR^{31}$, —$NR^{31}R^{32}$, —$NR^{34}R^{35}$, —$C(O)R^{31}$, —$CO_2R^{31}$, —$C(=O)NR^{31}R^{32}$, —$C(=O)$NNR$^{34}R^{35}$, —$NO_2$, —CN, —$S(O)_{0-2}R^{31}$, —$SO_2NR^{31}R^{32}$, —$SO_2NR^{34}R^{35}$, —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, —$C(=S)$$OR^{31}$, —$C(=O)SR^{31}$, —$NR^{31}C(=NR^{32})NR^{33}R^{32}$, —$NR^{31}C(=NR^{32})OR^{33}$, —$NR^{31}C(=NR^{32})SR^{33}$, —OC$(=O)OR^{33}$, —$OC(=O)NR^{31}R^{32}$, —$OC(=O)SR^{31}$, —SC$(=O)OR^{31}$, —$P(O)OR^{31}OR^{32}$, or —$SC(=O)NR^{31}R^{32}$ substituents.

In other embodiments for a compound of Formula X, each alkyl, cycloalkyl, heterocyclyl, or heteroalkyl forming all or part of $R^3$ is unsubstituted or substituted with one or more halo, —OH, —$R^{31}$, —$CF_3$, —$OCF_3$, —$OR^{31}$, —O-aryl, —$NR^{31}R^{32}$, —$NR^{34}R^{35}$, —$C(O)R^{31}$, —$CO_2R^{31}$, —$C(=O)$NNR$^{34}R^{35}$, —$C(=O)NR^{31}R^{32}$, $SO_2NR^{31}R^{32}$, or —$SO_2NR^{34}R^{35}$ substituents.

In some embodiments of a compound of Formula X, $R^4$ is hydrogen or halogen, such as chloro, bromo, fluoro or iodo. In other embodiments, $R^4$ is unsubstituted or substituted aryl (including but not limited to monocyclic or bicyclic aryl) or unsubstituted or substituted heteroaryl, including but not limited to monocyclic and bicyclic heteroaryl. Monocyclic heteroaryl $R^4$ includes but is not limited to pyrrolyl, thienyl, furyl, pyridinyl, pyranyl, imidazolyl, thiazolyl, pyrazolyl, and oxazolyl. Bicyclic heteroaryl $R^4$ includes but is not limited to benzothiophenyl, benzofuryl, indolyl, quinolinyl, isoquinolinyl, benzimidazolyl, benzoxazolyl, benzothiazolyl, quinazolinyl, azaindolyl, pyrazolopyrimidinyl, and purinyl $R^4$ is also unsubstituted or substituted $C_{1-10}$alkyl (including but not limited to $CH_3$, —$CH_2CH_3$, n-propyl, isopropyl, n-butyl, tert-butyl, sec-butyl, pentyl, hexyl, and heptyl) or unsubstituted or substituted $C_{3-8}$cycloalkyl (including but not limited to cyclopropyl, cyclobutyl, and cyclopentyl). In other embodiments, $R^4$ is -alkylcycloalkyl, -alkylaryl, -alkyl heteroaryl, or -alkyl-heterocyclyl. Alkyl, aryl, cycloalkyl, and heteroaryl are as described herein and the heterocyclyl is unsubstituted or substituted (non-limiting examples include pyrrolidinyl, tetrahydrofuranyl, piperidinyl, tetrahydropyranyl, thiazolidinyl, imidazolidinyl, morpholinyl, and piperazinyl) For $R^4$-alkylcycloalkyl, -alkylaryl, -alkyl heteroaryl, or -alkyl-heterocyclyl, connection to $W^1$ or to the compound of Formula I is through the alkyl portion of the moiety. In yet other embodiments, $R^4$ is unsubstituted or substituted alkenyl (including but not limited to unsubstituted or substituted $C_2$-$C_{10}$ alkenyl such as, for example, vinyl, allyl, 1-methyl propen-1-yl, butenyl, or pentenyl) or unsubstituted or substituted alkynyl (including but not limited to unsubstituted or substituted $C_2$-$C_{10}$alkynyl such as acetylenyl, propargyl, butynyl, or pentynyl).

For other Formula X compounds that are provided by the invention, wherein $R^4$ is -alkenylaryl, -alkenylheteroaryl, -alkenylheteroalkyl, -alkenylheterocyclcyl or -alkenylcycloalkyl, wherein alkenyl, aryl, heteroaryl, heteroalkyl, heterocyclyl, and cycloalkyl are as described herein. The $R^4$-alkenylaryl, -alkenylheteroaryl, -alkenylheteroalkyl, -alkenylheterocyclcyl, or -alkenylcycloalkyl moiety is attached to $W^1$ or to the compound of Formula I through the alkenyl portion of the moiety. In other embodiments, $R^4$ is -alkynylaryl, -alkynyl heteroaryl, -alkynylheteroalkyl, -alkynylheterocyclyl, -alkynylcycloalkyl, or -alkynylcycloalkenyl, wherein alkynyl, aryl, heteroaryl, heteroalkyl, heterocyclyl, cycloalkyl are as described herein. A $R^4$-cycloalkenyl moiety is unsubstituted or substituted $C_3$-$C_8$cycloalkenyl (including but not limited to cyclopentenyl and cyclohexenyl). The $R^4$ alkynylaryl, -alkynyl heteroaryl, -alkynylheteroalkyl, -alkynylheterocyclyl, -alkynylcycloalkyl, or -alkynylcycloalkenyl is attached to $W^1$ or to the compound of Formula I through the alkynyl portion of the moiety.

Some nonlimiting examples include 2-cyclopropylacetylenyl and 3-(morpholinyl)proparg-1-yl. Alternatively, $R^4$ is -cycloalkyl-alkyl, -cycloalkylalkynyl, or -cycloalkylalkenyl, wherein cycloalkyl, alkyl, alkenyl, and alkynyl are as described herein. The $R^4$-cycloalkyl-alkyl, -cycloalkylalkynyl, or -cycloalkylalkenyl is attached to $W^1$ or to the compound of Formula I through the cycloalkyl portion of the moiety. In some other embodiments, $R^4$ is -alkoxy alkyl, -alkoxyalkenyl, or -alkoxyalkynyl, wherein alkoxy, alkyl, alkenyl, and alkynyl are as described herein. The $R^4$-alkoxy alkyl, -alkoxyalkenyl, or -alkoxyalkynyl is attached to $W^1$ or to the compound of Formula I through the alkoxy portion of the moiety. Alternatively, $R^4$ is (unsubstituted or substituted heterocyclyl) wherein heterocyclyl includes but is not limited to azetidinyl, pyrrolidinyl, tetrahydrofuranyl, piperidinyl, tetrahydropyranyl, thiazolidinyl, imidazolidinyl, morpholinyl, and piperazinyl. Heterocyclyl includes but is not limited to morpholinyl, thiomorpholinyl, azetidinyl, pyrrolidinyl, tetrahydropyranyl, piperazinyl, and 4-NMe-piperazinyl. In some other embodiments, $R^4$ is -heterocyclylalkyl, -heterocyclylalkenyl, -heterocyclyl-alkynyl, -heterocyclylcycloalkyl or -heterocyclylheterocylyl wherein heterocyclyl, alkyl, alkenyl, cycloalkyl, and alkynyl are as described herein. The $R^4$-heterocyclylalkyl, -heterocyclylalkenyl, -heterocyclyl-alkynyl, -heterocyclylcycloalkyl or -heterocyclylheterocylyl is connected to $W^1$ or to the compound of Formula I through the heterocylyl portion of the moiety. In yet other embodiments, $R^4$ is -arylalkenyl, -arylalkynyl, or -aryl-heterocyclyl, wherein aryl, alkenyl, alkynyl or heterocyclyl is as described herein. The $R^4$-arylalkenyl, -arylalkynyl, or -aryl-heterocyclyl is attached to $W^1$ or to the compound of Formula I through the aryl portion of the moiety. Nonlimiting examples include 4-allylphen-1-yl, 2(morpholinyl)phenyl and 4-(piperidinyl)phenyl Alternatively, $R^4$ is -heteroaryl-alkyl, -heteroaryl-alkenyl, -heteroaryl-alkynyl, -heteroaryl-cycloalkyl, -heteroaryl-heteroalkyl, or -heteroaryl-heterocyclyl, wherein heteroaryl, alkyl, alkenyl, alkynyl, cycloalkyl, heteroalkyl, and heterocyclyl are as described herein. The $R^4$-heteroaryl-alkyl, -heteroaryl-alkenyl, -heteroaryl-alkynyl, -heteroaryl-cycloalkyl, -heteroaryl-heteroalkyl, or -heteroaryl-heterocyclyl is attached to $W^1$ or to the compound of Formula I through the heteroaryl portion of the moiety.

In some embodiments, each aryl or heteroaryl that forms part or all of $R^4$ is unsubstituted or is substituted with one or more independent halo, —OH, —$R^{31}$, —$CF_3$, —$OCF_3$, —$OR^{31}$, —$NR^{31}R^{32}$, —$NR^{34}R^{35}$, —$C(O)R^{31}$, —$CO_2R^{31}$, —$C(=O)NR^{31}R^{32}$, —$C(=O)NNR^{34}R^{35}$, —$NO_2$, —CN, —$S(O)_{0-2}R^{31}$, —$SO_2NR^{31}R^{32}$, —$SO_2NR^{34}R^{35}$, —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, —$C(=S)OR^{31}$, —$C(=O)SR^{31}$, —$NR^{31}C(=NR^{32})NR^{33}R^{32}$, —$NR^{31}C(=NR^{32})OR^{33}$, —$NR^{31}C(=NR^{32})SR^{33}$, —$OC(=O)OR^{33}$, —$OC(=O)NR^{31}R^{32}$, —$OC(=O)SR^{31}$, —$SC(=O)OR^{31}$, —P(O)$OR^{31}OR^{32}$, or —$SC(=O)NR^{31}R^{32}$ substituents.

In some embodiments, each alkyl, cycloalkyl, heterocyclyl, or heteroalkyl forming all or part of $R^4$ is unsubstituted or substituted with one or more halo, —OH, —$R^{31}$, —$CF_3$, —$OCF_3$, —$OR^{31}$, —O-aryl, —$NR^{31}R^{32}$, —$NR^{34}R^{35}$, —$C(O)R^{31}$, —$CO_2R^{31}$, —$C(=O)NNR^{34}R^{35}$, —$C(=O)NR^{31}R^{32}$, $SO_2NR^{31}R^{32}$, or —$SO_2NR^{34}R^{35}$ substituents.

In some embodiments of the invention, the compound of Formula X is a compound of Formula XI or XII:

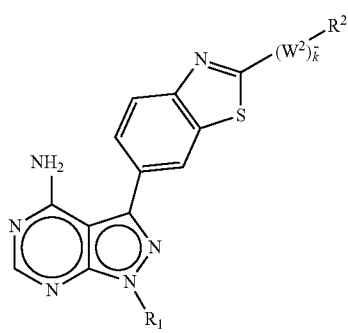

Formula XI

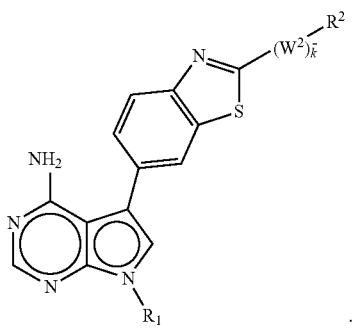

Formula XII

In some embodiments of the invention, the compound of Formula XI or Formula XII is a compound of Formula XI or XII:

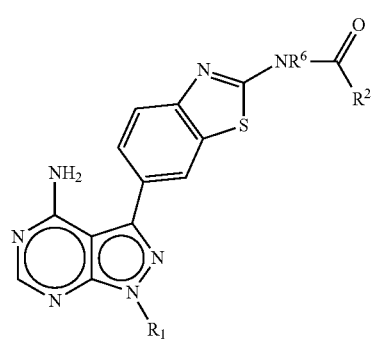

Formula XI-1

Formula XII-1

Formula XI-2

Formula XII-2

-continued

Formula XI-3
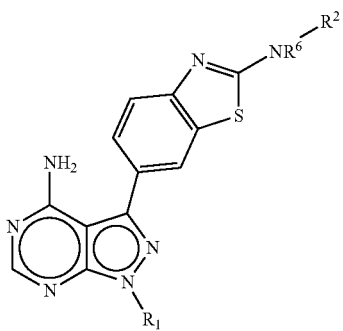

Formula XII-3
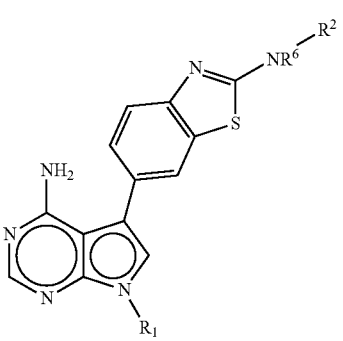

Formula XI-4
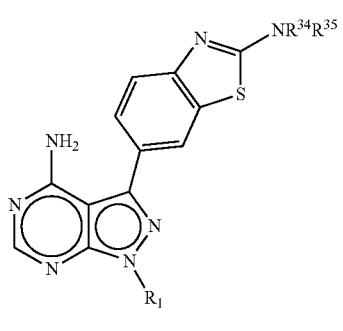

Formula XII-4
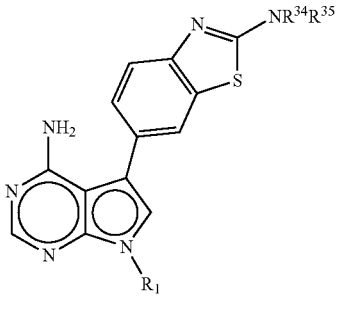

In some of the embodiments of the compounds of Formula XI-3 or XII-3, when $R^6$ or $R^2$ is phenyl, then the phenyl is a substituted phenyl. In other embodiments, when $R^6$ and/or $R^2$ is alkyl, then $R^6$ and/or $R^2$ is unsubstituted or substituted with one or more halo, —OH, —CF$_3$, —OCF$_3$, —OR$^{31}$, —O-aryl, —NR$^{31}$R$^{32}$, —NR$^{34}$R$^{35}$, —C(O)R$^{31}$, —CO$_2$R$^{31}$, —C(=O)NNR$^{34}$R$^{35}$, —NO$_2$, —CN, —S(O)$_{0-2}$R$^{31}$, —SO$_2$NR$^{31}$R$^{32}$, —SO$_2$NR$^{34}$R$^{35}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_{0-2}$R$^{32}$, —C(=S)OR$^{31}$, —C(=O)SR$^{31}$, —NR$^{31}$C(=NR$^{32}$)NR$^{33}$R$^{32}$, —NR$^{31}$C(=NR$^{32}$)OR$^{33}$, —NR$^{31}$C(=NR$^{32}$)SR$^{33}$, —OC(=O)OR$^{33}$, —OC(=O)NR$^{31}$R$^{32}$, —OC(=O)SR$^{31}$, —SC(=O)OR$^{31}$, —P(O)OR$^{31}$OR$^{32}$, or —SC(=O)NR$^{31}$R$^{32}$ substituents. In other embodiments, when $R^6$ and/or $R^2$ is alkyl, then $R^6$ and/or $R^2$ is substituted by cycloalkyl or heterocyclyl. In other embodiments, $R^6$ is hydrogen and $R^2$ is unsubstituted alkyl or hydrogen. In some embodiments, $R^6$ and $R^2$ are hydrogen.

In one aspect, a compound of Formula I or a pharmaceutically acceptable salt thereof, is provided wherein Formula I
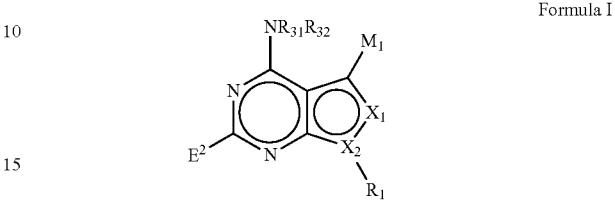

$M_1$ is benzothiazolyl substituted with —(W$^2$)$_k$—R$^2$; k is 0 or 1; $R_1$ is —H, -L-alkyl, -L-cycloalkyl, -L-alkyl-cycloalkyl, -L-aryl, -L-heteroaryl, -L-alkylaryl, -L-alkylheteroaryl, -L-alkylheterocylyl, -L-alkenyl, -L-alkynyl, -L-alkenyl-cycloalkyl, -L-alkynyl-cycloalkyl, or -L-heterocyclyl, each of which is unsubstituted or substituted by one or more independent $R^3$ substituents; L is absent, C=O, —C(=O)O—, —C(=O) NR$^{31}$—, —S—, —S(O)—, —S(O)$_2$—, —S(O)$_2$NR$^{31}$—, or —NR$^{31}$—; $X_1$ is N or C-E$^1$ and $X_2$ is N; or $X_1$ is NH or CH-E$^1$ and $X_2$ is C; E$^1$ and E$^2$ are independently —(W$^1$)$_j$—R$^4$; j, in each instance, is 0 or 1; W$^1$ is —O—, —NR$^6$—, —S(O)$_{0-2}$—, —C(O)—, —C(O)N(R$^6$)—, —N(R$^6$)C(O)—, —N(R$^6$)S(O)—, —N(R$^6$)S(O)$_2$—, —C(O)O—, —CH(R$^6$)N(C(O)OR$^7$)—, —CH(R$^7$)N(C(O)R$^7$)—, —CH(R$^6$)N(SO$_2$R$^7$)—, —CH(R$^6$)N(R$^7$)—, —CH(R$^6$)C(O)N(R$^7$)—, —CH(R$^6$)N(R$^7$)C(O)—, —CH(R$^6$)N(R$^7$)S(O)—, or —CH(R$^6$)N(R$^7$)S(O)$_2$—; W$^2$ is —O—, —NR$^6$—, —S(O)$_{0-2}$—, —C(O)—, —C(O)N(R$^6$)—, —N(R$^6$)C(O)—, —N(R$^6$)S(O)—, —N(R$^6$)S(O)$_2$—, —C(O)O—, —CH(R$^6$)N(C(O)OR$^7$)—, —CH(R$^7$)N(C(O)R$^7$)—, —CH(R$^6$)N(SO$_2$R$^7$)—, —CH(R$^6$)N(R$^7$)—, —CH(R$^6$)C(O)N(R$^7$)—, —CH(R$^6$)N(R$^7$)C(O)—, —CH(R$^6$)N(R$^7$)S(O)—, or —CH(R$^6$)N(R$^7$)S(O)$_2$—; $R^3$ and $R^4$ are independently hydrogen, halogen, aryl, heteroaryl, alkyl, cycloalkyl, -alkyl-cycloalkyl, -alkylheterocyclyl, C$_{2-10}$alkenyl, or C$_{2-10}$alkynyl; $R^2$ is hydrogen, bicyclic aryl, substituted monocyclic aryl, hetaryl, alkyl, cycloalkyl, -alkyl-cycloalkyl, -alkyl-monocyclic aryl, -alkylbicycloaryl, -alkylhetaryl, -alkylheterocyclyl, alkenyl, or alkynyl; $R^6$ and $R^7$ are each independently hydrogen, alkyl, alkenyl, aryl, heteroaryl, heterocyclyl or cycloalkyl, wherein each alkyl, alkenyl, aryl, heteroaryl, heterocyclyl or cycloalkyl is unsubstituted or substituted by one or more independent $R^8$ substituents; and $R^8$ is halo, —OR$^{31}$, —SH, NH$_2$, —NR$^{34}$R$^{35}$, —NR$^{31}$R$^{32}$, —CO$_2$R$^{31}$, —CO$_2$aryl-C(=O)NR$^{31}$R$^{32}$, —C(=O) NR$^{34}$R$^{35}$, —NO$_2$, —CN, —S(O)$_{0-2}$alkyl, —S(O)$_{0-2}$aryl, —SO$_2$NR$^{34}$R$^{35}$, —SO$_2$NR$^{31}$R$^{32}$, alkyl, alkenyl, or alkynyl; $R^{31}$, $R^{32}$, and $R^{33}$, in each instance, are independently H or alkyl; and $R^{34}$ and $R^{35}$ are taken together with the nitrogen atom to which they are attached to form a 3-10 membered ring.

In some embodiments, the compound is a compound wherein $E^2$ is —H. In some embodiments, wherein $E^2$ is —H, L is optionally —N(R$^{31}$)C(O)—. In other embodiments, wherein $E^2$ is —H, $R^3$ and $R^4$ are optionally alkoxy, heterocyclyl, —OH, —CF$_3$, —OCF$_3$, —OR$^{31}$, —NR$^{31}$R$^{32}$, —NR$^{34}$R$^{35}$, —C(O)R$^{31}$, —CO$_2$R$^{31}$, —C(=O)NR$^{31}$R$^{32}$, —C(=O)NNR$^{34}$R$^{35}$, —NO$_2$, —CN, —S(O)$_{0-2}$R$^{31}$, —SO$_2$NR$^{31}$R$^{32}$, —SO$_2$NR$^{34}$R$^{35}$, —NR$^{31}$C(=O)R$^{32}$, —NR³¹C(═O)OR³², —NR³¹C(═O)NR³²R³³, —NR³¹S(O)₀₋₂R³², —C(═S)OR³¹, —C(═O)SR³¹, —NR³¹C(═NR³²)NR³³R³², —NR³¹C(═NR³²)OR³³, —NR³¹C(═NR³²)SR³³, —OC(═O)OR³³, —OC(═O)NR³¹R³², —OC(═O)SR³¹, —SC(═O)OR³¹, —P(O)OR³¹OR³², or —SC(═O)NR³¹R³².

In yet other embodiments, wherein E² is —H, R² is optionally-alkyl-substituted monocyclic aryl, heterocyclyl, -cycloalkyl-heterocyclyl, or -heterocyclyl-heterocyclyl. In further embodiments, wherein E² is —H, W² is optionally —N(R⁶)C(O)N(R⁷)—, —CH(R⁷)C(O)—, or —NR³⁴R³⁵.

In a second aspect of the invention, a compound having a structure of Formula I, Formula II, Formula III, Formula IV, or Formula V, or a pharmaceutically acceptable salt thereof, shown below:

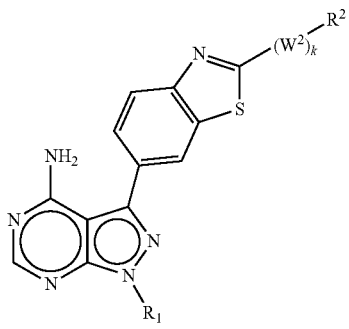

Formula II

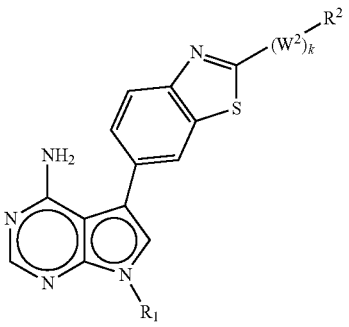

Formula III

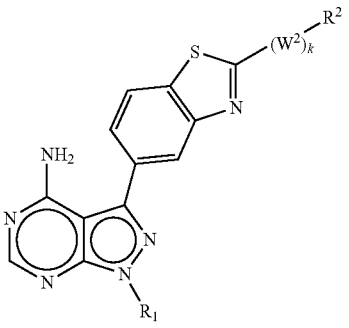

Formula IV

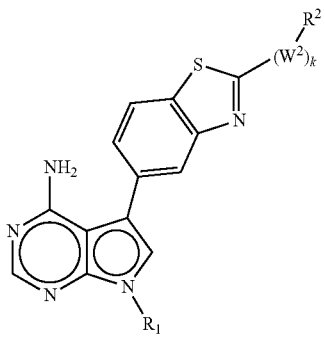

Formula V k is 0 or 1; $R_1$ is —H, -L-alkyl, -L-cycloalkyl, -L-alkylcycloalkyl, -L-aryl, -L-heteroaryl, -L-alkylaryl, -L-alkylheteroaryl, -L-alkylheterocyclyl, -L-alkenyl, -L-alkynyl, -L-alkenyl-cycloalkyl, -L-alkynyl-cycloalkyl, or -L-heterocyclyl, each of which is unsubstituted or substituted by one or more independent R³ substituents; L is absent, C═O, —C(═O)O—, —C(═O) NR³¹—, —S—, —S(O)—, —S(O)₂—, —S(O)₂NR³¹—, or —NR³¹; W² is —O—, —NR⁶—, —S(O)₀₋₂—, —C(O)—, —C(O)N(R⁶)—, —N(R⁶)C(O)—, —N(R⁶)S(O)—, —N(R⁶)S(O)₂—, —C(O)O—, —CH(R⁶)N(C(O)OR⁷)—, —CH(R⁷)N(C(O)R⁷)—, —CH(R⁶)N(SO₂R⁷)—, —CH(R⁶)N(R⁷)—, —CH(R⁶)C(O)N(R⁷)—, —CH(R⁶)N(R⁷)C(O)—, —CH(R⁶)N(R⁷)S(O)—, or CH(R⁶)N(R⁷)S(O)₂—; R³ and R⁴ are independently hydrogen, halogen, aryl, heteroaryl, alkyl, cycloalkyl, -alkylcycloalkyl, -alkylheterocyclyl, $C_{2-10}$alkenyl, or $C_{2-10}$alkynyl; R² is hydrogen, bicyclic aryl, substituted monocyclic aryl, hetaryl, alkyl, cycloalkyl, -alkyl-cycloalkyl, -alkyl-monocyclic aryl, -alkylbicycloaryl, -alkylhetaryl, -alkylheterocyclyl, alkenyl, or alkynyl; R⁶ and R⁷ are each independently hydrogen, alkyl, alkenyl, aryl, heteroaryl, heterocyclyl or cycloalkyl, wherein each alkyl, alkenyl, aryl, heteroaryl, heterocyclyl or cycloalkyl is unsubstituted or substituted by one or more independent R⁸ substituents; and R⁸ is halo, —OR³¹, —SH, —NH₂, —NR³⁴R³⁵, —NR³¹R³², —CO₂R³¹, —CO₂aryl-C(═O)NR³¹R³², C(═O) NR³⁴R³⁵, —NO₂, —CN, —S(O)₀₋₂ alkyl, —S(O)₂aryl, —SO₂NR³⁴R³⁵, —SO₂NR³¹R³², alkyl, alkenyl, or alkynyl; R³¹, R³², and R³³, in each instance, are independently H or alkyl; and R³⁴ and R³⁵ are taken together with the nitrogen atom to which they are attached to form a 3-10 membered ring.

In some embodiments, the compound of Formula II, Formula III, Formula IV, or Formula V, is a compound L is optionally —N(R³¹)C(O)—. In other embodiments, R³ and R⁴ are optionally alkoxy, heterocyclyl, —OH, —R³¹, —CF₃, —OCF₃, —OR³¹, —NR³¹R³², —NR³⁴R³⁵, —C(O) R³¹, —CO₂R³¹, —C(═O)NR³¹R³², —C(═O)NNR³⁴R³⁵, —NO₂, —CN, —S(O)₀₋₂R³¹, —SO₂NR³¹R³², —SO₂NR³⁴R³⁵, —NR³¹C(═O)R³², —NR³¹C(═O)OR³², —NR³¹C(═O)NR³²R³³, —NR³¹S(O)₀₋₂R³², —C(═S)OR³¹, —C(═O)SR³¹, —NR³¹C(═NR³²)NR³³R³², —NR³¹C(═NR³²)OR³³, —NR³¹C(═NR³²)SR³³, —OC(═O)OR³³, —OC(═O)NR³¹R³², —OC(═O)SR³¹, —SC(═O)OR³¹, —P(O)OR³¹OR³², or —SC(═O)NR³¹R³¹R³².

In yet other embodiments, R² is optionally-alkyl-substituted monocyclic aryl, heterocyclyl, -cycloalkyl-heterocyclyl, or -heterocyclyl-heterocyclyl. In further embodiments, W² is optionally —N(R⁶)C(O)N(R⁷)—, CH(R⁷)C(O)—, or —NR³⁴R³⁵.

In a third aspect of the invention, a compound of Formula II, Formula III, Formula IV, or Formula V, or a pharmaceutically acceptable salt thereof, is provided wherein $W^2$ is —$NR^6$—, —$N(R^6)C(O)$—, —$N(R^6)S(O)$—, or —$N(R^6)S(O)_2$.

In a fourth aspect of the invention, a compound of Formula X, or a pharmaceutically acceptable salt thereof, is provided wherein:

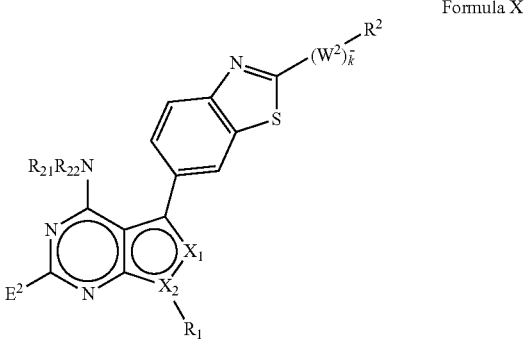

Formula X k, in each instance, is 0 or 1; $R_1$ is —H, -L-alkyl, -L-cycloalkyl, -L-alkyl-cycloalkyl, -L-aryl, -L-heteroaryl, -L-alkylaryl, -L-alkylheteroaryl, -L-alkylheterocylyl, -L-alkenyl, -L-alkynyl, -L-alkenyl-cycloalkyl, -L-alkynyl-cycloalkyl, or -L-heterocyclyl, each of which is unsubstituted or substituted by one or more independent $R^3$ substituents; L is absent, C=O, —C(=O)O—, —C(=O) $NR^{31}$—, —S—, —S(O)—, —S(O)$_2$—, —S(O)$_2NR^{31}$—, or —$NR^{31}$—; $X_1$ is N or C-$E^1$ and $X_2$ is N; or $X_1$ is NH or CH-$E^1$ and $X_2$ is C; $E^1$ and $E^2$ are independently —($W^1$)$_j$— $R^4$; j, in each instance, is 0 or 1; $W^1$ is —O—, —$NR^6$—, —S(O)$_{0-2}$—, —C(O)—, —C(O)N($R^6$)—, —N($R^6$)C(O)—, —N($R^6$)S(O)—, —N($R^6$)S(O)$_2$—, —C(O)O—, —CH($R^6$)N(C(O)O$R^7$)—, —CH($R^7$)N(C(O)$R^7$)—, —CH($R^6$)N(SO$_2R^7$)—, —CH($R^6$)N($R^7$)—, —CH($R^6$)C(O)N($R^7$)—, —CH($R^6$)N($R^7$)C(O)—, —CH($R^6$)N($R^7$)S(O)—, or —CH($R^6$)N($R^6$)S(O)$_2$—; $W^2$ is —O—, —$NR^6$—, —S(O)$_{0-2}$—, —C(O)—, —C(O)N($R^6$)—, —N($R^6$)C(O)—, —N($R^6$)S(O)—, —N($R^6$)S(O)$_2$—, —C(O)O—, —CH($R^6$)N(C(O)O$R^7$)—, —CH($R^7$)N(C(O)$R^7$)—, —CH($R^6$)N(SO$_2R^7$)—, —CH($R^6$)N($R^7$)—, —CH($R^6$)C(O)N($R^7$)—, —CH($R^6$)N ($R^7$)C(O)—, —CH($R^6$)N($R^7$)S(O)—, or —CH($R^6$)N($R^7$)S(O)$_2$—; $R^2$, $R^3$, and $R^4$ are independently hydrogen, halogen, aryl, heteroaryl, alkyl, cycloalkyl, alkenyl, alkynyl, heteroalkyl, heterocyclyl, alkyl-aryl, -alkyl-cycloalkyl, -alkylheterocyclyl, or -alkynyl-cycloalkyl; $R^6$ and $R^7$ are each independently hydrogen, alkyl, alkenyl, aryl, heteroaryl, heterocyclyl or cycloalkyl, wherein each alkyl, alkenyl, aryl, heteroaryl, heterocyclyl or cycloalkyl is unsubstituted or substituted by one or more independent $R^8$ substituents; $R^8$ is halo, —$OR^{31}$, —SH, NH$_2$, —$NR^{34}R^{35}$, —$NR^{31}R^{32}$, —$CO_2R^{31}$, $CO_2$aryl-C(=O)$NR^{31}R^{32}$, C(=O) $NR^{34}R^{35}$, —NO$_2$, —CN, —S(O)$_{0-2}$ alkyl, —S(O)$_{0-2}$aryl, —SO$_2NR^{34}R^{35}$, —SO$_2NR^{31}R^{32}$, alkyl, alkenyl, or alkynyl; $R^{31}$, $R^{32}$, and $R^{33}$, in each instance, are independently H or alkyl; and $R^{34}$ and $R^{35}$ are taken together with the nitrogen atom to which they are attached to form a 3-10 membered ring.

In some embodiments of the compound of Formula X, $E^2$ is —H. In some embodiments wherein $E^2$ is —H, L is optionally —N($R^{31}$)C(O)—. In other embodiments wherein $E^2$ is —H, $R^3$ and $R^4$ are optionally alkoxy, —OH, —$R^{31}$, CF$_3$, —OCF$_3$, —$OR^{31}$, —$NR^{31}R^{32}$, —$NR^{34}R^{35}$, —C(O)$R^{31}$, —CO$_2R^{31}$, —C(=O)$NR^{31}R^{32}$, —C(=O)NN$R^{34}R^{35}$, —NO$_2$, —CN, —S(O)$_{0-2}R^{31}$, —SO$_2NR^{31}R^{32}$, —SO$_2NR^{34}R^3$, —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, —C(=S) $OR^{31}$, —C(=O)$SR^{31}$, —$NR^{31}C(=NR^{32})NR^{33}R^{32}$, —$NR^{31}C(=NR^{32})OR^{33}$, —$NR^{31}C(=NR^{32})SR^{33}$, —OC(=O)$OR^{33}$, —OC(=O)$NR^{31}R^{32}$, —OC(=O)$SR^{31}$, —SC(=O)$OR^{31}$, —P(O)$OR^{31}OR^{32}$, or —SC(=O)$NR^{31}R^{32}$. In some other embodiments wherein $E^2$ is —H, $R^2$ is optionally -cycloalkyl-heterocyclyl, or -heterocyclyl-heterocyclyl. Alternatively, wherein $E^2$ is —H, $W^2$ is optionally —N($R^6$)C(O)N($R^7$)—, —CH($R^7$)C(O)—, or —$NR^{34}R^{35}$.

In a fifth aspect of the invention, a compound of Formula XI or Formula XII, or a pharmaceutically acceptable salt thereof, is provided wherein:

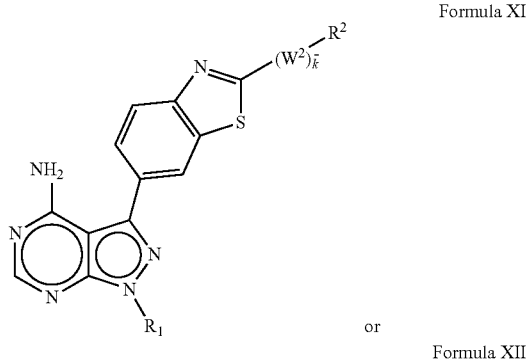

Formula XI or

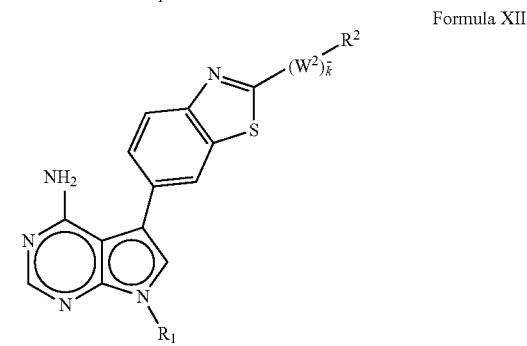

Formula XII k, in each instance, is 0 or 1; $R_1$ is H, L-alkyl, -L-cycloalkyl, -L-alkyl-cycloalkyl, -L-aryl, -L-heteroaryl, -L-alkylaryl, -L-alkylheteroaryl, -L-alkylheterocylyl, -L-alkenyl, -L-alkynyl, -L-alkenyl-cycloalkyl, -L-alkynyl-cycloalkyl, or -L-heterocylyl, each of which is unsubstituted or substituted by one or more independent $R^3$ substituents; L is absent, C=O, —C(=O)O—, —C(=O) $NR^{31}$—, —S—, —S(O)—, —S(O)$_2$—, —S(O)$_2NR^{31}$—, or —$NR^{31}$—; $W^2$ is —O—, —$NR^6$—, —S(O)$_{0-2}$—, —C(O)—, —C(O)N($R^6$)—, —N($R^6$)C(O)—, —N($R^6$)S(O)—, —N($R^6$)S(O)$_2$—, —C(O)O—, —CH($R^6$)N(C(O)O$R^7$)—, —CH($R^7$)N(C(O)$R^7$)—, —CH($R^6$)N(SO$_2R^7$)—, —CH($R^6$)N($R^7$)—, —CH($R^6$)C(O)N($R^7$)—, —CH($R^6$)N ($R^7$)C(O)—, —CH($R^6$)N($R^7$)S(O)—, or —CH($R^6$)N($R^7$)S(O)$_2$—; $R^2$, $R^3$, and $R^4$ are independently hydrogen, halogen, aryl, heteroaryl, alkyl, cycloalkyl, alkenyl, alkynyl, heteroalkyl, heterocyclyl, alkyl-aryl, -alkyl-cycloalkyl, -alkylheterocyclyl, or alkynyl-cycloalkyl; $R^6$ and $R^7$ are each independently hydrogen, alkyl, alkenyl, aryl, heteroaryl, heterocyclyl or cycloalkyl, wherein each alkyl, alkenyl, aryl, heteroaryl, heterocyclyl or cycloalkyl is unsubstituted or substituted by one or more independent $R^8$ substituents; $R^8$ is halo, —$OR^{31}$, —SH, —$NH_2$, —$NR^{34}R^{35}$, —$NR^{31}R^{32}$, —$CO_2R^{31}$, —$CO_2$aryl-C(=O)$NR^{31}R^{32}$, C(=O) $NR^{34}R^{35}$, —$NO_2$, —CN, —$S(O)_{0-2}$ alkyl, $S(O)_{0-2}$ aryl, $SO_2NR^{34}R^{35}$, —$SO_2NR^{31}R^{32}$, alkyl, alkenyl, or alkynyl; $R^{31}$, $R^{32}$, and $R^{33}$, in each instance, are independently H or alkyl; and $R^{34}$ and $R^{35}$ are taken together with the nitrogen atom to which they are attached to form a 3-10 membered ring.

In some embodiments of the compound of Formula XI or XII, L is optionally $N(R^{31})C(O)$. In other embodiments, $R^3$ and $R^4$ are optionally alkoxy, —OH, $R^{31}$, —$CF_3$, —$OCF_3$, —$OR^{31}$, $NR^{31}R^{32}$, $NR^{34}R^{35}$, —$C(O)R^{31}$, —$CO_2R^{31}$, —$C(=O)NR^{31}R^{32}$, —$C(=O)NNR^{34}R^{35}$, —$NO_2$, —CN, —$S(O)_{0-2}R^{31}$, —$SO_2NR^{31}R^{32}$, —$SO_2NR^{34}R^{35}$, —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, C(=S)$OR^{31}$, C(=O)$SR^{31}$, —$NR^{31}C(=NR^{32})NR^{33}R^{32}$, —$NR^{31}C(=NR^{32})OR^{33}$, —$NR^{31}C(=NR^{32})SR^{33}$, —$OC(=O)OR^{33}$, —$OC(=O)NR^{31}R^{31}R^{32}$, —$OC(=O)SR^{31}$, —$SC(=O)OR^{31}$, —$P(O)OR^{31}OR^{32}$, or —$SC(=O)NR^{31}R^{32}$. In some other embodiments, $R^2$ is optionally -cycloalkyl-heterocyclyl, or heterocyclyl-heterocyclyl. Alternatively, $W^2$ is optionally $N(R^6)C(O)N(R^7)$—, $CH(R^7)C(O)$—, or $NR^{34}R^{35}$.

Some illustrative compounds of the invention are described in the following tables. The compounds of the invention are not limited in any way to the compounds illustrated herein.

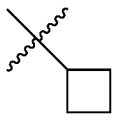 [SMILES: *C1CCC1]
Formula A

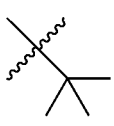 [SMILES: *C(C)(C)C]
Formula B

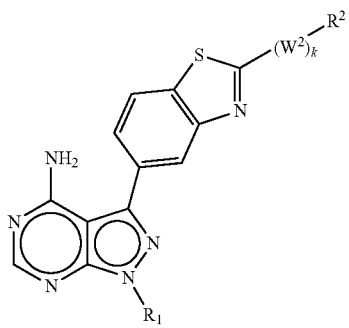
Formula C

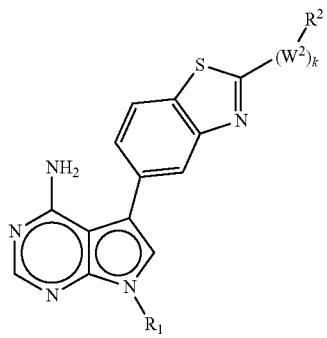
Formula D

Some exemplary non-limiting compounds of the present invention having a structure of Formula A, Formula B, Formula C, or Formula D include those in which $R_1$ is selected from any $R_1$ moiety described in Table 1, and in combination with any $(W^2)_k$—$R^2$ as described in Table 2. A compound of Formula A, Formula B, Formula C, or Formula D includes any combination of $R_1$ and $(W^2)_k$—$R^2$. Additional exemplary compounds of Formula A, Formula B, Formula C, or Formula D are illustrated in Table 5.

TABLE 1

Illustrative $R_1$ moieties of the compounds of Formula I.

| Subclass # | $R_1$ |
|---|---|
| R1-1 | H |
| | iso-propyl |
| R1-2 | Me |
| | n-propyl |
| R1-3 | Et |
| | iso-butyl |
| R1-4 | 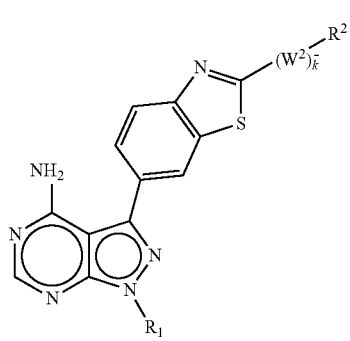 |
| R1-5 | 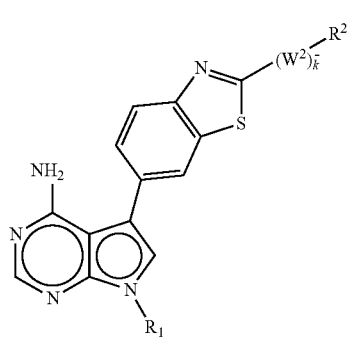 |
| R1-6 | 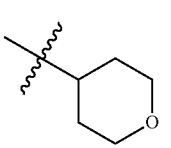 [SMILES: *C1CCOCC1] |

TABLE 1-continued

Illustrative R₁ moieties of the compounds of Formula I.

| Subclass # | R₁ |
|---|---|
| R1-7 | CH(CH₃)CH₂NH₂ (wedge bond) |
| R1-8 | CH₂CH=CH-phenyl (trans-cinnamyl) |
| R1-9 | 3-tetrahydrofuranyl |
| R1-10 | CH(CH₃)CH₂NH₂ (dashed wedge) |
| R1-11 | CH₂-(pyrrolidin-3-yl) |
| R1-12 | cycloheptyl |
| R1-13 | (CH₂)₄CN |
| R1-14 | CH₂CH₂-(piperidin-3-yl) |
| R1-15 | CH₂-(piperidin-4-yl) |
| R1-16 | (CH₂)₃CN |
| R1-17 | pyrrolidin-3-yl |
| R1-18 | CH₂-cyclopropyl |
| R1-19 | azetidin-3-yl |
| R1-20 | CH₂-(pyrrolidin-2-yl) |
| R1-21 | CH₂C≡CH |
| R1-22 | 3-methylcyclopentyl |
| R1-23 | CH₂CH(CH₃)CH₂OH |
| R1-24 | CH₂CH₂CH(CH₃)₂ |
| R1-25 | cyclopentyl |

TABLE 1-continued

Illustrative R₁ moieties of the compounds of Formula I.

| Subclass # | R₁ |
|---|---|
| R1-26 | (branched alkyl with HO) |
| R1-27 | benzyl |
| R1-28 | phenethyl |
| R1-29 | 2-pyridyl |
| R1-30 | 4-(NHCH₃)cyclohexyl |
| R1-31 | 1-methylpiperidin-4-yl |
| R1-32 | cyclopropylacetylene |
| R1-33 | 1-(SO₂Me)piperidin-4-yl |
| R1-34 | 1-(COMe)piperidin-4-yl |
| R1-35 | 4-(NHCH₃)cyclohexyl |
| R1-36 | 3-(NHCH₃)cyclobutyl |
| R1-37 | 2-morpholinoethyl |
| R1-38 | 2-(4-methylpiperazin-1-yl)ethyl |
| R1-39 | 1'-methyl-[1,4'-bipiperidin]-4-yl |

TABLE 1-continued

Illustrative R₁ moieties of the compounds of Formula I.

| Subclass # | R₁ |
|---|---|
| R1-40 | piperazine-N-SO₂Me attached via cyclobutyl |
| R1-41 | piperazine-N-CH₃ attached via cyclobutyl |
| R1-42 | piperazine-N-COMe attached via cyclobutyl |
| R1-43 | 4-(1-methylsulfonylpiperidin-4-yl)piperidine attached via cyclobutyl |
| R1-44 | 4-(1-acetylpiperidin-4-yl)piperidine |
| R1-45 | 4-morpholinocyclohexyl |
| R1-46 | 3-hydroxycyclobutyl |

TABLE 2

Illustrative (W²)ₖ—R² moieties of the compounds of Formula I.

| Subclass # | (W²)ₖ—R² |
|---|---|
| W-1 | —H |
| W-2 | —NH₂ |
| W-3 | —NHMe |
| W-4 | —N(Me)₂ |
| W-5 | —N(iso-propyl)₂ |
| W-6 | —N(Et)₂ |
| W-7 | —N(n-propyl)₂ |
| W-8 | —N(n-butyl)₂ |
| W-9 | —N(isobutyl)₂ |
| W-10 | —NH(cyclopropyl) |
| W-11 | —NH(cyclobutyl) |
| W-12 | —NH(cyclopentyl) |
| W-13 | —NH(CH₂cyclopentyl) |
| W-14 | —NH(CH₂cyclo-propyl) |
| W-15 | —NH(CH₂cyclobutyl) |
| W-16 | —NH(CH₂cyclohexyl) |
| W-17 | —NHCH₂CH₂OH |

TABLE 2-continued

Illustrative $(W^2)_k$—$R^2$ moieties of the compounds of Formula I.

| Subclass # | $(W^2)_k$—$R^2$ |
|---|---|
| W-18 | [structure: -CH2CH2-morpholinyl] |
| W-19 | [structure: -NH-CH2CH2-(4-methylpiperazinyl)] |
| W-20 | [structure: -NH-CH2CH2-(4-acetylpiperazinyl)] |
| W-21 | [structure: -NH-CH2CH2-(4-methylsulfonylpiperazinyl)] |
| W-22 | [structure: -NH-C(O)-CH2-morpholinyl] |
| W-23 | —NHC(O)Me |
| W-24 | —NHC(O)Et |
| W-25 | —NHC(O)isopropyl |
| W-26 | —NHC(O)isobutyl |
| W-27 | [structure: -NH-C(O)-cyclopropyl] |
| W-28 | —NHC(O)CH2-cyclopropyl |
| W-29 | —NHC(O)CH2-cyclobutyl |
| W-30 | —NHC(O)CH2-cyclopentyl |
| W-31 | —NHC(O)CH2-morpholinyl |
| W-32 | —NHC(O)CH2-(4-NMe)-piperazinyl |
| W-33 | —NHC(O)CH2-(4-NSO2Me)-piperazinyl |
| W-34 | —NHSO2Me |
| W-35 | —NHSO2Ph |
| W-36 | [structure: gem-dimethyl-morpholinyl] |
| W-37 | [structure: 4-methylpiperazinyl attached via N] |
| W-38 | [structure: 4-(SO2Me)-piperazinyl attached via N] |
| W-39 | [structure: 4-(COMe)-piperazinyl attached via N] |
| W-40 | [structure: 4-(1-methylpiperidin-4-yl)piperazinyl] |
| W-41 | [structure: -NH-C(O)-NH-CH3 urea] |

TABLE 2-continued
Illustrative $(W^2)_k$—$R^2$ moieties of the compounds of Formula I.
| Subclass # | $(W^2)_k$—$R^2$ |
|---|---|
| W-42 | 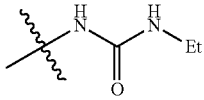 |
| W-43 | 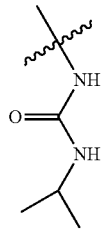 [SMILES: *NC(=O)NC(C)C] |
| W-44 | 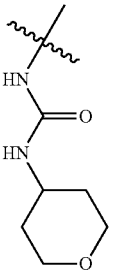 [SMILES: *NC(=O)NC1CCOCC1] |
| W-45 | 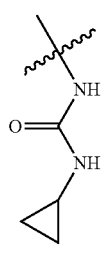 [SMILES: *NC(=O)NC1CC1] |
| W-46 | 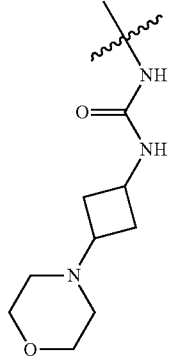 [SMILES: *NC(=O)NC1CC(N2CCOCC2)C1] |
| W-47 | 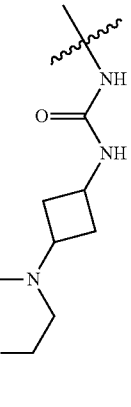 |
| W-48 | 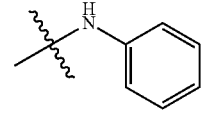 |
| W-49 | 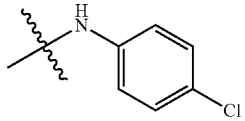 [SMILES: *Nc1ccc(Cl)cc1] |
| W-50 | 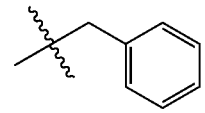 [SMILES: *Cc1ccccc1] |
| W-51 | 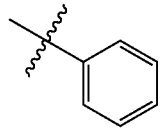 [SMILES: *c1ccccc1] |
Formula E
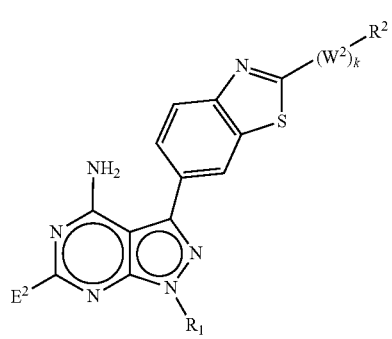

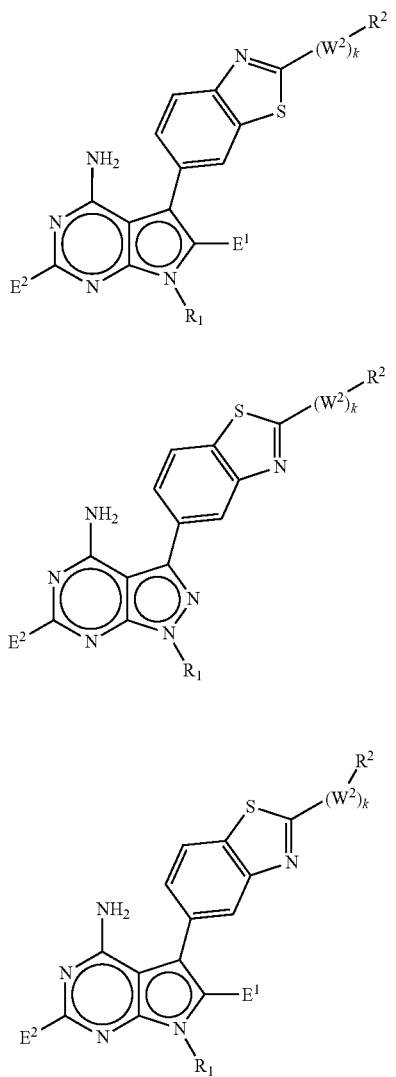

Formula F

Formula G

Formula H

Additional exemplary non-limiting compounds of the present invention having a structure of Formula E, Formula F, Formula G, or Formula H include those in which $R_1$ is selected from any $R_1$ moiety described in Table 1, in combination with any $(W^2)_k$—$R^2$ as described in Table 2, and in combination with $E^1$ and/or $E^2$, wherein $E^1$ and $E^2$ are selected independently from any E moiety as described in Table 3. A compound of Formula E, Formula F, Formula G, or Formula H includes any combination of $R_1$, $E^1$ and/or $E^2$, and $(W^2)_k$—$R^2$.

TABLE 3

Illustrative E moieties of the compounds of Formula I.

| Subclass # | E |
|---|---|
| E-1 | H |
| E-2 | Me |
| E-3 | Et |

TABLE 3-continued

Illustrative E moieties of the compounds of Formula I.

| Subclass # | E |
|---|---|
| E-4 | 2-pyridyl |
| E-5 | 5-pyrimidinyl |
| E-6 | 1-methyl-3-pyrazolyl |
| E-7 | 3-pyridyl |
| E-8 | —C(O)NH-iPr |
| E-9 | —C(O)NH-CH2CH2-morpholino |
| E-10 | iso-propyl |
| E-11 | n-propyl |
| E-12 | iso-butyl |
| E-13 | —F |
| E-14 | —CN |
| E-15 | —CF$_3$ |
| E-16 | —OMe |
| E-17 | —NHMe |
| E-18 | —NHEt |

TABLE 3-continued
Illustrative E moieties of the compounds of Formula I.
| Subclass # | E |
|---|---|
| E-19 | 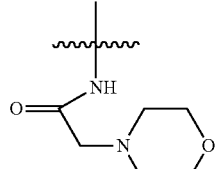 |
| E-20 |  |
| E-21 | 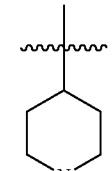 |
| E-22 | 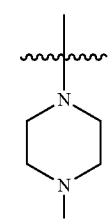 |
| E-23 | 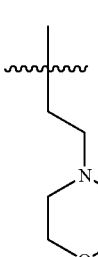 |
| E-24 | 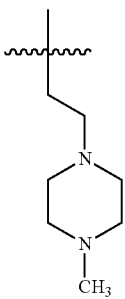 [SMILES: *CCN1CCN(C)CC1] |
| E-25 | 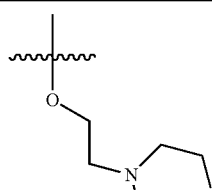 |
| E-26 | 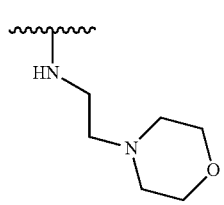 [SMILES: *NCCN1CCOCC1] |
| E-27 | 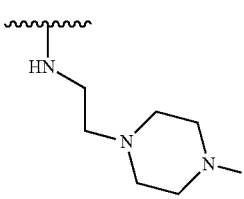 |
| E-28 | 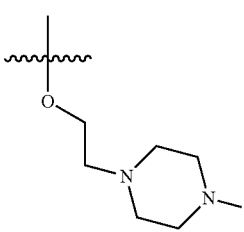 |
| E-29 | 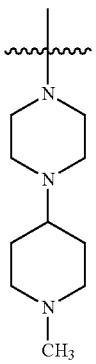 |

TABLE 3-continued
Illustrative E moieties of the compounds of Formula I.
| Subclass # | E |
|---|---|
| E-30 | 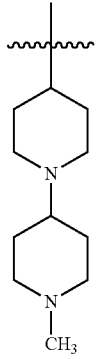 |
| E-31 | 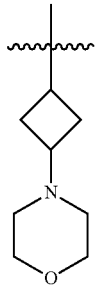 |
| E-32 | 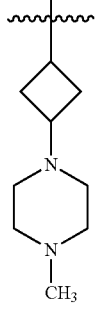 |
| E-33 | 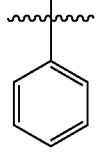 |
| E-34 | 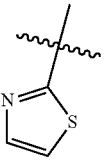 [SMILES: *c1nccs1] |
| E-35 | 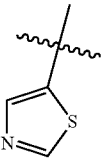 |
| E-36 | 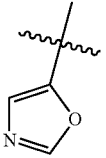 |
| E-37 | 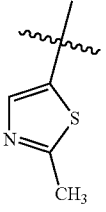 [SMILES: *c1cnc(C)s1] |
| E-38 | 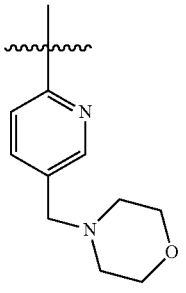 [SMILES: *c1ccc(CN2CCOCC2)cn1] |
| E-39 | 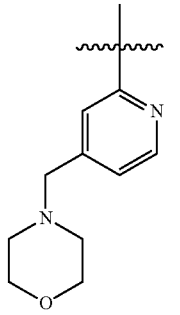 [SMILES: *c1cc(CN2CCOCC2)ccn1] |
| E-40 | 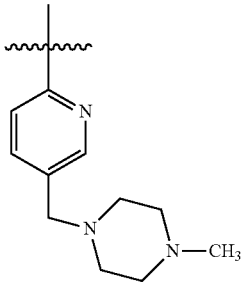 [SMILES: *c1ccc(CN2CCN(C)CC2)cn1] |

TABLE 3-continued
Illustrative E moieties of the compounds of Formula I.
| Subclass # | E |
|---|---|
| E-41 | 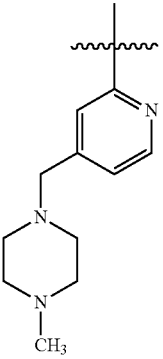 [SMILES: *c1cc(CN2CCN(C)CC2)ccn1] |
| E-42 | 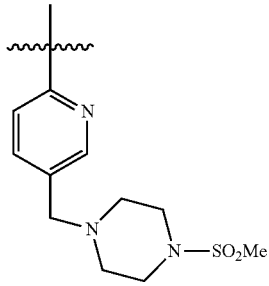 [SMILES: *c1ccc(CN2CCN(S(C)(=O)=O)CC2)cn1] |
| E-43 | 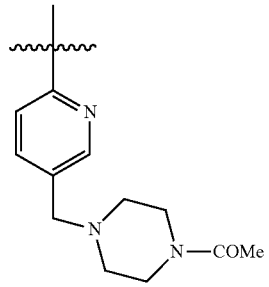 |
| E-44 | 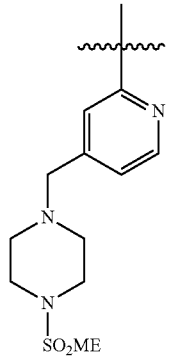 |
| E-45 | 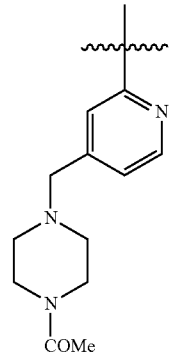 |
| E-46 | 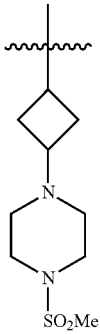 |
| E-47 | 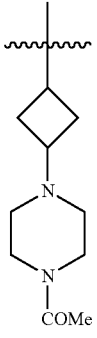 |
| E-48 | 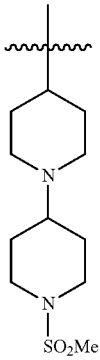 |

TABLE 3-continued
Illustrative E moieties of the compounds of Formula I.
| Subclass # | E |
|---|---|
| E-49 | 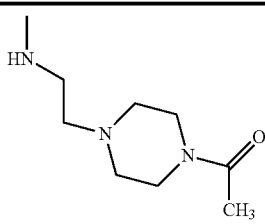 |
| E-50 | |
| E-51 | |
| E-52 | 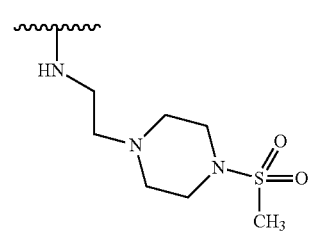 [SMILES: *NCCN1CCN(S(C)(=O)=O)CC1] |
| E-53 | |
TABLE 3-continued
Illustrative E moieties of the compounds of Formula I.
| Subclass # | E |
|---|---|
| E-54 | |
| E-55 | |
| E-56 | 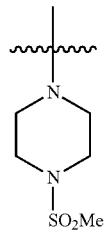 |
| E-57 | 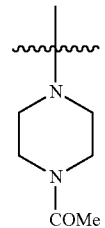 |
| E-58 | 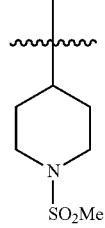 |
| E-59 | 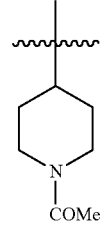 |
| E-60 | 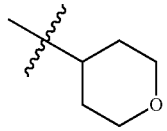 [SMILES: *C1CCOCC1] |

TABLE 3-continued

Illustrative E moieties of the compounds of Formula I.

| Subclass # | E |
|---|---|
| E-61 | azetidine (NH) |
| E-62 | piperidine-3-yl-ethyl (NH) |
| E-63 | tert-butyl |
| E-64 | 3-methylcyclopentyl |
| E-65 | pyrrolidin-3-yl (NH) |
| E-66 | isopentyl |
| E-67 | prop-2-ynyl |
| E-68 | (pyrrolidin-3-yl)methyl (NH) |
| E-69 | benzyl |
| E-70 | cyclobutyl |
| E-71 | (piperidin-4-yl)methyl (NH) |
| E-72 | cinnamyl |
| E-73 | cyclopropylmethyl |
| E-74 | cyclopentyl |
| E-75 | 4-(methylamino)cyclohexyl (NHCH$_3$) |
| E-76 | (pyridin-2-yl)methyl |
| E-77 | (pyridin-4-yl)methyl |
| E-78 | 4-morpholinocyclohexyl |

TABLE 3-continued

Illustrative E moieties of the compounds of Formula I.

| Subclass # | E |
|---|---|
| E-79 | cyclobutyl-OH |
| E-80 | 4-(morpholin-4-yl)pyridin-2-yl (attached at 4-position) |
| E-81 | 4-(4-(methylsulfonyl)piperazin-1-yl)pyridin-2-yl |
| E-82 | 4-(4-acetylpiperazin-1-yl)pyridin-2-yl |
| E-83 | 4-(4-methylpiperazin-1-yl)pyridin-2-yl |
| E-84 | 4-(thiomorpholin-4-yl)pyridin-2-yl |
| E-85 | 5-(morpholin-4-yl)pyridin-2-yl |
| E-86 | 5-(thiomorpholin-4-yl)pyridin-2-yl |

In some embodiments, one or more subject compounds bind specifically to a PI3 kinase or a protein kinase selected from the group consisting of mTor, DNA-dependent protein kinase DNA-dependent protein kinase (Pubmed protein accession number (PPAN) AAA79184), Abl tyrosine kinase (CAA52387), Bcr-Abl, hemopoietic cell kinase (PPAN CAI19695), Src (PPAN CAA24495), vascular endothelial growth factor receptor 2 (PPAN ABB82619), vascular endothelial growth factor receptor-2 (PPAN ABB82619), epidermal growth factor receptor (PPAN AG43241), EPH receptor B4 (PPAN EAL23820), stem cell factor receptor (PPAN AAF22141), Tyrosine-protein kinase receptor TIE-2 (PPAN Q02858), fms-related tyrosine kinase 3 (PPAN NP_004110), platelet-derived growth factor receptor alpha (PPAN NP_990080), RET (PPAN CAA73131), and any other protein kinases listed in the appended tables and figures, as well as any functional mutants thereof. In some embodiments, the IC50 of a subject compound for p110α, p110β, p110γ, or p110δ is less than about 1 uM, less than about 100 nM, less than about 50 nM, less than about 10 nM, less than 1 nM or even less than about 0.5 nM. In some embodiments, the IC50 of a subject compound for mTor is less than about 1 uM, less than about 100 nM, less than about 50 nM, less than about 10 nM, less than 1 nM, less than about 0.5 nM, or even less than about 0.1 nM. In some other embodiments, one or more subject compounds exhibit dual binding specificity and are capable of inhibiting a PI3 kinase (e.g., a class I PI3 kineaes) as well as a protein kinase (e.g., mTor) with an IC50 value less than about 1 uM, less than about 100 nM, less than about 50 nM, less than about 10 nM, less than 1 nM or even less than about 0.5 nM.

In a further embodiment, one or more subject compounds exhibits selective inhibition of mTor relative to one or more type I PI3Ks selected from the group consisting of p110α, p110β, p110γ, or p110δ. For instance, one or more mTor selective inhibitors of the present invention exhibits an IC50 value against mTor that is about 1, 2, 3, 5, 10, 100, or 1000 fold smaller than the IC50 value against one or more type I PI3Ks. In some embodiments, the subject inhibitors are selective for mTor, p110α, p110γ, and/or p110δ but not with respect to p110β. In other embodiments, the subject inhibitors are selective for mTor, p110β, p110γ, and/or p110δ but not with respect to p110α. In other embodiments, the subject inhibitors are selective for mTor, p110α, p110β, and/or p110δ but not with respect to p110γ. In yet other embodiments, the subject inhibitors are selective for mTor, p110α, p110β, and/or p110γ but not with respect to p110δ. In still other embodiments, the subject inhibitors are selective for mTor and p110γ and/or p110δ but not with respect to p110α and p110β. In some embodiments, the subject inhibitors are selective for mTor and p110γ, but not with respect to p110α, p110γ and p110β. In further embodiments, the subject inhibitors are selective for mTor and p110α, but not with respect to p110γ, p110δ and p110β.

In more embodiments, the subject inhibitors are selective for mTor and p110β, but not with respect to p110γ, p110δ and p110α. In more embodiments, the subject inhibitors are selective for mTor and p110δ, but not with respect to p110β, p110γ and p110α. In more embodiments, the subject inhibitors are selective for mTor and p110γ, but not with respect to p110δ, p110β and p110α. In yet another more embodiment, the subject inhibitors are selective for mTor and p110α, but not with respect to p110δ, p110β and p110γ.

One or more subject compounds are capable of inhibiting tyrosine kinases including, for example, DNA-dependent protein kinase DNA-dependent protein kinase (Pubmed protein accession number (PPAN) AAA79184), Abl tyrosine kinase (CAA52387), Bcr-Abl, hemopoietic cell kinase (PPAN CAI19695), Src (PPAN CAA24495), vascular endothelial growth factor receptor 2 (PPAN ABB82619), vascular endothelial growth factor receptor-2 (PPAN ABB82619), epidermal growth factor receptor (PPAN AG43241), EPH receptor B4 (PPAN EAL23820), stem cell factor receptor (PPAN AAF22141), Tyrosine-protein kinase receptor TIE-2 (PPAN Q02858), fms-related tyrosine kinase 3 (PPAN NP_004110), platelet-derived growth factor receptor alpha (PPAN NP_990080), RET (PPAN CAA73131), and functional mutants thereof. In some embodiments, the tyrosine kinase is Abl, Bcr-Abl, EGFR, or Flt-3, and any other kinases listed in the Tables herein.

The compounds of the invention can generally be synthesized by an appropriate combination of generally well known synthetic methods and the methods disclosed herein. Techniques useful in synthesizing these chemical entities are both readily apparent and accessible to those of skill in the relevant art, based on the instant disclosure.

Many of the optionally substituted starting compounds and other reactants are commercially available, e.g., from Aldrich Chemical Company (Milwaukee, Wis.) or can be readily prepared by those skilled in the art using commonly employed synthetic methodology.

Unless specified to the contrary, the reactions described herein take place at atmospheric pressure, generally within a temperature range from −10° C. to 200° C. Further, except as otherwise specified, reaction times and conditions are intended to be approximate, e.g., taking place at about atmospheric pressure within a temperature range of about −10° C. to about 110° C. over a period of about 1 to about 24 hours; reactions left to run overnight average a period of about 16 hours.

The discussion below is offered to illustrate certain of the diverse methods available for use in making the compounds of the invention and is not intended to limit the scope of reactions or reaction sequences that can be used in preparing the compounds of the present invention.

Scheme 1: Synthesis of pyrazolopyrimidine compounds of the invention.

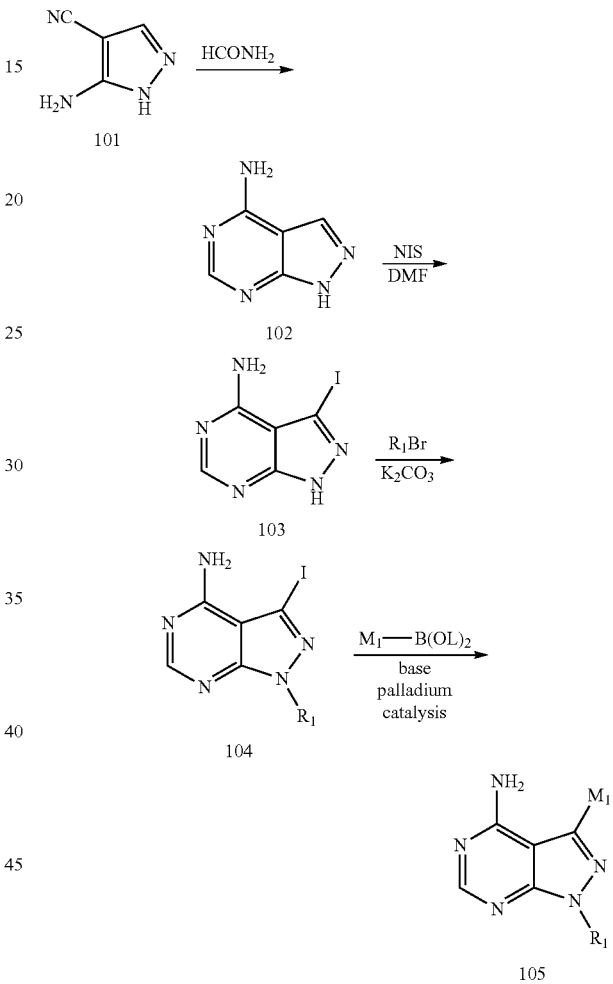

In one embodiment, compounds of Formula I are synthesized by condensing aminopyrazolocarbonitrile 101 with formamide, in refluxing excess formamide, to provide a pyrazolopyridine 102. The compound of Formula 103 is treated with N-iodosuccinimide, to produce a compound of Formula 103. The compound of Formula 103 is reacted with a suitable halogenated compound R₁Br in the presence of potassium carbonate in dimethylformamide to produce a compound of Formula 104. The compound of Formula 104 is coupled using suitable heteroaryl boronic acid or borolan reagents, in the presence of a suitable palladium catalyst, such as palladium acetate, and appropriate base, such as sodium carbonate, to provide compounds of the general formula 105.

Scheme 2: Synthesis of pyrrolopyrimidine compounds of the invention

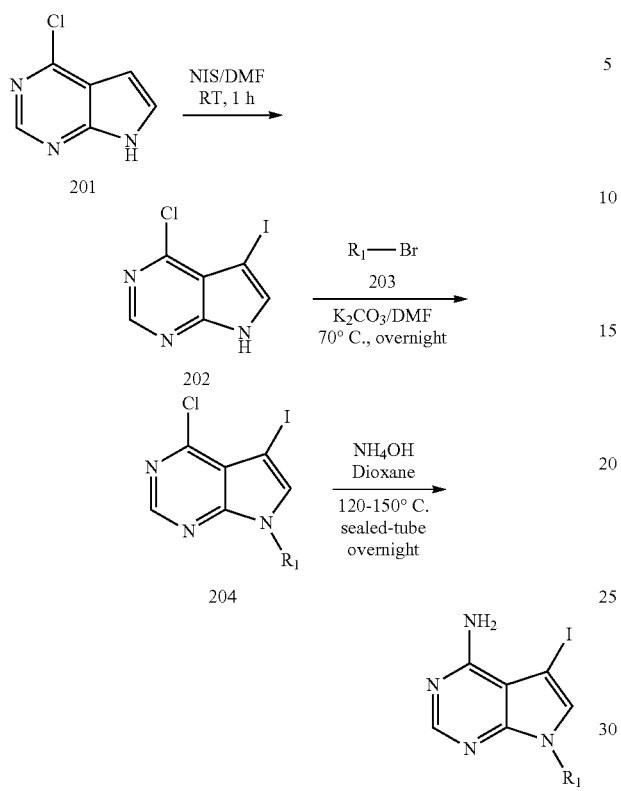

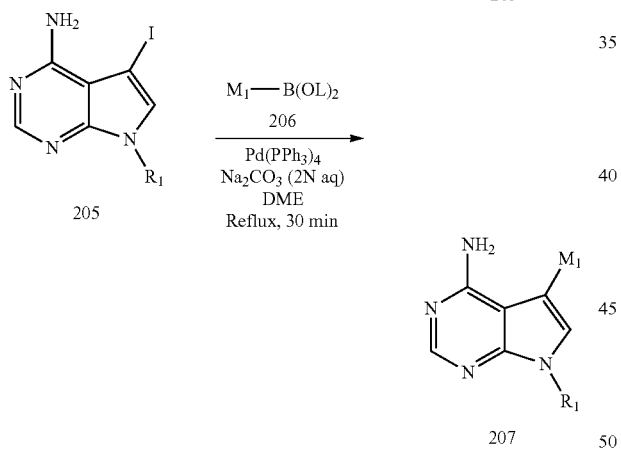

Compounds of the invention having a structure of a pyrrolopyrimidine may be synthesized by this route. The compound of Formula 201 is treated with, for example, N-iodosuccinimide, to produce a compound of Formula 202. The compound of Formula 202 is reacted with a suitable organobromide compound in the presence of a base, such as potassium carbonate in dimethylformamide to produce a compound of Formula 204. The compound of Formula 204 is treated with ammonia in a sealed tube at high temperature to produce a compound of Formula 205. The compound of Formula 205 is coupled with a suitable heteroaromatic boronic acid or borolan of Formula 206, with palladium tetrakistriphenylphosphine, a base, such as sodium carbonate to produce the compound of Formula 207.

Reaction Schemes H, I, and J illustrate methods of synthesis of borane reagents useful in preparing intermediates of use in synthesis of the compounds of the invention as described in Reaction Schemes 1 and 2 above, to introduce benzothiazolyl substituents.

Reaction Scheme H

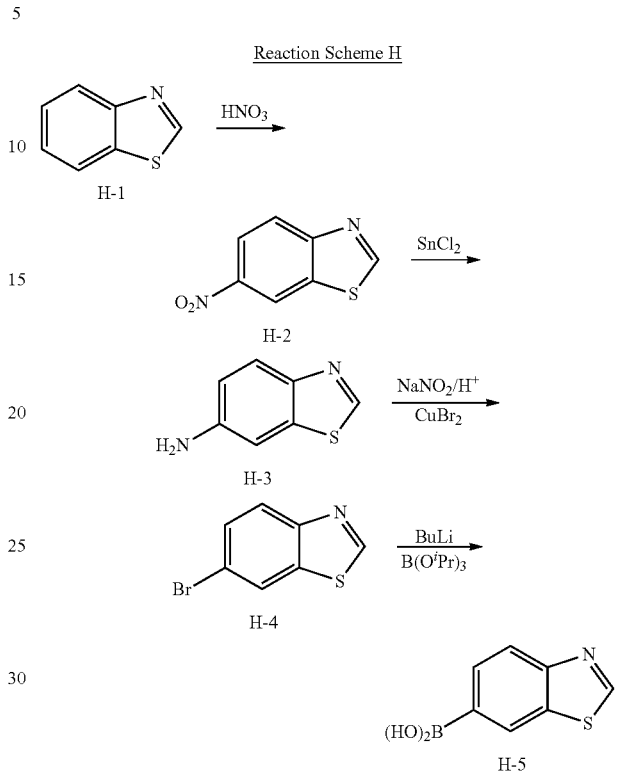

A compound of Formula H-1 is treated with, for example, nitric acid to produce a compound of Formula H-2. The compound of Formula H-2 is treated with a reducing agent such as stannous chloride to produce a compound of Formula H-3. The compound of H-3 is treated with sodium nitrate in acid and cupric bromide to produce a compound of Formula H-4. The compound of H-4 is treated a base such as butyl lithium and boron tris-isopropoxide to produce a compound of Formula H-5.

Reaction Scheme I

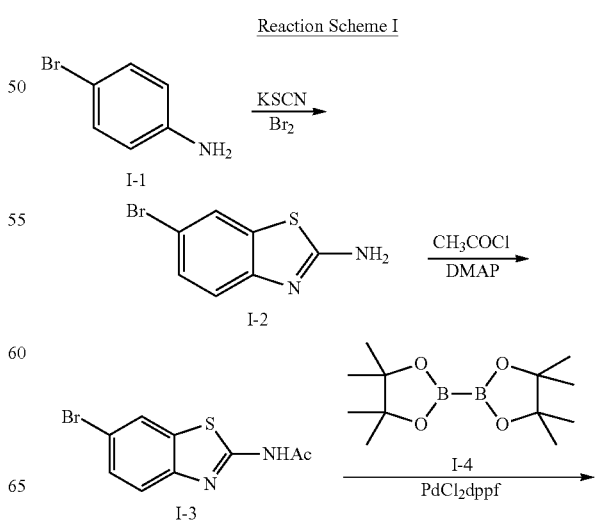

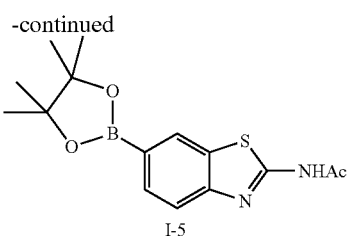

A compound of Formula I-1 is treated with, for example, potassium thiocyanate and bromine in acetic acid to produce a compound of Formula I-2. The compound of Formula I-2 is treated with an acteylating reagent such as acetyl chloride to produce a compound of Formula I-3. The compound of I-3 is reacted with, for example, bis(pinacolato)diboron (compound I-4) in the presence of a catalyst such as palladium chloride to produce a compound of Formula I-5.

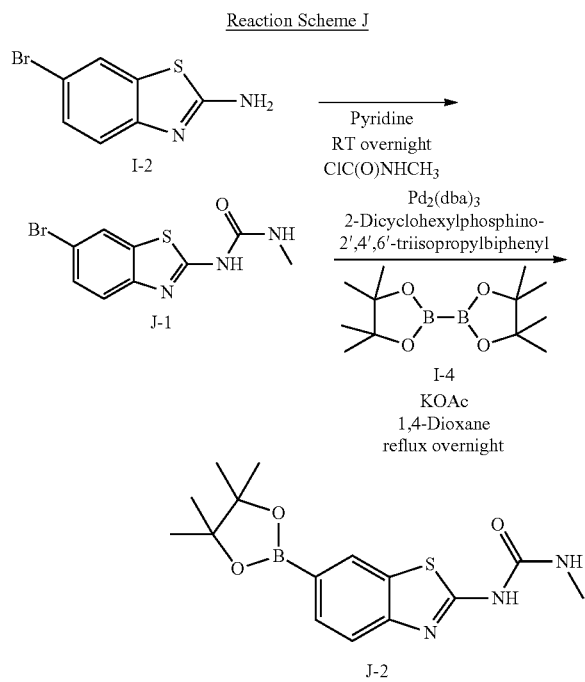

The compound of Formula I-2 is reacted with, for example, methyl carbamic acid chloride to produce a compound of Formula J-1. The compound of Formula J-1 is reacted with bis(pinacolato)diboron (compound I-4) in the presence of a catalyst such as $Pd_2(dba)_3$, 2-chlorohexylphosphino-2,4,6-triisopropylbiphenyl, a base such as potassium acetate, to produce the compound of Formula J-2.

The invention provides pharmaceutical compositions comprising one or more compounds of the present invention.

In some embodiments, the invention provides pharmaceutical compositions for the treatment of disorders such as hyperproliferative disorder including but not limited to cancer such as acute myeloid leukemia, thymus, brain, lung, squamous cell, skin, eye, retinoblastoma, intraocular melanoma, oral cavity and oropharyngeal, bladder, gastric, stomach, pancreatic, bladder, breast, cervical, head, neck, renal, kidney, liver, ovarian, prostate, colorectal, esophageal, testicular, gynecological, thyroid, CNS, PNS, AIDS related AIDS-Related (e.g. Lymphoma and Kaposi's Sarcoma) or Viral-Induced cancer. In some embodiments, said pharmaceutical composition is for the treatment of a non-cancerous hyperproliferative disorder such as benign hyperplasia of the skin (e.g., psoriasis), restenosis, or prostate (e.g., benign prostatic hypertrophy (BPH)).

In some embodiments, the invention provides pharmaceutical compositions for treating diseases or conditions related to an undesirable, over-active, harmful or deleterious immune response in a mammal. Such undesirable immune response can be associated with or result in, e.g., asthma, emphysema, bronchitis, psoriasis, allergy, anaphylaxsis, auto-immune diseases, rhuematoid arthritis, graft versus host disease, and lupus erythematosus. The pharmaceutical compositions of the present invention can be used to treat other respiratory diseases including but not limited to diseases affecting the lobes of lung, pleural cavity, bronchial tubes, trachea, upper respiratory tract, or the nerves and muscle for breathing.

The invention also provides compositions for the treatment of liver diseases (including diabetes), pancreatitis or kidney disease (including proliferative glomerulonephritis and diabetes-induced renal disease) or pain in a mammal.

The invention further provides a composition for the prevention of blastocyte implantation in a mammal.

The invention also relates to a composition for treating a disease related to vasculogenesis or angiogenesis in a mammal which can manifest as tumor angiogenesis, chronic inflammatory disease such as rheumatoid arthritis, inflammatory bowel disease, atherosclerosis, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

The subject pharmaceutical compositions are typically formulated to provide a therapeutically effective amount of a compound of the present invention as the active ingredient, or a pharmaceutically acceptable salt, ester, prodrug, solvate, hydrate or derivative thereof. Where desired, the pharmaceutical compositions contain pharmaceutically acceptable salt and/or coordination complex thereof, and one or more pharmaceutically acceptable excipients, carriers, including inert solid diluents and fillers, diluents, including sterile aqueous solution and various organic solvents, permeation enhancers, solubilizers and adjuvants.

The subject pharmaceutical compositions can be administered alone or in combination with one or more other agents, which are also typically administered in the form of pharmaceutical compositions. Where desired, the subject compounds and other agent(s) may be mixed into a preparation or both components may be formulated into separate preparations to use them in combination separately or at the same time.

In some embodiments, the concentration of one or more of the compounds provided in the pharmaceutical compositions of the present invention is less than 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v or v/v.

In some embodiments, the concentration of one or more of the compounds of the present invention is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v, or v/v.

In some embodiments, the concentration of one or more of the compounds of the present invention is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v. v/v.

In some embodiments, the concentration of one or more of the compounds of the present invention is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v.

In some embodiments, the amount of one or more of the compounds of the present invention is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of one or more of the compounds of the present invention is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

In some embodiments, the amount of one or more of the compounds of the present invention is in the range of 0.0001-10 g, 0.0005-9 g, 0.001-8 g, 0.005-7 g, 0.01-6 g, 0.05-5 g, 0.1-4 g, 0.5-4 g, or 1-3 g.

The compounds according to the invention are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. An exemplary dosage is 10 to 30 mg per day. The exact dosage will depend upon the route of administration, the form in which the compound is administered, the subject to be treated, the body weight of the subject to be treated, and the preference and experience of the attending physician.

A pharmaceutical composition of the present invention typically contains an active ingredient (e.g., a compound of the present invention or a pharmaceutically acceptable salt and/or coordination complex thereof, and one or more pharmaceutically acceptable excipients, carriers, including but not limited to inert solid diluents and fillers, diluents, sterile aqueous solution and various organic solvents, permeation enhancers, solubilizers and adjuvants.

Described below are non-limiting exemplary pharmaceutical compositions and methods for preparing the same.

Pharmaceutical compositions for oral administration. In some embodiments, the invention provides a pharmaceutical composition for oral administration containing a compound of the present invention, and a pharmaceutical excipient suitable for oral administration.

In some embodiments, the invention provides a solid pharmaceutical composition for oral administration containing: (i) an effective amount of a compound of the present invention; optionally (ii) an effective amount of a second agent; and (iii) a pharmaceutical excipient suitable for oral administration. In some embodiments, the composition further contains: (iv) an effective amount of a third agent.

In some embodiments, the pharmaceutical composition may be a liquid pharmaceutical composition suitable for oral consumption. Pharmaceutical compositions of the invention suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion. Such dosage forms can be prepared by any of the methods of pharmacy, but all methods include the step of bringing the active ingredient into association with the carrier, which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

This invention further encompasses anhydrous pharmaceutical compositions and dosage forms comprising an active ingredient, since water can facilitate the degradation of some compounds. For example, water may be added (e.g., 5%) in the pharmaceutical arts as a means of simulating long-term storage in order to determine characteristics such as shelf-life or the stability of formulations over time. Anhydrous pharmaceutical compositions and dosage forms of the invention can be prepared using anhydrous or low moisture containing ingredients and low moisture or low humidity conditions. Pharmaceutical compositions and dosage forms of the invention which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

An active ingredient can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the compositions of the invention to provide tablets that disintegrate when exposed to an aqueous environment. Too much of a disintegrant may produce tablets which may disintegrate in the bottle. Too little may be insufficient for disintegration to occur and may thus alter the rate and extent of release of the active ingredient(s) from the dosage form. Thus, a sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethylaureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

When aqueous suspensions and/or elixirs are desired for oral administration, the essential active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactant which can be used to form pharmaceutical compositions and dosage forms of the invention include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant may generally have an HLB value of at least 10, while suitable lipophilic surfactants may generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In one embodiment, the composition may include a solubilizer to ensure good solubilization and/or dissolution of the compound of the present invention and to minimize precipitation of the compound of the present invention. This can be especially important for compositions for non-oral use, e.g., compositions for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, .epsilon.-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, δ-valerolactone and isomers thereof, β-butyrolactone and isomers thereof; and other solubilizers known in the art, such as dimethyl acetamide, dimethyl isosorbide, N-methyl pyrrolidones, monooctanoin, diethylene glycol monoethyl ether, and water.

Mixtures of solubilizers may also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a patient using conventional techniques, such as distillation or evaporation. Thus, if present, the solubilizer can be in a weight ratio of 10%, 25%, 50%, 100%, or up to about 200% by weight, based on the combined weight of the drug, and other excipients. If desired, very small amounts of solubilizer may also be used, such as 5%, 2%, 1% or even less. Typically, the solubilizer may be present in an amount of about 1% to about 100%, more typically about 5% to about 25% by weight.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl)aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Example may include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

Pharmaceutical compositions for injection. In some embodiments, the invention provides a pharmaceutical composition for injection containing a compound of the present invention and a pharmaceutical excipient suitable for injection. Components and amounts of agents in the compositions are as described herein.

The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound of the present invention in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

Pharmaceutical compositions for topical (e.g., transdermal) delivery. In some embodiments, the invention provides a pharmaceutical composition for transdermal delivery containing a compound of the present invention and a pharmaceutical excipient suitable for transdermal delivery.

Compositions of the present invention can be formulated into preparations in solid, semi-solid, or liquid forms suitable for local or topical administration, such as gels, water soluble jellies, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation may provide more immediate exposure of the active ingredient to the chosen area.

The pharmaceutical compositions also may comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation. Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Another exemplary formulation for use in the methods of the present invention employs transdermal delivery devices ("patches"). Such transdermal patches may be used to provide continuous or discontinuous infusion of a compound of the present invention in controlled amounts, either with or without another agent.

The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

Pharmaceutical compositions for inhalation. Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

Other pharmaceutical compositions. Pharmaceutical compositions may also be prepared from compositions described herein and one or more pharmaceutically acceptable excipients suitable for sublingual, buccal, rectal, intraosseous, intraocular, intranasal, epidural, or intraspinal administration. Preparations for such pharmaceutical compositions are well-known in the art. See, e.g., See, e.g., Anderson, Philip O.; Knoben, James E.; Troutman, William G, eds., Handbook of Clinical Drug Data, Tenth Edition, McGraw-Hill, 2002; Pratt and Taylor, eds., *Principles of Drug Action*, Third Edition, Churchill Livingston, N.Y., 1990; Katzung, ed., *Basic and Clinical Pharmacology*, Ninth Edition, McGraw Hill, 20037ybg; Goodman and Gilman, eds., *The Pharmacological Basis of Therapeutics*, Tenth Edition, McGraw Hill, 2001; *Remingtons Pharmaceutical Sciences*, 20th Ed., Lippincott Williams & Wilkins., 2000; Martindale, *The Extra Pharmacopoeia*, Thirty-Second Edition (The Pharmaceutical Press, London, 1999); all of which are incorporated by reference herein in their entirety.

Administration of the compounds or pharmaceutical composition of the present invention can be effected by any method that enables delivery of the compounds to the site of action. These methods include oral routes, intraduodenal routes, parenteral injection (including intravenous, intraarterial, subcutaneous, intramuscular, intravascular, intraperitoneal or infusion), topical (e.g. transdermal application), rectal administration, via local delivery by catheter or stent or through inhalation. Compounds can also abe administered intraadiposally or intrathecally.

The amount of the compound administered will be dependent on the mammal being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to 7 g/day, preferably about 0.05 to about 2.5 g/day. In some instances, dosage levels below the lower limit of the aforesaid range may be more than adequate, while in other cases still larger doses may be employed without causing any harmful side effect, e.g. by dividing such larger doses into several small doses for administration throughout the day.

In some embodiments, a compound of the invention is administered in a single dose. Typically, such administration will be by injection, e.g., intravenous injection, in order to introduce the agent quickly. However, other routes may be used as appropriate. A single dose of a compound of the invention may also be used for treatment of an acute condition.

In some embodiments, a compound of the invention is administered in multiple doses. Dosing may be about once, twice, three times, four times, five times, six times, or more than six times per day. Dosing may be about once a month, once every two weeks, once a week, or once every other day. In another embodiment a compound of the invention and another agent are administered together about once per day to about 6 times per day.

In another embodiment the administration of a compound of the invention and an agent continues for less than about 7 days. In yet another embodiment the administration continues for more than about 6, 10, 14, 28 days, two months, six months, or one year. In some cases, continuous dosing is achieved and maintained as long as necessary.

Administration of the agents of the invention may continue as long as necessary. In some embodiments, an agent of the invention is administered for more than 1, 2, 3, 4, 5, 6, 7, 14, or 28 days. In some embodiments, an agent of the invention is administered for less than 28, 14, 7, 6, 5, 4, 3, 2, or 1 day. In some embodiments, an agent of the invention is administered chronically on an ongoing basis, e.g., for the treatment of chronic effects.

An effective amount of a compound of the invention may be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, or as an inhalant.

The compositions of the invention may also be delivered via an impregnated or coated device such as a stent, for example, or an artery-inserted cylindrical polymer. Such a method of administration may, for example, aid in the prevention or amelioration of restenosis following procedures such as balloon angioplasty. Without being bound by theory, compounds of the invention may slow or inhibit the migration and proliferation of smooth muscle cells in the arterial wall which contribute to restenosis. A compound of the invention may be administered, for example, by local delivery from the struts of a stent, from a stent graft, from grafts, or from the cover or sheath of a stent. In some embodiments, a compound of the invention is admixed with a matrix. Such a matrix may be a polymeric matrix, and may serve to bond the compound to the stent. Polymeric matrices suitable for such use, include, for example, lactone-based polyesters or copolyesters such as polylactide, polycaprolactonglycolide, polyorthoesters, polyanhydrides, polyaminoacids, polysaccharides, polyphosphazenes, poly (ether-ester) copolymers (e.g. PEO-PLLA); polydimethylsiloxane, poly(ethylene-vinylacetate), acrylate-based polymers or copolymers (e.g. polyhydroxyethyl methylmethacrylate, polyvinyl pyrrolidinone), fluorinated polymers such as polytetrafluoroethylene and cellulose esters. Suitable matrices may be nondegrading or may degrade with time, releasing the compound or compounds. Compounds of the invention may be applied to the surface of the stent by various methods such as dip/spin coating, spray coating, dip-coating, and/or brush-coating. The compounds may be applied in a solvent and the solvent may be allowed to evaporate, thus forming a layer of compound onto the stent. Alternatively, the compound may be located in the body of the stent or graft, for example in microchannels or micropores. When implanted, the compound diffuses out of the body of the stent to contact the arterial wall. Such stents may be prepared by dipping a stent manufactured to contain such micropores or microchannels into a solution of the compound of the invention in a suitable solvent, followed by evaporation of the solvent. Excess drug on the surface of the stent may be removed via an additional brief solvent wash. In yet other embodiments, compounds of the invention may be covalently linked to a stent or graft. A covalent linker may be used which degrades in vivo, leading to the release of the compound of the invention. Any bio-labile linkage may be used for such a purpose, such as ester, amide or anhydride linkages. Compounds of the invention may additionally be administered intravascularly from a balloon used during angioplasty. Extravascular administration of the compounds via the pericard or via advential application of formulations of the invention may also be performed to decrease restenosis.

A variety of stent devices which may be used as described are disclosed, for example, in the following references, all of which are hereby incorporated by reference: U.S. Pat. Nos. 5,451,233; 5,040,548; 5,061,273; 5,496,346; 5,292,331; 5,674,278; 3,657,744; 4,739,762;5,195,984; 5,292,331; 5,674,278; 5,879,382; and 6,344,053.

The compounds of the invention may be administered in dosages. It is known in the art that due to intersubject variability in compound pharmacokinetics, individualization of dosing regimen is necessary for optimal therapy. Dosing for a compound of the invention may be found by routine experimentation in light of the instant disclosure.

When a compound of the invention, is administered in a composition that comprises one or more agents, and the agent has a shorter half-life than the compound of the invention unit dose forms of the agent and the compound of the invention may be adjusted accordingly.

The subject pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compound in sterile aqueous solutions, for example, aqueous propylene glycol or dextrose solutions. Such dosage forms can be suitably buffered, if desired.

The invention also provides kits. The kits include a compound or compounds of the present invention as described herein, in suitable packaging, and written material that can include instructions for use, discussion of clinical studies, listing of side effects, and the like. Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. The kit may further contain another agent. In some embodiments, the compound of the present invention and the agent are provided as separate compositions in separate containers within the kit. In some embodiments, the compound of the present invention and the agent are provided as a single composition within a container in the kit. Suitable packaging and additional articles for use (e.g., measuring cup for liquid preparations, foil wrapping to minimize exposure to air, and the like) are known in the art and may be included in the kit. Kits described herein can be provided, marketed and/or promoted to health providers, including physicians, nurses, pharmacists, formulary officials, and the like. Kits may also, in some embodiments, be marketed directly to the consumer.

The invention also provides methods of using the compounds or pharmaceutical compositions of the present invention to treat disease conditions, including but not limited to diseases associated with malfunctioning of one or more types of PI3 kinase and/or mTOR. A detailed description of conditions and disorders mediated by p110δ kinase activity is set forth in Sadu et al., WO 01/81346, which is incorporated herein by reference in its entirety for all purposes.

The invention also relates to a method of treating a hyperproliferative disorder in a mammal that comprises administering to said mammal a therapeutically effective amount of a compound of the present invention, or a pharmaceutically acceptable salt, ester, prodrug, solvate, hydrate or derivative thereof. In some embodiments, said method relates to the treatment of cancer such as acute myeloid leukemia, *thymus*, brain, lung, squamous cell, skin, eye, retinoblastoma, intraocular melanoma, oral cavity and oropharyngeal, bladder, gastric, stomach, pancreatic, bladder, breast, cervical, head, neck, renal, kidney, liver, ovarian, prostate, colorectal, esophageal, testicular, gynecological, thyroid, CNS, PNS, AIDS-related (e.g. Lymphoma and Kaposi's Sarcoma) or viral-induced cancer. In some embodiments, said method relates to the treatment of a non-cancerous hyperproliferative disorder such as benign hyperplasia of the skin (e.g., psoriasis), restenosis, or prostate (e.g., benign prostatic hypertrophy (BPH)).

The treatment methods provided herein comprise administering to the subject a therapeutically effective amount of a compound of the invention. In one embodiment, the present invention provides a method of treating an inflammation disorder, including autoimmune diseases in a mammal. The method comprises administering to said mammal a therapeutically effective amount of a compound of the present invention, or a pharmaceutically acceptable salt, ester, prodrug, solvate, hydrate or derivative thereof. Examples of autoimmune diseases includes but is not limited to acute disseminated encephalomyelitis (ADEM), Addison's disease, antiphospholipid antibody syndrome (APS), aplastic anemia, autoimmune hepatitis, coeliac disease, Crohn's disease, Diabetes mellitus (type 1), Goodpasture's syndrome, Graves' disease, Guillain-Barrd syndrome (GBS), Hashimoto's disease, lupus erythematosus, multiple sclerosis, myasthenia gravis, opsoclonus myoclonus syndrome (OMS), optic neuritis, Ord's thyroiditis, oemphigus, polyarthritis, primary biliary cirrhosis, psoriasis, rheumatoid arthritis, Reiter's syndrome, Takayasu's arteritis, temporal arteritis (also known as "giant cell arteritis"), warm autoimmune hemolytic anemia, Wegener's granulomatosis, alopecia universalis, Chagas' disease, chronic fatigue syndrome, dysautonomia, endometriosis, hidradenitis suppurativa, interstitial cystitis, neuromyotonia, sarcoidosis, scleroderma, ulcerative colitis, vitiligo, and vulvodynia. Other disorders include bone-resorption disorders and thrombosis.

In some embodiments, the method of treating inflammatory or autoimmune diseases comprises administering to a subject (e.g. a mammal) a therapeutically effective amount of one or more compounds of the present invention that selectively inhibit PI3K-δ and/or PI3K-γ as compared to all other type I PI3 kinases. Such selective inhibition of PI3K-δ and/or PI3K-γ may be advantageous for treating any of the diseases or conditions described herein. For example, selective inhibition of PI3K-δ may inhibit inflammatory responses associated with inflammatory diseases, autoimmune disease, or diseases related to an undesirable immune response including but not limited to asthma, emphysema, allergy, dermatitis, rheumatoid arthritis, psoriasis, lupus erythematosus, or graft versus host disease. Selective inhibition of PI3K-δ may further provide for a reduction in the inflammatory or undesirable immune response without a concomitant reduction in the ability to reduce a bacterial, viral, and/or fungal infection. Selective inhibition of both PI3K-δ and PI3K-γ may be advantageous for inhibiting the inflammatory response in the subject to a greater degree than that would be provided for by inhibitors that selectively inhibit PI3K-δ or PI3K-γ alone. In one aspect, one or more of the subject methods are effective in reducing antigen specific antibody production in vivo by about 2-fold, 3-fold, 4-fold, 5-fold, 7.5-fold, 10-fold, 25-fold, 50-fold, 100-fold, 250-fold, 500-fold, 750-fold, or about 1000-fold or more. In another aspect, one or more of the subject methods are effective in reducing antigen specific IgG3 and/or IgGM production in vivo by about 2-fold, 3-fold, 4-fold, 5-fold, 7.5-fold, 10-fold, 25-fold, 50-fold, 100-fold, 250-fold, 500-fold, 750-fold, or about 1000-fold or more.

In one aspect, one of more of the subject methods are effective in ameliorating symptoms associated with rheumatoid arthritis including but not limited to a reduction in the swelling of joints, a reduction in serum anti-collagen levels, and/or a reduction in joint pathology such as bone resorption, cartilage damage, pannus, and/or inflammation. In another aspect, the subject methods are effective in reducing ankle inflammation by at least about 2%, 5%, 10%, 15%, 20%, 25%, 30%, 50%, 60%, or about 75% to 90%. In another aspect, the subject methods are effective in reducing knee inflammation by at least about 2%, 5%, 10%, 15%, 20%, 25%, 30%, 50%, 60%, or about 75% to 90% or more. In still another aspect, the subject methods are effective in reducing serum anti-type II collagen levels by at least about 10%, 12%, 15%, 20%, 24%, 25%, 30%, 35%, 50%, 60%, 75%, 80%, 86%, 87%, or about 90% or more. In another aspect, the subject methods are effective in reducing ankle histopathology scores by about 5%, 10%, 15%, 20%, 25%, 30%, 40%, 50%, 60%, 75%, 80%, 90% or more. In still another aspect, the subject methods are effective in reducing knee histopathology scores by about 5%, 10%, 15%, 20%, 25%, 30%, 40%, 50%, 60%, 75%, 80%, 90% or more.

In other embodiments, the present invention provides methods of using the compounds or pharmaceutical compositions to treat respiratory diseases including but not limited to diseases affecting the lobes of lung, pleural cavity, bronchial tubes, trachea, upper respiratory tract, or the nerves and muscle for breathing. For example, methods are provided to treat obstructive pulmonary disease. Chronic obstructive pulmonary disease (COPD) is an umbrella term for a group of respiratory tract diseases that are characterized by airflow obstruction or limitation. Conditions included in this umbrella term are: chronic bronchitis, emphysema, and bronchiectasis.

In another embodiment, the compounds described herein are used for the treatment of asthma. Also, the compounds or pharmaceutical compositions described herein may be used for the treatment of endotoxemia and sepsis. In one embodiment, the compounds or pharmaceutical compositions described herein are used to for the treatment of rheumatoid arthritis (RA). In yet another embodiment, the compounds or pharmaceutical compositions described herein is used for the treatment of contact or atopic dermatitis. Contact dermatitis includes irritant dermatitis, phototoxic dermatitis, allergic dermatitis, photoallergic dermatitis, contact urticaria, systemic contact-type dermatitis and the like. Irritant dermatitis can occur when too much of a substance is used on the skin of when the skin is sensitive to certain substance. Atopic dermatitis, sometimes called eczema, is a kind of dermatitis, an atopic skin disease.

The invention also relates to a method of treating diseases related to vasculogenesis or angiogenesis in a mammal that comprises administering to said mammal a therapeutically effective amount of a compound of the present invention, or a pharmaceutically acceptable salt, ester, prodrug, solvate, hydrate or derivative thereof. In some embodiments, said method is for treating a disease selected from the group consisting of tumor angiogenesis, chronic inflammatory disease such as rheumatoid arthritis, atherosclerosis, inflammatory bowel disease, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

Patients that can be treated with compounds of the present invention, or pharmaceutically acceptable salt, ester, prodrug, solvate, hydrate or derivative of said compounds, according to the methods of this invention include, for example, patients that have been diagnosed as having psoriasis; restenosis; atherosclerosis; BPH; breast cancer such as a ductal carcinoma in duct tissue in a mammary gland, medullary carcinomas, colloid carcinomas, tubular carcinomas, and inflammatory breast cancer; ovarian cancer, including epithelial ovarian tumors such as adenocarcinoma in the ovary and an adenocarcinoma that has migrated from the ovary into the abdominal cavity; uterine cancer; cervical cancer such as adenocarcinoma in the cervix epithelial including squamous cell carcinoma and adenocarcinomas; prostate cancer, such as a prostate cancer selected from the following: an adenocarcinoma or an adenocarinoma that has migrated to the bone; pancreatic cancer such as epitheliod carcinoma in the pancreatic duct tissue and an adenocarcinoma in a pancreatic duct; bladder cancer such as a transitional cell carcinoma in urinary bladder, urothelial carcinomas (transitional cell carcinomas), tumors in the urothelial cells that line the bladder, squamous cell carcinomas, adenocarcinomas, and small cell cancers; leukemia such as acute myeloid leukemia (AML), acute lymphocytic leukemia, chronic lymphocytic leukemia, chronic myeloid leukemia, hairy cell leukemia, myelodysplasia, myeloproliferative disorders, acute myelogenous leukemia (AML), chronic myelogenous leukemia (CML), mastocytosis, chronic lymphocytic leukemia (CLL), multiple myeloma (MM), and myelodysplastic syndrome (MDS); bone cancer; lung cancer such as non-small cell lung cancer (NSCLC), which is divided into squamous cell carcinomas, adenocarcinomas, and large cell undifferentiated carcinomas, and small cell lung cancer; skin cancer such as basal cell carcinoma, melanoma, squamous cell carcinoma and actinic keratosis, which is a skin condition that sometimes develops into squamous cell carcinoma; eye retinoblastoma; cutaneous or intraocular (eye) melanoma; primary liver cancer (cancer that begins in the liver); kidney cancer; thyroid cancer such as papillary, follicular, medullary and anaplastic; AIDS-related lymphoma such as diffuse large B-cell lymphoma, B-cell immunoblastic lymphoma and small non-cleaved cell lymphoma; Kaposi's Sarcoma; viral-induced cancers including hepatitis B virus (HBV), hepatitis C virus (HCV), and hepatocellular carcinoma; human lymphotropic virus-type 1 (HTLV-1) and adult T-cell leukemia/lymphoma; and human papilloma virus (HPV) and cervical cancer; central nervous system cancers (CNS) such as primary brain tumor, which includes gliomas (astrocytoma, anaplastic astrocytoma, or glioblastoma multiforme), Oligodendroglioma, Ependymoma, Meningioma, Lymphoma, Schwannoma, and Medulloblastoma; peripheral nervous system (PNS) cancers such as acoustic neuromas and malignant peripheral nerve sheath tumor (MPNST) including neurofibromas and schwannomas, malignant fibrous cytoma, malignant fibrous histiocytoma, malignant meningioma, malignant mesothelioma, and malignant mixed Müllerian tumor; oral cavity and oropharyngeal cancer such as, hypopharyngeal cancer, laryngeal cancer, nasopharyngeal cancer, and oropharyngeal cancer; stomach cancer such as lymphomas, gastric stromal tumors, and carcinoid tumors; testicular cancer such as germ cell tumors (GCTs), which include seminomas and nonseminomas, and gonadal stromal tumors, which include Leydig cell tumors and Sertoli cell tumors; thymus cancer such as to thymomas, thymic carcinomas, Hodgkin disease, non-Hodgkin lymphomas carcinoids or carcinoid tumors; rectal cancer; and colon cancer.

The invention also relates to a method of treating diabetes in a mammal that comprises administering to said mammal a therapeutically effective amount of a compound of the present invention, or a pharmaceutically acceptable salt, ester, prodrug, solvate, hydrate or derivative thereof.

In addition, the compounds described herein may be used to treat acne.

In addition, the compounds described herein may be used for the treatment of arteriosclerosis, including atherosclerosis. Arteriosclerosis is a general term describing any hardening of medium or large arteries.

Atherosclerosis is a hardening of an artery specifically due to an atheromatous plaque.

Further the compounds described herein may be used for the treatment of glomerulonephritis. Glomerulonephritis is a primary or secondary autoimmune renal disease characterized by inflammation of the glomeruli. It may be asymptomatic, or present with hematuria and/or proteinuria. There are many recognized types, divided in acute, subacute or chronic glomerulonephritis. Causes are infectious (bacterial, viral or parasitic pathogens), autoimmune or paraneoplastic.

Additionally, the compounds described herein may be used for the treatment of bursitis, lupus, acute disseminated encephalomyelitis (ADEM), addison's disease, antiphospholipid antibody syndrome (APS), aplastic anemia, autoimmune hepatitis, coeliac disease, crohn's disease, diabetes mellitus (type 1), goodpasture's syndrome, graves' disease, guillain-barré syndrome (GBS), hashimoto's disease, inflammatory bowel disease, lupus erythematosus, myasthenia gravis, opsoclonus myoclonus syndrome (OMS), optic neuritis, ord's thyroiditis, ostheoarthritis, uveoretinitis, pemphigus, polyarthritis, primary biliary cirrhosis, reiter's syndrome, takayasu's arteritis, temporal arteritis, warm autoimmune hemolytic anemia, wegener's granulomatosis, alopecia universalis, chagas' disease, chronic fatigue syndrome, dysautonomia, endometriosis, hidradenitis suppurativa, interstitial cystitis, neuromyotonia, sarcoidosis, scleroderma, ulcerative colitis, vitiligo, vulvodynia, appendicitis, arteritis, arthritis, blepharitis, bronchiolitis, bronchitis, cervicitis, cholangitis, cholecystitis, chorioamnionitis, colitis, conjunctivitis, cystitis, dacryoadenitis, dermatomyositis, endocarditis, endometritis, enteritis, enterocolitis, epicondylitis, epididymitis, fasciitis, fibrositis, gastritis, gastroenteritis, gingivitis, hepatitis, hidradenitis, ileitis, iritis, laryngitis, mastitis, meningitis, myelitis, myocarditis, myositis, nephritis, omphalitis, oophoritis, orchitis, osteitis, otitis, pancreatitis, parotitis, pericarditis, peritonitis, pharyngitis, pleuritis, phlebitis, pneumonitis, proctitis, prostatitis, pyelonephritis, rhinitis, salpingitis, sinusitis, stomatitis, synovitis, tendonitis, tonsillitis, uveitis, vaginitis, vasculitis, or vulvitis.

The invention also relates to a method of treating a cardiovascular disease in a mammal that comprises administering to said mammal a therapeutically effective amount of a compound of the present invention, or a pharmaceutically acceptable salt, ester, prodrug, solvate, hydrate or derivative thereof. Examples of cardiovascular conditions include, but are not limited to, atherosclerosis, restenosis, vascular occlusion and carotid obstructive disease.

In another aspect, the present invention provides methods of disrupting the function of a leukocyte or disrupting a function of an osteoclast. The method includes contacting the leukocyte or the osteoclast with a function disrupting amount of a compound of the invention.

In another aspect of the present invention, methods are provided for treating ophthalmic disease by administering one or more of the subject compounds or pharmaceutical compositions to the eye of a subject.

Methods are further provided for administering the compounds of the present invention via eye drop, intraocular injection, intravitreal injection, topically, or through the use of a drug eluting device, microcapsule, implant, or microfluidic device. In some cases, the compounds of the present invention are administered with a carrier or excipient that increases the intraocular penetrance of the compound such as an oil and water emulsion with colloid particles having an oily core surrounded by an interfacial film.

In some cases, the colloid particles include at least one cationic agent and at least one non-ionic sufactant such as a poloxamer, tyloxapol, a polysorbate, a polyoxyethylene castor oil derivative, a sorbitan ester, or a polyoxyl stearate. In some cases, the cationic agent is an alkylamine, a tertiary alkyl amine, a quarternary ammonium compound, a cationic lipid, an amino alcohol, a biguanidine salt, a cationic compound or a mixture thereof. In some cases the cationic agent is a biguanidine salt such as chlorhexidine, polyaminopropyl biguanidine, phenformin, alkylbiguanidine, or a mixture thereof. In some cases, the quaternary ammonium compound is a benzalkonium halide, lauralkonium halide, cetrimide, hexadecyltrimethylammonium halide, tetradecyltrimethylammonium halide, dodecyltrimethylammonium halide, cetrimonium halide, benzethonium halide, behenalkonium halide, cetalkonium halide, cetethyldimonium halide, cetylpyridinium halide, benzododecinium halide, chlorallyl methenamine halide, rnyristylalkonium halide, stearalkonium halide or a mixture of two or more thereof. In some cases, cationic agent is a benzalkonium chloride, lauralkonium chloride, benzododecinium bromide, benzethenium chloride, hexadecyltrimethylammonium bromide, tetradecyltrimethylammonium bromide, dodecyltrimethylammonium bromide or a mixture of two or more thereof. In some cases, the oil phase is mineral oil and light mineral oil, medium chain triglycerides (MCT), coconut oil; hydrogenated oils comprising hydrogenated cottonseed oil, hydrogenated palm oil, hydrogenate castor oil or hydrogenated soybean oil; polyoxyethylene hydrogenated castor oil derivatives comprising poluoxyl-40 hydrogenated castor oil, polyoxyl-60 hydrogenated castor oil or polyoxyl-100 hydrogenated castor oil.

The invention further provides methods of modulating a PI3K and/or mTor kinase activity by contacting the kinase with an amount of an effective amount of compound of the invention. Modulate can be inhibiting or activating kinase activity. In some embodiments, the invention provides methods of inhibiting kinase activity by contacting the kinase with an amount of an effective amount of a compound of the invention in solution. In some embodiments, the invention provides methods of inhibiting the kinase activity by contacting a cell, tissue, organ that express the kinase of interest. In some embodiments, the invention provides methods of inhibiting kinase activity in subject including but not limited to rodents and mammal (e.g., human) by administering into the subject an effective amount of a compound of the invention. In some embodiments, the percentage of inhibiting exceeds 50%, 60%, 70%, 80%, or 90%.

In some embodiments, the kinase is selected from the group consisting of PI3 kinase including different isorforms such as PI3 kinase α, PI3 kinase β, PI3 kinase γ, PI3 kinase δ; DNA-PK; mTor; Abl, VEGFR, Ephrin receptor B4 (EphB4); TEK receptor tyrosine kinase (TIE2); FMS-related tyrosine kinase 3 (FLT-3); Platelet derived growth factor receptor (PDGFR); RET; ATM; ATR; hSmg-1; Hck; Src; Epidermal growth factor receptor (EGFR); KIT; Inulsin Receptor (IR) and IGFR.

The present invention also provides methods for combination therapies in which an agent known to modulate other pathways, or other components of the same pathway, or even overlapping sets of target enzymes are used in combination with a compound of the present invention, or a pharmaceutically acceptable salt, ester, prodrug, solvate, hydrate or derivative thereof. In one aspect, such therapy includes but is not limited to the combination of the subject compound with chemotherapeutic agents, therapeutic antibodies, and radiation treatment, to provide a synergistic or additive therapeutic effect.

In one aspect, the compounds or pharmaceutical compositions of the present invention may present synergistic or additive efficacy when administered in combination with agents that inhibit IgE production or activity. Such combination can reduce the undesired effect of high level of IgE associated with the use of one or more PI3Kδ inhibitors, if such effect occurs. This may be particularly useful in treatment of autoimmune and inflammatory disorders (AIID) such as rheumatoid arthritis. Additionally, the administration of PI3Kδ or PI3Kδ/γ inhibitors of the present invention in combination with inhibitors of mTOR may also exhibit synergy through enhanced inhibition of the PI3K pathway.

In a separate but related aspect, the present invention provides a combination treatment of a disease associated with PI3Kδ comprising administering to a PI3Kδ inhibitor and an agent that inhibits IgE production or activity. Other exemplary PI3Kδ inhibitors are applicable and they are described, e.g., U.S. Pat. No. 6,800,620. Such combination treatment is particularly useful for treating autoimmune and inflammatory diseases (AIID) including but not limited to rheumatoid arthritis.

Agents that inhibit IgE production are known in the art and they include but are not limited to one or more of TEI-9874, 2-(4-(6-cyclohexyloxy-2-naphtyloxy)phenylacetamide)benzoic acid, rapamycin, rapamycin analogs (i.e. rapalogs), TORC1 inhibitors, TORC2 inhibitors, and any other compounds that inhibit mTORC1 and mTORC2. Agents that inhibit IgE activity include, for example, anti-IgE antibodies such as for example Omalizumab and TNX-901.

For treatment of autoimmune diseases, the subject compounds or pharmaceutical compositions can be used in combination with commonly prescribed drugs including but not limited to Enbrel®, Remicade®, Humira®, Avonex®, and Rebif®. For treatment of respiratory diseaseses, the subject compounds or pharmaceutical compositions can be administered in combination with commonly prescribed drugs including but not limited to Xolair®, Advair®, Singulair®, and Spiriva®.

The compounds of the invention may be formulated or administered in conjunction with other agents that act to relieve the symptoms of inflammatory conditions such as encephalomyelitis, asthma, and the other diseases described herein. These agents include non-steroidal anti-inflammatory drugs (NSAIDs), e.g. acetylsalicylic acid; ibuprofen; naproxen; indomethacin; nabumetone; tolmetin; etc. Corticosteroids are used to reduce inflammation and suppress activity of the immune system. The most commonly prescribed drug of this type is Prednisone. Chloroquine (Aralen) or hydroxychloroquine (Plaquenil) may also be very useful in some individuals with lupus. They are most often prescribed for skin and joint symptoms of lupus. Azathioprine (Imuran) and cyclophosphamide (Cytoxan) suppress inflammation and tend to suppress the immune system. Other agents, e.g. methotrexate and cyclosporin are used to control the symptoms of lupus. Anticoagulants are employed to prevent blood from clotting rapidly. They range from aspirin at very low dose which prevents platelets from sticking, to heparin/coumadin.

In another one aspect, this invention also relates to methods and pharmaceutical compositions for inhibiting abnormal cell growth in a mammal which comprises an amount of a compound of the present invention, or a pharmaceutically acceptable salt, ester, prodrug, solvate, hydrate or derivative thereof, in combination with an amount of an anti-cancer agent (e.g. a chemotherapeutic agent). Many chemotherapeutics are presently known in the art and can be used in combination with the compounds of the invention.

In some embodiments, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens. Non-limiting examples are chemotherapeutic agents, cytotoxic agents, and non-peptide small molecules such as Gleevec (Imatinib Mesylate), Velcade (bortezomib), Casodex (bicalutamide), Iressa (gefitinib), and Adriamycin as well as a host of chemotherapeutic agents. Non-limiting examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, Casodex™, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK.R™; razoxane; sizofiran; spirogermanium; tenuazonic acid; triaziquone; 2,2',2"-trichlorotriethyla-mine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL™, Bristol-Myers Squibb Oncology, Princeton, N.J.) and docetaxel (TAXOTERE™, Rhone-Poulenc Rorer, Antony, France); retinoic acid; esperamicins; capecitabine; and pharmaceutically acceptable salts, acids or derivatives of any of the above. Also included as suitable chemotherapeutic cell conditioners are anti-hormonal agents that act to regulate or inhibit hormone action on tumors such as anti-estrogens including for example tamoxifen (Nolvadex™), raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; camptothecin-11 (CPT-11); topoisomerase inhibitor RFS 2000; difluoromethylornithine (DMFO). Where desired, the compounds or pharmaceutical composition of the present invention can be used in combination with commonly prescribed anti-cancer drugs such as Herceptin®, Avastin®, Erbitux®, Rituxan®, Taxol®, Arimidex®, Taxotere®, and Velcade®.

This invention further relates to a method for using the compounds or pharmaceutical composition in combination with radiation therapy in inhibiting abnormal cell growth or treating the hyperproliferative disorder in the mammal. Techniques for administering radiation therapy are known in the art, and these techniques can be used in the combination therapy described herein. The administration of the compound of the invention in this combination therapy can be determined as described herein.

Radiation therapy can be administered through one of several methods, or a combination of methods, including without limitation external-beam therapy, internal radiation therapy, implant radiation, stereotactic radiosurgery, systemic radiation therapy, radiotherapy and permanent or temporary interstitial brachytherapy. The term "brachytherapy," as used herein, refers to radiation therapy delivered by a spatially confined radioactive material inserted into the body at or near a tumor or other proliferative tissue disease site. The term is intended without limitation to include exposure to radioactive isotopes (e.g. At-211, I-131, I-125, Y-90, Re-186, Re-188, Sm-153, Bi-212, P-32, and radioactive isotopes of Lu). Suitable radiation sources for use as a cell conditioner of the present invention include both solids and liquids. By way of non-limiting example, the radiation source can be a radionuclide, such as I-125, I-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide(s), e.g., a solution of I-125 or I-131, or a radioactive fluid can be produced using a slurry of a suitable fluid containing small particles of solid radionuclides, such as Au-198, Y-90. Moreover, the radionuclide(s) can be embodied in a gel or radioactive micro spheres.

Without being limited by any theory, the compounds of the present invention can render abnormal cells more sensitive to treatment with radiation for purposes of killing and/or inhibiting the growth of such cells. Accordingly, this invention further relates to a method for sensitizing abnormal cells in a mammal to treatment with radiation which comprises administering to the mammal an amount of a compound of the present invention or pharmaceutically acceptable salt, ester, prodrug, solvate, hydrate or derivative thereof, which amount is effective is sensitizing abnormal cells to treatment with radiation. The amount of the compound, salt, or solvate in this method can be determined according to the means for ascertaining effective amounts of such compounds described herein.

The compounds or pharmaceutical compositions of the present invention can be used in combination with an amount of one or more substances selected from anti-angiogenesis agents, signal transduction inhibitors, and anti-proliferative agents.

Anti-angiogenesis agents, such as MMP-2 (matrix-metalloprotienase 2) inhibitors, MMP-9 (matrix-metalloprotienase 9) inhibitors, and COX-11 (cyclooxygenase 11) inhibitors, can be used in conjunction with a compound of the present invention and pharmaceutical compositions described herein. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931, 788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain Patent Application No. 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. Preferred MMP-2 and MMP-9 inhibitors are those that have little or no activity inhibiting MMP-1. More preferred, are those that selectively inhibit MMP-2 and/or AMP-9 relative to the other matrix-metalloproteinases (i.e., MAP-1, MMP-3, MMP-4, MMP-5, MMP-6, MMP-7, MMP-8, MMP-10, MMP-11, MMP-12, andMMP-13). Some specific examples of MMP inhibitors useful in the present invention are AG-3340, RO 32-3555, and RS 13-0830.

The invention also relates to a method of and to a pharmaceutical composition of treating a cardiovascular disease in a mammal which comprises an amount of a compound of the present invention, or a pharmaceutically acceptable salt, ester, prodrug, solvate, hydrate or derivative thereof, or an isotopically-labeled derivative thereof, and an amount of one or more therapeutic agents use for the treatment of cardiovascular diseases.

Exemplary agents for use in cardiovascular disease applications are anti-thrombotic agents, e.g., prostacyclin and salicylates, thrombolytic agents, e.g., streptokinase, urokinase, tissue plasminogen activator (TPA) and anisoylated plasminogen-streptokinase activator complex (APSAC), anti-platelets agents, e.g., acetyl-salicylic acid (ASA) and clopidrogel, vasodilating agents, e.g., nitrates, calcium channel blocking drugs, anti-proliferative agents, e.g., colchicine and alkylating agents, intercalating agents, growth modulating factors such as interleukins, transformation growth factor-beta and congeners of platelet derived growth factor, monoclonal antibodies directed against growth factors, anti-inflammatory agents, both steroidal and non-steroidal, and other agents that can modulate vessel tone, function, arteriosclerosis, and the healing response to vessel or organ injury post intervention.

Antibiotics can also be included in combinations or coatings comprised by the invention. Moreover, a coating can be used to effect therapeutic delivery focally within the vessel wall. By incorporation of the active agent in a swellable polymer, the active agent will be released upon swelling of the polymer.

The compounds describe herein may be formulated or administered in conjunction with liquid or solid tissue barriers also known as lubricants. Examples of tissue barriers include, but are not limited to, polysaccharides, polyglycans, seprafilm, interceed and hyaluronic acid.

Medicaments which may be administered in conjunction with the compounds described herein include any suitable drugs usefully delivered by inhalation for example, analgesics, e.g. codeine, dihydromorphine, ergotamine, fentanyl or morphine; anginal preparations, e.g. diltiazem; antiallergics, e.g. cromoglycate, ketotifen or nedocromil; anti-infectives, e.g. cephalosporins, penicillins, streptomycin, sulphonamides, tetracyclines or pentamidine; antihistamines, e.g. methapyrilene; anti-inflammatories, e.g. beclomethasone, flunisolide, budesonide, tipredane, triamcinolone acetonide or fluticasone; antitussives, e.g. noscapine; bronchodilators, e.g. ephedrine, adrenaline, fenoterol, formoterol, isoprenaline, metaproterenol, phenylephrine, phenylpropanolamine, pirbuterol, reproterol, rimiterol, salbutamol, salmeterol, terbutalin, isoetharine, tulobuterol, orciprenaline or (−)-4-amino-3,5-dichloro-α-[[[6-[2-(2-pyridinyl)ethoxy]hexyl]-amino]methyl]benzenemethanol; diuretics, e.g. amiloride; anticholinergics e.g. ipratropium, atropine or oxitropium; hormones, e.g. cortisone, hydrocortisone or prednisolone; xanthines e.g. aminophylline, choline theophyllinate, lysine theophyllinate or theophylline; and therapeutic proteins and peptides, e.g. insulin or glucagon. It will be clear to a person skilled in the art that, where appropriate, the medicaments may be used in the form of salts (e.g. as alkali metal or amine salts or as acid addition salts) or as esters (e.g. lower alkyl esters) or as solvates (e.g. hydrates) to optimize the activity and/or stability of the medicament.

Other exemplary therapeutic agents useful for a combination therapy include but are not limited to agents as described above, radiation therapy, hormone antagonists, hormones and their releasing factors, thyroid and antithyroid drugs, estrogens and progestins, androgens, adrenocorticotropic hormone; adrenocortical steroids and their synthetic analogs; inhibitors of the synthesis and actions of adrenocortical hormones, insulin, oral hypoglycemic agents, and the pharmacology of the endocrine pancreas, agents affecting calcification and bone turnover: calcium, phosphate, parathyroid hormone, vitamin D, calcitonin, vitamins such as water-soluble vitamins, vitamin B complex, ascorbic acid, fat-soluble vitamins, vitamins A, K, and E, growth factors, cytokines, chemokines, muscarinic receptor agonists and antagonists; anticholinesterase agents; agents acting at the neuromuscular junction and/or autonomic ganglia; catecholamines, sympathomimetic drugs, and adrenergic receptor agonists or antagonists; and 5-hydroxytryptamine (5-HT, serotonin) receptor agonists and antagonists.

Therapeutic agents can also include agents for pain and inflammation such as histamine and histamine antagonists, bradykinin and bradykinin antagonists, 5-hydroxytryptamine (serotonin), lipid substances that are generated by biotransformation of the products of the selective hydrolysis of membrane phospholipids, eicosanoids, prostaglandins, thromboxanes, leukotrienes, aspirin, nonsteroidal anti-inflammatory agents, analgesic-antipyretic agents, agents that inhibit the synthesis of prostaglandins and thromboxanes, selective inhibitors of the inducible cyclooxygenase, selective inhibitors of the inducible cyclooxygenase-2, autacoids, paracrine hormones, somatostatin, gastrin, cytokines that mediate interactions involved in humoral and cellular immune responses, lipid-derived autacoids, eicosanoids, 3-adrenergic agonists, ipratropium, glucocorticoids, methylxanthines, sodium channel blockers, opioid receptor agonists, calcium channel blockers, membrane stabilizers and leukotriene inhibitors.

Additional therapeutic agents contemplated herein include diuretics, vasopressin, agents affecting the renal conservation of water, rennin, angiotensin, agents useful in the treatment of myocardial ischemia, anti-hypertensive agents, angiotensin converting enzyme inhibitors, 3-adrenergic receptor antagonists, agents for the treatment of hypercholesterolemia, and agents for the treatment of dyslipidemia.

Other therapeutic agents contemplated include drugs used for control of gastric acidity, agents for the treatment of peptic ulcers, agents for the treatment of gastroesophageal reflux disease, prokinetic agents, antiemetics, agents used in irritable bowel syndrome, agents used for diarrhea, agents used for constipation, agents used for inflammatory bowel disease, agents used for biliary disease, agents used for pancreatic disease.

Therapeutic agents used to treat protozoan infections, drugs used to treat Malaria, Amebiasis, Giardiasis, Trichomoniasis, Trypanosomiasis, and/or Leishmaniasis, and/or drugs used in the chemotherapy of helminthiasis.

Other therapeutic agents include antimicrobial agents, sulfonamides, trimethoprim-sulfamethoxazole quinolones, and agents for urinary tract infections, penicillins, cephalosporins, and other, 3-Lactam antibiotics, an agent comprising an aminoglycoside, protein synthesis inhibitors, drugs used in the chemotherapy of tuberculosis, mycobacterium avium complex disease, and leprosy, antifungal agents, antiviral agents including nonretroviral agents and antiretroviral agents.

Examples of therapeutic antibodies that can be combined with a subject compound include but are not limited to anti-receptor tyrosine kinase antibodies (cetuximab, panitumumab, trastuzumab), anti CD20 antibodies (rituximab, tositumomab), and other antibodies such as alemtuzumab, bevacizumab, and gemtuzumab.

Moreover, therapeutic agents used for immunomodulation, such as immunomodulators, immunosuppressive agents, tolerogens, and immunostimulants are contemplated by the methods herein. In addition, therapeutic agents acting on the blood and the blood-forming organs, hematopoietic agents, growth factors, minerals, and vitamins, anticoagulant, thrombolytic, and antiplatelet drugs.

Further therapeutic agents that can be combined with a subject compound may be found in Goodman and Gilman's "The Pharmacological Basis of Therapeutics" Tenth Edition edited by Hardman, Limbird and Gilman or the Physician's Desk Reference, both of which are incorporated herein by reference in their entirety.

The compounds described herein can be used in combination with the agents disclosed herein or other suitable agents, depending on the condition being treated. Hence, in some embodiments the compounds of the invention will be co-administer with other agents as described above. When used in combination therapy, the compounds described herein may be administered with the second agent simultaneously or separately. This administration in combination can include simultaneous administration of the two agents in the same dosage form, simultaneous administration in separate dosage forms, and separate administration. That is, a compound described herein and any of the agents described above can be formulated together in the same dosage form and administered simultaneously. Alternatively, a compound of the present invention and any of the agents described above can be simultaneously administered, wherein both the agents are present in separate formulations. In another alternative, a compound of the present invention can be administered just followed by and any of the agents described above, or vice versa. In the separate administration protocol, a compound of the present invention and any of the agents described above may be administered a few minutes apart, or a few hours apart, or a few days apart.

Administration of the compounds of the present invention can be effected by any method that enables delivery of the compounds to the site of action. An effective amount of a compound of the invention may be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

The amount of the compound administered will be dependent on the mammal being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to 7 g/day, preferably about 0.05 to about 2.5 g/day. In some instances, dosage levels below the lower limit of the aforesaid range may be more than adequate, while in other cases still larger doses may be employed without causing any harmful side effect, e.g. by dividing such larger doses into several small doses for administration throughout the day.

In some embodiments, a compound of the invention is administered in a single dose. Typically, such administration will be by injection, e.g., intravenous injection, in order to introduce the agent quickly. However, other routes may be used as appropriate. A single dose of a compound of the invention may also be used for treatment of an acute condition.

In some embodiments, a compound of the invention is administered in multiple doses. Dosing may be about once, twice, three times, four times, five times, six times, or more than six times per day. Dosing may be about once a month, once every two weeks, once a week, or once every other day. In another embodiment a compound of the invention and another agent are administered together about once per day to about 6 times per day.

In another embodiment the administration of a compound of the invention and an agent continues for less than about 7 days. In yet another embodiment the administration continues for more than about 6, 10, 14, 28 days, two months, six months, or one year. In some cases, continuous dosing is achieved and maintained as long as necessary.

Administration of the agents of the invention may continue as long as necessary. In some embodiments, an agent of the invention is administered for more than 1, 2, 3, 4, 5, 6, 7, 14, or 28 days. In some embodiments, an agent of the invention is administered for less than 28, 14, 7, 6, 5, 4, 3, 2, or 1 day. In some embodiments, an agent of the invention is administered chronically on an ongoing basis, e.g., for the treatment of chronic effects.

When a compound of the invention, is administered in a composition that comprises one or more agents, and the agent has a shorter half-life than the compound of the invention unit dose forms of the agent and the compound of the invention may be adjusted accordingly.

The examples and preparations provided below further illustrate and exemplify the compounds of the present invention and methods of preparing such compounds. It is to be understood that the scope of the present invention is not limited in any way by the scope of the following examples and preparations. In the following examples molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

EXAMPLES

Example 1

1-(6-(4-amino-7-isopropyl-7H-pyrrolo[2,3-d]pyrimidin-5-yl)benzo[d]thiazol-2-yl)-3-methylurea Scheme 3. The synthesis of 1-(6-(4-amino-7-isopropyl-7H-pyrrolo[2,3-d]pyrimidin-5-yl)benzo[d]thiazol-2-yl)-3-methylurea

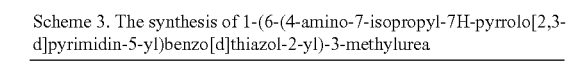
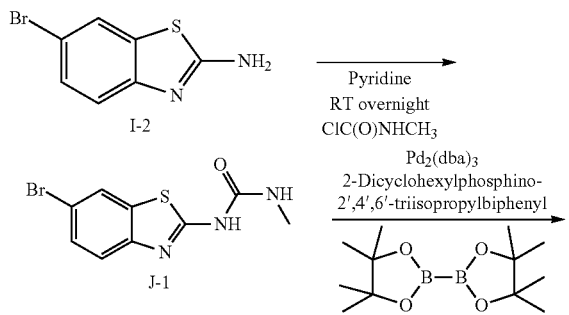
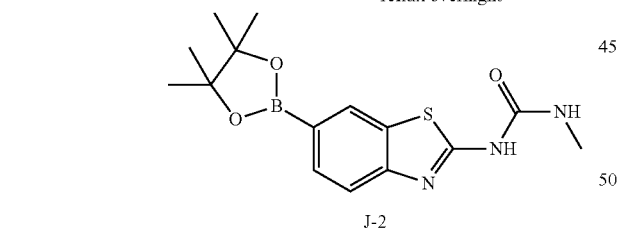
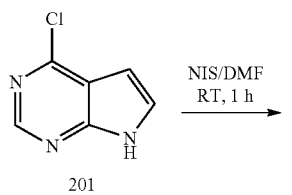
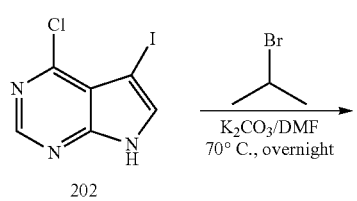
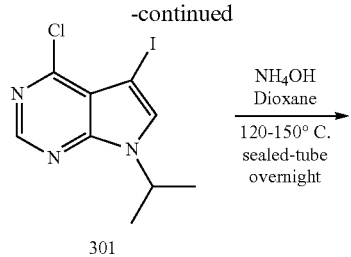
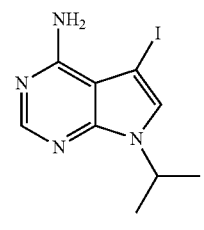
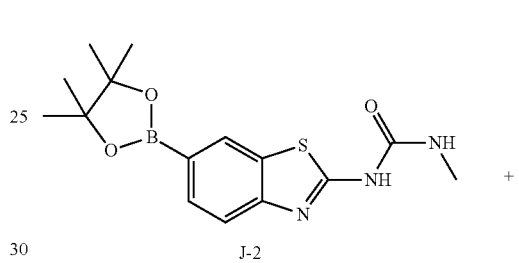
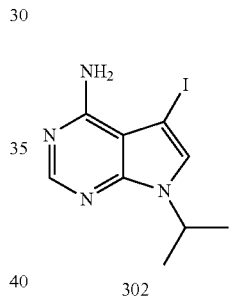
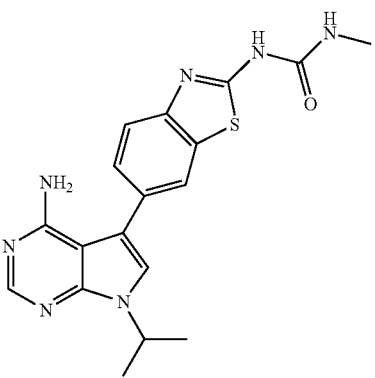

A solution of 6-bromobenzo[d]thiazol-2-amine (I-2) (750 mg, 3.3 mmol) in DMF(50 mL) was cooled to 0° C., methylcarbamic chloride (1.23 g, 13.2 mmol, 4 eq) was added slowly, and the mixture was stirred at room temperature overnight. The mixture was concentrated in vacuo, then water (20 mL) was added. The resulting solid was collected by filtration and dried in vacuo to afford the desired product, 1-(6-bromobenzo[d]thiazol-2-yl)-3-methylurea (J-1) (900 mg, 95.7%) as a white solid. The product obtained was used directly in the next step without further purification.

1-(6-bromobenzo[d]thiazol-2-yl)-3-methylurea (J–1) (800 mg, 2.8 mmol), bis(pinacolato)diboron (853 mg, 3.36 mmol), Pd$_2$(dba)$_3$ (51 mg, 0.056 mmol), 2-dicyclohexylphosphino-2',4',6'-triisopropylbiphenyl (80 mg, 0.168 mmol) and potassium acetate (440 mg, 1.6 mmol) were dissolved in 1,4-dioxane (15 mL) and heated to reflux for overnight under argon. The mixture was allowed to cool to room temperature, filtered, and the cake was washed with 1,4-dioxane. The combined filtrate was concentrated in vacuo and the residue was purified by flash column chromatography eluting with MeOH/DCM (1/50) to afford the desired product, 1-methyl-3-(6-(4,4,5,5-tetramethyl-1,3,2-dioxaborolan-2-yl)benzo[d]thiazol-2-yl)urea (J-2) (800 mg, 85%) as a white solid. ESI-MS m/z: 333.95 [M+1]$^+$ A solution of 4-chloro-7H-pyrrolo[2,3-d]pyrimidine (201) (500 mg, 3.25 mmol) and NIS (805 mg, 1.1 eq, 3.6 mmol) in DMF (1 mL) was stirred at room temperature for 1 h. The mixture was concentrated in vacuo, then water (10 mL) was added. The resulting solid was collected by filtration. Then dried in vacuo to afford the desired product, 4-chloro-5-iodo-7H-pyrrolo[2,3-d]pyrimidine (202) (900 mg, 99% yield) as a off-white solid. ESI-MS m/z: 277.85 [M–H]$^-$. The product obtained was used directly in the next step without purification.

A solution of 4-chloro-5-iodo-7H-pyrrolo[2,3-d]pyrimidine (202) (900 mg, 3.22 mmol) in DMF (50 mL) was heated to 70° C., K$_2$CO$_3$ (890 mg, 2 eq, 6.45 mmol) was added slowly and then 2-bromopropane (363 uL, 3.87 mmol, 1.2 eq) was added dropwise. The mixture was stirred overnight at 70° C. The mixture was cooled to room temperature and concentrated in vacuo. Then water (20 mL) was added. The resulting solid was collected by filtration and dried in vacuo to afford the desired product, 4-chloro-5-iodo-7-isopropyl-7H-pyrrolo[2,3-d]pyrimidine (301) (850 mg, 82% yield) as a white solid. The product obtained was used directly in the next step without purification.

A solution of 4-chloro-5-iodo-7-isopropyl-7H-pyrrolo[2,3-d]pyrimidine (301) (850 mg, 2.64 mmol) and NH$_4$OH (5 mL) in 1.4-dioxane (6 mL) was stirred in a sealed-tube at 120-150° C. for 24 h. The mixture was allowed to cool to room temperature and concentrated in vacuo, then water (20 mL) was added. The resulting solid was collected by filtration and dried in vacuo to afford the desired product, 5-iodo-7-isopropyl-7H-pyrrolo[2,3-d]pyrimidin-4-amine (302) (640 mg, 80% yield) as a white solid. The product obtained was used directly in the next step without further purification. ESI-MS m/z: 302.85 [M+H]$^+$.

A mixture of 5-iodo-7-isopropyl-7H-pyrrolo[2,3-d]pyrimidin-4-amine (302) (200 mg, 0.66 mmol), 1-methyl-3-(6-(4,4,5,5-tetramethyl-1,3,2-dioxaborolan-2-yl)benzo[d]thiazol-2-yl)urea (J-2)(333 mg, 1.5 eq, 1.0 mmol), Pd(PPh$_3$)$_4$ (76 mg, 0.1 eq, 0.066 mmol) and Na$_2$CO$_3$ (2 N, 2 mL) in DME (10 mL) was stirred at reflux for 30 min under Ar. The mixture was cooled to room temperature, and then concentrated in vacuo. Brine (10 mL) was added to the residue and then extracted with ethyl acetate (3×30 mL). The combined organic layer was washed with brine (10 mL), dried over MgSO$_4$ and filtered. The filtrate was concentrated in vacuo and the residue was purified by flash column chromatography eluting with MeOH/DCM (1/30) to afford the desired product, 1-(6-(4-amino-7-isopropyl-7H-pyrrolo[2,3-d]pyrimidin-5-yl)benzo[d]thiazol-2-yl)-3-methylurea (303) (147 mg 58% yield) as a white solid ESI-MS m/z: 382.00 [M+1]$^+$.

Example 2

1-(6-(4-amino-7-(tetrahydro-2H-pyran-4-yl)-7H-pyrrolo[2,3-d]pyrimidin-5-yl)benzo[d]thiazol-2-yl)-3-methylurea Scheme 4: Synthesis of 1-(6-(4-amino-7-(tetrahydro-2H-pyran-4-yl)-7H-pyrrolo[2,3-d]pyrimidin-5-yl)benzo[d]thiazol-2-yl)-3-methylurea.

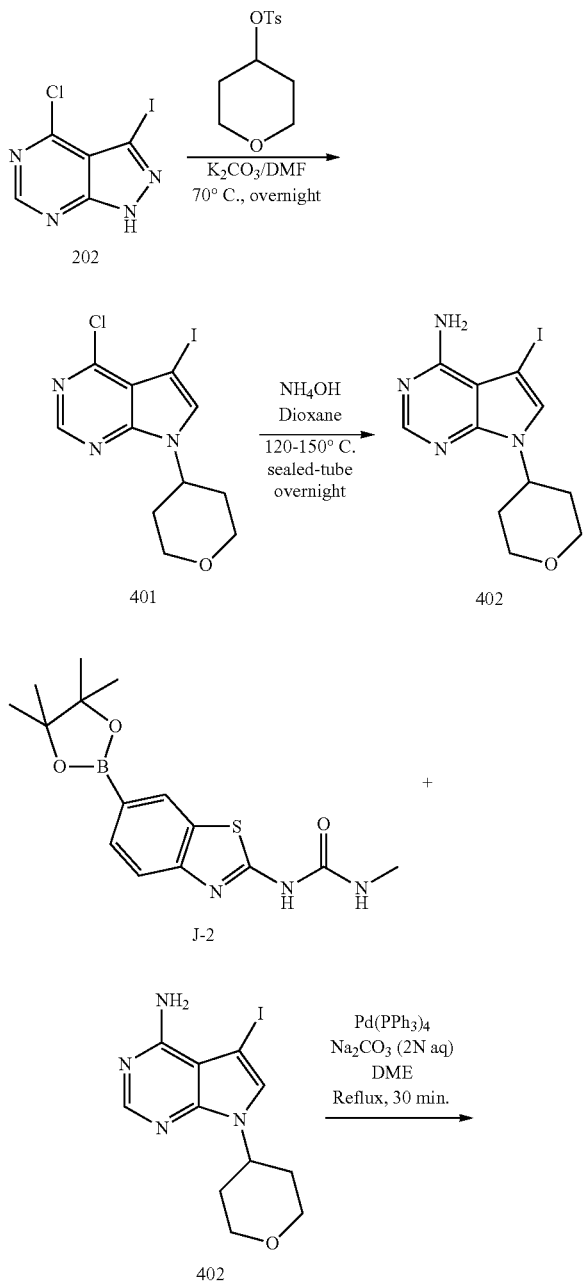

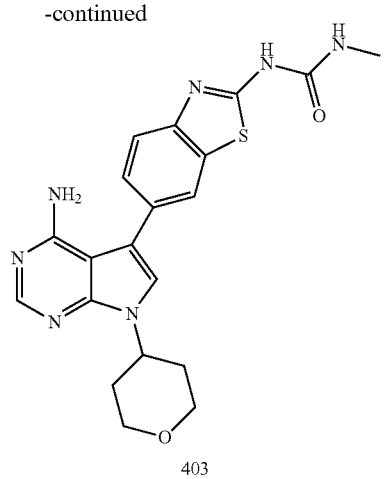

403

A solution of 4-chloro-5-iodo-7H-pyrrolo[2,3-d]pyrimidine (202) (1.842 g, 6.602 mmol) in DMF (50 mL) was heated to 70° C., K₂CO₃ (1.78 g, 2 eq, 13.2 mmol) was added slowly and then tetrahydro-2H-pyran-4-yl 4-methylbenzenesulfonate (2.2 g, 8.583 mmol, 1.3 eq) was added dropwise. The solution was stirred overnight at 70° C. The mixture was concentrated in vacuo. Then water (20 mL) was added. The resulting solid was collected by filtration and dried in vacuo to afford the desired product, 4-chloro-5-iodo-7-(tetrahydro-2H-pyran-4-yl)-7H-pyrrolo[2,3-d]pyrimidine (401) (1.7 g, 82% yield) as a white solid. The product obtained was used directly in the next step without further purification.

A solution of 4-chloro-5-iodo-7-(tetrahydro-2H-pyran-4-yl)-7H-pyrrolo[2,3-d]pyrimidine (401) (1.7 g, 2.64 mmol) and NH₄OH (15 mL) in 1,4-dioxane (5 mL) was stirred in a sealed-tube at 120-150° C. for 24 h. The mixture was allowed to cool to room temperature and then concentrated in vacuo, then water (30 mL) was added. The resulting solid was collected by filtration. Then dried in vacuo to afford the desired product, 5-iodo-7-(tetrahydro-2H-pyran-4-yl)-7H-pyrrolo[2,3-d]pyrimidin-4-amine (402) (1.6 g, 80% yield) as a white solid. The product obtained was used directly in the next step without further purification. ESI-MS m/z: 344.90 [M+H]⁺.

A mixture of 5-iodo-7-(tetrahydro-2H-pyran-4-yl)-7H-pyrrolo[2,3-d]pyrimidin-4-amine (402) (100 mg, 0.29 mmol), 1-methyl-3-(6-(4,4,5,5-tetramethyl-1,3,2-dioxaborolan-2-yl)benzo[d]thiazol-2-yl)urea (J-2)(127 mg, 1.3 eq, 0.38 mmol), Pd(PPh₃)₄ (38 mg, 0.1 eq, 0.03 mmol) and Na₂CO₃ (2 N, 2 mL) in DME (10 mL) was stirred at reflux for 30 min. under argon. The mixture was cooled to room temperature, and then concentrated in vacuo. Brine (10 mL) was added to the residue and then extracted with ethyl acetate (3×30 mL). The combined organic layer was washed with brine (10 mL), dried over MgSO₄ and filtered. The filtrate was concentrated in vacuo and the residue was purified by flash column chromatography eluting with MeOH/DCM (1/30) to afford the desired product, 1-(6-(4-amino-7-(tetrahydro-2H-pyran-4-yl)-7H-pyrrolo[2,3-d]pyrimidin-5-yl)benzo[d]thiazol-2-yl)-3-methylurea (403) (60 mg 58% yield) as a white solid. ESI-MS m/z: 424.05 [M+1]⁺.

Example 3

N-(6-(4-amino-1-isopropyl-1H-pyrazolo[3,4-d]pyrimidin-3-yl)benzo[d]thiazol-2-yl)acetamide Scheme 5: Synthesis of N-(6-(4-amino-1-isopropyl-1H-pyrazolo[3,4-d]pyrimidin-3-yl)benzo[d]thiazol-2-yl)acetamide

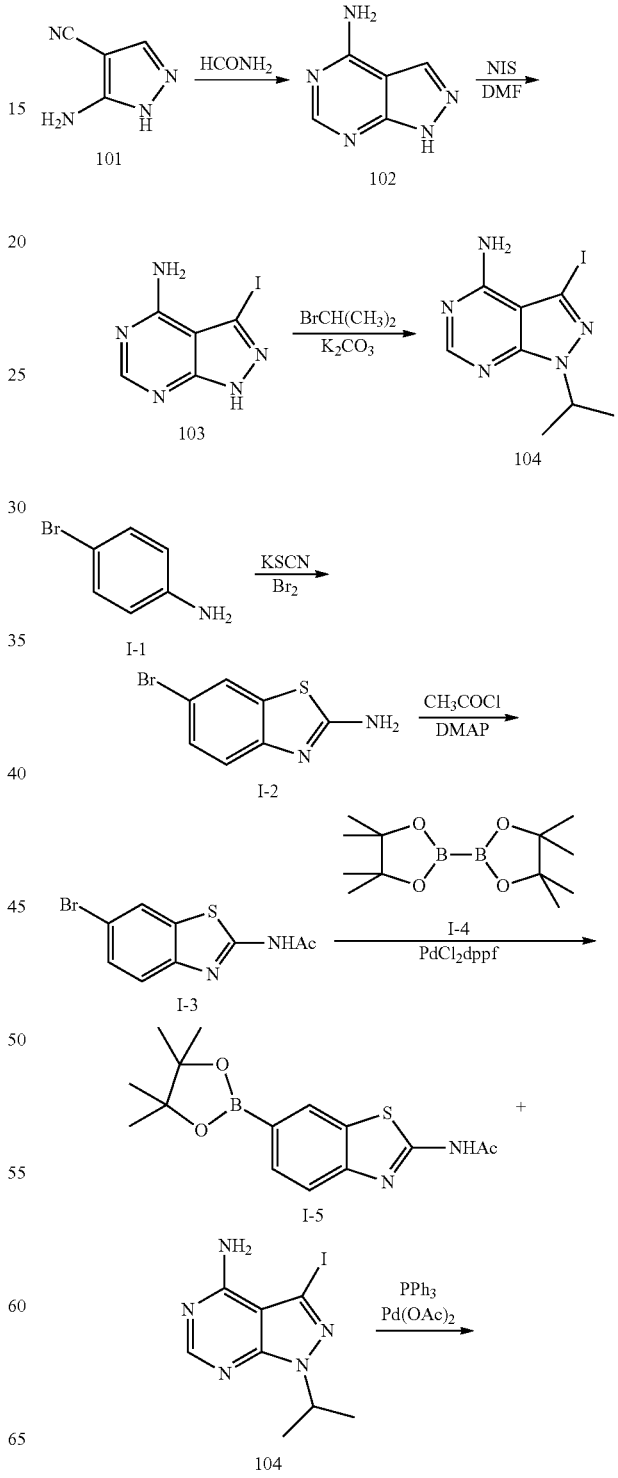

135
-continued

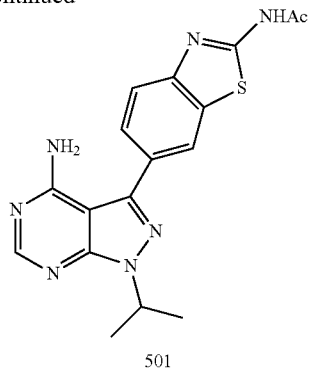

501

A solution of 200 mL of formamide and 3-amino-4-pyrazolecarbonitrile (101) (55 g, 0.509 mol) was stirred at reflux for 1 h. The reaction mixture was cooled to room temperature and 800 mL of water was added. The resulting solid was collected by filtration, rinsed with water and dried in vacuo to yield the desired product, 1H-pyrazolo[3,4-d]pyrimidin-4-amine (102) (64 g, 93% yield) as an off-white solid. ESI-MS (M+H)+m/z: 135.95

A solution of 3H-pyrazolo[3,4-d]pyrimidin-4-amine (102) (22.8 g, 0.169 mol) and N-iodo-succinamide (45.3 g, 0.201 mol, 1.2 eq.) in DMF (100 mL) was stirred at 80 OC for 7-8 h. The resulting solid was collected by filtration, rinsed with EtOH (100 mL) and dried in vacuo overnight to yield the desired product, 3-iodo-1H-pyrazolo[3,4-d]pyrimidin-4-amine (103) (31.7 g, 71.9% yield). ESI-MS (M+H)+ m/z: 261.8

To a suspension of 3-iodo-1H-pyrazolo[3,4-d]pyrimidin-4-amine (103) (2.0 g, 7.66 mmol) in anhydrous N,N-dimethylformamide (50 mL) under an argon atmosphere, potassium carbonate (4.23 g, 30.6 mmol) and 2-bromopropane (0.79 mL, 8.43 mmol) were added sequentially. The resulting mixture was stirred at 80 OC for 5 h and then was allowed to cool to room temperature. The mixture was filtered. The filtrate was concentrated in vacuo to half volume and then partitioned between water and ethyl acetate. The organic layer was washed with brine, dried over sodium sulfate and filtered. The filtrate was concentrated in vacuo to afford the desired product, 3-iodo-1-isopropyl-1H-pyrazolo[3,4-d]pyrimidin-4-amine (4) (1.86 g, 80.2% yield) as a yellow solid. ESI-MS (M+H)+m/z: 303.9.

4-Bromoaniline (I-1) (120 g, 0.697 mol) and KSCN (69 g, 0.697 mol) were dissolved in a mixture of THF (500 mL) and AcOH (450 mL). The mixture was stirred at RT for 30 min. and then was cooled to −30° C., solid NBS (124 g, 0.697 mol) was added slowly. The resulting mixture was stirred at −30° C. for 30 min., and then was allowed to warm to RT and stirred overnight. The solution was poured into stirred ice-water (3000 mL), ammonia solution was added to adjust the pH value to 9 and then filtered. The filtrate was extracted with ethyl acetate (2000 mL), washed with water (500 mL), dried over Na$_2$SO$_4$ and filtered. The filtrate was heated to reflux for 20 min., and then cooled to 0° C. The mixture was filtered through silica gel (10 g), and the filtrate was concentrated in vacuo. The crude product was taken in chloroform (1500 mL), heated to reflux for 30 min., and then cooled to 0° C. The precipitate was collected by filtration and further dried in vacuo to afford the desired product, 6-bromobenzo[d]thiazol-2-amine I-2 (78 g, 49% yield) as a white solid. ESI-MS (M+H)+m/z: 230.90

136

To a stirred solution of 6-bromobenzo[d]thiazol-2-amine I-2 (229 g, 1.0 mol), pyridine (237 g, 3.0 mol) and DMAP (1.0 g) in anhydrous THF (1800 mL) at 10° C., CH$_3$COCl (87 g, 1.1 mol) was added dropwise and the temperature was kept below 20° C. The resulting mixture was allowed to warm to RT and stirred overnight. The mixture was poured into H$_2$O (2000 mL) and extracted with ethyl acetate (2000 mL). The organic layer was dried over Na$_2$SO$_4$ and filtered. The filtrate was concentrated in vacuo. The crude product was suspended in chloroform (1200 mL), heated to reflux for 20 min. and then cooled to RT. The precipitate was collected by filtration and further dried in vacuo to afford the desired product, N-(6-bromobenzo[d]thiazol-2-yl) acetamide (I-3) (231 g, 85% yield) as a white solid. ESI-MS (M+H)+ m/z: 270.95

To a stirred mixture of N-(6-bromobenzo[d]thiazol-2-yl) acetamide (I-3) (32.5 g, 120 mmol) and 4,4,4',4',5,5,5',5'-octamethyl-2,2'-bi(1,3,2-dioxaborolane) (I-4) (36.5 g, 144 mmol) in 1,4-dioxane (1000 mL), dppf(PdCl$_2$) (10 g, 12 mmol) and KOAc (70 g, 720 mmol) were added sequentially. The resulting mixture was degassed and back-filled with argon three times and then stirred at 110° C. for 2 h. The mixture was allowed to cool to RT, filtered through silica gel (10 g) and concentrated in vacuo. The residue was purified by flash column chromatography on silica gel (10-50% ethyl acetate/petroether) to afford the desired product, N-(6-(4,4,5,5-tetramethyl-1,3,2-dioxaborolan-2-yl)benzo[d]thiazol-2-yl)acetamide (I-5) (35 g, 93% yield) as a white solid. ESI-MS (M+H)+ m/z: 317.05.

A mixture of 3-iodo-1-isopropyl-1H-pyrazolo[3,4-d]pyrimidin-4-amine (104) (1.88 g, 6.2 mmol), N-(6-(4,4,5,5-tetramethyl-1,3,2-dioxaborolan-2-yl)benzo[d]thiazol-2-yl) acetamide (I-5) (2.0 g, 6.3 mmol), Pd(OAc)$_2$ (0.28 g, 1.24 mmol), triphenyl phosphine (0.98 g, 3.7 mmol) and Na$_2$CO$_3$ (3.3 g, 31 mmol) was dissolved in a mixture of DMF (5 mL), EtOH (2 mL) and H$_2$O (2 mL). The resulting mixture was degassed and back-filled with argon three times and then stirred at 80° C. for 4 h. The mixture was allowed to cool to room temperature and filtered. The filtrate was concentrated in vacuo. The crude product was purified by chromatography eluting with DCM/MeOH (20/1) on a silica gel column (200-300 mesh) to afford the desired product N-(6-(4-amino-1-isopropyl-1H-pyrazolo[3,4-d]pyrimidin-3-yl)benzo[d]thiazol-2-yl)acetamide (501) (1.1 g, 48.2%) as a white solid. ESI-MS (M+H)+ m/z: 368.4.

Example 4

N-(6-(4-amino-1-cyclopentyl-1H-pyrazolo[3,4-d]pyrimidin-3-yl)benzo[d]thiazol-2-yl)acetamide Scheme 6: Synthesis of N-(6-(4-amino-1-cyclopentyl-1H-pyrazolo[3,4-d]pyrimidin-3-yl)benzo[d]thiazol-2-yl)acetamide.

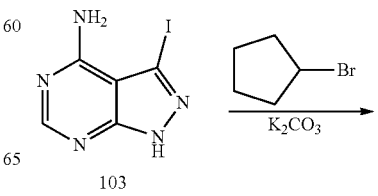

103

Example 5

1-isopropyl-3-(2-(methylamino)benzo[d]thiazol-6-yl)-1H-pyrazolo[3,4-d]pyrimidin-4-amine Scheme 7: Synthesis of 1-isopropyl-3-(2-(methylamino)benzo[d]thiazol-6-yl)-1H-pyrazolo[3,4-d]pyrimidin-4-amine

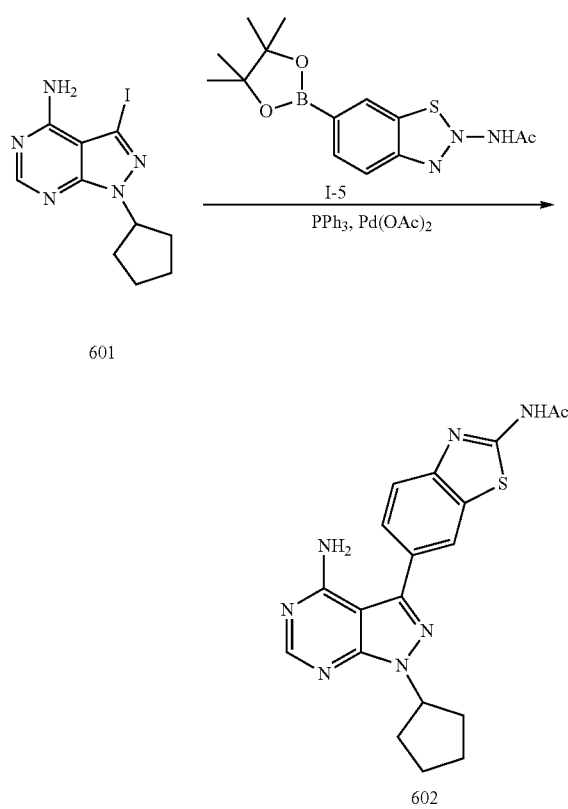

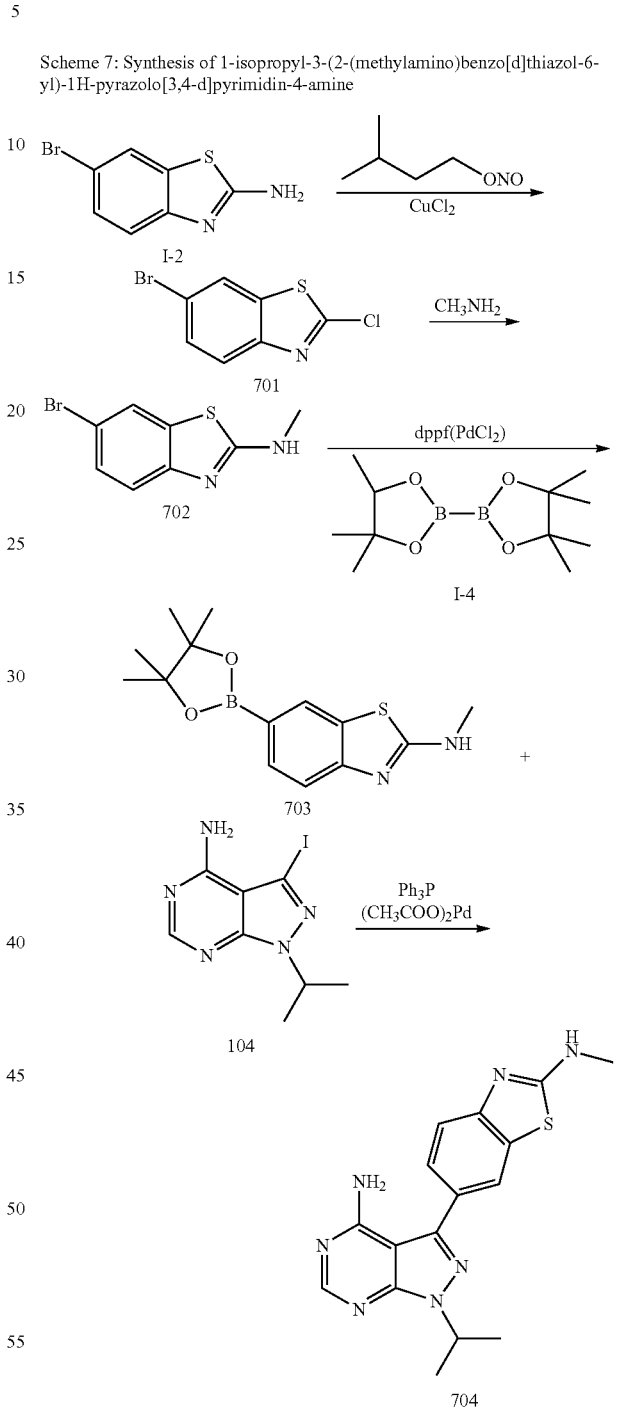

To a suspension of 3-iodo-1H-pyrazolo[3,4-d]pyrimidin-4-amine (103) (2.0 g, 7.66 mmol) in anhydrous N,N-dimethylformamide (50 mL) under an argon atmosphere, potassium carbonate (4.23 g, 30.6 mmol) and bromocyclopentane (1.37 g, 9.20 mmol, 1.2 eq) were added sequentially. The resulting mixture was stirred at 80° C. for 5 h and then was allowed to cool to room temperature. The mixture was filtered and the filtrate was concentrated to half volume in vacuo and then partitioned between water and ethyl acetate. The organic layer was dried over sodium sulfate, filtered and concentrated in vacuo to afford the desired product, 1-cyclopentyl-3-iodo-1H-pyrazolo[3,4-d]pyrimidin-4-amine (601) (1.27 g, 50.4% yield) as a yellow solid. ESI-MS (M+H)+ m/z: 330.1.

A mixture of 3-iodo-1-isopropyl-1H-pyrazolo[3,4-d]pyrimidin-4-amine (601 (1.21 g, 3.68 mmol), N-(6-(4,4,5,5-tetramethyl-1,3,2-dioxaborolan-2-yl)benzo[d]thiazol-2-yl)acetamide (I-5) (1.18 g, 3.71 mmol), Pd(OAc)$_2$ (0.17 g, 0.75 mmol), triphenyl phosphine (0.59 g, 2.22 mmol) and Na$_2$CO$_3$ (1.98 g, 18.6 mmol) was dissolved in a mixture of DMF (3 mL), EtOH (1.5 mL) and H$_2$O (1.5 mL). The resulting mixture was degassed and back-filled with argon three times and then stirred at 80° C. for 4 h. The mixture was allowed to cool to room temperature and filtered. The filtrate was concentrated in vacuo. The crude product was purified by flash column chromatography on silica gel (200-300 mesh) eluting with DCM/MeOH (20/1) to give the desired product, N-(6-(4-amino-1-cyclopentyl-1H-pyrazolo[3,4-d]pyrimidin-3-yl)benzo[d]thiazol-2-yl)acetamide (602) (0.52 g, 35.9%) as an off-white solid. ESI-MS (M+H)+m/z: 394.1.

Iso-Pentyl nitrite (0.9 mL, 6.8 mmol) and copper (II) chloride (0.938 g, 5.5 mmol) were suspended in CH$_3$CN (25 mL), and the mixture was stirred at 65° C. for 30 min. A solution of 6-bromobenzo[d]thiazol-2-amine (I-2) (1 g, 4.37 mmol) in THF (20 mL) was added dropwise, and the resulting mixture was stirred at 85° C. for 1 h. The mixture was allowed to cool to RT, poured into 20% HCl (200 mL), filtered, and the cake was washed with water (50 mL). The crude product was purified by flash column chromatography on silica gel (200-300 mesh) eluting with petroether/ethyl acetate (40/1) to give the desired product, 6-bromo-2-chlorobenzo[d]thiazole (701) (0.58 g, 53.7% yield) as a pale solid. ESI-MS (M+H)+m/z: 247.9. [00394] 6-Bromo-2-chlorobenzo[d]thiazole (701) (0.5 g, 2.0 mmol) was dissolved in methanamine solution (20 ml) in a sealed tube, and the resulting mixture was stirred at 60° C. overnight. The mixture was allowed to cool to RT, concentrated in vacuo and water (20 mL) was added. The solid was collected by filtration to afford the desired product, 6-bromo-N-methyl-benzo[d]thiazol-2-amine (702) (0.43 g, 87.9% yield). ESI-MS (M+H)+m/z: 242.8.

To a stirred mixture of 6-bromo-N-methylbenzo[d]thiazol-2-amine (702) (70 mg, 0.29 mmol) and 4,4,4',4',5,5,5',5'-octamethyl-2,2'-bi(1,3,2-dioxaborolane) (I-4)(88 mg, 0.35 mmol) in 1,4-dioxane (7 mL), dppf(PdCl$_2$) (24 mg, 0.029 mmol) and KOAc (45 mg, 0.46 mmol) were added sequentially. The resulting mixture was degassed and back-filled with argon three times and then stirred at 110° C. for 8 h. The mixture was allowed to cool to RT and concentrated in vacuo. The residue was purified by flash column chromatography on silica gel (DCM/MeOH=80/1) to afford N-methyl-6-(4,4,5,5-tetramethyl-1,3,2-dioxaborolan-2-yl) benzo[d]thiazol-2-amine (703) (40 mg, 47.6% yield) as a pale solid. ESI-MS (M+H)$^+$ m/z: 291.00.

A mixture of 3-iodo-1-isopropyl-1H-pyrazolo[3,4-d]pyrimidin-4-amine (104) (47 mg, 0.16 mmol), N-methyl-6-(4,4,5,5-tetramethyl-1,3,2-dioxaborolan-2-yl)benzo[d]thiazol-2-amine (703 (37 mg, 0.13 mmol), Pd(OAc)$_2$ (6 mg, 0.027 mmol), triphenyl phosphine (20 mg, 0.076 mmol) and Na$_2$CO$_3$ (69 mg, 0.65 mmol) was dissolved in a mixture of DMF (4 mL), EtOH (4 mL) and H$_2$O (2 mL). The resulting mixture was degassed and back-filled with argon three times and then stirred at 90° C. for 1.5 h. The mixture was allowed to cool to room temperature and filtered. The filtrate was concentrated in vacuo. The crude product was purified by flash chromatography on silica gel (200-300 mesh) eluting with DCM/MeOH (20/1) to give the desired product 1-isopropyl-3-(2-(methylamino)benzo[d]thiazol-6-yl)-1H-pyrazolo[3,4-d]pyrimidin-4-amine (704) (15 mg, 34.1%) as a pale solid. ESI-MS (M+H)$^+$ m/z: 340.05.

Example 6

In Vitro Activity of Selected Compounds of Formula I

TABLE 5

Structures corresponding to the compound number listed in Table 4.

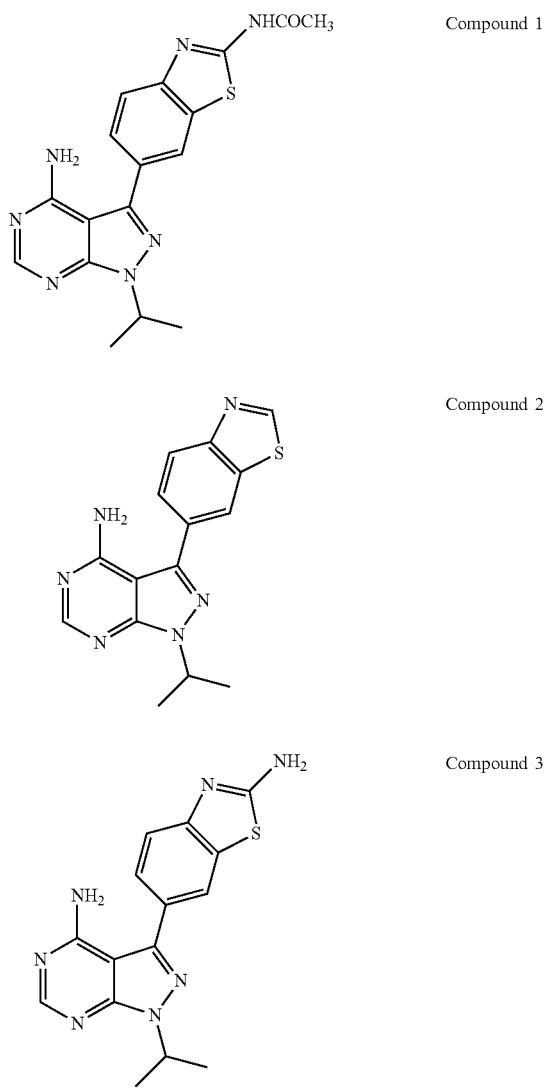

TABLE 4

IC50 values for selected assays.

| IC$_{50}$ results | 50 nm or less (Compound #) | 100 nm or less (Compound #) | 500 nm or less (Compound #) | 1000 nm or less (Compound #) | >1000 nm (Compound #) |
|---|---|---|---|---|---|
| mTORC | 1, 3, 4, 5, 11, 19, 20, 21, 22, 23 | 10 | 8, 9, 12, 15, | 15, 16, 17, | 2, 6, 7, 13, 14, 18 |
| PI3K alpha | 4, 20, 21, 22, 23 | 5, 10, 11, | 1, 3, 9, 12, 19, 30 | 6, 8, 16, | 2, 7, 13, 14, 15, 17, 18 |
| PI3K beta | 21, 22, | 23 | 20 | | 1, 3, 4, 5, 10, 11, 12, 15, 18,19 |
| PI3K gamma | 1, 3, 4, 5, 10, 11, 19, 20, 21, 22, 23, | | 12, | | 18 |
| PI3K delta | 1, 4, 5, 19, 20, 21, 22, 23 | 3, 10, | 11, | 12, | 18 |
| PC3 proliferation | | 22 | | 21 | 23 |

TABLE 5-continued
Structures corresponding to the compound number listed in Table 4.
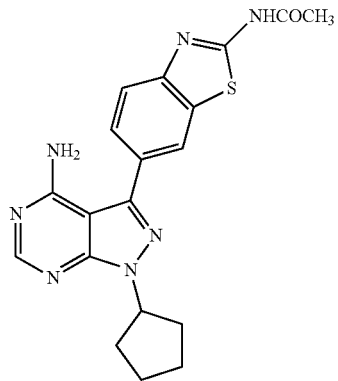 Compound 4
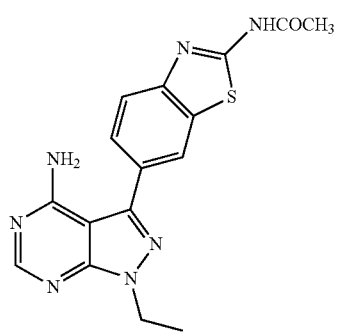 Compound 5
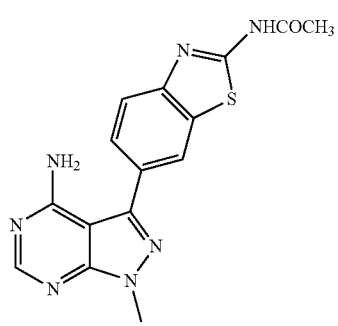 Compound 6
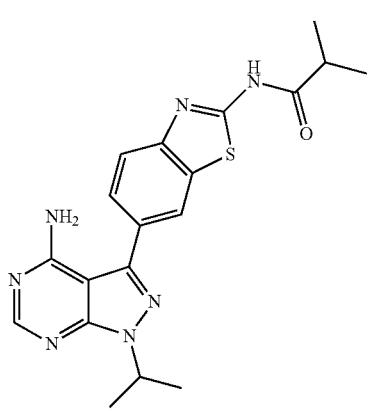 [SMILES: CC(C)C(=O)Nc1nc2ccc(-c3nn(C(C)C)c4ncnc(N)c34)cc2s1] Compound 7
TABLE 5-continued
Structures corresponding to the compound number listed in Table 4.
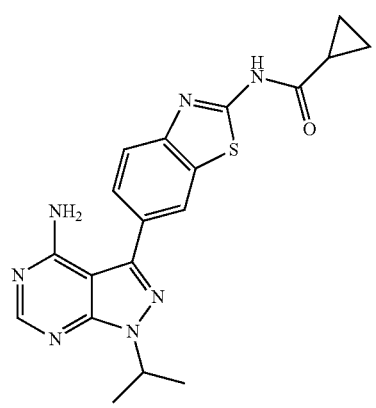 [SMILES: CC(C)n1nc(-c2ccc3nc(NC(=O)C4CC4)sc3c2)c2c(N)ncnc21] Compound 8
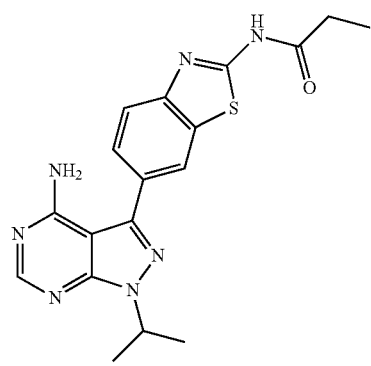 [SMILES: CCC(=O)Nc1nc2ccc(-c3nn(C(C)C)c4ncnc(N)c34)cc2s1] Compound 9
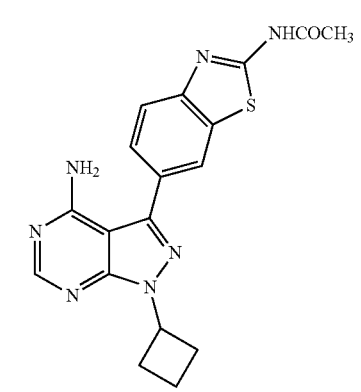 Compound 10
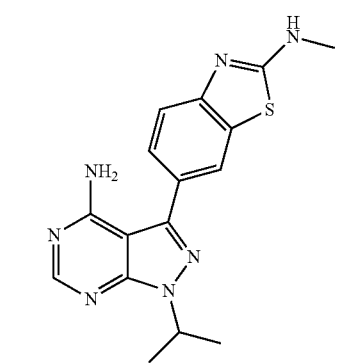 [SMILES: CNc1nc2ccc(-c3nn(C(C)C)c4ncnc(N)c34)cc2s1] Compound 11

TABLE 5-continued
Structures corresponding to the compound number listed in Table 4.
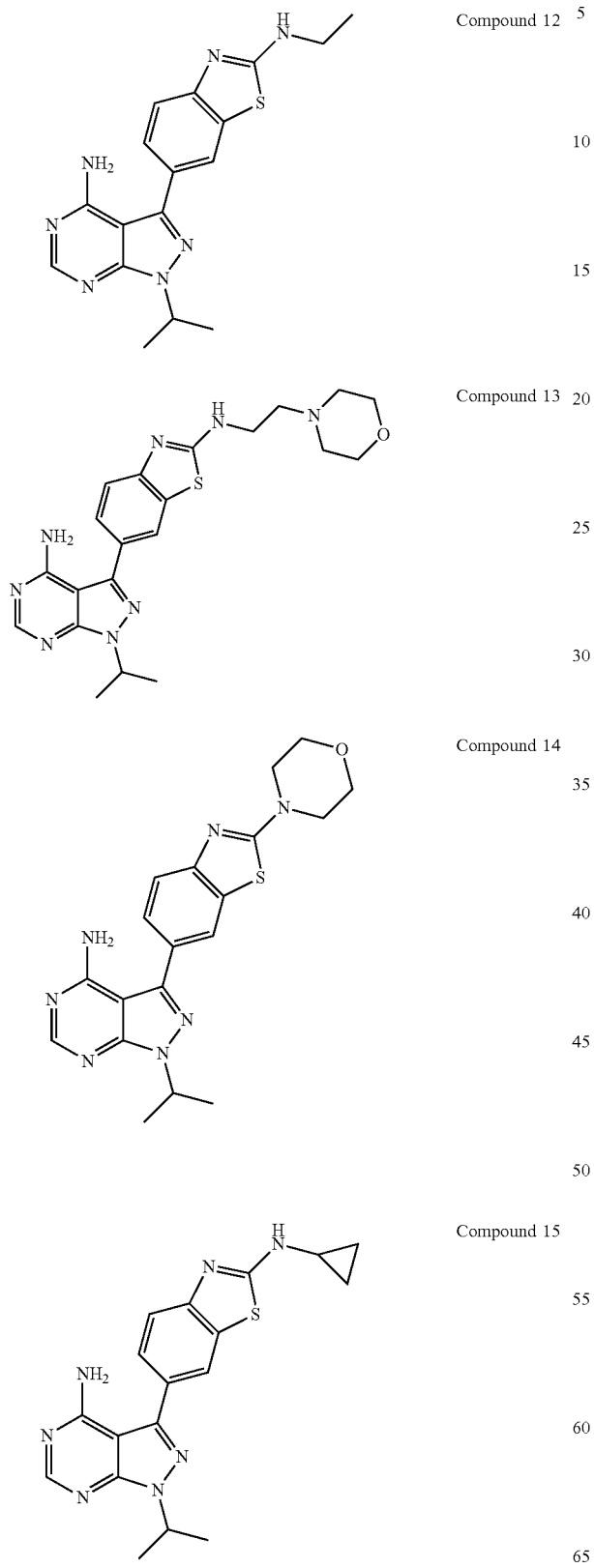
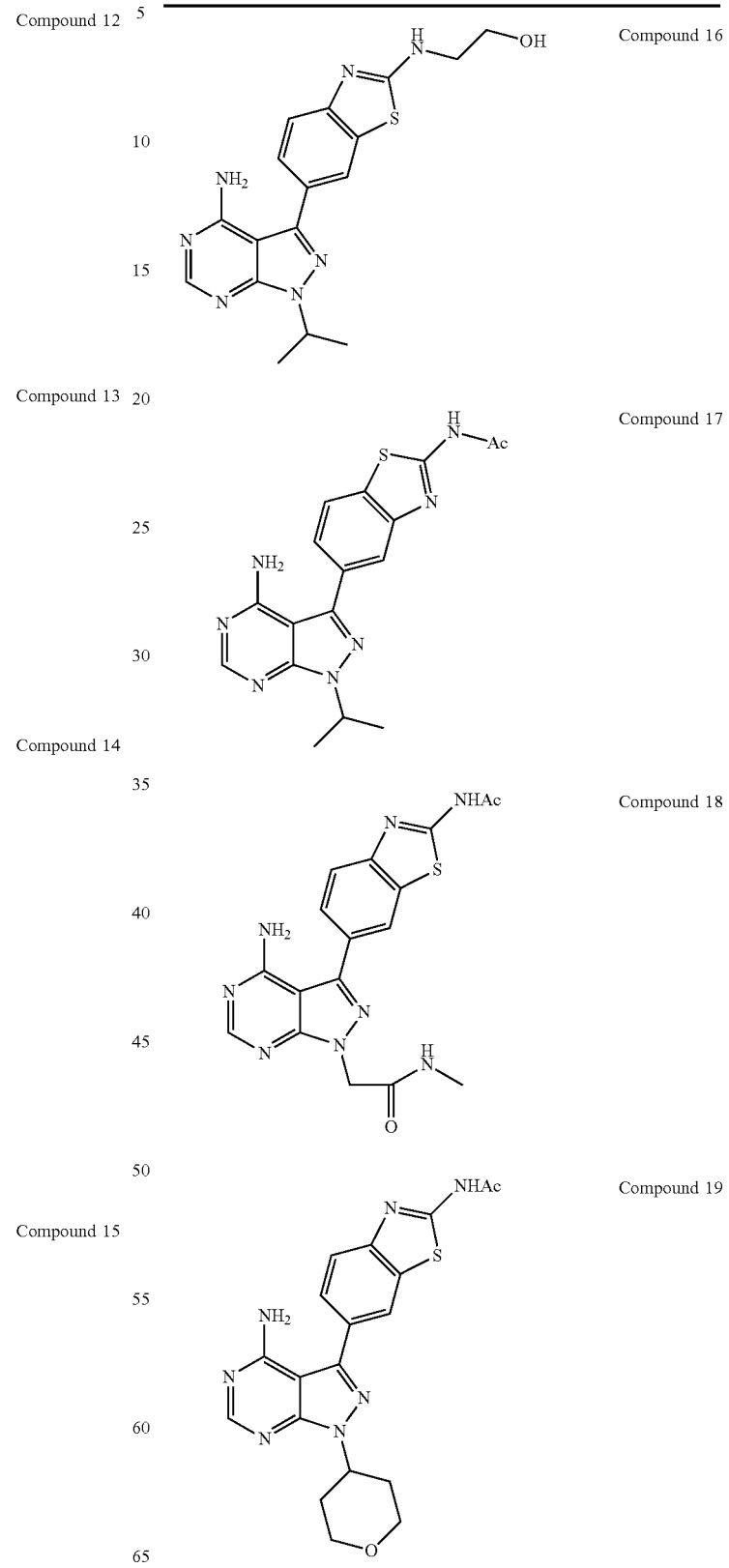

TABLE 5-continued

Structures corresponding to the compound number listed in Table 4.

Compound 20

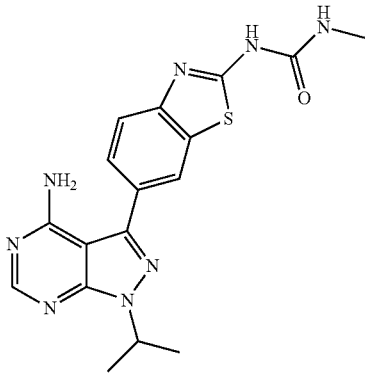 [SMILES: CNC(=O)Nc1nc2ccc(-c3nn(C(C)C)c4ncnc(N)c34)cc2s1]

Compound 21

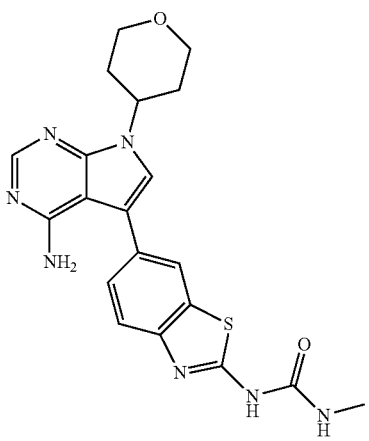 [SMILES: CNC(=O)Nc1nc2ccc(-c3cn(C4CCOCC4)c4ncnc(N)c34)cc2s1]

Compound 22

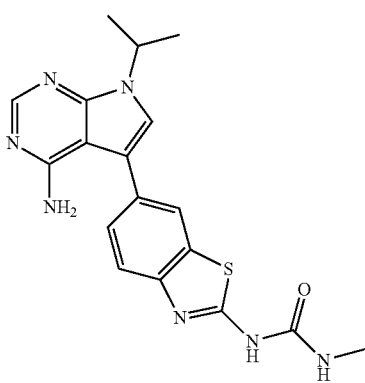 [SMILES: CNC(=O)Nc1nc2ccc(-c3cn(C(C)C)c4ncnc(N)c34)cc2s1]

TABLE 5-continued

Structures corresponding to the compound number listed in Table 4.

Compound 23

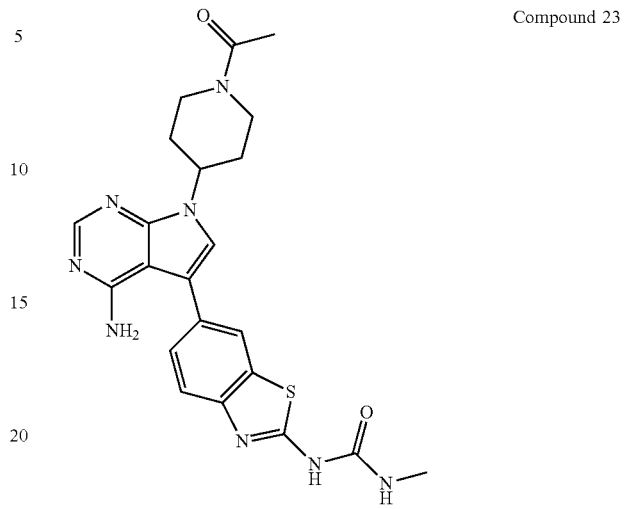

Example 7

Expression and Inhibition Assays of p110α/p85α, p110β/p85α, p110δ/p85α, and p110γ

Class I PI3-Ks can be either purchased (p110α/p85α, p110β/p85a, p110δ/p85 (from Upstate, and p110γ from Sigma) or expressed as previously described (Knight et al., 2004). IC50 values are measured using either a standard TLC assay for lipid kinase activity (described below) or a high-throughput membrane capture assay. Kinase reactions are performed by preparing a reaction mixture containing kinase, inhibitor (2% DMSO final concentration), buffer (25 mM HEPES, pH 7.4, 10 mM MgCl2), and freshly sonicated phosphatidylinositol (100 g/ml). Reactions are initiated by the addition of ATP containing 10 μCi of γ-32P-ATP to a final concentration 10 or 100 μM and allowed to proceed for 5 minutes at room temperature. For TLC analysis, reactions are then terminated by the addition of 105 μl 1N HCl followed by 160 μl CHC13:MeOH (1:1). The biphasic mixture is vortexed, briefly centrifuged, and the organic phase is transferred to a new tube using a gel loading pipette tip precoated with CHCl₃. This extract is spotted on TLC plates and developed for 3-4 hours in a 65:35 solution of n-propanol:1M acetic acid. The TLC plates are then dried, exposed to a phosphorimager screen (Storm, Amersham), and quantitated. For each compound, kinase activity is measured at 10-12 inhibitor concentrations representing two-fold dilutions from the highest concentration tested (typically, 200 μM). For compounds showing significant activity, IC50 determinations are repeated two to four times, and the reported value is the average of these independent measurements.

Other commercial kits or systems for assaying PI3-K activities are available. The commercially available kits or systems can be used to screen for inhibitors and/or agonists of PI3-Ks including but not limited to PI 3-Kinase α, β, δ, and γ. Anr exemplary system is PI 3-Kinase (human) HTRF™ Assay from Upstate. The assay can be carried out according to the procedures suggested by the manufacturer. Briefly, the assay is a time resolved FRET assay that indirectly measures PIP3 product formed by the activity of a PI3-K. The kinase reaction is performed in a microtitre plate (e.g., a 384 well microtitre plate). The total reaction volume is approximately 20 ul per well. In the first step, each well receives 2 ul of test compound in 20% dimethylsulphoxide resulting in a 2% DMSO final concentration. Next, approximately 14.5 ul of a kinase/PIP2 mixture (diluted in 1× reaction buffer) is added per well for a final concentration of 0.25-0.3 ug/ml kinase and 10 uM PIP2. The plate is sealed and incubated for 15 minutes at room temperature. To start the reaction, 3.5 ul of ATP (diluted in 1× reaction buffer) is added per well for a final concentration of 10 uM ATP. The plate is sealed and incubated for 1 hour at room temperature. The reaction is stopped by adding 5 ul of Stop Solution per well and then 5 ul of Detection Mix is added per well. The plate is sealed, incubated for 1 hour at room temperature, and then read on an appropriate plate reader. Data is analyzed and IC50s are generated using GraphPad Prism 5.

Example 8

Expression and Inhibition Assays of Abl

The compounds described herein can be assayed in triplicate against recombinant full-length Abl or Abl (T315I) (Upstate) in an assay containing 25 mM HEPES, pH 7.4, 10 mM MgCl2, 200 μM ATP (2.5 μCi of γ-32P-ATP), and 0.5 mg/mL BSA. The optimized Abl peptide substrate EAIYAAPFAKKK is used as phosphoacceptor (200 μM). Reactions are terminated by spotting onto phosphocellulose sheets, which are washed with 0.5% phosphoric acid (approximately 6 times, 5-10 minutes each). Sheets are dried and the transferred radioactivity quantitated by phosphorimaging.

Example 9

Expression and Inhibition Assays of Hck

The compounds described herein can be assayed in triplicate against recombinant full-length Hck in an assay containing 25 mM HEPES, pH 7.4, 10 mM MgCl2, 200 μM ATP (2.5 μCi of γ-32P-ATP), and 0.5 mg/mL BSA. The optimized Src family kinase peptide substrate EIYGEFKKK is used as phosphoacceptor (200 μM). Reactions are terminated by spotting onto phosphocellulose sheets, which are washed with 0.5% phosphoric acid (approximately 6 times, 5-10 minutes each). Sheets are dried and the transferred radioactivity quantitated by phosphorimaging.

Example 10

Expression and Inhibition Assays of Inulsin Receptor (IR)

The compounds described herein can be assayed in triplicate against recombinant insulin receptor kinase domain (Upstate) in an assay containing 25 mM HEPES, pH 7.4, 10 mM MgCl2, 10 mM MnCl2, 200 μM ATP (2.5 μCi of γ-32P-ATP), and 0.5 mg/mL BSA. Poly E-Y (Sigma; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Example 11

Expression and Inhibition Assays of Src

The compounds described herein can be assayed in triplicate against recombinant full-length Src or Src (T338I) in an assay containing 25 mM HEPES, pH 7.4, 10 mM MgCl2, 200 μM ATP (2.5 μCi of γ-32P-ATP), and 0.5 mg/mL BSA. The optimized Src family kinase peptide substrate EIYGEFKKK is used as phosphoacceptor (200 μM). Reactions are terminated by spotting onto phosphocellulose sheets, which are washed with 0.5% phosphoric acid (approximately 6 times, 5-10 minutes each). Sheets were dried and the transferred radioactivity quantitated by phosphorimaging.

Example 12

Expression and Inhibition Assays of DNA-PK (DNAK)

DNA-PK can be purchased from Promega and assayed using the DNA-PK Assay System (Promega) according to the manufacturer's instructions.

Example 13

Expression and Inhibition Assays mTOR

The compounds described herein can be tested against recombinant mTOR (Invitrogen) in an assay containing 50 mM HEPES, pH 7.5, 1 mM EGTA, 10 mM MgCl2, 2.5 mM, 0.01% Tween, 10 μM ATP (2.5 μCi of μ-32P-ATP), and 3 μg/mL BSA. Rat recombinant PHAS-1/4EBP1 (Calbiochem; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Other kits or systems for assaying mTOR activity are commercially avaiable. For instance, one can use Invitrogen's LanthaScreen™ Kinase assay to test the inhibitors of mTOR disclosed herein. This assay is a time resolved FRET platform that measures the phosphorylation of GFP labeled 4EBP1 by mTOR kinase. The kinase reaction is performed in a white 384 well microtitre plate. The total reaction volume is 20 ul per well and the reaction buffer composition is 50 mM HEPES pH7.5, 0.01% Polysorbate 20, 1 mM EGTA, 10 mM MnC12, and 2 mM DTT. In the first step, each well receives 2 ul of test compound in 20% dimethylsulphoxide resulting in a 2% DMSO final concentration. Next, 8 ul of mTOR diluted in reaction buffer is added per well for a 60 ng/ml final concentration. To start the reaction, 10 ul of an ATP/GFP-4EBP1 mixture (diluted in reaction buffer) is added per well for a final concentration of 10 uM ATP and 0.5 uM GFP-4EBP1. The plate is sealed and incubated for 1 hour at room temperature. The reaction is stopped by adding 10 ul per well of a Tb-anti-pT46 4EBP1 antibody/EDTA mixture (diluted in TR-FRET buffer) for a final concentration of 1.3 nM antibody and 6.7 mM EDTA. The plate is sealed, incubated for 1 hour at room temperature, and then read on a plate reader set up for LanthaScreen™ TR-FRET. Data is analyzed and IC50s are generated using GraphPad Prism 5.

Example 14

Expression and Inhibition Assays of Vascular Endothelial Growth Receptor

The compounds described herein can be tested against recombinant KDR receptor kinase domain (Invitrogen) in an assay containing 25 mM HEPES, pH 7.4, 10 mM MgCl2, 0.1% BME, 10 μM ATP (2.5 μCi of μ-32P-ATP), and 3 μg/mL BSA. Poly E-Y (Sigma; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Example 15

Expression and Inhibition Assays of Ephrin receptor B4 (EphB4)

The compounds described herein can be tested against recombinant Ephrin receptor B4 kinase domain (Invitrogen) in an assay containing 25 mM HEPES, pH 7.4, 10 mM MgCl2, 0.1% BME, 10 μM ATP (2.5 μCi of μ-32P-ATP), and 3 μg/mL BSA. Poly E-Y (Sigma; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Example 16

Expression and Inhibition Assays of Epidermal Growth Factor Receptor (EGFR)

The compounds described herein can be tested against recombinant EGF receptor kinase domain (Invitrogen) in an assay containing 25 mM HEPES, pH 7.4, 10 mM MgCl2, 0.1% BME, 10 μM ATP (2.5 μCi of μ-32P-ATP), and 3 μg/mL BSA. Poly E-Y (Sigma; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Example 17

Expression and Inhibition Assays of KIT Assay

The compounds described herein can be tested against recombinant KIT kinase domain (Invitrogen) in an assay containing 25 mM HEPES, pH 7.4, 10 mM MgCl2, 1 mM DTT, 10 mM MnC12, 10 μM ATP (2.5 μCi of μ-32P-ATP), and 3 μg/mL BSA. Poly E-Y (Sigma; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Example 18

Expression and Inhibition Assays of RET

The compounds described herein can be tested against recombinant RET kinase domain (Invitrogen) in an assay containing 25 mM HEPES, pH 7.4, 10 mM MgCl2, 2.5 mM DTT, 10 μM ATP (2.5 μCi of μ-32P-ATP), and 3 μg/mL BSA. The optimized Abl peptide substrate EAIYAAP-FAKKK is used as phosphoacceptor (200 μM). Reactions are terminated by spotting onto phosphocellulose sheets, which are washed with 0.5% phosphoric acid (approximately 6 times, 5-10 minutes each). Sheets are dried and the transferred radioactivity quantitated by phosphorimaging.

Example 19

Expression and Inhibition Assays of Platelet derived growth factor receptor (PDGFR)

The compounds described herein can be tested against recombinant PDG receptor kinase domain (Invitrogen) in an assay containing 25 mM HEPES, pH 7.4, 10 mM MgCl2, 2.5 mM DTT, 10 μM ATP (2.5 μCi of μ-32P-ATP), and 3 μg/mL BSA. The optimized Abl peptide substrate EAIYAAPFAKKK is used as phosphoacceptor (200 μM). Reactions are terminated by spotting onto phosphocellulose sheets, which are washed with 0.5% phosphoric acid (approximately 6 times, 5-10 minutes each). Sheets are dried and the transferred radioactivity quantitated by phosphorimaging.

Example 20

Expression and Inhibition Assays of FMS-related tyrosine kinase 3 (FLT-3)

The compounds described herein can be tested against recombinant FLT-3 kinase domain (Invitrogen) in an assay containing 25 mM HEPES, pH 7.4, 10 mM MgCl2, 2.5 mM DTT, 10 μM ATP (2.5 μCi of μ-32P-ATP), and 3 μg/mL BSA. The optimized Abl peptide substrate EAIYAAP-FAKKK is used as phosphoacceptor (200 μM). Reactions are terminated by spotting onto phosphocellulose sheets, which are washed with 0.5% phosphoric acid (approximately 6 times, 5-10 minutes each). Sheets are dried and the transferred radioactivity quantitated by phosphorimaging.

Example 21

Expression and Inhibition Assays of TEK Receptor Tyrosine Kinase (TIE2)

The compounds described herein can be tested against recombinant TIE2 kinase domain (Invitrogen) in an assay containing 25 mM HEPES, pH 7.4, 10 mM MgCl2, 2 mM DTT, 10 mM MnCl2, 10 μM ATP (2.5 μCi of μ-32P-ATP), and 3 μg/mL BSA. Poly E-Y (Sigma; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Example 22

B Cell Activation and Proliferation Assay

The ability of one or more subject compounds to inhibit B cell activitation and proliferation is determined according to standard procedures known in the art. For example, an in vitro cellular proliferation assay is established that measures the metabolic activity of live cells. The assay is performed in a 96 well microtiter plate using Alamar Blue reduction. Balb/c splenic B cells are purified over a Ficoll-Paque™ PLUS gradient followed by magnetic cell separation using a MACS B cell Isolation Kit (Miletenyi). Cells are plated in 90 ul at 50,000 cells/well in B Cell Media (RPMI+10% FBS+Penn/Strep+50 uM bME+5 mM HEPES). A compound disclosed herein is diluted in B Cell Media and added in a 10 ul volume. Plates are incubated for 30 min at 37 C and 5% $CO_2$ (0.2% DMSO final concentration). A 50 ul B cell stimulation cocktail is then added containing either 10 ug/ml LPS or 5 ug/ml F(ab')2 Donkey anti-mouse IgM plus 2 ng/ml recombinant mouse IL4 in B Cell Media. Plates are incubated for 72 hours at 37° C. and 5% $CO_2$. A volume of 15 uL of Alamar Blue reagent is added to each well and plates are incubated for 5 hours at 37 C and 5% $CO_2$. Alamar Blue fluoresce is read at 560Ex/590Em, and IC50 values are calculated using GraphPad Prism 5.

Example 23

Tumor Cell Line Proliferation Assay

The ability of one or more subject compounds to inhibit tumor cell line proliferation is determined according to standard procedures known in the art. For instance, an in vitro cellular proliferation assay can be performed to measure the metabolic activity of live cells. The assay is performed in a 96 well microtiter plate using Alamar Blue reduction. Human tumor cell lines are obtained from ATCC (e.g., MCF7, U-87 MG, MDA-MB-468, PC-3), grown to confluency in T75 flasks, trypsinized with 0.25% trypsin, washed one time with Tumor Cell Media (DMEM+10% FBS), and plated in 90 ul at 5,000 cells/well in Tumor Cell Media. A compound disclosed herein is diluted in Tumor Cell Media and added in a 10 ul volume. Plates are incubated for 72 hours at 37 C and 5% $CO_2$. A volume of 10 uL of Alamar Blue reagent is added to each well and plates are incubated for 3 hours at 37 C and 5% $CO_2$. Alamar Blue fluoresce is read at 560Ex/590Em, and IC50 values are calculated using GraphPad Prism 5.

Example 24

Antitumor Activity In Vivo

The compounds described herein can be evaluated in a panel of human and murine tumor models.
Paclitaxel-Refractory Tumor Models
1. Clinically-Derived Ovarian Carcinoma Model.
This tumor model is established from a tumor biopsy of an ovarian cancer patient. Tumor biopsy is taken from the patient.
The compounds described herein are administered to nude mice bearing staged tumors using an every 2 days.times.5 schedule.
2. A2780Tax Human Ovarian Carcinoma Xenograft (Mutated Tubulin)
A2780Tax is a paclitaxel-resistant human ovarian carcinoma model. It is derived from the sensitive parent A2780 line by co-incubation of cells with paclitaxel and verapamil, an MDR-reversal agent. Its resistance mechanism has been shown to be non-MDR related and is attributed to a mutation in the gene encoding the beta-tubulin protein.
The compounds described herein can be administered to mice bearing staged tumors on an every 2 days.times.5 schedule.

3. HCT116/VM46 Human Colon Carcinoma Xenograft (Multi-Drug Resistant).
HCT116/VM46 is an MDR-resistant colon carcinoma developed from the sensitive HCT116 parent line. In vivo, grown in nude mice, HCT116/VM46 has consistently demonstrated high resistance to paclitaxel.
The compounds described herein can be administered to mice bearing staged tumors on an every 2 days×5 schedule.
4. M5076 Murine Sarcoma Model
M5076 is a mouse fibrosarcoma that is inherently refractory to paclitaxel in vivo.
The compounds described herein can be administered to mice bearing staged tumors on an every 2 days×5 schedule.
One or more compounds of the invention can be used in combination other therapeutic agents in vivo in the multi-drug resistant human colon carcinoma xenografts HCT/VM46 or any other model known in the art including those described herein.

Example 25

Microsome Stability Assay

The stability of one or more subject compounds is determined according to standard procedures known in the art. For example, stability of one or more subject compounds is established by an in vitro assay. In particular, an in vitro microsome stability assay is established that measures stability of one or more subject compounds when reacting with mouse, rat or human microsomes from liver. The microsome reaction with compounds is performed in 1.5 mL Eppendorf tube. Each tube contains 0.1 µL of 10.0 mg/ml NADPH; 75 µL of 20.0 mg/ml mouse, rat or human liver microsome; 0.4 µL of 0.2 M phosphate buffer, and 425 µL of dd$H_2O$. Negative control (without NADPH) tube contains 75 µL of 20.0 mg/ml mouse, rat or human liver microsome; 0.4 µL of 0.2 M phosphate buffer, and 525 µL of dd$H_2O$. The reaction is started by adding 1.0 µL of 10.0 mM tested compound. The reaction tubes are incubated at 37° C. 100 µL sample is collected into new Eppendorf tube containing 300 µL cold Methanol at 0, 5, 10, 15, 30 and 60 minutes of reaction. Samples are centrifuged at 15,000 rpm to remove protein. Supernatant of centrifuged sample is transferred to new tube. Concentration of stable compound after reaction with microsome in the supernatant is measured by Liquid Chromatography/Mass Spectrometry (LC-MS).

Example 26

Plasma Stability Assay

The stability of one or more subject compounds in plasma is determined according to standard procedures known in the art. See, e.g., *Rapid Commun. Mass Spectrom.*, 10: 1019-1026. The following procedure is an HPLC-MS/MS assay using human plasma; other species including monkey, dog, rat, and mouse are also available. Frozen, heparinized human plasma is thawed in a cold water bath and spun for 10 minutes at 2000 rpm at 4° C. prior to use. A subject compound is added from a 400 µM stock solution to an aliquot of pre-warmed plasma to give a final assay volume of 400 µL (or 800 µL for half-life determination), containing 5 µM test compound and 0.5% DMSO. Reactions are incubated, with shaking, for 0 minutes and 60 minutes at 37° C., or for 0, 15, 30, 45 and 60 minutes at 37 C for half life determination. Reactions are stopped by transferring 50 µL of the incubation mixture to 200 µL of ice-cold acetonitrile and mixed by shaking for 5 minutes. The samples are centrifuged at 6000×g for 15 minutes at 4° C. and 120 μL of supernatant removed into clean tubes. The samples are then evaporated to dryness and submitted for analysis by HPLC-MS/MS.

Where desired, one or more control or reference compounds (5 μM) are tested simultaneously with the test compounds: one compound, propoxycaine, with low plasma stability and another compound, propantheline, with intermediate plasma stability.

Samples are reconstituted in acetonitrile/methanol/water (1/1/2, v/v/v) and analyzed via (RP)HPLC-MS/MS using selected reaction monitoring (SRM). The HPLC conditions consist of a binary LC pump with autosampler, a mixed-mode, C12, 2×20 mm column, and a gradient program. Peak areas corresponding to the analytes are recorded by HPLC-MS/MS. The ratio of the parent compound remaining after 60 minutes relative to the amount remaining at time zero, expressed as percent, is reported as plasma stability. In case of half-life determination, the half-life is estimated from the slope of the initial linear range of the logarithmic curve of compound remaining (%) vs. time, assuming first order kinetics.

Example 27

Chemical Stability

The chemical stability of one or more subject compounds is determined according to standard procedures known in the art. The following details an exemplary procedure for ascertaining chemical stability of a subject compound. The default buffer used for the chemical stability assay is phosphate-buffered saline (PBS) at pH 7.4; other suitable buffers can be used. A subject compound is added from a 100 μM stock solution to an aliquot of PBS (in duplicate) to give a final assay volume of 400 μL, containing 5 μM test compound and 1% DMSO (for half-life determination a total sample volume of 700 μL is prepared). Reactions are incubated, with shaking, for 0 minutes and 24 hours at 37° C.; for half-life determination samples are incubated for 0, 2, 4, 6, and 24 hours. Reactions are stopped by adding immediately 100 μL of the incubation mixture to 100 μL of acetonitrile and vortexing for 5 minutes. The samples are then stored at −20° C. until analysis by HPLC-MS/MS. Where desired, a control compound or a reference compound such as chlorambucil (5 jM) is tested simultaneously with a subject compound of interest, as this compound is largely hydrolyzed over the course of 24 hours. Samples are analyzed via (RP)HPLC-MS/MS using selected reaction monitoring (SRM). The HPLC conditions consist of a binary LC pump with autosampler, a mixed-mode, C12, 2×20 mm column, and a gradient program. Peak areas corresponding to the analytes are recorded by HPLC-MS/MS. The ratio of the parent compound remaining after 24 hours relative to the amount remaining at time zero, expressed as percent, is reported as chemical stability. In case of half-life determination, the half-life is estimated from the slope of the initial linear range of the logarithmic curve of compound remaining (%) vs. time, assuming first order kinetics.

Example 28

Akt Kinase Assay

Cells comprising components of the Akt/mTOR pathway, including but not limited to L6 myoblasts, B-ALL cells, B-cells, T-cells, leukemia cells, bone marrow cells, p190 transduced cells, philladelphia chromosome positive cells (Ph+), and mouse embryonic fibroblasts, are typically grown in cell growth media such as DMEM supplemented with fetal bovine serum and/or antibiotics, and grown to confluency.

In order to compare the effect of one or more compounds disclosed herein on Akt activation, said cells are serum starved overnight and incubated with one or more compounds disclosed herein or about 0.1% DMSO for approximately 1 minute to about 1 hour prior to stimulation with insulin (e.g. 100 nM) for about 1 minutes to about 1 hour. Cells are lysed by scraping into ice cold lysis buffer containing detergents such as sodium dodecyl sulfate and protease inhibitors (e.g., PMSF). After contacting cells with lysis buffer, the solution is briefly sonicated, cleared by centrifugation, resolved by SDS-PAGE, transferred to nitrocellulose or PVDF and immunoblotted using antibodies to phospho-Akt S473, phospho-Akt T308, Akt, and β-actin (Cell Signaling Technologies).

When tested under these conditions, one or more compounds of the present disclosure are expected to inhibit insulin stimulated phosphorylation of Akt at S473. Alternatively, some compounds disclosed herein are expected to additionally inhibit insulin stimulated phosphorylation of Akt at T308. Such class of compounds may inhibit Akt more effectively than rapamycin.

Example 29

Kinase Signaling in Blood

PI3K/Akt/mTor signaling is measured in blood cells using the phosflow method (Methods Enzymol. 2007; 434:131-54). The advantage of this method is that it is by nature a single cell assay so that cellular heterogeneity can be detected rather than population averages. This allows concurrent dinstinction of signaling states in different populations defined by other markers. Phosflow is also highly quantitative. To test the effects of one or more compounds disclosed herein, unfractionated splenocytes, or peripheral blood mononuclear cells are stimulated with anti-CD3 to initiate T-cell receptor signaling. The cells are then fixed and stained for surface markers and intracellular phosphoproteins. It is expected that inhibitors disclosed herein inhibit anti-CD3 mediated phosphorylation of Akt-S473 and S6, whereas rapamycin inhibits S6 phosphorylation and enhances Akt phosphorylation under the conditions tested.

Similarly, aliquots of whole blood are incubated for 15 minutes with vehicle (e.g. 0.1% DMSO) or kinase inhibitors at various concentrations, before addition of stimuli to crosslink the T cell receptor (TCR) (anti-CD3 with secondary antibody) or the B cell receptor (BCR) using anti-kappa light chain antibody (Fab'2 fragments). After approximately 5 and 15 minutes, samples are fixed (e.g. with cold 4% paraformaldehyde) and used for phosflow. Surface staining is used to distinguish T and B cells using antibodies directed to cell surface markers that are known to the art. The level of phosphrylation of kinase substrates such as Akt and S6 are then measured by incubating the fixed cells with labeled antibodies specific to the phosphorylated isoforms of these proteins. The population of cells is then analyzed by flow cytometry.

This assay can be employed to demonstrate that one or more of the compounds of the present invention are potent and selective inhibitors of one or more members of one or more of PI3K, mTOR, and/or Akt signaling in blood cells under the conditions tested.

Example 30

Colony Formation Assay

Murine bone marrow cells freshly transformed with a p190 BCR-Abl retrovirus (herein referred to as p190 transduced cells) are plated in the presence of various drug combinations in M3630 methylcellulose media for about 7 days with recombinant human IL-7 in about 30% serum, and the number of colonies formed is counted by visual examination under a microscope.

Alternatively, human peripheral blood mononuclear cells are obtained from Philadelphia chromosome positive (Ph+) and negative (Ph−) patients upon initial diagnosis or relapse. Live cells are isolated and enriched for CD19+CD34+B cell progenitors. After overnight liquid culture, cells are plated in methocult GF+H4435, Stem Cell Technologies) supplemented with cytokines (IL-3, IL-6, IL-7, G-CSF, GM-CSF, CF, Flt3 ligand, and erythropoietin) and various concentrations of known chemotherapeutic agents in combination with either compounds of the present disclosure. Colonies are counted by microscopy 12-14 days later. This method can be used to test for evidence of additive or synergistic activity.

One or more of the compounds of the present invention are expected to be potent and selective inhibitors of p190 transduced cell colony formation under the conditions tested.

Example 31

In Vivo Effect of Kinase Inhibitors on Leukemic Cells

Female recipient mice are lethally irradiated from a γ source in two doses about 4 hr apart, with approximately 5Gy each. About 1 hr after the second radiation dose, mice are injected i.v. with about $1 \times 10^6$ leukemic cells (e.g. Ph+ human or murine cells, or p190 transduced bone marrow cells). These cells are administered together with a radioprotective dose of about $5 \times 10^6$ normal bone marrow cells from 3-5 week old donor mice. Recipients are given antibiotics in the water and monitored daily. Mice who become sick after about 14 days are euthanized and lymphoid organs are harvested for analysis. Kinase inhibitor treatment begins about 10 days after leukemic cell injection and continues daily until the mice become sick or a maximum of approximately 35 days post-transplant. Inhibitors are given by oral lavage.

Peripheral blood cells are collected approximately on day 10 (pre-treatment) and upon euthanization (post treatment), contacted with labeled anti-hCD4 antibodies and counted by flow cytometry. This method can be used to demonstrate that the synergistic effect of one or more compounds disclosed herein in combination with known chemotherapeutic agents significantly reduce leukemic blood cell counts as compared to treatment with known chemotherapeutic agents (e.g. Gleevec) alone under the conditions tested.

Example 32

Treatment of Lupus Disease Model Mice

Mice lacking the inhibitory receptor FcγRIIb that opposes PI3K signaling in B cells develop lupus with high penetrance. FcγRIIb knockout mice (R2KO, Jackson Labs) are considered a valid model of the human disease as some lupus patients show decreased expression or function of FcγRIIb (S. Bolland and J. V. Ravtech 2000. *Immunity* 12:277-285).

The R2KO mice develop lupus-like disease with antinuclear antibodies, glomerulonephritis and proteinurea within about 4-6 months of age. For these experiments, the rapamycin analogue RAD001 (available from LC Laboratories) is used as a benchmark compound, and administered orally. This compound has been shown to ameliorate lupus symptoms in the B6.Sle1z.Sle3z model (T. Wu et al. *J. Clin Invest.* 117:2186-2196).

Lupus disease model mice such as R2KO, BXSB or MLR/lpr are treated at about 2 months old, approximately for about two months. Mice are given doses of: vehicle, RAD001 at about 10 mg/kg, or compounds disclosed herein at approximately 1 mg/kg to about 500 mg/kg. Blood and urine samples are obtained at approximately throughout the testing period, and tested for antinuclear antibodies (in dilutions of serum) or protein concentration (in urine). Serum is also tested for anti-ssDNA and anti-dsDNA antibodies by ELISA. Animals are euthanized at day 60 and tissues harvested for measuring spleen weight and kidney disease. Glomerulonephritis is assessed in kidney sections stained with H&E. Other animals are studied for about two months after cessation of treatment, using the same endpoints.

This model can be employed to demonstrate that the kinase inhibitors disclosed herein can suppress or delay the onset of lupus symptoms in lupus disease model mice.

Example 33

Murine Bone Marrow Transplant Assay

Female recipient mice are lethally irradiated from a γ ray source. About 1 hr after the radiation dose, mice are injected with about $1 \times 106$ leukemic cells from early passage p190 transduced cultures (e.g. as described in *Cancer Genet Cytogenet.* 2005 August; 161(1):51-6). These cells are administered together with a radioprotective dose of approximately $5 \times 106$ normal bone marrow cells from 3-5 wk old donor mice. Recipients are given antibiotics in the water and monitored daily. Mice who become sick after about 14 days are euthanized and lymphoid organs harvested for flow cytometry and/or magnetic enrichment. Treatment begins on approximately day 10 and continues daily until mice become sick, or after a maximum of about 35 days post-transplant. Drugs are given by oral gavage (p.o.). In a pilot experiment a dose of chemotherapeutic that is not curative but delays leukemia onset by about one week or less is identified; controls are vehicle-treated or treated with chemotherapeutic agent, previously shown to delay but not cure leukemogenesis in this model (e.g. imatinib at about 70 mg/kg twice daily). For the first phase p190 cells that express eGFP are used, and postmortem analysis is limited to enumeration of the percentage of leukemic cells in bone marrow, spleen and lymph node (LN) by flow cytometry. In the second phase, p190 cells that express a tailless form of human CD4 are used and the postmortem analysis includes magnetic sorting of hCD4+ cells from spleen followed by immunoblot analysis of key signaling endpoints: p Akt-T308 and S473; pS6 and p4EBP-1. As controls for immunoblot detection, sorted cells are incubated in the presence or absence of kinase inhibitors of the present disclosure inhibitors before lysis. Optionally, "phosflow" is used to detect p Akt-S473 and pS6-S235/236 in hCD4-gated cells without prior sorting. These signaling studies are particularly useful if, for example, drug-treated mice have not developed clinical leukemia at the 35 day time point. Kaplan-Meier plots of survival are generated and statistical analysis done according to methods known in the art. Results from p190 cells are analyzed separated as well as cumulatively.

Samples of peripheral blood (100-200 µl) are obtained weekly from all mice, starting on day 10 immediately prior to commencing treatment. Plasma is used for measuring drug concentrations, and cells are analyzed for leukemia markers (eGFP or hCD4) and signaling biomarkers as described herein.

This general assay may be used to demonstrate that effective therapeutic doses of the compounds disclosed herein can be used for inhibiting the proliferation of leukemic cells.

Example 34

TNP-Ficoll T-cell Independent B-cell Activation Assay

To test the effects of the compounds of the present invention in suppressing T cell independent antibody production, the TNP-Ficoll B-cell activation assay is used as described herein. Compounds of the present invention are dissolved in an appropriate vehicle (e.g. 5% 1-methyl-2-pyrrolidinone, 85% polyethylene glycol 400, 10% Solutor). Compounds are administered orally approximately 1hr before TNP-Ficoll treatment to 4-10 week old mice.

To study the effects of the compounds on B-cell activation, one set of mice are grouped according to the following table:

| Group # | Mice/ group | Comp treated | Group | Antigen injection at day-1 TNP-F | Route | Compound Administration from day-1 to day-7 (mg/kg) | Route | Regimen |
|---|---|---|---|---|---|---|---|---|
| 1 | 4 | Vehicle | Antigen only | 200 uL | ip | 0 | PO | BID for 7 days |
| 2 | 8 | — | Antigen only | (0.5 mg/ml) | | 0 | | |
| 3 | 8 | Reference compound #1 | reference | | | 30 | | |
| 4 | 8 | Test compound | Antigen + cmp | | | 1 | | |
| 5 | 8 | | | | | 3 | | |
| 6 | 8 | | | | | 10 | | |
| 7 | 8 | | | | | 30 | | |
| 8 | 8 | | | | | 60 | | |

Four animals in group 1, and eight animals in groups 2 to 7 are euthanized in $CO_2$ 2 hours after the last compound administration on day 7. Blood is immediately collected by cadio-puncture and kept at 37° C. for 1 hr to clot followed by overnight incubation at 4° C. to allow the clot to contract. The following day, serum is collected by decanting and centrifugation at 3000 rpm for 10 min. The collected serum is then frozen at −80° C. for future analysis.

Serum samples are analyzed for anti-TNP antibody titers by ELISA as described herein. TNP-BSA is coated onto a Nunc Maxisorb microtiter plate with 100 µl/well at a concentration of 10 µg/ml in phosphate buffered saline (PBS). The Maxisorb plate is incubated for 1.5 hours at room temperature and the solution is removed. 200 µl/well of blocking buffer (e.g. 1% BSA in PBS) is added to each well and incubated 1hr at room temperature. The plate is washed once with 200 µl/well of PBS 0.05% Tween-20 (wash buffer). A 1:2 dilution of serum from each mouse in blocking buffer is added to each well in the first column (1) of the microtiter plate. The serum in each well of column 1 is then diluted 3-fold in blocking buffer and added to column 2. The serum in each well of column 2 is diluted 3-fold in blocking buffer and added to column 3. The procedure is repeated across the twelve columns of the microtiter plate. The microtiter plate is incubated 1 hr at room temperature. Serum is removed from the plate and the plate is washed three times with wash buffer. 100 µl/well of goat anti-mouse IgG3-HRP diluted 1:250 in blocking buffer is added to each well and incubated 1 hr at room temperature. The anti-mouse IgG3-HRP is removed from the microtiter plate and the plate is washed six times with wash buffer. HRP substrate (200 µl ABTS solution+30% $H_2O_2$+10 ml citrate buffer) is added to each well at 100 µl/well, incubated 2-20 minutes in the dark and the amount of anti-TNP IgG3 is determined spectrophotometrically at 405 nm. Similarly, anti-TNP IgM and total anti-TNP Ab are determined using anti-mouse IgM-HRP and anti-mouse Ig-HRP respectively.

This model can be employed to demonstrate that the test compounds are capable of reducing IgG3 levels relative to vehicle control mice at the tested dose levels.

Example 35

Rat Developing Type II Collagen Induced Arthritis Assay

In order to study the effects of the compounds of the present invention on the autoimmune disease arthritis, a collagen induced developing arthritis model is used. Female Lewis rats are given collagen injections at day 0. Bovine type II collagen is prepared as a 4 mg/ml solution in 0.01N acetic acid. Equal volumes of collagen and Freund's incomplete adjuvant are emulsified by hand mixing until a bead of the emulsified material holds its form in water. Each rodent receives a 300 µl injection of the mixture at each injection time spread over three subcutaneous sites on the back.

Oral compound administration begins on day 0 and continues through day 16 with vehicle (5% NMP, 85% PEG 400, 10% Solutol) or compounds of the present invention in vehicle or control (e.g. methotrexate) at 12 hour intervals daily. Rats are weighed on days 0, 3, 6, 9-17 and caliper measurements of ankles are taken on days 9-17. Final body weights are taken, and then the animals are euthanized on day 17. After euthanization, blood is drawn and hind paws and knees are removed. Blood is further processed for pharmacokinetics experiments as well as an anti-type II collagen antibody ELISA assay. Hind paws are weighed and then, with the knees, preserved in 10% formalin. The paws and knees are subsequently processed for microscopy. Livers, spleen and *thymus* are weighed. Sciatic nerves are prepared for histopathology.

Knee and ankle joints are fixed for 1-2 days and decalcified for 4-5 days. Ankle joints are cut in half longitudinally, and knees are cut in half along the frontal plane. Joints are processed, embedded, sectioned and stained with toluidine blue. Scoring of the joints is done according to the following criteria:
Knee and Ankle Inflammation
0=Normal
1=Minimal infiltration of inflammatory cells in synovium/periarticular tissue
2=Mild infiltration
3=Moderate infiltration with moderate edema
4=Marked infiltration with marked edema
5=Severe infiltration with severe edema
Ankle Pannus
0=Normal
1=Minimal infiltration of pannus in cartilage and subchondral bone
2=Mild infiltration (<¼ of tibia or tarsals at marginal zones)
3=Moderate infiltration (¼ to ⅓ of tibia or small tarsals affected at marginal zones)
4=Marked infiltration (½-¾ of tibia or tarsals affected at marginal zones)
5=Severe infiltration (>¾ of tibia or tarsals affected at marginal zones, severe distortion of overall architecture)
Knee Pannus
0=Normal
1=Minimal infiltration of pannus in cartilage and subchondral bone
2=Mild infiltration (extends over up to ¼ of surface or subchondral area of tibia or femur)
3=Moderate infiltration (extends over >¼ but <½ of surface or subchondral area of tibia or femur)
4=Marked infiltration (extends over ½ to ¾ of tibial or femoral surface)
5=Severe infiltration (covers >¾ of surface)
Cartilage Damage (Ankle, Emphasis on Small Tarsals)
0=Normal
1=Minimal=minimal to mild loss of toluidine blue staining with no obvious chondrocyte loss or collagen disruption
2=Mild=mild loss of toluidine blue staining with focal mild (superficial) chondrocyte loss and/or collagen disruption
3=Moderate=moderate loss of toluidine blue staining with multifocal moderate (depth to middle zone) chondrocyte loss and/or collagen disruption, smaller tarsals affected to ½-¾ depth
4=Marked=marked loss of toluidine blue staining with multifocal marked (depth to deep zone) chondrocyte loss and/or collagen disruption, 1 or more small tarsals have full thickness loss of cartilage
5=Severe=severe diffuse loss of toluidine blue staining with multifocal severe (depth to tide mark) chondrocyte loss and/or collagen disruption
Cartilage Damage (Knee, emphasis on femoral condyles)
0=Normal
1=Minimal=minimal to mild loss of toluidine blue staining with no obvious chondrocyte loss or collagen disruption
2=Mild=mild loss of toluidine blue staining with focal mild (superficial) chondrocyte loss and/or collagen disruption
3=Moderate=moderate loss of toluidine blue staining with multifocal to diffuse moderate (depth to middle zone) chondrocyte loss and/or collagen disruption
4=Marked=marked loss of toluidine blue staining with multifocal to diffuse marked (depth to deep zone) chondrocyte loss and/or collagen disruption or single femoral surface with total or near total loss
5=Severe=severe diffuse loss of toluidine blue staining with multifocal severe (depth to tide mark) chondrocyte loss and/or collagen disruption on both femurs and/or tibias
Bone Resorption (Ankle)
0=Normal
1=Minimal=small areas of resorption, not readily apparent on low magnification, rare osteoclasts
2=Mild=more numerous areas of resorption, not readily apparent on low magnification, osteoclasts more numerous, <¼ of tibia or tarsals at marginal zones resorbed
3=Moderate=obvious resorption of medullary trabecular and cortical bone without full thickness defects in cortex, loss of some medullary trabeculae, lesion apparent on low magnification, osteoclasts more numerous, ¼ to ⅓ of tibia or tarsals affected at marginal zones
4=Marked=Full thickness defects in cortical bone, often with distortion of profile of remaining cortical surface, marked loss of medullary bone, numerous osteoclasts, ½-¾ of tibia or tarsals affected at marginal zones
5=Severe=Full thickness defects in cortical bone, often with distortion of profile of remaining cortical surface, marked loss of medullary bone, numerous osteoclasts, >¾ of tibia or tarsals affected at marginal zones, severe distortion of overall architecture
Bone Resorption (Knee)
0=Normal
1=Minimal=small areas of resorption, not readily apparent on low magnification, rare osteoclasts
2=Mild=more numerous areas of resorption, definite loss of subchondral bone involving ¼ of tibial or femoral surface (medial or lateral)
3=Moderate=obvious resorption of subchondral bone involving >¼ but <½ of tibial or femoral surface (medial or lateral)
4=Marked=obvious resorption of subchondral bone involving ≥½ but <¾ of tibial or femoral surface (medial or lateral)
5=Severe=distortion of entire joint due to destruction involving >¾ of tibial or femoral surface (medial or lateral)
1. Statistical analysis of body/paw weights, paw AUC parameters and histopathologic parameters were evaluated using a Student's t-test or other appropriate (ANOVA with post-test) with significance set at the 5% significance level. Percent inhibition of paw weight and AUC was calculated using the following formula:

$$\% \text{ Inhibition} = A - B/A \times 100$$

A=Mean Disease Control−Mean Normal
B=Mean Treated−Mean Normal

This model can be employed to demonstrate that one or more compounds of the present invention are capable of ameliorating arthritis induced ankle diameter increase over time, and reduction of ankle histopathology in at least one or more of the categories of inflammation, pannus, cartilage damage, and bone resorption as described above. The results are expected to show that one or more compounds of the present invention may be useful for the treatment and reduction of arthritis disease symptoms. The model can be employed to demonstrate that one or more compounds of the present invention may not only be useful for treating arthritis disease symptoms, but may also be useful for the inhibition of the autoimmune reaction itself.

Example 36

Rat Established Type II Collagen Induced Arthritis Assay

In order to examine the dose responsive efficacy of the compounds of the present invention in inhibiting the inflammation, cartilage destruction and bone resorption of 10 day established type II collagen induced arthritis in rats, compounds are administered orally daily or twice daily for 6 days.

Female Lewis rats are anesthetized and given collagen injections prepared and administered as described previously on day 0. On day 6, animals are anesthetized and given a second collagen injection. Caliper measurements of normal (pre-disease) right and left ankle joints are performed on day 9. On days 10-11, arthritis typically occurs and rats arerandomized into treatment groups. Randomization is performed after ankle joint swelling is obviously established and there is evidence of bilateral disease.

After an animal is selected for enrollment in the study, treatment is initiated by the oral route. Animals are given vehicle, control (Enbrel) or compound doses, twice daily or once daily (BID or QD respectively). Administration is performed on days 1-6 using a volume of 2.5 ml/kg (BID) or 5 ml/kg (QD) for oral solutions. Rats are weighed on days 1-7 following establishment of arthritis and caliper measurements of ankles taken every day. Final body weights are taken on day 7 and animals are euthanized.

This model can be employed to demonstrate that the kinase inhibitors disclosed herein can reduce mean ankle diameter increase over time with a once daily administration or twice daily administration under the conditions tested. This suggests that the compounds of the present invention may be useful for the treatment of autoimmune diseases such as arthritis.

Example 37

Adjuvant Induced Arthritis Assay

Intrathecal Catheterization of Rats

Isoflurane-anesthetized Lewis rats (200-250 g) are implanted with an intrathecal (IT) catheter. After a 6 d recovery period, all animals except those that appeared to have sensory or motor abnormalities (generally fewer than 5% of the total number) are used for experiments. For IT administration, 10 μl of drug or saline followed by 10 μl of isotonic saline is injected through the catheter.

Adjuvant Arthritis and Drug Treatment

Lewis rats are immunized at the base of the tail with 0.1 ml of complete Freund's adjuvant (CFA) on day 0 several days after catheter implantation (n=6/group). Drug (e.g. one or more compounds of the present invention or or vehicle) treatment is generally started on day 8 and is continued daily until day 20. Clinical signs of arthritis generally begin on day 10, and paw swelling is determined every second day by water displacement plethysmometry.

This model can be used to show that selected test compounds (e.g., one or more compounds of the present invention) demonstrate a dose dependent reduction in the average paw volume increase as measured in this adjuvant induced arthritis model system. These results would suggest that one or more of the compounds of the present invention may be useful for the treatment of one or more of the diseases or conditions described herein.

The results would also suggest that selected test compounds (one or more compounds of the present invention) do not exhibit toxicity or other adverse reaction under the conditions tested as measured by a lack of weight loss.

Example 38

Rodent Pharmacokinetic Assay

In order to study the pharmacokinetics of the compounds of the present invention a set of 4-10 week old mice are grouped according to the following table:

| Group # | Mice/ group | Compound Administration from day-1 to day-7 | | |
|---|---|---|---|---|
| | | (mg/kg) | Route | Regimen |
| 1 | 3 | 1 | Po | BID for 7 days |
| 2 | 3 | 3 | | |
| 3 | 3 | 10 | | |
| 4 | 3 | 30 | | |
| 5 | 3 | 60 | | |

ICompounds of the present invention are dissolved in an appropriate vehicle (e.g. 5% 1-methyl-2-pyrrolidinone, 85% polyethylene glycol 400, 10% Solutor) and administered orally at 12 hour intervals daily. All animals are euthanized in $CO_2$ 2 hours after the final compound is administered. Blood is collected immediately and kept on ice for plasma isolation. Plasma is isolated by centrifuging at 5000 rpm for 10 minutes. Harvested plasma is frozen for pharmacokinetic detection.

This assay are expected to demonstrate the pharmacokinetic parameters such as absorption, distribution, metabolism, excretion, and toxicity for the compounds of the present invention.

Example 39

Basotest Assay

The basotest assay is performed using Orpegen Pharma Basotest reagent kit. Heparinized whole blood is pre-incubated with test compound or solvent at 37 C for 20 min. Blood is then incubated with assay kit stimulation buffer (to prime cells for response) followed by allergen (dust mite extract or grass extract) for 20 min. The degranulation process is stopped by incubating the blood samples on ice. The cells are then labeled with anti-IgE-PE to detect basophilic granulocytes, and anti-gp53-FITC to detect gp53 (a glycoprotein expressed on activated basophils). After staining red blood cells are lysed by addition of Lysing Solution. Cells are washed, and analyzed by flow cytometry. This assay can be used to show that under the conditions tested some of the compound of the present invention are potent inhibitors of allergen induced activation of basophils.

Example 40

Combination Use of PI3Kδ Inhibitors and Agents that Inhibit IgE Production or Activity The compounds of the present invention may present synergistic or additive efficacy when administered in combination with agents that inhibit IgE production or activity. Agents that inhibit IgE production include, for example, one or more of TEI-9874, 2-(4-(6-cyclohexyloxy-2-naphtyloxy)phenylacetamide)benzoic acid, rapamycin, rapamycin analogs (i.e. rapalogs), TORC1 inhibitors, TORC2 inhibitors, and any other compounds that inhibit mTORC1 and mTORC2. Agents that inhibit IgE activity include, for example, anti-IgE antibodies such as Omalizumab and TNX-901.

One or more of the subject compounds capable of inhibiting PI3Kδ are efficacious in treatment of autoimmune and inflammatory disorders (AIID) for example rheumatoid arthritis. If any of the compounds causes an undesired level of IgE production, one may choose to administer it in combination with an agent that inhibits IgE production or IgE activity. Additionally, the administration of PI3Kδ or PI3Kδ/γ inhibitors of the present invention in combination with inhibitors of existing mTOR or mTOR inhibitors provided by the present invention may also exhibit synergy through enhanced inhibition of the PI3K pathway. Various in vivo and in vitro models may be used to establish the effect of such combination treatment on AIID including but not limited to (a) in vitro B-cell antibody production assay, (b) in vivo TNP assay, and (c) rodent collagen induced arthritis model.

(a) B-cell Assay

Mice are euthanized, and the spleens are removed and dispersed through a nylon mesh to generate a single-cell suspension. The splenocytes are washed (following removal of erythrocytes by osmotic shock) and incubated with anti-CD43 and anti-Mac-1 antibody-conjugated microbeads (Miltenyi Biotec). The bead-bound cells are separated from unbound cells using a magnetic cell sorter. The magnetized column retains the unwanted cells and the resting B cells are collected in the flow-through. Purified B-cells are stimulated with lipopolysaccharide or an anti-CD40 antibody and interleukin 4. Stimulated B-cells are treated with vehicle alone or with PI3K inhibitors of the present invention with and without known mTOR inhibitors such as rapamycin, rapalogs, or mTORC1/C2 inhibitors. The results are expected to show that in the presence of mTOR inhibitors (e.g., rapamycin) alone, there is little to no substantial effect on IgG and IgE response. However, in the presence of PI3Kδ and mTOR inhibitors, the B-cells are expected to exhibit a decreased IgG response as compared to the B-cells treated with vehicle alone, and the B-cells are expected to exhibit a decreased IgE response as compared to the response from B-cells treated with PI3Kδ inhibitors alone.

(b) TNP Assay

Mice are immunized with TNP-Ficoll or TNP-KHL and treated with: vehicle, a PI3Kδ inhibitor, an mTOR inhibitor, for example rapamycin, or a PI3Kδ inhibitor in combination with an mTOR inhibitor such as rapamycin. Antigen-specific serum IgE is measured by ELISA using TNP-BSA coated plates and isotype specific labeled antibodies. This assay can be used to demonstrate that mice treated with an mTOR inhibitor alone exhibit little or no substantial effect on antigen specific IgG3 response and no statistically significant elevation in IgE response as compared to the vehicle control. This assay can be used to demonstrate that mice treated with both PI3Kδ inhibitor and mTOR inhibitor exhibit a reduction in antigen specific IgG3 response as compared to the mice treated with vehicle alone. Additionally, This assay can be used to demonstrate that the mice treated with both PI3Kδ inhibitor and mTOR inhibitor exhibit a decrease in IgE response as compared to the mice treated with PI3Kδ inhibitor alone.

(c) Rat Collagen Induced Arthritis Model

Female Lewis rats are anesthetized and given collagen injections prepared and administered as described previously on day 0. On day 6, animals are anesthetized and given a second collagen injection. Caliper measurements of normal (pre-disease) right and left ankle joints are performed on day 9. On days 10-11, arthritis typically occurs and rats are randomized into treatment groups. Randomization is performed after ankle joint swelling is obviously established and there is good evidence of bilateral disease.

After an animal is selected for enrollment in the study, treatment is initiated. Animals are given vehicle, PI3Kδ inhibitor, or PI3Kδ inhibitor in combination with rapamycin. Dosing is administered on days 1-6. Rats are weighed on days 1-7 following establishment of arthritis and caliper measurements of ankles taken every day. Final body weights are taken on day 7 and animals are euthanized.

This assay can be used to show that the combination treatment using PI3Kδ inhibitor and rapamycin provides greater efficacy than treatment with PI3Kδ inhibitor alone.

Example 41

Use of the Compounds of the Present Invention for Inhibition of Tumor Growth

Cell Lines. Cell lines of interest (A549, U87, ZR-75-1 and 786-O) are obtained from American Type Culture Collection (ATCC, Manassas, Va.). Cells are proliferated and preserved cryogenically at early passage (e.g. passage 3). One aliquot is used for further proliferation to get enough cells for one TGI study (at about passage 9).

Animals. Female athymic nude mice are supplied by Harlan. Mice are received at 4 to 6 weeks of age. All mice are acclimated for about one day to two weeks prior to handling. The mice are housed in microisolator cages and maintained under specific pathogen-free conditions. The mice are fed with irradiated mouse chow and freely available autoclaved water is provided.

Tumor Xenograft Model. Mice are inoculated subcutaneously in the right flank with 0.01 to 0.5 ml of tumor cells (approximately $1.0 \times 10^5$ to $1.0 \times 10^8$ cells/mouse). Five to 10 days following inoculation, tumors are measured using calipers and tumor weight is calculated, for example using the animal study management software, such as Study Director V.1.6.70 (Study Log). Mice with tumor sizes of about 120 mg are pair-matched into desired groups using Study Director (Day 1). Body weights are recorded when the mice are pair-matched. Tumor volume and bodyweight measurements are taken one to four times weekly and gross observations are made at least once daily. On Day 1, compounds of the present invention and reference compounds as well as vehicle control are administered by oral gavage or iv as indicated. At the last day of the experiment, mice are sacrificed and their tumors are collected 1-4 hours after the final dose. The tumors are excised and cut into two sections. One third of the tumor is fixed in formalin and embedded in paraffin blocks and the remaining two thirds of tumor is snap frozen and stored at −80° C.

Data and Statistical Analysis

Mean tumor growth inhibition (TGI) is calculated utilizing the following formula:

$$TGI = \left[1 - \frac{(\overline{X}_{Treated(Final)} - \overline{X}_{Treated(Day1)})}{(\overline{X}_{Control(Final)} - \overline{X}_{Control(Day1)})}\right] \times 100\%$$

Tumors that regress from the Day 1 starting size are removed from the calculations. Individual tumor shrinkage (TS) is calculated using the formula below for tumors that show regression relative to Day 1 tumor weight. The mean tumor shrinkage of each group is calculated and reported.

$$TS = \left[1 - \frac{(\text{Tumor Weight}_{(Final)})}{(\text{Tumor Weight}_{(Day1)})}\right] \times 100\%$$

This assay can be employed to show that one or more compounds of the present invention inhibit tumor cell growth including but not limited to renal carcinomoa cell growth, breast cancer cell growth, lung cancer cell growth, or glioblastoma cell growth with an $IC_{50}$ of less than about 10 to about 0.5 mg/kg at a once per day dosage under the conditions tested.

The invention claimed is:

1. A compound of Formula I

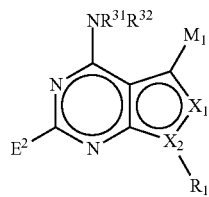

Formula I or a pharmaceutically acceptable salt thereof, wherein:
$M_1$ is benzothiazolyl substituted with $-(W^2)_k-R^2$;
k, in each instance, is 0 or 1;
$R_1$ is —H, -L-alkyl, -L-cycloalkyl, -L-alkyl-cycloalkyl, -L-aryl, -L-heteroaryl, -L-alkylaryl, -L-alkylheteroaryl, -L-alkylheterocyclyl, -L-alkenyl, -L-alkynyl, -L-alkenyl-cycloalkyl, -L-alkynyl-cycloalkyl, or -L-heterocyclyl, each of which is unsubstituted or substituted by one or more independent $R^3$ substituents;
L is a bond, —C(=O)—, —C(=O)O—, —C(=O)NR$^{31}$—, —S—, —S(O)—, —S(O)$_2$—, —S(O)$_2$NR$^{31}$—, or —NR$^{31}$—;
$X_1$ is C-$E^1$ and $X_2$ is N;
$E^1$ and $E^2$ are independently —(W$^1$)$_j$—R$^4$;
j, in each instance, is 0 or 1;
$W^1$ is —O—, —NR$^6$—, —S(O)$_{0-2}$—, —C(=O)—, —C(=O)N(R$^6$)—, —N(R$^6$)C(=O)—, —N(R$^6$)S(O)—, —N(R$^6$)S(O)$_2$—, —C(=O)O—, —CH(R$^6$)N(C(=O)OR$^7$)—, —CH(R$^7$)N(C(=O)R$^7$)—, —CH(R$^6$)N(SO$_2$R$^7$)—, —CH(R$^6$)N(R$^7$)—, —CH(R$^6$)C(=O)N(R$^7$)—, —CH(R$^6$)N(R$^7$)C(=O)—, —CH(R$^6$)N(R$^7$)S(O)—, or —CH(R$^6$)N(R$^7$)S(O)$_2$—;
$W^2$ is —O—, —NR$^6$—, —S(O)$_{0-2}$—, —C(=O)—, —C(=O)N(R$^6$)—, —N(R$^6$)C(=O)—, —N(R$^6$)C(=O)N(R$^7$)—, —N(R$^6$)S(O)—, —N(R$^6$)S(O)$_2$—, —C(=O)O—, —CH(R$^6$)N(C(=O)OR$^7$)—, —CH(R$^7$)N(C(=O)R$^7$)—, —CH(R$^6$)N(SO$_2$R$^7$)—, —CH(R$^6$)N(R$^7$)—, —CH(R$^6$)C(=O)N(R$^7$)—, —CH(R$^6$)N(R$^7$)C(=O)—, —CH(R$^6$)N(R$^7$)S(O)—, or —CH(R$^6$)N(R$^7$)S(O)$_2$—;
$R^2$ is hydrogen, bicyclic aryl, substituted monocyclic aryl, hetaryl, alkyl, cycloalkyl, -alkyl-cycloalkyl, -alkyl-monocyclic aryl, -alkylbicycloaryl, -alkylhetaryl, -alkylheterocyclyl, -alkenyl, or -alkynyl;
$R^3$ and $R^4$ are independently hydrogen, halogen, —OH, —R$^{31}$, —CF$_3$, —OCF$_3$, —OR$^{31}$, —NR$^{31}$R$^{32}$, —NR$^{34}$R$^{35}$, —C(=O)R$^{31}$, —CO$_2$R$^{31}$, —C(=O)NR$^{31}$R$^{32}$, —C(=O)NNR$^{34}$R$^{35}$, —NO$_2$, —CN, —S(O)$_{0-2}$R$^{31}$, —SO$_2$NR$^{31}$R$^{32}$, —SO$_2$NR$^{34}$R$^{35}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_{0-2}$R$^{32}$, —C(=S)OR$^{31}$, —C(=O)SR$^{31}$, —NR$^{31}$C(=NR$^{32}$)NR$^{33}$R$^{32}$, —NR$^{31}$C(=NR$^{32}$)OR$^{33}$, —NR$^{31}$C(=NR$^{32}$)SR$^{33}$, —OC(=O)OR$^{33}$, —OC(=O)NR$^{31}$R$^{32}$, —OC(=O)SR$^{31}$, —SC(=O)OR$^{31}$, —P(O)OR$^{31}$OR$^{32}$, or —SC(=O)NR$^{31}$R$^{32}$;

$R^6$ and $R^7$ are each independently hydrogen, alkyl, alkenyl, aryl, heteroaryl, heterocyclyl or cycloalkyl, wherein each alkyl, alkenyl, aryl, heteroaryl, heterocyclyl or cycloalkyl is unsubstituted or substituted by one or more independent $R^8$ substituents;
$R^8$ is halo, —OR$^{31}$, —SH, —NH$_2$, —NR$^{34}$R$^{35}$, —NR$^{31}$R$^{32}$, —CO$_2$R$^{31}$, —CO$_2$aryl-C(=O)NR$^{31}$R$^{32}$, —C(=O)NR$^{34}$R$^{35}$, —NO$_2$, —CN, —S(O)$_{0-2}$ alkyl, —S(O)$_{0-2}$aryl, —SO$_2$NR$^{34}$R$^{35}$, —SO$_2$NR$^{31}$R$^{32}$, alkyl, alkenyl, or alkynyl;
$R^{31}$, $R^{32}$, and $R^{33}$, in each instance, are independently H or alkyl; and
$R^{34}$ and $R^{35}$ are taken together with the nitrogen atom to which they are attached to form a 3-10 membered ring.

2. The compound or pharmaceutically acceptable salt of claim 1, wherein $E^2$ is —H.

3. The compound or pharmaceutically acceptable salt of claim 2, wherein k is 1.

4. The compound or pharmaceutically acceptable salt of claim 2, wherein —(W$^2$)$_k$— is —N(R$^6$)C(=O)N(R$^7$)—.

5. The compound or pharmaceutically acceptable salt of claim 2, wherein $R^1$ is alkyl, or heterocyclyl, each of which is unsubstituted or substituted by $R^3$, and wherein $R^3$ is —C(=O)NR$^{31}$R$^{32}$.

6. The compound of claim 1, wherein $M_1$ is 6-benzothiazolyl substituted at the 2-position with —(W$^2$)$_k$—R$^2$.

7. A compound of claim 1, wherein the compound is of Formula XII

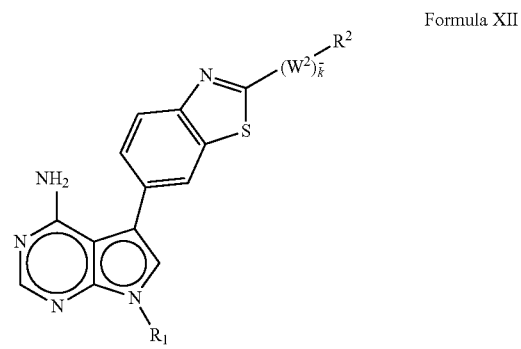

Formula XII or a pharmaceutically acceptable salt thereof.

8. The compound or pharmaceutically acceptable salt of claim 7, wherein k is 1.

9. The compound or pharmaceutically acceptable salt of claim 7, wherein $R_1$ is $C_{1-4}$alkyl.

10. The compound or pharmaceutically acceptable salt of claim 7, wherein $R_1$ is heterocyclyl, which is unsubstituted or substituted with $R^3$.

11. The compound or pharmaceutically acceptable salt of claim 10, wherein —(W$^2$)$_k$— is —NHC(=O)NH—.

12. The compound or pharmaceutically acceptable salt of claim 11, wherein $R^2$ is $C_{1-4}$alkyl.

13. A pharmaceutical composition comprising a compound claim of 1 or claim 7 and a pharmaceutically acceptable carrier.

14. A method of inhibiting activity of mTor, PI3α PI3β, PI3γ, PI3δ, and prostate cancer cells proliferation present in a cell, comprising contacting said cell with an effective amount of a compound of claim 1 or claim 7.

15. The method of claim 14, wherein the inhibiting activity takes place in a subject suffering from a disorder selected from of cancer, bone disorder, inflammatory disease, immune disease, nervous system disease, metabolic disease, respiratory disease, or cardiac disease.

16. The method of claim 15, further comprising administering a second therapeutic agent.

17. A method for inhibiting prostate cancer cell proliferation comprising contacting a cell with a compound of claim 1 or claim 7.

18. A method of ameliorating transplant rejection, mantle cell lymphoma, renal cell carcinoma, endometrial cancer, and restenosis, comprising administering to a subject in need thereof a therapeutically effective amount of a compound of claim 1 or claim 7.

19. A compound of formula or a pharmaceutically acceptable salt thereof, wherein the formula is:

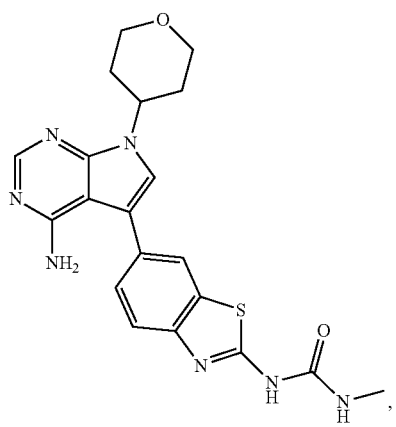

,

-continued

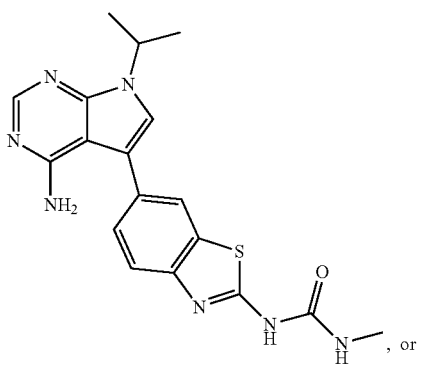

, or

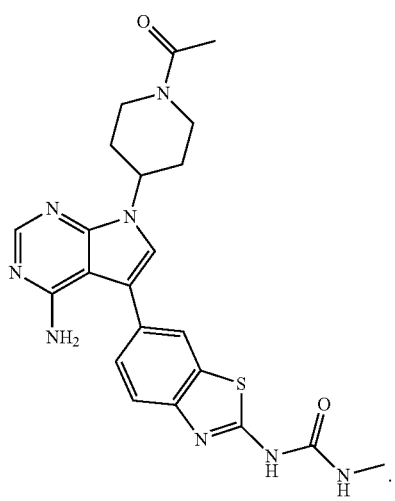

.

* * * * *